(12) United States Patent
Zemel et al.

(10) Patent No.: US 10,344,002 B2
(45) Date of Patent: Jul. 9, 2019

(54) COMPOSITIONS AND METHODS FOR TREATING METABOLIC DISORDERS

(71) Applicant: NuSirt Sciences, Inc., Nashville, TN (US)

(72) Inventors: Michael Zemel, Knoxville, TN (US); Antje Bruckbauer, Knoxville, TN (US)

(73) Assignee: NuSirt Sciences, Inc., Nashville, TN (US)

( * ) Notice: Subject to any disclaimer, the term of this patent is extended or adjusted under 35 U.S.C. 154(b) by 0 days.

(21) Appl. No.: 15/715,702

(22) Filed: Sep. 26, 2017

(65) Prior Publication Data

US 2018/0105498 A1 Apr. 19, 2018

Related U.S. Application Data

(60) Provisional application No. 62/399,973, filed on Sep. 26, 2016.

(51) Int. Cl.
*C07D 233/88* (2006.01)
*A61P 3/00* (2006.01)

(52) U.S. Cl.
CPC .............. *C07D 233/88* (2013.01); *A61P 3/00* (2018.01)

(58) Field of Classification Search
None
See application file for complete search history.

(56) References Cited

U.S. PATENT DOCUMENTS

| | | | |
|---|---|---|---|
| 5,679,712 | A | 10/1997 | Schwark et al. |
| 6,372,790 | B1 | 4/2002 | Bonhomme et al. |
| 2003/0162784 | A1 | 8/2003 | Mylari |
| 2004/0092495 | A1 | 5/2004 | Moinet et al. |
| 2005/0124693 | A1 | 6/2005 | Taka et al. |
| 2008/0177074 | A1 | 7/2008 | Naddaka et al. |
| 2009/0203653 | A1 | 8/2009 | Garvey |
| 2011/0275561 | A1 | 11/2011 | Graefe-Mody et al. |
| 2014/0179660 | A1 | 6/2014 | Kim et al. |
| 2015/0025006 | A1 | 1/2015 | Laria et al. |
| 2016/0038525 | A1 | 2/2016 | Broedl et al. |

FOREIGN PATENT DOCUMENTS

| | | |
|---|---|---|
| DE | 2205744 A1 | 8/1973 |
| EP | 0589336 A1 | 3/1994 |
| EP | 0590455 A1 | 4/1994 |
| EP | 0612723 A1 | 8/1994 |
| EP | 0699663 A1 | 3/1996 |
| FR | 2222375 A1 | 10/1974 |
| FR | 2840302 A1 | 12/2003 |
| WO | WO-9943663 A1 | 9/1999 |
| WO | WO-2004083218 A1 | 9/2004 |
| WO | WO-2007097276 A1 | 8/2007 |
| WO | WO-2008090550 A2 | 7/2008 |
| WO | WO-2013103384 A1 | 7/2013 |
| WO | WO-2013149258 A2 | 10/2013 |
| WO | WO-2013156608 A1 | 10/2013 |
| WO | WO-2016049236 A1 | 3/2016 |
| WO | WO-2018058109 A1 | 3/2018 |

OTHER PUBLICATIONS

Bogdanova, et al., New barbituric acid derivatives with basic substituents at the nitrogen atom; Roczniki Chemii; vol. 47, Issue 1, pp. 115-121, Journal, 1973.
Burdarov, et al., Antimicrobial action of 5,5-disubstituted barbituric acids with basic substituents in the nitrogen atom; Doklady Bolgarskoi Akademii Nauk; vol. 27, Issue 5, pp. 695-698, Journal, 1974.
CAS Registry No. 1026025-24-0.
CAS Registry No. 1332605-26-1.
CAS Registry No. 1348810-39-8.
CAS Registry No. 1350248-43-9.
CAS Registry No. 1368442-88-9.
CAS Registry No. 1505854-50-1.
CAS Registry No. 1508525-07-2.
CAS Registry No. 1555308-12-7.
CAS Registry No. 1556935-23-9.
CAS Registry No. 1854873-11-2.
CAS Registry No. 1858385-50-8.
CAS Registry No. 1861683-63-7.
CAS Registry No. 1876534-58-5.
CAS Registry No. 1877827-85-4.
CAS Registry No. 1899228-55-7.
CAS Registry No. 46744-34-7.
CAS Registry No. 802874-46-0.
Cesnek, et al., Synthesis of 9-alkyl and 9-heteroalkyl substituted 2-amino-6-guanidinopurines and their influence on the NO-production in macrophages; Bioorganic & Medicinal Chemistry; vol. 13, Issue 8, pp. 2917-2926, 2005.
Doleckova, et al., Synthesis and biological evaluation of guanidino analogues of roscovitine; European Journal of Medicinal Chemistry; vol. 62; pp. 443-452; 2013.
International Search Report dated Nov. 16, 2017 for International Patent Application No. PCT/US2017/053448.
Mahto, et al., Admet & molecular docking studies of novel Zanamivir analogs as Neuraminidase inhibitors; International Journal of Pharmaceutical Sciences Review and Research; vol. 13, Issue 1, pp. 91-94, Journal, 2012.
Nacheva, et al., Derivatives of barbituric acid with basic substituents at the nitrogen atom. III. Determination of ionization constants of some N-(2-benzylaminoethyl)-N-(2-aminoethyl), and N-(2-guanidinoethyl)-5,5-disubstituted barbituric acids in mixed water-ethanol solutions; Farmatsiya (Sofia, Bulgaria); vol. 23, Issue 2, pp. 6-14, Journal 1973.

(Continued)

*Primary Examiner* — Heidi Reese
(74) *Attorney, Agent, or Firm* — Wilson Sonsini Goodrich & Rosati

(57) ABSTRACT

Methods and compounds useful for reducing, treating, preventing, or sustaining the reduction of a metabolic disease or disorder are provided herein. Also provided herein are compositions and kits for practicing any of the methods described herein.

32 Claims, 14 Drawing Sheets
(3 of 14 Drawing Sheet(s) Filed in Color)

(56) References Cited

OTHER PUBLICATIONS

Soliman, et al., Synthesis of Novel Modified Guanidines: Reaction of Dicyandiamide with Amino Acids, Amides, and Amines in Aqueous Medium; Journal of Heterocyclic Chemistry; Sep. 2014: vol. 51, Issue 5, pp. 1322-1326.

Ulbricht, H., 2-Aminooxazoles as potential hydrogen-bonding virucides. Part 1. N-Unsubstituted and N-substituted 2-aminooxazoles; Pharmazie; vol. 42, Issue 9, pp. 598-601, Journal, 1987.

Yamamoto, et al., Design, synthesis and quantitative structure-activity relationship study of N-(3-oxo-3,4-dihydro-2H-benzo[1,4]oxazine-7-carbonyl)guanidine derivatives as potent Na/H exchange inhibitors; Chemical & Pharmaceutical Bulletin, vol. 45, Issue 12, pp. 1975-1983, Journal, 1997.

Fig. 14A
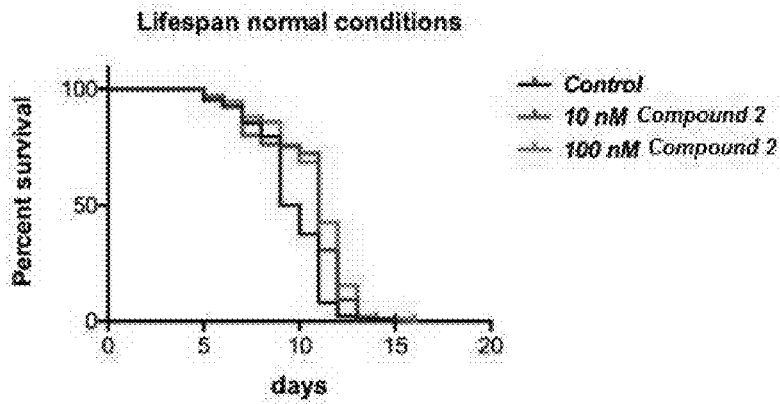
Fig. 14B
|  | Control | 10 nM Compound 2 | 100 nM Compound 2 |
| --- | --- | --- | --- |
| median survival (days) | 9 | 11 | 11 |
| max lifespan (days) | 15 | 13 | 16 |
| p-value (Log-rank) from Control |  | <0.0001 | 0.0002 |
Fig. 14C
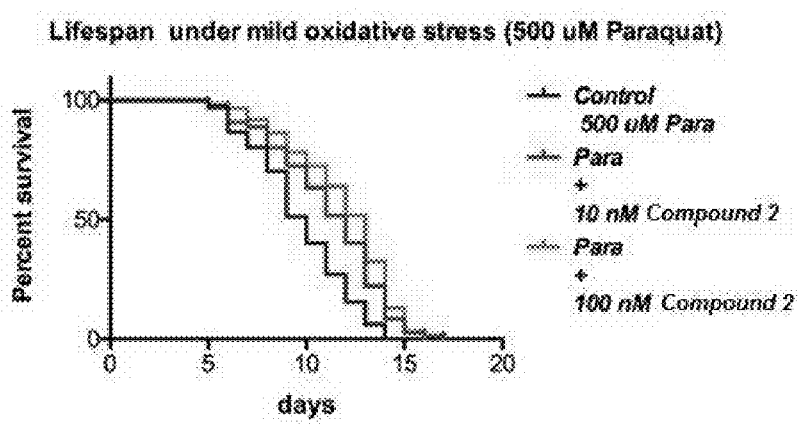
Fig. 14D
|  | Paraquat 500 uM | | |
| --- | --- | --- | --- |
|  | Control | 10 nM Compound 2 | 100 nM Compound 2 |
| median survival (days) | 10 | 12 | 13 |
| max lifespan (days) | 14 | 16 | 16 |
| p-value to Para-Control |  | <0.0001 | <0.0001 |

COMPOSITIONS AND METHODS FOR TREATING METABOLIC DISORDERS

CROSS-REFERENCE

This application claims priority to U.S. Provisional Application 62/399,973, filed on Sep. 26, 2016, the entire content of which is incorporated herein by reference.

BACKGROUND OF THE INVENTION

Metabolic disorders, such as hyperlipidemia, diabetes, high cholesterol, arteriosclerosis, hypertension and obesity, and the related diseases present a significant burden to public health. For instance, obesity, clinically defined as a body mass index of over 30 $kg/m^2$, is estimated to affect 35.7% of the U.S. adult population. In the U.S., obesity is estimated to cause roughly 110,000-365,000 deaths per year. Obesity can result in hyperlipidemia, characterized by an excess of lipids, including cholesterol, cholesterol esters, phospholipids, and triglycerides, in the bloodstream. Additionally, obesity can result in diabetes and other related diseases. Diabetes is a metabolic disorder characterized by high blood glucose levels or low glucose tolerance, and is estimated to affect 8% of the U.S. population. Obesity is also associated with vascular disease, cancer, renal disease, infectious diseases, external causes, intentional self-harm, nervous system disorders, and chronic pulmonary disease (N Engl J Med 2011; 364:829-841). Metabolic syndrome, in which subjects present with central obesity and at least two other metabolic disorders (such as high triglycerides, high blood pressure, or diabetes), is estimated to affect 25% of the U.S. population.

Hepatic steatosis, also sometimes referred to as fatty liver disease, is a condition generally characterized by an abnormal retention of lipids in cells of the liver. Hepatic steatosis affects millions of people worldwide. The prevalence of fatty liver disease has been estimated to range from 10-24% in various countries around the globe. Fatty liver disease can be classified into several categories. For example, non-alcoholic fatty liver disease (NAFLD) generally refers to a spectrum of hepatic lipid disorders characterized by hepatic steatosis with no known secondary cause. NAFLD can be subcategorized into (a) non-alcoholic fatty liver (NAFL), defined as the presence of steatosis in the absence of histological evidence of hepatocellular injury, and (b) non-alcoholic steatohepatitis (NASH), hepatic steatosis accompanied by hepatocyte injury and inflammation. NASH may occur with or without fibrosis, but may progress to fibrosis and cirrhosis. NAFLD is generally associated with energy metabolism pathologies, including obesity, dyslipidemia, diabetes and metabolic syndrome. The prevalence of NAFLD in the general population is estimated at 20%, with prevalence of NASH estimated to be 3-5%. Among patients with obesity (or diabetes) and patients with dyslipidemias, the prevalence rate of NAFLD is estimated 70% and 50%, respectively.

Nicotinic acid, a form of vitamin B3 (niacin), has been used to treat hyperlipidemia which is one of the symptoms of obesity and other conditions. When taken in high doses (1-4 g/day typically; maximum clinical dose is 6 g/day), nicotinic acid can treat hyperlipidemia, as it can lower total lipid, LDL, cholesterol, triglycerides, and lipoprotein, or raise HDL lipoprotein in the bloodstream. It can also reduce atherosclerotic plaque progression and coronary heart disease morbidity and mortality.

Diabetes, also sometimes associate with obesity, can be treated with anti-diabetic agents such as metformin. Metformin, along with phenformin and buformin, is a form of biguanide, which is a guanide. When ingested (1000-2550 mg/day), metformin can treat diabetes by increasing insulin sensitivity, increasing glucose uptake in the gut, increasing glucose utilization, and lowering blood glucose level. Metformin does not increase the amount of insulin produced by the body and thus generally does not cause hypoglycemia, as many other diabetes medications can do.

Many efforts have been attempted to develop treatments for metabolic disorders such as hyperlipidemia and diabetes. However, both nicotinic acid and metformin can have significant side-effect and hence can be generally poorly tolerated. For instance, one significant side-effect of nicotinic acid involves severe cutaneous vasodilation and flushing responses. Such well-documented side-effects have limited the prescription of nicotinic acid. (Carlson L A. Nicotinic acid: the broad-spectrum lipid drug. A 50th anniversary review. J Int Med 2005; 258:94-114). Current anti-diabetic agents such as metformin can be associated with other adverse effects. Amongst them are common adverse gastro-intestinal effects that cause discomfort and limit effective dosing, as well as the rare but serious adverse event of lactic acidosis. While side effects are somewhat attenuated in sustained (SR) and extended (ER) release preparations, the side effects persist sufficiently to limit the usage of these otherwise effective drugs.

SUMMARY OF THE INVENTION

The present disclosure provides for methods, compounds, compositions, and kits for reducing, treating, preventing, or sustaining the reduction of a metabolic disease or disorder, including but not limited to, diabetes, metabolic syndrome, obesity, hyperlipidemia, high cholesterol, arteriosclerosis, hypertension, non-alcoholic steatohepatitis, non-alcoholic fatty liver, non-alcoholic fatty liver disease, or hepatic steatosis in a subject in need thereof.

Sirtuins are highly conserved protein deacetylases and/or ADP-ribosyltransferases that have been shown to extend lifespan in lower model organisms, such as yeast, *C. elegans*, and drosophila. In mammals, sirtuins have been shown to act as metabolic sensors, responding to environmental signals to coordinate the activity of genes that regulate multiple energy homeostasis pathways. For example, studies have shown that sirtuin activation mimics the effects of caloric restriction, an intervention demonstrated to significantly extend lifespan, and activates genes that improve glucose homeostasis and the conversion of fat to energy by fatty acid oxidation. Sirtuin pathway activators can include any agents which activate one or more components of a sirtuin pathway. The sirtuin pathway includes, without limitation, signaling molecules such as, Sirt1, Sirt3, and AMPK. The output of the pathway can be determined by the expression level and/or the activity of the pathway and/or a physiological effect. In some embodiments, activation of the Sirt1 pathway includes stimulation of PGC1-α and/or subsequent stimulation of mitochondrial biogenesis and fatty acid oxidation. An increase or activation of a sirtuin pathway can be observed by an increase in the activity of a pathway component protein. For example, the protein can be Sirt1, PGC1-α, AMPK, Epacl, Adenylyl cyclase, Sirt3, or any other proteins and their respective associated proteins along the signaling pathway depicted in FIG. 1 (Park et. al., "Resveratrol Ameliorates Aging-Related Metabolic Phenotypes by Inhibiting cAMP Phosphodiesterases," Cell 148, 421-433 Feb. 3, 2012). Non-limiting examples of physiological effects that can serve as measures of sirtuin pathway output include mitochondrial biogenesis, fatty acid oxidation, glucose uptake, palmitate uptake, oxygen consumption, carbon dioxide production, weight loss, heat production, visceral adipose tissue loss, respiratory exchange ratio, insulin sensitivity, inflammation marker level, vasodilation, browning of fat cells, and irisin production. Examples of indicia of browning of fat cells include, without limitation, increased fatty acid oxidation, and expression of one or more brown-fat-selective genes (e.g., Ucp1, Cidea, Prdm16, and Ndufs1). In some embodiments, changes in one or more physiological effects that can serve as measures of sirtuin pathway output are induced by increasing irisin production.

The sirtuin pathway may further be defined as any pathway incorporating or converging upon pathways mediated by phosphodiesterases (PDEs). PDEs are enzymes that interact with cyclic adenosine monophosphates (cAMPs) and cyclic guanosine monophosphates (cGMPs). The PDE family of enzymes comprises multiple subclasses, including PDE 1-11 in humans. Inhibitors of these phosphodiesterases can prevent the inactivation of cAMPs and cGMPs, and can have a variety of different physiological effects. The PDE inhibitors can be selective, by preferentially inhibiting one PDE subclass as compared to another subclass, or non-selective, which have a substantially lower degree of selectivity for individual PDE subclasses. Sildenafil is an example of a selective PDE inhibitor that has shown selective inhibition of PDE5. Sildenafil is a pharmaceutically active agent that has been used to treat pulmonary hypertension, erectile dysfunction, and altitude sickness.

The sirtuin pathway can be activated by sirtuin pathway activators, including but not limited to biguanides (e.g., metformin), to treat metabolic diseases. Co-administration of a sirtuin pathway activator (e.g., metformin) and the branched-chain amino acid leucine activates the sirtuin pathway to a greater extent than administration of any one of the agents alone. Co-administration of these agents has a synergistic effect, e.g., activating the sirtuin pathway, treating a metabolic disease, and/or reducing or preventing NASH or hepatic steatosis to a greater extent than an additive effect of administering the sirtuin pathway activator alone or administering the leucine in free amino acid form (or metabolite thereof) alone.

Greater potency may be achievable by covalently linking the active moieties of synergistic agents. For example, combining active moieties of two synergistic agents, such as a guanidine group or biguanidine group from a sirtuin pathway activator (e.g., metformin) and a branched alkyl chain (e.g., isobutyl group, sec-butyl group, tert-butyl group, isopropyl group) from a branched chain amino acid (e.g., leucine), in a single compound may retain the synergistic effect of the two separate agents or may have an even greater effect. Compounds can be designed to treat metabolic diseases or disorders, including but not limited to hyperlipidemia, diabetes, high cholesterol, arteriosclerosis, hypertension, obesity, metabolic syndrome, hepatic steatosis, NAFLD, NAFL, and NASH, by combining sirtuin activating elements of one or more sirtuin pathway activators and/or synergistic agents to activate the sirtuin pathway.

Provided herein is a method of treating a metabolic disease or disorder in a subject in need thereof, the method comprising administering to the subject a compound of Formula (I-a) or Formula (II-a):

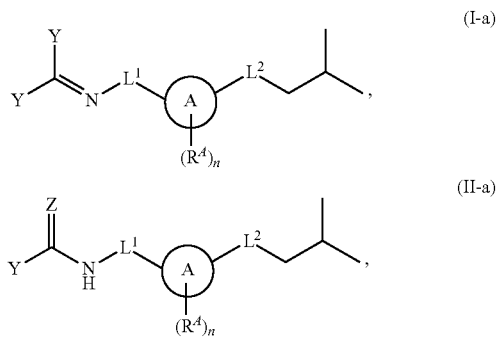

or a pharmaceutically acceptable salt thereof, wherein:

A is selected from a bond, $C_{3-12}$ carbocycle, and 3- to 12-membered heterocycle, wherein the carbocycle or heterocycle is monocyclic or multicyclic;

Y is selected from $N(R^1)_2$, $C(R^B)_3$, $OR^3$, and $SR^3$;

Z is selected from $NR^1$, $C(R^B)_2$, O, and S;

each of $L^1$ and $L^2$ is independently selected from a bond, —O—, —S—, —N(R$^1$)—, —N(R$^1$)CH$_2$—, —C(O)—, —C(O)O—, —OC(O)—, —OC(O)O—, —C(O)N(R$^1$)—, —C(O)N(R$^1$)C(O)—, —C(O)N(R$^1$)C(O)N(R$^1$)—, —N(R$^1$)C(O)—, —N(R$^1$)C(O)N(R$^1$)—, —N(R$^1$)C(O)O—, —OC(O)N(R$^1$)—, —C(NR$^1$)—, —N(R$^1$)C(NR$^1$)—, —C(NR$^1$)N(R$^1$)—, —N(R$^1$)C(NR$^1$)N(R$^1$)—, —S(O)$_2$—, —OS(O)—, —S(O)O—, —S(O)—, —OS(O)$_2$—, —S(O)$_2$O—, —N(R$^1$)S(O)$_2$—, —S(O)$_2$N(R$^1$)—, —N(R$^1$)S(O)—, —S(O)N(R$^1$)—, —N(R$^1$)S(O)$_2$N(R$^1$)—, —N(R$^1$)S(O)N(R$^1$)—, alkylene, alkenylene, alkynylene, heteroalkylene, heteroalkenylene, and heteroalkynylene, wherein one or more hydrogen atoms are optionally substituted with $R^2$ and wherein two $R^2$ groups attached to the same atom or different atoms can optionally join together to form a $C_{3-8}$ carbocycle or 3- to 8-membered heterocycle;

$R^A$ is independently selected at each occurrence from $R^2$;

n is an integer from 0 to 10;

$R^B$ is independently selected at each occurrence from hydrogen and $R^2$, and/or two $R^B$ groups attached to the same atom can optionally join together to form a $C_{3-8}$ carbocycle or 3- to 8-membered heterocycle;

$R^1$ is independently selected at each occurrence from: hydrogen, —C(O)R$^3$, —C(O)OR$^3$, —C(O)N(R$^3$)$_2$, —C(O)NR$^4$R$^5$;

$C_{1-6}$ alkyl, $C_{2-6}$ alkenyl, and $C_{2-6}$ alkynyl, each of which is independently optionally substituted at each occurrence with one or more substituents selected from halogen, —NO$_2$, —CN, —OR$^3$, —SR$^3$, —N(R$^3$)$_2$, —NR$^4$R$^5$, —S(=O)R$^3$, —S(=O)$_2$R$^3$, —S(=O)$_2$N(R$^3$)$_2$, —S(=O)$_2$NR$^4$R$^5$, —NR$^3$S(=O)$_2$R$^3$, —NR$^3$S(=O)$_2$N(R$^3$)$_2$, —NR$^3$S(=O)$_2$NR$^4$R$^5$, —C(O)R$^3$, —C(O)OR$^3$, —OC(O)R$^3$, —OC(O)OR$^3$, —OC(O)N(R$^3$)$_2$, —OC(O)NR$^4$R$^5$, —NR$^3$C(O)R$^3$, —NR$^3$C(O)OR$^3$, —NR$^3$C(O)N(R$^3$)$_2$, —NR$^3$C(O)NR$^4$R$^5$, —C(O)N(R$^3$)$_2$, —C(O)NR$^4$R$^5$, —P(O)(OR$^3$)$_2$, —P(O)(R$^3$)$_2$, =O, =S, =N(R$^3$), $C_{3-12}$ carbocycle and 3- to 12-membered heterocycle; and $C_{3-12}$ carbocycle and 3- to 12-membered heterocycle, wherein each $C_{3-12}$ carbocycle and 3- to 12-membered heterocycle in $R^1$ is independently optionally substituted with one or more substituents selected from halogen, —NO$_2$, —CN, —OR$^3$, —SR$^3$, —N(R$^3$)$_2$, —NR$^4$R$^5$, —S(=O)R$^3$, —S(=O)$_2$R$^3$, —S(=O)$_2$N(R$^3$)$_2$, —S(=O)$_2$NR$^4$R$^5$, —NR$^3$S(=O)$_2$R$^3$, —NR$^3$S (=O)₂N(R³)₂, —NR³S(=O)₂NR⁴R⁵, —C(O)R³, —C(O)OR³, —OC(O)R³, —OC(O)OR³, —OC(O)N(R³)₂, —OC(O)NR⁴R⁵, —NR³C(O)R³, —NR³C(O)OR³, —NR³C(O)N(R³)₂, —NR³C(O)NR⁴R⁵, —C(O)N(R³)₂, —C(O)NR⁴R⁵, —P(O)(OR³)₂, —P(O)(R³)₂, =O, =S, =N(R³), C₁₋₆ alkyl, C₁₋₆ haloalkyl, C₂₋₆ alkenyl, and C₂₋₆ alkynyl;

R² is independently selected at each occurrence from: halogen, —NO₂, —CN, —OR³, —SR³, —N(R³)₂, —NR⁴R⁵, —S(=O)R³, —S(=O)₂R³, —S(=O)₂N(R³)₂, —S(=O)₂NR⁴R⁵, —NR³S(=O)₂R³, —NR³S(=O)₂N(R³)₂, —NR³S(=O)₂NR⁴R⁵, —C(O)R³, —C(O)OR³, —OC(O)R³, —OC(O)OR³, —OC(O)N(R³)₂, —OC(O)NR⁴R⁵, —NR³C(O)R³, —NR³C(O)OR³, —NR³C(O)N(R³)₂, —NR³C(O)NR⁴R⁵, —C(O)N(R³)₂, —C(O)NR⁴R⁵, —P(O)(OR³)₂, —P(O)(R³)₂, =O, =S, =N(R³);

C₁₋₁₀ alkyl, C₂₋₁₀ alkenyl, and C₂₋₁₀ alkynyl, each of which is independently optionally substituted at each occurrence with one or more substituents selected from halogen, —NO₂, —CN, —OR³, —SR³, —N(R³)₂, —NR⁴R⁵, —S(=O)R³, —S(=O)₂R³, —S(=O)₂N(R³)₂, —S(=O)₂NR⁴R⁵, —NR³S(=O)₂R³, —NR³S(=O)₂N(R³)₂, —NR³S(=O)₂NR⁴R⁵, —C(O)R³, —C(O)OR³, —OC(O)R³, —OC(O)OR³, —OC(O)N(R³)₂, —OC(O)NR⁴R⁵, —NR³C(O)R³, —NR³C(O)OR³, —NR³C(O)N(R³)₂, —NR³C(O)NR⁴R⁵, —C(O)N(R³)₂, —C(O)NR⁴R⁵, —P(O)(OR³)₂, —P(O)(R³)₂, =O, =S, =N(R³), C₃₋₁₂ carbocycle, and 3- to 12-membered heterocycle; and C₃₋₁₂ carbocycle and 3- to 12-membered heterocycle, wherein each C₃₋₁₂ carbocycle and 3- to 12-membered heterocycle in R² is independently optionally substituted with one or more substituents selected from halogen, —NO₂, —CN, —OR³, —SR³, —N(R³)₂, —NR⁴R⁵, —S(=O)R³, —S(=O)₂R³, —S(=O)₂N(R³)₂, —S(=O)₂NR⁴R⁵, —NR³S(=O)₂R³, —NR³S(=O)₂N(R³)₂, —NR³S(=O)₂NR⁴R⁵, —C(O)R³, —C(O)OR³, —OC(O)R³, —OC(O)OR³, —OC(O)N(R³)₂, —OC(O)NR⁴R⁵, —NR³C(O)R³, —NR³C(O)OR³, —NR³C(O)N(R³)₂, —NR³C(O)NR⁴R⁵, —C(O)N(R³)₂, —C(O)NR⁴R⁵, —P(O)(OR³)₂, —P(O)(R³)₂, =O, =S, =N(R³), C₁₋₆ alkyl, C₁₋₆ haloalkyl, C₂₋₆ alkenyl, and C₂₋₆ alkynyl;

R³ is independently selected at each occurrence from hydrogen; and C₁₋₂₀ alkyl, C₂₋₂₀ alkenyl, C₂₋₂₀ alkynyl, 1- to 6-membered heteroalkyl, C₃₋₁₂ carbocycle, and 3- to 12-membered heterocycle, each of which is optionally substituted by halogen, —CN, —NO₂, —NH₂, —NHCH₃, —NHCH₂CH₃, =O, —OH, —OCH₃, —OCH₂CH₃, C₃₋₁₂ carbocycle, or 3- to 6-membered heterocycle; and R⁴ and R⁵ are taken together with the nitrogen atom to which they are attached to form a 3- to 8-membered heterocycle, optionally substituted with one or more R²;

thereby treating the metabolic disease or disorder in the subject.

In some cases of a method described herein, the compound is a compound of Formula (I-b) or Formula (II-b):

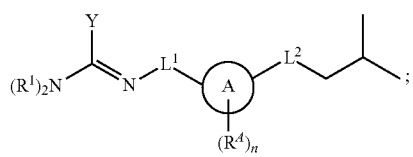
(I-b)

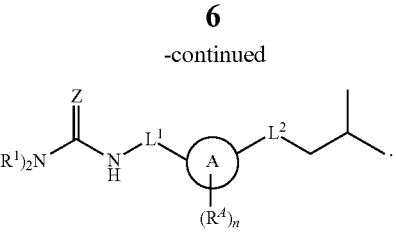
(II-b)

In some cases of a method described herein, the compound is a compound of Formula (I-c) or Formula (II-c):

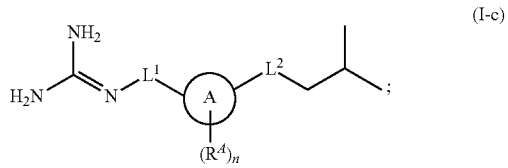
(I-c)

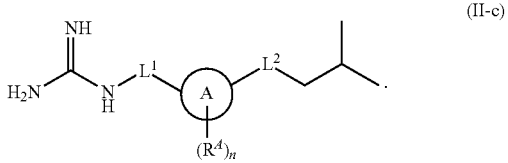
(II-c)

In some cases of a method described herein, the compound is a compound of Formula (III):

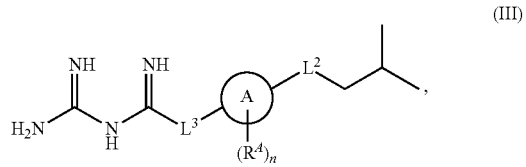
(III)

or a pharmaceutically acceptable salt thereof, wherein:

L³ is selected from a bond, —O—, —S—, —N(R¹)—, —N(R¹)CH₂—, —C(O)—, —C(O)O—, —OC(O)—, —OC(O)O—, —C(O)N(R¹)—, —C(O)N(R¹)C(O)—, —C(O)N(R¹)C(O)N(R¹)—, —N(R¹)C(O)—, —N(R¹)C(O)N(R¹)—, —N(R¹)C(O)O—, —OC(O)N(R¹)—, —C(NR¹)—, —N(R¹)C(NR¹)—, —C(NR¹)N(R¹)—, —N(R¹)C(NR¹)N(R¹)—, —S(O)₂—, —OS(O)—, —S(O)O—, —S(O)—, —OS(O)₂—, —S(O)₂O—, —N(R¹)S(O)₂—, —S(O)₂N(R¹)—, —N(R¹)S(O)—, —S(O)N(R¹)—, —N(R¹)S(O)₂N(R¹)—, —N(R¹)S(O)N(R¹)—, alkylene, alkenylene, alkynylene, heteroalkylene, heteroalkenylene, and heteroalkynylene, wherein one or more hydrogen atoms of L³ are optionally substituted with R² and wherein two R² groups attached to the same atom or different atoms of L³ can optionally join together to form a C₃₋₈ carbocycle or 3- to 8-membered heterocycle.

In some cases of a method described herein, the compound is a compound of Formula (IV):

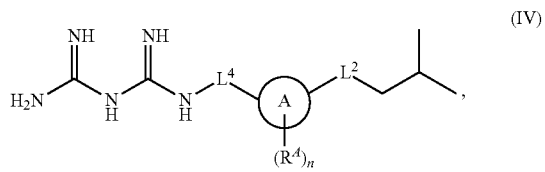
(IV)

or a pharmaceutically acceptable salt thereof, wherein:

$L^4$ is selected from a bond, —O—, —S—, —N($R^1$)—, —N($R^1$)CH$_2$—, —C(O)—, —C(O)O—, —OC(O)—, —OC(O)O—, —C(O)N($R^1$)—, —C(O)N($R^1$)C(O)—, —C(O)N($R^1$)C(O)N($R^1$)—, —N($R^1$)C(O)—, —N($R^1$)C(O)N($R^1$)—, —N($R^1$)C(O)O—, —OC(O)N($R^1$)—, —C(N$R^1$)—, —N($R^1$)C(N$R^1$)—, —C(N$R^1$)N($R^1$)—, —N($R^1$)C(N$R^1$)N($R^1$)—, —S(O)$_2$—, —OS(O)—, —S(O)O—, —S(O)—, —OS(O)$_2$—, —S(O)$_2$O—, —N($R^1$)S(O)$_2$—, —S(O)$_2$N($R^1$)—, —N($R^1$)S(O)—, —S(O)N($R^1$)—, —N($R^1$)S(O)$_2$N($R^1$)—, —N($R^1$)S(O)N($R^1$)—, alkylene, alkenylene, alkynylene, heteroalkylene, heteroalkenylene, and heteroalkynylene, wherein one or more hydrogen atoms of $L^4$ are optionally substituted with $R^2$ and wherein two $R^2$ groups attached to the same atom or different atoms of $L^4$ can optionally join together to form a $C_{3-8}$ carbocycle or 3- to 8-membered heterocycle.

In some cases of a method described herein, the compound is a biguanide.

In some cases of a method described herein, A is a bond. In some cases of a method described herein, A is monocyclic. In some cases of a method described herein, A is multicyclic. In some cases of a method described herein, A is a $C_{3-8}$ carbocycle or 3- to 8-membered heterocycle. In some cases of a method described herein, A is a $C_{3-6}$ carbocycle or 3- to 6-membered heterocycle. In some cases of a method described herein, A is a $C_{5-6}$ carbocycle or 5- to 6-membered heterocycle. In some cases of a method described herein, A is a $C_{3-12}$ carbocycle. In some cases of a method described herein, A is a 3- to 12-membered heterocycle. In some cases of a method described herein, A is a monocyclic heterocycle. In some cases of a method described herein, A is a 5-membered or 6-membered heterocycle.

In some cases of a method described herein, $L^2$ is a bond. In some cases of a method described herein, $L^2$ is an alkylene. In some cases of a method described herein, $L^2$ is a $C_{5-6}$ alkylene.

In some cases of a method described herein, the compound is a compound of Formula (V):

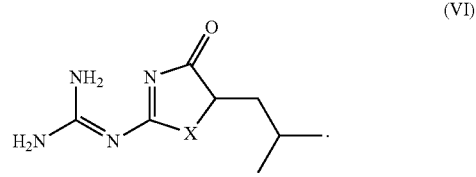

(V)

wherein:
each of W and X is independently selected from the group consisting of —O—, —S—, —N($R^1$)—, —N($R^1$)CH$_2$—, —C(O)—, —C(O)O—, —OC(O)—, —OC(O)O—, —C(O)N($R^1$)—, —C(O)N($R^1$)C(O)—, —C(O)N($R^1$)C(O)N($R^1$)—, —N($R^1$)C(O)—, —N($R^1$)C(O)N($R^1$)—, —N($R^1$)C(O)O—, —OC(O)N($R^1$)—, —C(N$R^1$)—, —N($R^1$)C(N$R^1$)—, —C(N$R^1$)N($R^1$)—, —N($R^1$)C(N$R^1$)N($R^1$)—, —S(O)$_2$—, —OS(O)—, —S(O)O—, —S(O)—, —OS(O)$_2$—, —S(O)$_2$O—, —N($R^1$)S(O)$_2$—, —S(O)$_2$N($R^1$)—, —N($R^1$)S(O)—, —S(O)N($R^1$)—, —N($R^1$)S(O)$_2$N($R^1$)—, —N($R^1$)S(O)N($R^1$)—, $C_{1-8}$ alkylene, $C_{1-8}$ alkenylene, $C_{1-8}$ alkynylene, $C_{1-7}$ heteroalkylene, $C_{1-7}$ heteroalkenylene, and $C_{1-7}$ heteroalkynylene, wherein one or more hydrogen atoms are optionally substituted with $R^2$ and wherein two $R^2$ groups attached to the same atom or different atoms can optionally join together to form a $C_{3-8}$ carbocycle or 3- to 8-membered heterocycle.

In some cases of a method described herein, W is selected from the group consisting of —C(O)— and —C($R^B$)$_2$—.

In some cases of a method described herein, the compound is a compound of Formula (VI):

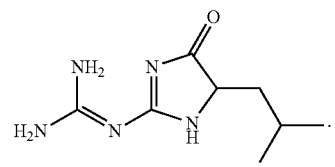

(VI)

In some cases of a method described herein, X is selected from the group consisting of —O—, —S—, —N($R^1$)—, —C($R^B$)$_2$—, and any combination thereof.

In some cases of a method described herein, the compound is

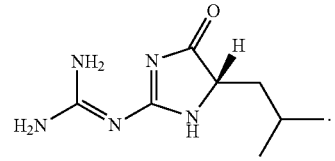

In some cases of a method described herein, the compound is

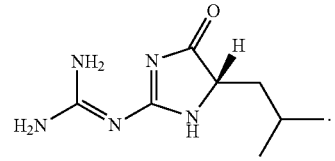

Provided herein is a method of treating a metabolic disease or disorder in a subject in need thereof, the method comprising administering to the subject a compound selected from Table 1 or Table 3, or a pharmaceutically acceptable salt thereof, thereby treating the metabolic disease or disorder in the subject.

In some cases of a method described herein, the metabolic disease or disorder is selected from the group consisting of diabetes, metabolic syndrome, obesity, hyperlipidemia, high cholesterol, arteriosclerosis, hypertension, non-alcoholic steatohepatitis, non-alcoholic fatty liver, non-alcoholic fatty liver disease, hepatic steatosis, and any combination thereof.

In some cases of a method described herein, the method further comprises administering a second therapeutic agent. In some cases of a method described herein, the second therapeutic agent is selected from the group consisting of a phosphodiesterase (PDE) inhibitor, sirtuin pathway activator, anti-diabetic agent, anti-hyperlipidemic agent, glucagon-like peptide-1 (GLP-1) agonist, dipeptidyl peptidase-4 (DPP-4) inhibitor, sodium-glucose cotransporter-2 (SGLT2) inhibitor or gliflozin, a fibrate, a nitric oxide (NO) donor, nicotinic acid, nicotinamide riboside, nicotinic acid metabolite, and any combination thereof. In some cases of a method described herein, the second therapeutic agent is selected from the group consisting of sildenafil, nicotinic acid, nicotinamide riboside, and nicotinic acid metabolite.

In some cases of a method described herein, the compound is administered to the subject at a dose of about 0.1-5,000 mg/day. In some cases of a method described herein, the compound is administered to the subject to achieve a circulating concentration in the subject within the range of about 1 nM to about 5 mM.

Provided herein is a compound of Formula (V):

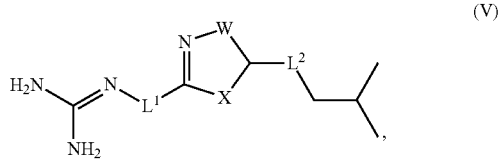

(V)

wherein:
each of $L^1$ and $L^2$ is independently selected from a bond, —O—, —S—, —N($R^1$)—, —N($R^1$)CH$_2$—, —C(O)—, —C(O)O—, —OC(O)—, —OC(O)O—, —C(O)N($R^1$)—, —C(O)N($R^1$)C(O)—, —C(O)N($R^1$)C(O)N($R^1$)—, —N($R^1$)C(O)—, —N($R^1$)C(O)N($R^1$)—, —N($R^1$)C(O)O—, —OC(O)N($R^1$)—, —C(N$R^1$)—, —N($R^1$)C(N$R^1$)—, —C(N$R^1$)N($R^1$)—, —N($R^1$)C(N$R^1$)N($R^1$)—, —S(O)$_2$—, —OS(O)—, —S(O)O—, —S(O)—, —OS(O)$_2$—, —S(O)$_2$O—, —N($R^1$)S(O)$_2$—, —S(O)$_2$N($R^1$)—, —N($R^1$)S(O)—, —S(O)N($R^1$)—, —N($R^1$)S(O)$_2$N($R^1$)—, —N($R^1$)S(O)N($R^1$)—, alkylene, alkenylene, alkynylene, heteroalkylene, heteroalkenylene, and heteroalkynylene, wherein one or more hydrogen atoms are optionally substituted with $R^2$ and wherein two $R^2$ groups attached to the same atom or different atoms can optionally join together to form a $C_{3-8}$ carbocycle or 3- to 8-membered heterocycle;

$R^1$ is independently selected at each occurrence from:
hydrogen, —C(O)$R^3$, —C(O)O$R^3$, —C(O)N($R^3$)$_2$, —C(O)N$R^4R^5$;
$C_{1-6}$ alkyl, $C_{2-6}$ alkenyl, and $C_{2-6}$ alkynyl, each of which is independently optionally substituted at each occurrence with one or more substituents selected from halogen, —NO$_2$, —CN, —OR$^3$, —SR$^3$, —N(R$^3$)$_2$, —NR$^4$R$^5$, —S(=O)R$^3$, —S(=O)$_2$R$^3$, —S(=O)$_2$N(R$^3$)$_2$, —S(=O)$_2$NR$^4$R$^5$, —NR$^3$S(=O)$_2$R$^3$, —NR$^3$S(=O)$_2$N(R$^3$)$_2$, —NR$^3$S(=O)$_2$NR$^4$R$^5$, —C(O)R$^3$, —C(O)OR$^3$, —OC(O)R$^3$, —OC(O)OR$^3$, —OC(O)N(R$^3$)$_2$, —OC(O)NR$^4$R$^5$, —NR$^3$C(O)R$^3$, —NR$^3$C(O)OR$^3$, —NR$^3$C(O)N(R$^3$)$_2$, —NR$^3$C(O)NR$^4$R$^5$, —C(O)N(R$^3$)$_2$, —C(O)NR$^4$R$^5$, —P(O)(OR$^3$)$_2$, —P(O)(R$^3$)$_2$, =O, =S, =N(R$^3$), $C_{3-12}$ carbocycle and 3- to 12-membered heterocycle; and
$C_{3-12}$ carbocycle and 3- to 12-membered heterocycle, wherein each $C_{3-12}$ carbocycle and 3- to 12-membered heterocycle in $R^1$ is independently optionally substituted with one or more substituents selected from halogen, —NO$_2$, —CN, —OR$^3$, —SR$^3$, —N(R$^3$)$_2$, —NR$^4$R$^5$, —S(=O)R$^3$, —S(=O)$_2$R$^3$, —S(=O)$_2$N(R$^3$)$_2$, —S(=O)$_2$NR$^4$R$^5$, —NR$^3$S(=O)$_2$R$^3$, —NR$^3$S(=O)$_2$N(R$^3$)$_2$, —NR$^3$S(=O)$_2$NR$^4$R$^5$, —C(O)R$^3$, —C(O)OR$^3$, —OC(O)R$^3$, —OC(O)OR$^3$, —OC(O)N(R$^3$)$_2$, —OC(O)NR$^4$R$^5$, —NR$^3$C(O)R$^3$, —NR$^3$C(O)OR$^3$, —NR$^3$C(O)N(R$^3$)$_2$, —NR$^3$C(O)NR$^4$R$^5$, —C(O)N(R$^3$)$_2$, —C(O)NR$^4$R$^5$, —P(O)(OR$^3$)$_2$, —P(O)(R$^3$)$_2$, =O, =S, =N(R$^3$), $C_{1-6}$ alkyl, $C_{1-6}$ haloalkyl, $C_{2-6}$ alkenyl, and $C_{2-6}$ alkynyl;

$R^2$ is independently selected at each occurrence from:
halogen, —NO$_2$, —CN, —OR$^3$, —SR$^3$, —N(R$^3$)$_2$, —NR$^4$R$^5$, —S(=O)R$^3$, —S(=O)$_2$R$^3$, —S(=O)$_2$N(R$^3$)$_2$, —S(=O)$_2$NR$^4$R$^5$, —NR$^3$S(=O)$_2$R$^3$, —NR$^3$S(=O)$_2$N(R$^3$)$_2$, —NR$^3$S(=O)$_2$NR$^4$R$^5$, —C(O)R$^3$, —C(O)OR$^3$, —OC(O)R$^3$, —OC(O)OR$^3$, —OC(O)N(R$^3$)$_2$, —OC(O)NR$^4$R$^5$, —NR$^3$C(O)R$^3$, —NR$^3$C(O)OR$^3$, —NR$^3$C(O)N(R$^3$)$_2$, —NR$^3$C(O)NR$^4$R$^5$, —C(O)N(R$^3$)$_2$, —C(O)NR$^4$R$^5$, —P(O)(OR$^3$)$_2$, —P(O)(R$^3$)$_2$, =O, =S, =N(R$^3$);
$C_{1-10}$ alkyl, $C_{2-10}$ alkenyl, and $C_{2-10}$ alkynyl, each of which is independently optionally substituted at each occurrence with one or more substituents selected from halogen, —NO$_2$, —CN, —OR$^3$, —SR$^3$, —N(R$^3$)$_2$, —NR$^4$R$^5$, —S(=O)R$^3$, —S(=O)$_2$R$^3$, —S(=O)$_2$N(R$^3$)$_2$, —S(=O)$_2$NR$^4$R$^5$, —NR$^3$S(=O)$_2$R$^3$, —NR$^3$S(=O)$_2$N(R$^3$)$_2$, —NR$^3$S(=O)$_2$NR$^4$R$^5$, —C(O)R$^3$, —C(O)OR$^3$, —OC(O)R$^3$, —OC(O)OR$^3$, —OC(O)N(R$^3$)$_2$, —OC(O)NR$^4$R$^5$, —NR$^3$C(O)R$^3$, —NR$^3$C(O)OR$^3$, —NR$^3$C(O)N(R$^3$)$_2$, —NR$^3$C(O)NR$^4$R$^5$, —C(O)N(R$^3$)$_2$, —C(O)NR$^4$R$^5$, —P(O)(OR$^3$)$_2$, —P(O)(R$^3$)$_2$, =O, =S, =N(R$^3$), $C_{3-12}$ carbocycle, and 3- to 12-membered heterocycle; and
$C_{3-12}$ carbocycle and 3- to 12-membered heterocycle, wherein each $C_{3-12}$ carbocycle and 3- to 12-membered heterocycle in $R^2$ is independently optionally substituted with one or more substituents selected from halogen, —NO$_2$, —CN, —OR$^3$, —SR$^3$, —N(R$^3$)$_2$, —NR$^4$R$^5$, —S(=O)R$^3$, —S(=O)$_2$R$^3$, —S(=O)$_2$N(R$^3$)$_2$, —S(=O)$_2$NR$^4$R$^5$, —NR$^3$S(=O)$_2$R$^3$, —NR$^3$S(=O)$_2$N(R$^3$)$_2$, —NR$^3$S(=O)$_2$NR$^4$R$^5$, —C(O)R$^3$, —C(O)OR$^3$, —OC(O)R$^3$, —OC(O)OR$^3$, —OC(O)N(R$^3$)$_2$, —OC(O)NR$^4$R$^5$, —NR$^3$C(O)R$^3$, —NR$^3$C(O)OR$^3$, —NR$^3$C(O)N(R$^3$)$_2$, —NR$^3$C(O)NR$^4$R$^5$, —C(O)N(R$^3$)$_2$, —C(O)NR$^4$R$^5$, —P(O)(OR$^3$)$_2$, —P(O)(R$^3$)$_2$, =O, =S, =N(R$^3$), $C_{1-6}$ alkyl, $C_{1-6}$ haloalkyl, $C_{2-6}$ alkenyl, and $C_{2-6}$ alkynyl;

$R^3$ is independently selected at each occurrence from hydrogen; and $C_{1-20}$ alkyl, $C_{2-20}$ alkenyl, $C_{2-20}$ alkynyl, 1- to 6-membered heteroalkyl, $C_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, $C_{3-12}$ carbocycle, or 3- to 6-membered heterocycle; and $R^4$ and $R^5$ are taken together with the nitrogen atom to which they are attached to form a heterocycle, optionally substituted with one or more $R^2$;

each of W and X is independently selected from the group consisting of —O—, —S—, —N($R^1$)—, —N($R^1$)CH$_2$—, —C(O)—, —C(O)O—, —OC(O)—, —OC(O)O—, —C(O)N($R^1$)—, —C(O)N($R^1$)C(O)—, —C(O)N($R^1$)C(O)N($R^1$)—, —N($R^1$)C(O)—, —N($R^1$)C(O)N($R^1$)—, —N($R^1$)C(O)O—, —OC(O)N($R^1$)—, —C(N$R^1$)—, —N($R^1$)C(N$R^1$)—, —C(N$R^1$)N($R^1$)—, —N($R^1$)C(N$R^1$)N($R^1$)—, —S(O)$_2$—, —OS(O)—, —S(O)O—, —S(O)—, —OS(O)$_2$—, —S(O)$_2$O—, —N($R^1$)S(O)$_2$—, —S(O)$_2$N($R^1$)—, —N($R^1$)S(O)—, —S(O)N($R^1$)—, —N($R^1$)S(O)$_2$N($R^1$)—, —N($R^1$)S(O)N($R^1$)—, $C_{1-8}$ alkylene, $C_{1-8}$ alkenylene, $C_{1-8}$ alkynylene, $C_{1-7}$ heteroalkylene, $C_{1-7}$ heteroalkenylene, and $C_{1-7}$ heteroalkynylene, wherein one or more hydrogen atoms are optionally substituted with $R^2$ and wherein two $R^2$ groups attached to the same atom or different atoms can optionally join together to form a $C_{3-8}$ carbocycle or 3- to 8-membered heterocycle.

In some cases of a method described herein, W is selected from the group consisting of —C(O)— and —C($R^B$)$_2$—.

In some cases of a method described herein, the compound is a compound of Formula (VI):

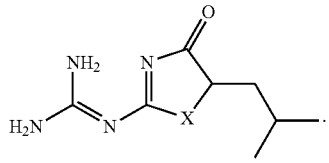
(VI)

In some cases of a method described herein, X is selected from the group consisting of —O—, —S—, —N(R$^1$)—, —C(R$^B$)$_2$—, and any combination thereof.

In some cases of a method described herein, the compound is

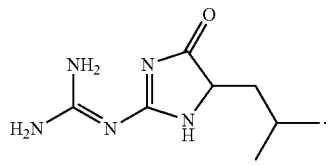

In some cases of a method described herein, the compound is

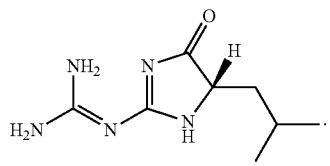

Provided herein is a compound selected from Table 1 or a pharmaceutically acceptable salt thereof.

Provided herein is a pharmaceutical composition comprising a compound described herein and a pharmaceutically acceptable carrier. In some cases of a pharmaceutical composition described herein, the pharmaceutical composition is formulated for oral administration. In some cases of a pharmaceutical composition described herein, the pharmaceutical composition is formulated for injection.

Provided herein is a kit comprising a pharmaceutical composition described herein and instructions for using the composition to treat a subject suffering from a disease or condition.

Provided herein is a method of treating a disease or condition in a subject in need thereof, the method comprising: administering to the subject a therapeutically effective amount of a compound described herein.

Provided herein is a method of treating a disease or condition in a subject, comprising administering to the subject a therapeutically effective amount of a pharmaceutical composition of a compound described herein. In some cases of a method described herein, the disease or condition is selected from the group consisting of diabetes, metabolic syndrome, obesity, hyperlipidemia, high cholesterol, arteriosclerosis, hypertension, non-alcoholic steatohepatitis, non-alcoholic fatty liver, non-alcoholic fatty liver disease, hepatic steatosis, and any combination thereof.

Provided herein is a composition comprising:
(a) a compound of Formula (I-a) or Formula (II-a):

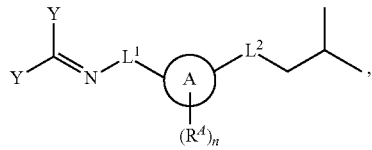
(I-a)

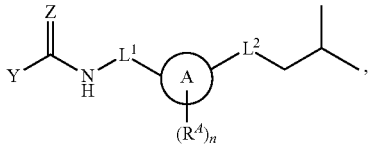
(II-a)

or a pharmaceutically acceptable salt thereof, wherein:
A is selected from a bond, C$_{3-12}$ carbocycle, and 3- to 12-membered heterocycle, wherein the carbocycle or heterocycle is monocyclic or multicyclic;
Y is selected from N(R$^1$)$_2$, C(R$^B$)$_3$, OR$^3$, and SR$^3$;
Z is selected from NR$^1$, C(R$^B$)$_2$, O, and S;
each of L$^1$ and L$^2$ is independently selected from a bond, —O—, —S—, —N(R$^1$)—, —N(R$^1$)CH$_2$—, —C(O)—, —C(O)O—, —OC(O)—, —OC(O)O—, —C(O)N(R$^1$)—, —C(O)N(R$^1$)C(O)—, —C(O)N(R$^1$)C(O)N(R$^1$)—, —N(R$^1$)C(O)—, —N(R$^1$)C(O)N(R$^1$)—, —N(R$^1$)C(O)O—, —OC(O)N(R$^1$)—, —C(NR$^1$)—, —N(R$^1$)C(NR$^1$)—, —C(NR$^1$)N(R$^1$)—, —N(R$^1$)C(NR$^1$)N(R$^1$)—, —S(O)$_2$—, —OS(O)—, —S(O)O—, —S(O)—, —OS(O)$_2$—, —S(O)$_2$O—, —N(R$^1$)S(O)$_2$—, —S(O)$_2$N(R$^1$)—, —N(R$^1$)S(O)—, —S(O)N(R$^1$)—, —N(R$^1$)S(O)$_2$N(R$^1$)—, —N(R$^1$)S(O)N(R$^1$)—, alkylene, alkenylene, alkynylene, heteroalkylene, heteroalkenylene, and heteroalkynylene, wherein one or more hydrogen atoms are optionally substituted with R$^2$ and wherein two R$^2$ groups attached to different atoms can optionally join together to form a C$_{3-8}$ carbocycle or 3- to 8-membered heterocycle;
R$^A$ is independently selected at each occurrence from R$^2$;
n is an integer from 0 to 10;
R$^B$ is independently selected at each occurrence from hydrogen and R$^2$, and/or two R$^B$ groups attached to the same atom can optionally join together to form a C$_{3-8}$ carbocycle or 3- to 8-membered heterocycle;
R$^1$ is independently selected at each occurrence from: hydrogen, —C(O)R$^3$, —C(O)OR$^3$, —C(O)N(R$^3$)$_2$, —C(O)NR$^4$R$^5$;
C$_{1-6}$ alkyl, C$_{2-6}$ alkenyl, and C$_{2-6}$ alkynyl, each of which is independently optionally substituted at each occurrence with one or more substituents selected from halogen, —NO$_2$, —CN, —OR$^3$, —SR$^3$, —N(R$^3$)$_2$, —NR$^4$R$^5$, —S(=O)R$^3$, —S(=O)$_2$R$^3$, —S(=O)$_2$N(R$^3$)$_2$, —S(=O)$_2$NR$^4$R$^5$, —NR$^3$S(=O)$_2$R$^3$, —NR$^3$S(=O)$_2$N(R$^3$)$_2$, —NR$^3$S(=O)$_2$NR$^4$R$^5$, —C(O)R$^3$, —C(O)OR$^3$, —OC(O)R$^3$, —OC(O)OR$^3$, —OC(O)N(R$^3$)$_2$, —OC(O)NR$^4$R$^5$, —NR$^3$C(O)R$^3$, —NR$^3$C(O)OR$^3$, —NR$^3$C(O)N(R$^3$)$_2$, —NR$^3$C(O)NR$^4$R$^5$, —C(O)N(R$^3$)$_2$, —C(O)NR$^4$R$^5$, —P(O)(OR$^3$)$_2$, —P(O)(R$^3$)$_2$, =O, =OS, =N(R$^3$), C$_{3-12}$ carbocycle and 3- to 12-membered heterocycle; and
C$_{3-12}$ carbocycle and 3- to 12-membered heterocycle, wherein each C$_{3-12}$ carbocycle and 3- to 12-membered heterocycle in R$^1$ is independently optionally substituted with one or more substituents selected from halogen, —NO$_2$, —CN, —OR$^3$, —SR$^3$, —N(R$^3$)$_2$, —NR$^4$R$^5$, —S(=O)R$^3$, —S(=O)$_2$R$^3$, —S(=O)$_2$N(R$^3$)$_2$, —S(=O)$_2$NR$^4$R$^5$, —NR$^3$S(=O)$_2$R$^3$, —NR$^3$S (=O)$_2$N(R$^3$)$_2$, —NR$^3$S(=O)$_2$NR$^4$R$^5$, —C(O)R$^3$, —C(O)OR$^3$, —OC(O)R$^3$, —OC(O)OR$^3$, —OC(O)N(R$^3$)$_2$, —OC(O)NR$^4$R$^5$, —NR$^3$C(O)R$^3$, —NR$^3$C(O)OR$^3$, —NR$^3$C(O)N(R$^3$)$_2$, —NR$^3$C(O)NR$^4$R$^5$, —C(O)N(R$^3$)$_2$, —C(O)NR$^4$R$^5$, —P(O)(OR$^3$)$_2$, —P(O)(R$^3$)$_2$, =O, =S, =N(R$^3$), C$_{1-6}$ alkyl, C$_{1-6}$ haloalkyl, C$_{2-6}$ alkenyl, and C$_{2-6}$ alkynyl;

R$^2$ is independently selected at each occurrence from:

halogen, —NO$_2$, —CN, —OR$^3$, —SR$^3$, —N(R$^3$)$_2$, —NR$^4$R$^5$, —S(=O)R$^3$, —S(=O)$_2$R$^3$, —S(=O)$_2$N(R$^3$)$_2$, —S(=O)$_2$NR$^4$R$^5$, —NR$^3$S(=O)$_2$R$^3$, —NR$^3$S(=O)$_2$N(R$^3$)$_2$, —NR$^3$S(=O)$_2$NR$^4$R$^5$, —C(O)R$^3$, —C(O)OR$^3$, —OC(O)R$^3$, —OC(O)OR$^3$, —OC(O)N(R$^3$)$_2$, —OC(O)NR$^4$R$^5$, —NR$^3$C(O)R$^3$, —NR$^3$C(O)OR$^3$, —NR$^3$C(O)N(R$^3$)$_2$, —NR$^3$C(O)NR$^4$R$^5$, —C(O)N(R$^3$)$_2$, —C(O)NR$^4$R$^5$, —P(O)(OR$^3$)$_2$, —P(O)(R$^3$)$_2$, =O, =S, =N(R$^3$);

C$_{1-10}$ alkyl, C$_{2-10}$ alkenyl, and C$_{2-10}$ alkynyl, each of which is independently optionally substituted at each occurrence with one or more substituents selected from halogen, —NO$_2$, —CN, —OR$^3$, —SR$^3$, —N(R$^3$)$_2$, —NR$^4$R$^5$, —S(=O)R$^3$, —S(=O)$_2$R$^3$, —S(=O)$_2$N(R$^3$)$_2$, —S(=O)$_2$NR$^4$R$^5$, —NR$^3$S(=O)$_2$R$^3$, —NR$^3$S(=O)$_2$N(R$^3$)$_2$, —NR$^3$S(=O)$_2$NR$^4$R$^5$, —C(O)R$^3$, —C(O)OR$^3$, —OC(O)R$^3$, —OC(O)OR$^3$, —OC(O)N(R$^3$)$_2$, —OC(O)NR$^4$R$^5$, —NR$^3$C(O)R$^3$, —NR$^3$C(O)OR$^3$, —NR$^3$C(O)N(R$^3$)$_2$, —NR$^3$C(O)NR$^4$R$^5$, —C(O)N(R$^3$)$_2$, —C(O)NR$^4$R$^5$, —P(O)(OR$^3$)$_2$, —P(O)(R$^3$)$_2$, =O, =S, =N(R$^3$), C$_{3-12}$ carbocycle, and 3- to 12-membered heterocycle; and C$_{3-12}$ carbocycle and 3- to 12-membered heterocycle, wherein each C$_{3-12}$ carbocycle and 3- to 12-membered heterocycle in R$^2$ is independently optionally substituted with one or more substituents selected from halogen, —NO$_2$, —CN, —OR$^3$, —SR$^3$, —N(R$^3$)$_2$, —NR$^4$R$^5$, —S(=O)R$^3$, —S(=O)$_2$R$^3$, —S(=O)$_2$N(R$^3$)$_2$, —S(=O)$_2$NR$^4$R$^5$, —NR$^3$S(=O)$_2$R$^3$, —NR$^3$S(=O)$_2$N(R$^3$)$_2$, —NR$^3$S(=O)$_2$NR$^4$R$^5$, —C(O)R$^3$, —C(O)OR$^3$, —OC(O)R$^3$, —OC(O)OR$^3$, —OC(O)N(R$^3$)$_2$, —OC(O)NR$^4$R$^5$, —NR$^3$C(O)R$^3$, —NR$^3$C(O)OR$^3$, —NR$^3$C(O)N(R$^3$)$_2$, —NR$^3$C(O)NR$^4$R$^5$, —C(O)N(R$^3$)$_2$, —C(O)NR$^4$R$^5$, —P(O)(OR$^3$)$_2$, —P(O)(R$^3$)$_2$, =O, =S, =N(R$^3$), C$_{1-6}$ alkyl, C$_{1-6}$ haloalkyl, C$_{2-6}$ alkenyl, and C$_{2-6}$ alkynyl;

R$^3$ is independently selected at each occurrence from hydrogen; and C$_{1-20}$ alkyl, C$_{2-20}$ alkenyl, C$_{2-20}$ alkynyl, 1- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle; and R$^4$ and R$^5$ are taken together with the nitrogen atom to which they are attached to form a 3- to 8-membered heterocycle, optionally substituted with one or more R$^2$; and (b) one or more agents selected from the group consisting of a phosphodiesterase (PDE) inhibitor, sirtuin pathway activator, anti-diabetic agent, anti-hyperlipidemic agent, glucagon-like peptide-1 (GLP-1) agonist, dipeptidyl peptidase-4 (DPP-4) inhibitor, sodium-glucose cotransporter-2 (SGLT2) inhibitor or gliflozin, a fibrate, a nitric oxide (NO) donor, nicotinic acid, nicotinamide riboside, nicotinic acid metabolite, and any combination thereof.

In some cases of a composition described herein, the compound is a compound of Formula (I-b) or Formula (II-b):

(I-b)

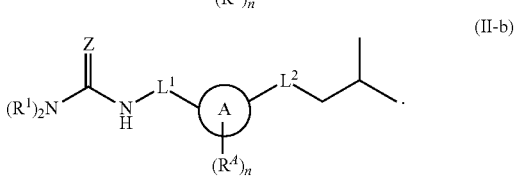
(II-b)

In some cases of a composition described herein, the compound is a compound of Formula (I-c) or Formula (II-c):

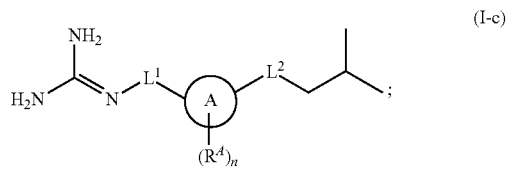
(I-c)

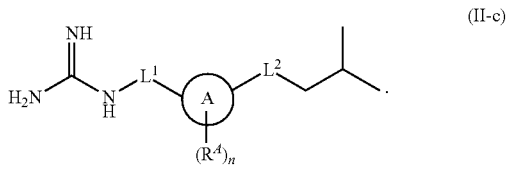
(II-c)

In some cases of a composition described herein, the compound is a compound of Formula (III):

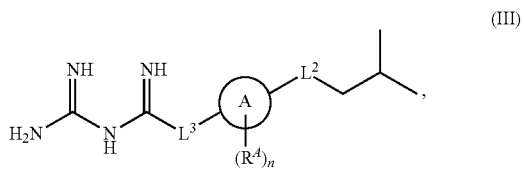
(III)

or a pharmaceutically acceptable salt thereof, wherein:

L$^3$ is selected from a bond, —O—, —S—, —N(R$^1$)—, —N(R$^1$)CH$_2$—, —C(O)—, —C(O)O—, —OC(O)—, —OC(O)O—, —C(O)N(R$^1$)—, —C(O)N(R$^1$)C(O)—, —C(O)N(R$^1$)C(O)N(R$^1$)—, —N(R$^1$)C(O)—, —N(R$^1$)C(O)N(R$^1$)—, —N(R$^1$)C(O)O—, —OC(O)N(R$^1$)—, —C(NR$^1$)—, —N(R$^1$)C(NR$^1$)—, —C(NR$^1$)N(R$^1$)—, —N(R$^1$)C(NR$^1$)N(R$^1$)—, —S(O)$_2$—, —OS(O)—, —S(O)O—, —S(O)—, —OS(O)$_2$—, —S(O)$_2$O—, —N(R$^1$)S(O)$_2$—, —S(O)$_2$N(R$^1$)—, —N(R$^1$)S(O)—, —S(O)N(R$^1$)—, —N(R$^1$)S(O)$_2$N(R$^1$)—, —N(R$^1$)S(O)N(R$^1$)—, alkylene, alkenylene, alkynylene, heteroalkylene, heteroalkenylene, and heteroalkynylene, wherein one or more hydrogen atoms of L$^3$ are optionally substituted with R$^2$ and wherein two R$^2$ groups attached to the same atom or different atoms of L$^3$ can optionally join together to form a C$_{3-8}$ carbocycle or 3- to 8-membered heterocycle.

In some cases of a composition described herein, the compound is a compound of Formula (IV):

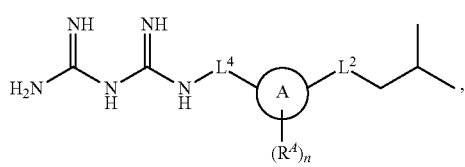

or a pharmaceutically acceptable salt thereof, wherein:

$L^4$ is selected from a bond, —O—, —S—, —N($R^1$)—, —N($R^1$)$CH_2$—, —C(O)—, —C(O)O—, —OC(O)—, —OC(O)O—, —C(O)N($R^1$)—, —C(O)N($R^1$)C(O)—, —C(O)N($R^1$)C(O)N($R^1$)—, —N($R^1$)C(O)—, —N($R^1$)C(O)N($R^1$)—, —N($R^1$)C(O)O—, —OC(O)N($R^1$)—, —C(N$R^1$)—, —N($R^1$)C(N$R^1$)—, —C(N$R^1$)N($R^1$)—, —N($R^1$)C(N$R^1$)N($R^1$)—, —S(O)$_2$—, —OS(O)—, —S(O)O—, —S(O)—, —OS(O)$_2$—, —S(O)$_2$O—, —N($R^1$)S(O)$_2$—, —S(O)$_2$N($R^1$)—, —N($R^1$)S(O)—, —S(O)N($R^1$)—, —N($R^1$)S(O)$_2$N($R^1$)—, —N($R^1$)S(O)N($R^1$)—, alkylene, alkenylene, alkynylene, heteroalkylene, heteroalkenylene, and heteroalkynylene, wherein one or more hydrogen atoms of $L^4$ are optionally substituted with $R^2$ and wherein two $R^2$ groups attached to the same atom or different atoms of $L^4$ can optionally join together to form a $C_{3-8}$ carbocycle or 3- to 8-membered heterocycle.

In some cases of a composition described herein, the compound is a biguanide.

In some cases of a composition described herein, A is a bond. In some cases of a composition described herein, A is a $C_{3-12}$ carbocycle. In some cases of a composition described herein, A is a 3- to 12-membered heterocycle. In some cases of a composition described herein, A is a monocyclic heterocycle. In some cases of a composition described herein, A is a 5-membered or 6-membered heterocycle.

In some cases of a composition described herein, $L^2$ is a bond. In some cases of a composition described herein, $L^2$ is an alkylene. In some cases of a composition described herein, $L^2$ is a $C_{1-6}$ alkylene.

In some cases of a composition described herein, the compound is a compound of Formula (V):

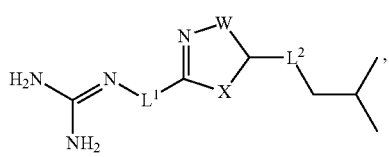

wherein:
each of W and X is independently selected from the group consisting of —O—, —S—, —N($R^1$)—, —N($R^1$)$CH_2$—, —C(O)—, —C(O)O—, —OC(O)—, —OC(O)O—, —C(O)N($R^1$)—, —C(O)N($R^1$)C(O)—, —C(O)N($R^1$)C(O)N($R^1$)—, —N($R^1$)C(O)—, —N($R^1$)C(O)N($R^1$)—, —N($R^1$)C(O)O—, —OC(O)N($R^1$)—, —C(N$R^1$)—, —N($R^1$)C(N$R^1$)—, —C(N$R^1$)N($R^1$)—, —N($R^1$)C(N$R^1$)N($R^1$)—, —S(O)$_2$—, —OS(O)—, —S(O)O—, —S(O)—, —OS(O)$_2$—, —S(O)$_2$O—, —N($R^1$)S(O)$_2$—, —S(O)$_2$N($R^1$)—, —N($R^1$)S(O)—, —S(O)N($R^1$)—, —N($R^1$)S(O)$_2$N($R^1$)—, —N($R^1$)S(O)N($R^1$)—, $C_{1-8}$ alkylene, $C_{1-8}$ alkenylene, $C_{1-8}$ alkynylene, $C_{1-7}$ heteroalkylene, $C_{1-7}$ heteroalkenylene, and $C_{1-7}$ heteroalkynylene, wherein one or more hydrogen atoms are optionally substituted with $R^2$ and wherein two $R^2$ groups attached to the same atom or different atoms can optionally join together to form a $C_{3-8}$ carbocycle or 3- to 8-membered heterocycle.

In some cases of a composition described herein, W is selected from the group consisting of —C(O)— and —C($R^B$)$_2$—.

In some cases of a composition described herein, the compound is a compound of Formula (VI):

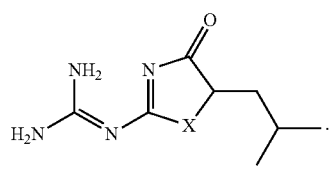

In some cases of a composition described herein, X is selected from the group consisting of —O—, —S—, —N($R^1$)—, —C($R^B$)$_2$—, and any combination thereof.

In some cases of a composition described herein, the compound is

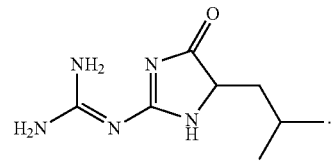

In some cases of a composition described herein, the compound is

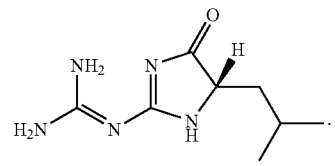

In some cases of a composition described herein, the phosphodiesterase (PDE) inhibitor is a phosphodiesterase type 5 (PDE5) inhibitor. In some cases of a composition described herein, the phosphodiesterase type 5 (PDE5) inhibitor is selected from the group consisting of avanafil, iodenafil, mirodenafil, sildenafil, tadalafil, icariin, vardenafil, udenafil, zaprinst, benzamidenafil, dasantafil, and any combination thereof.

In some cases of a composition described herein, the sirtuin pathway activator is a biguanide, resveratrol, a sirtuin activator, an AMPK activator, or a PGC-1α activator. In some cases of a composition described herein, the PGC-1a activator is a thiazolidinedione. In some cases of a composition described herein, the thiazolidinedione is selected from the group consisting of rosiglitazone, pioglitazone, lobeglitazone, and any combination thereof.

In some cases of a composition described herein, the anti-diabetic agent is selected from the group consisting of biguanide, meglitinide, sulfonylurea, thiazolidinedione, alpha glucosidase inhibitor, ergot alkaloid, and any combination thereof. In some cases of a composition described herein, the sulfonylurea is glipizide. In some cases of a composition described herein, the biguanide is metformin.

In some cases of a composition described herein, the glucagon-like peptide-1 (GLP-1) agonist is selected from the group consisting of exenatide, liraglutide, lixisenatide, albiglutide, dulaglutide, taspoglutide, semaglutide, and any combination thereof.

In some cases of a composition described herein, the dipeptidyl peptidase-4 (DPP-4) inhibitor is selected from the group consisting of sitagliptin, vildagliptin, saxagliptin, linagliptin, gemigliptin, anagliptin, teneligliptin, alogliptin, trelagliptin, dutogliptin, omarigliptin, berberine, lupeol, and any combination thereof.

In some cases of a composition described herein, the sodium-glucose cotransporter-2 (SGLT2) inhibitor or gliflozin is selected from the group consisting of dapagliflozin, empagliflozin, canagliflozin, ipragliflozin, tofogliflozin, sergliflozin etabonate, remogliflozin etabonate, ertugliflozin, and any combination thereof.

In some cases of a composition described herein, the fibrate is selected from the group consisting of bezafibrate, ciprofibrate, clofibrate, aluminium clofibrate, etofibrate, gemfibrozil, fenofibrate, clinofibrate, and any combination thereof.

In some cases of a composition described herein, the nitric oxide (NO) donor is selected from the group consisting of an organic nitrate, a diazeniumdiolate (NONOate), an S-nitrosothiol, an active pharmaceutical agent comprising an NO group, an NO-zeolite, arginine, sodium nitroprusside (SNP), and any combination thereof. In some cases of a composition described herein, the organic nitrate is selected from the group consisting of:

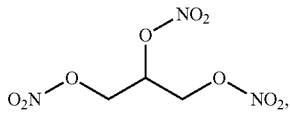

(glyceryl trinitrate (GTN))

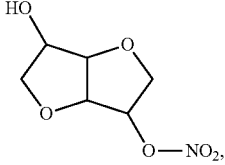

(isosorbide mononitrate (ISMN))

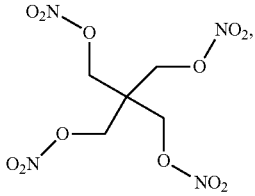

(pentaerythritol tetranitrate (PETN))

and BiDil (isosorbide dinitrate with hydralazine). In some cases of a composition described herein, the diazeniumdiolate is selected from the group consisting of:

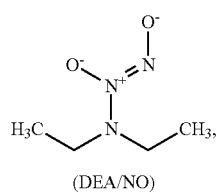

(DEA/NO)

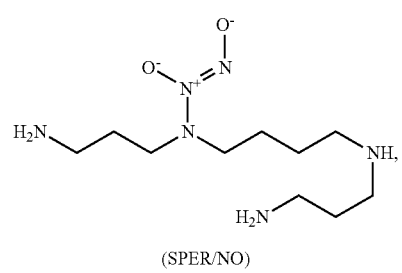

(SPER/NO)

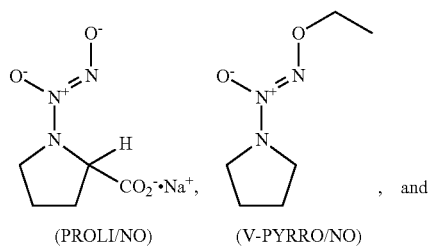

(PROLI/NO)    (V-PYRRO/NO)    , and

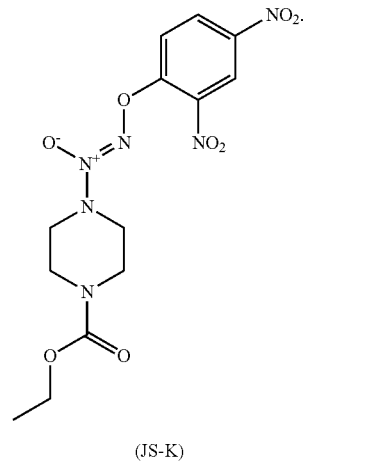

(JS-K)

In some cases of a composition described herein, the S-nitrosothiol is selected from the group consisting of:

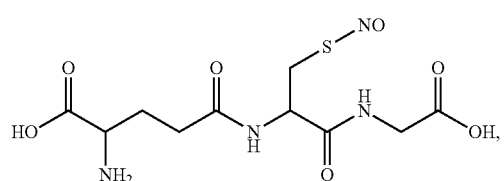

(S-nitroso-glutathione (GSNO))

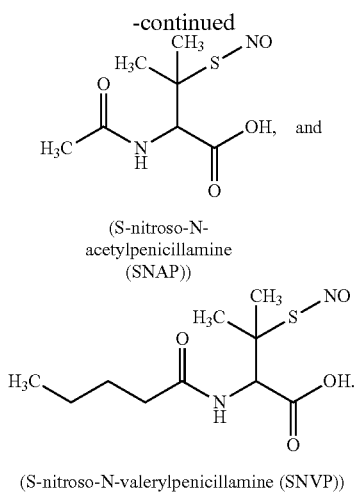

(S-nitroso-N-acetylpenicillamine (SNAP))

(S-nitroso-N-valerylpenicillamine (SNVP))

In some cases of a composition described herein, the component (b) in the composition is sildenafil. In some cases of a composition described herein, the component (b) in the composition is selected from the group consisting of nicotinic acid

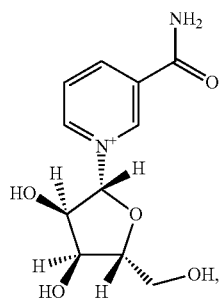 [SMILES: NC(=O)c1ccc[n+]([C@@H]2O[C@H](CO)[C@@H](O)[C@H]2O)c1]

nicotinamide riboside and nicotinic acid metabolite.

In some cases of a composition described herein, the amount of the one or more agents selected from the group consisting of nicotinic acid, nicotinamide riboside, and nicotinic acid metabolite is at least about 1 mg, at least about 5 mg, or at least about 10 mg. In some cases of a composition described herein, the amount of the one or more agents selected from the group consisting of nicotinic acid, nicotinamide riboside, and nicotinic acid metabolite is less than about 250 mg, less than about 500 mg, less than about 750 mg, or less than about 1 g. In some cases of a composition described herein, the amount of the one or more agents selected from the group consisting of nicotinic acid, nicotinamide riboside, and nicotinic acid metabolite is between about 1-100 mg. In some cases of a composition described herein, the component (b) in the composition is nicotinic acid. In some cases of a composition described herein, the composition is substantially free of nicotinamide. In some cases of a composition described herein, the composition does not contain nicotinamide. In some cases of a composition described herein, the composition is substantially free of nicotinic acid metabolites. In some cases of a composition described herein, the composition is substantially free of each of nicotinyl CoA, nicotinuric acid, nicotinate mononucleotide, nicotinate adenine dinucleotide, and nicotinamide adenine dinucleotide.

In some cases of a composition described herein, the composition is substantially free of non-branched amino acids. In some cases of a composition described herein, the composition is substantially free of each amino acid selected from the group consisting of alanine, arginine, asparagine, aspartic acid, cysteine, glutamic acid, glutamine, glycine, histidine, lysine, methionine, phenylalanine, proline, serine, threonine, tryptophan, valine, isoleucine and tyrosine. In some cases of a composition described herein, the composition contains less than about 0.1% of each free amino acid selected from the group consisting of alanine, arginine, asparagine, aspartic acid, cysteine, glutamic acid, glutamine, glycine, histidine, lysine, methionine, phenylalanine, proline, serine, threonine, tryptophan, valine, isoleucine and tyrosine. In some cases of a composition described herein, the composition is substantially free of each of alanine, glycine, glutamic acid, and proline. In some cases of a composition described herein, the composition is substantially free of amino acids.

In some cases of a composition described herein, the amount of the one or more agents selected from the group consisting of nicotinic acid, nicotinamide riboside, and nicotinic acid metabolite, when administered to a subject, yields a serum level of such agent(s) that is between about 1-1000 nM, between about 10-500 nM, or between about 1-100 nM.

In some cases of a composition described herein, the amount of nicotinic acid and/or nicotinic acid metabolites is insufficient to reduce lipid content in the absence of component (a). In some cases of a composition described herein, the amount of component (a) and (b) synergistically lowers lipid accumulation, increases fat oxidation, increases insulin sensitivity, increases glucose utilization, or increases activation of one or more components in the sirtuin pathway in said subject when administered to the subject as compared to administering component (a) or component (b) alone. In some cases of a composition described herein, the one or more components in the sirtuin pathway is SIRT1, and/or SIRT3, and/or AMPK, and/or PCG1α. In some cases of a composition described herein, the amount of component (a) and (b) synergistically increases fat oxidation in said subject when administered to the subject as compared to administering component (a) or component (b) alone.

In some cases of a composition described herein, the composition is formulated for oral administration. In some cases of a composition described herein, the composition is a tablet, a capsule, a pill, a granule, an emulsion, a gel, a plurality of beads encapsulated in a capsule, a powder, a suspension, a liquid, a semi-liquid, a semi-solid, a syrup, a slurry, or a chewable form. In some cases of a composition described herein, the composition is formulated in a unit dosage form.

In some cases of a composition described herein, component (a) and component (b) are separately packaged. In some cases of a composition described herein, component (a) and component (b) are mixed.

In some cases of a composition described herein, the composition further comprises one or more therapeutic agents that are capable of lowering lipid accumulation, and/or increasing fat oxidation, and/or increasing insulin sensitivity, and/or increasing glucose utilization.

In some cases of a composition described herein, the composition is administered at least once a day, twice a day, three times a day, or more.

Provided herein is a kit comprising a multi-day supply of unit dosages of a composition described herein and instructions directing the administration of said multi-day supply over a period of multiple days.

Provided herein is a method of reducing atherosclerotic plaque size in a subject in need thereof, comprising administering to said subject a dose of a composition described herein comprising an amount of a compound described herein and an amount of nicotinic acid and/or nicotinic acid metabolites to effect a reduction of the total atherosclerotic plaque size in the subject.

Provided herein is a method of reducing adiposity in a subject in need thereof, comprising administering to said subject a compound described herein, a pharmaceutical composition described herein, or a composition described herein to effect a reduction of adiposity in the subject.

Provided herein is a method of increasing insulin sensitivity in a subject in need thereof, comprising administering to said subject a compound described herein, a pharmaceutical composition described herein, or a composition described herein to effect increasing insulin sensitivity in the subject. In some embodiments, the increase in insulin sensitivity is at least about a 1-fold increase (e.g., at least about 1, 2, 3, 4, 5, 6, 8, 10, 15, 20, or 50 fold).

Provided herein is a method of increasing glucose utilization in a subject in need thereof, comprising administering to said subject a compound described herein, a pharmaceutical composition described herein, or a composition described herein to effect increasing glucose utilization in the subject.

Provided herein is a method of increasing fat oxidation in a subject in need thereof, comprising administering to said subject a compound described herein, a pharmaceutical composition described herein, or a composition described herein to effect increasing fat oxidation in the subject.

Provided herein is a method of treating diabetes and/or hyperlipidemia comprising administering to the subject a compound described herein, a pharmaceutical composition described herein, or a composition described herein over a time period, during which the subject exhibits one or more of (1) an increase in insulin sensitivity, glucose utilization, or fat oxidation or (2) a reduction in lipid accumulation.

Provided herein is a method of reducing atherosclerotic plaque size in a subject in need thereof, comprising administering to said subject a dose of a compound described herein, a pharmaceutical composition described herein, or a composition described herein to effect a reduction in total atherosclerotic plaque size in the subject.

Provided herein is a method of reducing non-alcoholic steatohepatitis (NASH) in a subject in need thereof, comprising administering to said subject a dose of a compound described herein, a pharmaceutical composition described herein, or a composition described herein to effect a reduction in non-alcoholic steatohepatitis (NASH) in the subject.

Provided herein is a method of reducing, treating, preventing, or sustaining a reduction of a metabolic disease or disorder in a subject in need thereof, comprising administering to said subject a dose of a compound described herein, a pharmaceutical composition described herein, or a composition described herein to effect a reduction, treatment, prevention, or sustainment in reduction of the metabolic disease or disorder.

Provided herein is a method of reducing, treating, preventing, or sustaining a reduction of a metabolic disease or disorder in a subject in need thereof, comprising administering to the subject:
  a) an amount of a compound of Formula (I-a) or Formula (II-a); and
  b) an amount of a phosphodiesterase (PDE) inhibitor, sirtuin pathway activator, anti-diabetic agent, anti-hyperlipidemic agent, glucagon-like peptide-1 (GLP-1) agonist, dipeptidyl peptidase-4 (DPP-4) inhibitor, sodium-glucose cotransporter-2 (SGLT2) inhibitor or gliflozin, a fibrate, a nitric oxide (NO) donor, nicotinic acid, nicotinamide riboside, or nicotinic acid metabolite;
  wherein the administering of (a) and (b) reduces, treats, prevents, or sustains a reduction of the metabolic disease or disorder to a greater extent than administration of (a) alone, thereby reducing, treating, preventing, or sustaining a reduction of the metabolic disease or disorder in the subject.

Provided herein is a method of preventing a metabolic disease or disorder in a subject exhibiting a propensity to the metabolic disease or disorder comprising administering to the subject prior to manifestation of the metabolic disease or disorder symptom:
  a) a compound of Formula (I-a) or Formula (II-a); and
  b) an amount of a phosphodiesterase (PDE) inhibitor, sirtuin pathway activator, anti-diabetic agent, anti-hyperlipidemic agent, glucagon-like peptide-1 (GLP-1) agonist, dipeptidyl peptidase-4 (DPP-4) inhibitor, sodium-glucose cotransporter-2 (SGLT2) inhibitor or gliflozin, a fibrate, a nitric oxide (NO) donor, nicotinic acid, nicotinamide riboside, or nicotinic acid metabolite;
  wherein the administering of (a) and (b) reduces the metabolic disease or disorder to a greater extent than administration of (a) alone, thereby preventing the metabolic disease or disorder in the subject.

In some cases of a method described herein, wherein the compound of Formula (I-a) or Formula (II-a) is

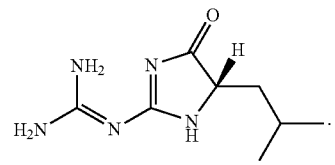

In some cases of a method described herein, the metabolic disease or disorder is selected from the group consisting of diabetes, metabolic syndrome, obesity, hyperlipidemia, high cholesterol, arteriosclerosis, hypertension, non-alcoholic steatohepatitis, non-alcoholic fatty liver, non-alcoholic fatty liver disease, hepatic steatosis, and any combination thereof. In some cases of a method described herein, the compound of Formula (I-a) or Formula (II-a) is selected from Table 1 or Table 3.

In some cases of a method described herein, the method further comprises administering to the subject (c) a second sirtuin pathway activator. In some cases of a method described herein, the sirtuin pathway activator comprises a biguanide and the second sirtuin pathway activator comprises a sirtuin activator. In some cases of a method described herein, the sirtuin pathway activator comprises a sirtuin activator and the second sirtuin pathway activator comprises a thiazolidinedione. In some cases of a method described herein, the sirtuin pathway activator comprises a sirtuin activator and the second sirtuin pathway activator comprises a PDE5-specific inhibitor. In some cases of a method described herein, the sirtuin pathway activator comprises a biguanide and the second sirtuin pathway activator comprises a thiazolidinedione. In some cases of a method described herein, the sirtuin pathway activator comprises a biguanide and the second sirtuin pathway activator comprises a PDE5-specific inhibitor. In some cases of a method described herein, the sirtuin pathway activator comprises a thiazolidinedione and the second sirtuin pathway activator comprises a PDE5-specific inhibitor.

In some cases of a method described herein, the subject is administered periodically a composition comprising components (a), (b), and (c) over a course of at least 2 months.

In some cases of a method described herein, the subject has been diagnosed with said non-alcoholic steatohepatitis (NASH). In some cases of a method described herein, the non-alcoholic steatohepatitis (NASH) is evidenced by reduction in hepatic fat, inflammation and/or fibrosis detectable by one or more methods selected from the group consisting of ultrasonography, computed tomography (CT), magnetic resonance imaging, measurement of serum alanine transaminase and aspartate transaminase, biopsy, transient elastography, magnetic resonance elastography, and related techniques. In some cases of a method described herein, the reduction of non-alcoholic steatohepatitis (NASH) in the subject is evidenced by a reduction in hepatic fat detectable by one or more methods selected from the group consisting of ultrasonography, computed tomography (CT), magnetic resonance imaging measurement of serum alanine transaminase and aspartate transaminase, and biopsy.

In some cases of a method described herein, the subject exhibits a non-alcoholic fatty liver disease (NAFLD). In some cases of a method described herein, the NAFLD is selected from the group consisting of non-alcoholic fatty liver (NAFL), NASH-related cirrhosis, and hepatic steatosis.

In some cases of a method described herein, the subject exhibits one or more symptoms of non-alcoholic steatohepatitis (NASH) selected from the group consisting of weakness, fatigue, unexplained weight loss, ache and jaundice.

In some cases of a method described herein, a wt % of the sirtuin pathway activator in the composition, excluding fillers, is 5-50 wt %. In some cases of a method described herein, the sirtuin pathway activator is a sirtuin activator. In some cases of a method described herein, the sirtuin activator is resveratrol. In some cases of a method described herein, the amount of resveratrol administered to the subject is 0.5-100 mg/day. In some cases of a method described herein, the sirtuin activator is a polyphenol selected from the group consisting of chlorogenic acid, resveratrol, caffeic acid, polyphenols, stilbenes, cinnamic acid, hydroxycinnamic acids, ferulic acid, piceatannol, ellagic acid, epigallocatechin gallate, grape seed extract, and any analog thereof. In some cases of a method described herein, the amount of chlorogenic acid, caffeic acid, polyphenols, stilbenes, cinnamic acid, hydroxycinnamic acids, ferulic acid, piceatannol, ellagic acid, epigallocatechin gallate, or grape seed extract, or any analog thereof administered to the subject is 0.5-500 mg/day.

In some cases of a method described herein, the phosphodiesterase (PDE) inhibitor is selected from the group consisting of icariin, sildenafil, tadalafil, vardenafil, avanafil, lodenafil, mirodenafil, udenafil, zaprinast, and any combination thereof. In some cases of a method described herein, the amount of icariin administered to the subject is 1-2000 mg/day. In some cases of a method described herein, the amount of sildenafil administered to the subject is 0.05-100 mg/day. In some cases of a method described herein, the amount of tadalafil administered to the subject is 0.01-20 mg/day. In some cases of a method described herein, the amount of vardenafil administered to the subject is 0.01-20 mg/day. In some cases of a method described herein, the amount of avanafil administered to the subject is 1-200 mg/day. In some cases of a method described herein, the amount of lodenafil administered to the subject is 1-200 mg/day. In some cases of a method described herein, the amount of mirodenafil administered to the subject is 1-100 mg/day. In some cases of a method described herein, the amount of udenafil administered to the subject is 1-200 mg/day. In some cases of a method described herein, the amount of zaprinast administered to the subject is 1-2000 mg/day.

In some cases of a method described herein, the sirtuin pathway activator is a biguanide, resveratrol, a sirtuin activator, an AMPK activator, or a PGC-1α activator. In some cases of a method described herein, the sirtuin pathway activator is an AMPK activator. In some cases of a method described herein, the AMPK activator is a biguanide.

In some cases of a method described herein, the sirtuin pathway activator is a PGC-1α activator. In some cases of a method described herein, the PGC-1α activator is a thiazolidinedione. In some cases of a method described herein, the thiazolidinedione is selected from the group consisting of rosiglitazone and pioglitazone. In some cases of a method described herein, the amount of rosiglitazone administered is 0.1-4 mg. In some cases of a method described herein, the amount of pioglitazone administered is 0.1-45 mg.

In some cases of a method described herein, the amount of sirtuin pathway activator is a sub-therapeutic amount.

In some cases of a method described herein, the reduction in non-alcoholic steatohepatitis (NASH) is characterized by a reduction in hepatic steatosis, inflammation, ballooning, and/or fibrosis.

In some cases of a method described herein, the amount of (a) or (b) is a therapeutic amount. In some cases of a method described herein, the amount of (a) or (b) is a sub-therapeutic amount. In some cases of a method described herein, the amounts of (a) and (b) are co-administered. In some cases of a method described herein, the amounts of (a) and (b) are administered simultaneously as a single composition. In some cases of a method described herein, the amounts of (a) and (b) are administered sequentially. In some cases of a method described herein, all of the amounts are administered sequentially within 15 minutes, 60 minutes or 2 hours. In some cases of a method described herein, all components of the composition are administered within 15 minutes, 60 minutes or 2 hours. In some cases of a method described herein, the method comprises administering (a) and (b) 1, 2, 3, 4, 5, or more than 5 times per day. In some cases of a method described herein, the method comprises administering (a) and (b) 3 times daily and the liver mass of the subject is decreased by 25% within 6 weeks.

In some cases of a method described herein, the subject is a human. In some cases of a method described herein, the subject is a mammal, non-human mammal, non-human primate, domesticated animal, or non-domesticated animal. In some cases of a method described herein, the domesticated animal is a laboratory animal, household pet, or livestock. In some cases of a method described herein, the subject is a dog, cat, rodent, mouse, hamster, cow, bird, chicken, pig, horse, goat, sheep, rabbit, ape, monkey, or chimpanzee.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The patent application file contains at least one drawing executed in color. Copies of this patent or patent application with color drawing(s) will be provided by the Office upon request and payment of the necessary fee.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3A shows the effect of the baseline OCR on C2C12 muscle cells. FIG. 3B shows the effect of the palmitate induced OCR on C2C12 muscle cells.

FIG. 10A shows the effect of baseline OCR on 3T3L1 adipocytes. FIG. 10B shows the effect of palmitate induced OCR on 3T3L1 adipocytes.

FIG. 13A represents the effect of the control and FIG. 13B represents the effect of 100 nM of Compound 2 on lipid accumulation in *C. elegans*.

FIGS. 14A, 14B, 14C and 14D show the effects of 10 nM and 100 nM Compound 2 on lifespan in *C. elegans* under normal and mild oxidative stress (500 uM Paraquat) conditions. FIG. 14A depicts the graphical representation of the effects of the different concentrations of Compound 2 on lifespan in *C. elegans* under normal conditions, and FIG. 14B shows the results of the effects of the different concentrations of Compound 2 on lifespan in *C. elegans* under normal conditions, as represented by median survival and max lifespan. FIG. 14C depicts the graphical representation of the effects of the different concentrations of Compound 2 on lifespan in *C. elegans* under mild oxidative stress conditions, and FIG. 14B shows the results of the effects of the different concentrations of Compound 2 on lifespan in *C. elegans* under mild oxidative stress conditions, as represented by median survival and max lifespan.

DETAILED DESCRIPTION OF THE INVENTION

Figure 1:
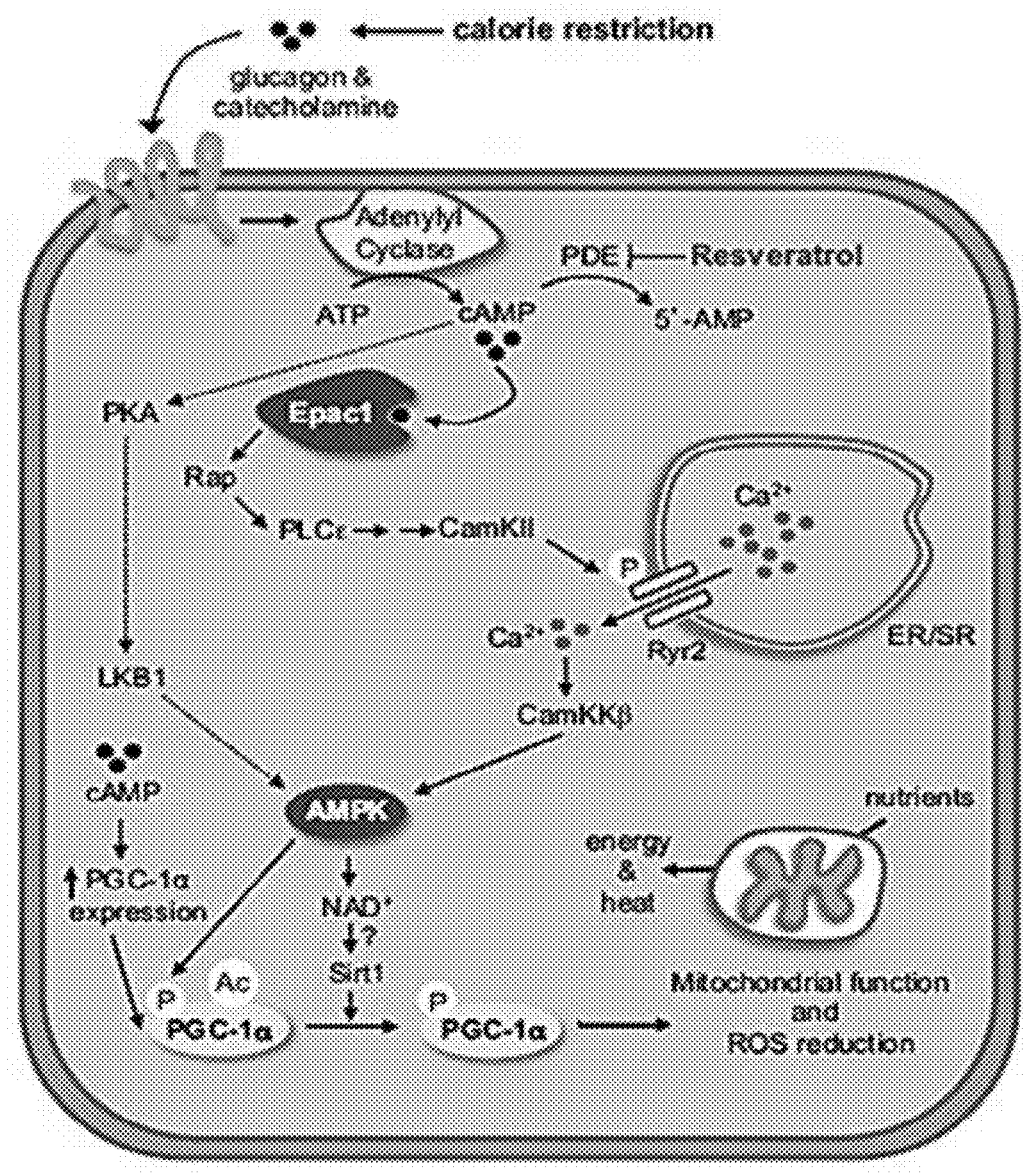
FIG. 1 depicts a sirtuin pathway.

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. Unless stated otherwise, the present invention is not limited by the illustrated ordering of acts or events, as some acts may occur in different orders and/or concurrently with other acts or events. Furthermore, not all illustrated acts or events are required to implement a methodology in accordance with the present invention. The concentration of various components in the disclosed compositions is exemplary and not meant to be limited to the recited concentration per se.

As used herein, the singular forms "a", "an" and "the" include plural references unless the context clearly dictates otherwise. For example, the term "a cell" includes a plurality of cells, including mixtures thereof.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The terms "determining", "measuring", "evaluating", "assessing," "assaying," "interrogating," and "analyzing" are used interchangeably herein to refer to any form of measurement, and include determining if an element is present or not. These terms include both quantitative and/or qualitative determinations that can be relative or absolute.

As used herein, the term "subject" or "individual" includes mammals. Non-limiting examples of mammals include humans and mice, including transgenic and non-transgenic mice. The methods described herein can be useful in human therapeutics, pre-clinical studies, and veterinary applications. In some embodiments, the subject is a mammal, and in some embodiments, the subject is human. Other mammals include, and are not limited to, apes, chimpanzees, orangutans, monkeys; domesticated animals (e.g., pets) such as dogs, cats, guinea pigs, hamsters, mice, rats, rabbits, and ferrets; domesticated farm animals such as cows, buffalo, bison, horses, donkey, swine, sheep, and goats; or exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, pandas, giant pandas, hyena, seals, sea lions, and elephant seals. The subject may have diabetes. The subject may have NASH or hepatic steatosis. In some cases, the subject is diagnosed with NASH or hepatic steatosis, NAFLD or NASH-related cirrhosis. In some cases, the subject exhibits a propensity for having NASH or hepatic steatosis, NAFLD or NASH-related cirrhosis.

As used herein, "agent", "therapeutic agent", or "biologically active agent" refers to a biological, pharmaceutical, or chemical compound or other moiety. Non-limiting examples include simple or complex organic or inorganic molecule, a peptide, a protein, a peptide nucleic acid (PNA), an oligonucleotide (including e.g., aptamer and polynucleotides), an antibody, an antibody derivative, antibody fragment, a vitamin derivative, a carbohydrate, a toxin, a branched chain amino acid in free amino acid form or metabolite thereof, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents.

The terms "administer", "administered", "administers" and "administering" are defined as providing a composition to a subject via a route known in the art, including but not limited to intravenous, intraarterial, oral, parenteral, buccal, topical, transdermal, rectal, intramuscular, subcutaneous, intraosseous, transmucosal, or intraperitoneal routes of administration. In certain embodiments, oral routes of administering a composition can be used.

As used herein, the terms "co-administration", "administered in combination with" and their grammatical equivalents are meant to encompass administration of a composition and additional therapeutic agent to a single subject. Co-administration can encompass administration of two or more agents to an animal so that both agents and/or their metabolites are present in the subject at the same time. Co-administration can encompass treatment regimens in which the composition and additional therapeutic agent are administered by the same or different route of administration or at the same or different times. Co-administration can include simultaneous administration of the agents in separate compositions, administration at different times in separate compositions, and/or administration in a single composition comprising each of the agents to be co-administered.

The term "effective amount" or "therapeutically effective amount" refers to that amount of a compound described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term can also apply to a dose that can induce a particular response in target cells, e.g., reduction of proliferation or down regulation of activity of a target protein. The specific dose can vary depending on the particular compounds chosen, the dosing regimen to be followed, whether it is administered in combination with other compounds, timing of administration, the tissue to which it is administered, and the physical delivery system in which it is carried.

The term "energy metabolism," as used herein, refers to the transformation of energy that accompanies biochemical reactions in the body, including cellular metabolism and mitochondrial biogenesis. Energy metabolism can be quantified using the various measurements described herein, for example and without limitations, weight-loss, fat-loss, insulin sensitivity, fatty acid oxidation, glucose utilization, triglyceride content, Sirt 1 expression level, Sirt 2, 3, 4, 5 or 6 expression level, AMPK expression level, oxidative stress, and mitochondrial biomass.

The term "isolated", as applied to the subject components, for example, a compound of Formula I-a, I-b, I-c, II-a, II-b, II-c, III, IV, V, or VI or a compound listed in Table 1 or 3, a phosphodiesterase (PDE) inhibitor, sirtuin pathway activator, anti-diabetic agent, anti-hyperlipidemic agent, glucagon-like peptide-1 (GLP-1) agonist, dipeptidyl peptidase-4 (DPP-4) inhibitor, sodium-glucose cotransporter-2 (SGLT2) inhibitor or gliflozin, a fibrate, a nitric oxide (NO) donor, nicotinic acid, nicotinamide riboside, nicotinic acid metabolite, and resveratrol, refers to a preparation of the substance devoid of at least some of the other components that may also be present where the substance or a similar substance naturally occurs or is initially obtained from. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. In certain embodiments, increasing enrichment of any of the components can be used. Thus, for example, a 2-fold enrichment, 10-fold enrichment, 100-fold enrichment, or 1000-fold enrichment can be used. A substance can also be provided in an isolated state by a process of artificial assembly, such as by chemical synthesis.

A "modulator" of a pathway refers to a substance or agent which modulates the activity of one or more cellular proteins mapped to the same specific signal transduction pathway. A modulator may augment or suppress the activity and/or expression level or pattern of a signaling molecule. A modulator can activate a component in a pathway by directly binding to the component. A modulator can also indirectly activate a component in a pathway by interacting with one or more associated components. The output of the pathway can be measured in terms of the expression or activity level of proteins. The expression level of a protein in a pathway can be reflected by levels of corresponding mRNA or related transcription factors as well as the level of the protein in a subcellular location. For instance, certain proteins can be activated by translocating in or out of a specific subcellular component, including but not limited to nucleus, mitochondria, endosome, lysosome or other membranous structure of a cell. The output of the pathway can also be measured in terms of physiological effects, such as mitochondrial biogenesis, fatty acid oxidation, or glucose uptake.

An "activator" refers to a modulator that influences a pathway in a manner that increases the pathway output. Activation of a particular target may be direct (e.g., by interaction with the target) or indirect (e.g., by interaction with a protein upstream of the target in a signaling pathway including the target).

The term "selective inhibition" or "selectively inhibit" as referred to a biologically active agent refers to the agent's ability to preferentially reduce the target signaling activity as compared to off-target signaling activity, via direct or interact interaction with the target.

The term "substantially free", as used herein, refers to compositions that have less than about 10%, less than about 5%, less than about 1%, less than about 0.5%, less than 0.1% or even less of a specified component. For example, a composition that is substantially free of non-branched chain amino acids may have less than about 1% of the non-branched chain amino acid lysine. For example, substantially free of a non-branched chain amino acid can be evidenced by less than 1% of the non-branched chain amino acid when compared to the rest of the amino acids in a given composition.

A "sub-therapeutic amount" of an agent, an activator or a therapy is an amount less than the effective amount for that agent, activator or therapy, but when combined with an effective or sub-therapeutic amount of another agent or therapy can produce a desired result, due to, for example, synergy in the resulting efficacious effects, and/or reduced side effects. A sub-therapeutic amount of the agent or component can be such that it is an amount below which would be considered therapeutic. For example, FDA guidelines can suggest a specified level of dosing to treat a particular condition, and a sub-therapeutic amount would be any level that is below the FDA suggested dosing level. The sub-therapeutic amount can be about 1, 5, 10, 15, 20, 25, 30, 35, 50, 75, 90, or 95% less than the amount that is considered to be a therapeutic amount. The therapeutic amount can be assessed for individual subjects, or for groups of subjects. The group of subjects can be all potential subjects, or subjects having a particular characteristic such as age, weight, race, gender, or physical activity level.

A "synergistic" or "synergizing" effect can be such that the one or more effects of the combination compositions are greater than the one or more effects of each component alone at a comparable dosing level, or they can be greater than the predicted sum of the effects of all of the components at a comparable dosing level, assuming that each component acts independently. The synergistic effect can be about, or greater than about 10, 20, 30, 50, 75, 100, 110, 120, 150, 200, 250, 350, or 500% or even more than the effect on a subject with one of the components alone, or the additive effects as measured when each of the components when administered individually. The effect can be any of the measurable effects described herein.

Quantification of the therapeutic effect can show that the effect of a synergistic composition that comprises component (a), component (b), and component (c) is greater than the predicted effect of administering (a) or (b) or (c) alone, assuming simple additive effects of (a) and (b) and (c), and thus the effect is synergistic. The synergistic effect can be quantified as the measured effect above the predicted simple additive effect of the components of the composition. For example, if administration of component (a) alone yields an effect of 10% relative to control, administration of component (b) alone yields an effect of 15% relative to control, administration of component (c) alone yields an effect of 15% relative to control, and administration of a composition comprising both (a) and (b) and (c) yields an effect of 60% relative to control, the synergistic effect would be 60%–(15%+10%+15%), or 25%.

As described herein, a "biological marker", or a "biomarker", generally refers to a measurable indicator of some biological state or condition. Biological markers are often measured and evaluated to examine normal biological processes, pathogenic processes, or pharmacologic responses to a therapeutic intervention. Accordingly, the biomarkers can relate to genes, mRNAs, and proteins corresponding to the biomarkers as described herein.

As used herein, "treatment" or "treating" refers to an approach for obtaining beneficial or desired results with respect to a disease, disorder, or medical condition including but not limited to a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. In certain embodiments, for prophylactic benefit, the compositions are administered to a subject at risk of developing a particular disease, or to a subject reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The terms "antagonist" and "inhibitor" are used interchangeably, and they refer to a compound having the ability to inhibit a biological function (e.g., activity, expression, binding, protein-protein interaction) of a target protein (e.g., menin, MLL1, MLL2, and/or an MLL fusion protein). Accordingly, the terms "antagonist" and "inhibitor" are defined in the context of the biological role of the target protein. While preferred antagonists herein specifically interact with (e.g., bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor.

The term "agonist" as used herein refers to a compound having the ability to initiate or enhance a biological function of a target protein, whether by inhibiting the activity or expression of the target protein. Accordingly, the term "agonist" is defined in the context of the biological role of the target polypeptide. While preferred agonists herein specifically interact with (e.g., bind to) the target, compounds that initiate or enhance a biological activity of the target polypeptide by interacting with other members of the signal transduction pathway of which the target polypeptide is a member are also specifically included within this definition.

"Signal transduction" is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator may augment (agonist) or suppress (antagonist) the activity of a signaling molecule.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

As used herein, the term "nitric oxide donor" or "NO donor" refers to compounds suitable to increase nitric oxide (NO) levels or bioactivity directly or indirectly, e.g., by increasing the amount or level of available substrate or enzymes for NO production. Examples of nitric oxide donors include compounds that release NO or a related redox species under physiological or any disease treatment conditions, compounds that provide nitric oxide bioactivity, e.g., vasorelaxation or stimulation or inhibition of a receptor protein, or compounds, after non-enzymatic or enzymatic reaction, release nitric oxide. It is noted that a "NO donor" may or may not include a nitric oxide chemical group. Particular examples thereof include L-arginine, SNP, organic nitrate, compounds inhibiting arginase, e.g., arginase II, a competitor of the NO synthase (NOS). Other examples comprise compounds stimulating the activity of NO synthase, in particular, of the eNOS, either by increasing the amount or level of NOS or the turnover rate of the enzyme. These compounds may act directly or indirectly through affecting the level of natural eNOS stimulators, like sphinogine 1-phospate.

The term "organic nitric oxide donor" means an organic compound or mixture of compounds with at least one of such compound(s) which are NO donors, such as compound that can release nitric oxide under physiological or any disease treatment conditions.

As used herein, an "organic nitrate" refers to a compound of formula R—$ONO_2$, wherein R is an alkyl, alkenyl, alkynyl, aryl, arylalkyl, arylalkenyl, arylalkynyl, alkylaryl, alkenylaryl or alkynylaryl group, each of which can optionally be substituted, optionally with one or more further —$ONO_2$ groups, and each of which may optionally include one or more heteroatoms N, O or S in its carbon skeleton.

As used herein, an "organic nitrite" refers to a compound of formula $R^b$—ONO, wherein $R^b$ is an alkyl, alkenyl, alkynyl, aryl, arylalkyl, arylalkenyl, arylalkynyl, alkylaryl, alkenylaryl or alkynylaryl group, each of which may optionally be substituted, optionally with one or more further —ONO groups, and each of which may optionally include one or more heteroatoms N, O or S in its carbon skeleton.

The term "$C_{x-y}$" or "$C_x$—$C_y$" when used in conjunction with a chemical moiety, such as alkyl, alkenyl, or alkynyl is meant to include groups that contain from x to y carbons in the chain. For example, the term "$C_{x-y}$ alkyl" refers to substituted or unsubstituted saturated hydrocarbon groups, including straight-chain alkyl and branched-chain alkyl groups that contain from x to y carbons in the chain. The terms "$C_{x-y}$ alkenyl" and "$C_{x-y}$ alkynyl" refer to substituted or unsubstituted straight-chain or branched-chain unsaturated hydrocarbon groups that contain at least one double or triple bond respectively. Unless stated otherwise specifically in the specification, a $C_{x-y}$ alkyl, $C_{x-y}$ alkenyl, or $C_{x-y}$ alkynyl is optionally substituted by one or more substituents such as those substituents described herein.

"Carbocycle" refers to a saturated, unsaturated or aromatic ring in which each atom of the ring is a carbon atom. Carbocycle may include 3- to 10-membered monocyclic rings, 6- to 12-membered bicyclic rings, and 6- to 12-membered bridged rings. Each ring of a bicyclic carbocycle may be selected from saturated, unsaturated, and aromatic rings. In some embodiments, the carbocycle is an aryl. In some embodiments, the carbocycle is a cycloalkyl. In some embodiments, the carbocycle is a cycloalkenyl. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, are included in the definition of carbocyclic. Exemplary carbocycles include cyclopentyl, cyclohexyl, cyclohexenyl, adamantyl, phenyl, indanyl, and naphthyl. Unless stated otherwise specifically in the specification, a carbocycle is optionally substituted by one or more substituents such as those substituents described herein.

"Heterocycle" refers to a saturated, unsaturated or aromatic ring comprising one or more heteroatoms. Exemplary heteroatoms include N, O, Si, P, B, and S atoms. Heterocycles include 3- to 10-membered monocyclic rings, 6- to 12-membered bicyclic rings, and 6- to 12-membered bridged rings. Each ring of a bicyclic heterocycle may be selected from saturated, unsaturated, and aromatic rings. The heterocycle may be attached to the rest of the molecule through any atom of the heterocycle, valence permitting, such as a carbon or nitrogen atom of the heterocycle. In some embodiments, the heterocycle is a heteroaryl. In some embodiments, the heterocycle is a heterocycloalkyl. In an exemplary embodiment, a heterocycle, e.g., pyridyl, may be fused to a saturated or unsaturated ring, e.g., cyclohexane, cyclopentane, or cyclohexene.

"Heteroaryl" refers to a 3- to 12-membered aromatic ring that comprises at least one heteroatom wherein each heteroatom may be independently selected from N, O, and S. As used herein, the heteroaryl ring may be selected from monocyclic or bicyclic and fused or bridged ring systems rings wherein at least one of the rings in the ring system is aromatic, i.e., it contains a cyclic, delocalized (4n+2) π-electron system in accordance with the Hückel theory. The heteroatom(s) in the heteroaryl may be optionally oxidized. One or more nitrogen atoms, if present, are optionally quaternized. The heteroaryl may be attached to the rest of the molecule through any atom of the heteroaryl, valence permitting, such as a carbon or nitrogen atom of the heteroaryl. Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryls as defined above which are optionally substituted by one or more substituents such as those substituents described herein.

Compounds of the present disclosure also include crystalline and amorphous forms of those compounds, pharmaceutically acceptable salts, and active metabolites of these compounds having the same type of activity, including, for example, polymorphs, pseudopolymorphs, solvates, hydrates, unsolvated polymorphs (including anhydrates), conformational polymorphs, and amorphous forms of the compounds, as well as mixtures thereof.

The compounds described herein may exhibit their natural isotopic abundance, or one or more of the atoms may be artificially enriched in a particular isotope having the same atomic number, but an atomic mass or mass number different from the atomic mass or mass number predominantly found in nature. All isotopic variations of the compounds of the present disclosure, whether radioactive or not, are encompassed within the scope of the present disclosure. For example, hydrogen has three naturally occurring isotopes, denoted $^1$H (protium), $^2$H (deuterium), and $^3$H (tritium). Protium is the most abundant isotope of hydrogen in nature. Enriching for deuterium may afford certain therapeutic advantages, such as increased in vivo half-life and/or exposure, or may provide a compound useful for investigating in vivo routes of drug elimination and metabolism. Isotopically-enriched compounds may be prepared by conventional techniques well known to those skilled in the art.

"Isomers" are different compounds that have the same molecular formula. "Stereoisomers" are isomers that differ only in the way the atoms are arranged in space. "Enantiomers" are a pair of stereoisomers that are non superimposable mirror images of each other. A 1:1 mixture of a pair of enantiomers is a "racemic" mixture. The term "(±)" is used to designate a racemic mixture where appropriate. "Diastereoisomers" or "diastereomers" are stereoisomers that have at least two asymmetric atoms but are not mirror images of each other. The absolute stereochemistry is specified according to the Cahn-Ingold-Prelog R—S system. When a compound is a pure enantiomer, the stereochemistry at each chiral carbon can be specified by either R or S. Resolved compounds whose absolute configuration is unknown can be designated (+) or (−) depending on the direction (dextro- or levorotatory) in which they rotate plane polarized light at the wavelength of the sodium D line. Certain compounds described herein contain one or more asymmetric centers and can thus give rise to enantiomers, diastereomers, and other stereoisomeric forms, the asymmetric centers of which can be defined, in terms of absolute stereochemistry, as (R)- or (S)-. The present chemical entities, pharmaceutical compositions and methods are meant to include all such possible stereoisomers, including racemic mixtures, optically pure forms, mixtures of diastereomers and intermediate mixtures. Optically active (R)- and (S)-isomers can be prepared using chiral synthons or chiral reagents, or resolved using conventional techniques. The optical activity of a compound can be analyzed via any suitable method, including but not limited to chiral chromatography and polarimetry, and the degree of predominance of one stereoisomer over the other isomer can be determined.

Chemical entities having carbon-carbon double bonds or carbon-nitrogen double bonds may exist in Z- or E-form (or cis- or trans-form). Furthermore, some chemical entities may exist in various tautomeric forms. Unless otherwise specified, chemical entities described herein are intended to include all Z-, E- and tautomeric forms as well.

The term "substituted" refers to moieties having substituents replacing a hydrogen on one or more carbons or heteroatoms of the structure. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, a carbocycle, a heterocycle, a cycloalkyl, a heterocycloalkyl, an aromatic and heteroaromatic moiety. In some embodiments, substituents may include any substituents described herein, for example: halogen, hydroxy, oxo (=O), thioxo (=S), cyano (—CN), nitro (—NO$_2$), imino (=N—H), oximo (=N—OH), hydrazino (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2), and —R$^b$—S(O)$_t$N(R$^a$)$_2$ (where t is 1 or 2); and alkyl, alkenyl, alkynyl, aryl, aralkyl, aralkenyl, aralkynyl, cycloalkyl, cycloalkylalkyl, heterocycloalkyl, heterocycloalkylalkyl, heteroaryl, and heteroarylalkyl any of which may be optionally substituted by alkyl, alkenyl, alkynyl, halogen, hydroxy, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); wherein each R$^a$ is independently selected from hydrogen, alkyl, cycloalkyl, cycloalkylalkyl, aryl, aralkyl, heterocycloalkyl, heterocycloalkylalkyl, heteroaryl, or heteroarylalkyl, wherein each R$^a$, valence permitting, may be optionally substituted with alkyl, alkenyl, alkynyl, halogen, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); and wherein each R$^b$ is independently selected from a direct bond or a straight or branched alkylene, alkenylene, or alkynylene chain, and each R$^c$ is a straight or branched alkylene, alkenylene or alkynylene chain.

It will be understood by those skilled in the art that substituents can themselves be substituted, if appropriate. Unless specifically stated as "unsubstituted," references to chemical moieties herein are understood to include substituted variants. For example, reference to a "heteroaryl" group or moiety implicitly includes both substituted and unsubstituted variants.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "salt" or "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

"Prodrug" is meant to indicate a compound that may be converted under physiological conditions or by solvolysis to a biologically active compound described herein (e.g., compound of Formula I-a, I-b, I-c, II-a, II-b, II-c, III, IV, V, or VI or a compound listed in Table 1 or 3). Thus, the term "prodrug" refers to a precursor of a biologically active compound that is pharmaceutically acceptable. In some aspects, a prodrug is inactive when administered to a subject but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam); Higuchi, T., et al., "Pro-drugs as Novel Delivery Systems," (1987) A.C.S. Symposium Series, Vol. 14; and Bioreversible Carriers in Drug Design, ed. Edward B. Roche, American Pharmaceutical Association and Pergamon Press) each of which is incorporated in full by reference herein. The term "prodrug" is also meant to include any covalently bonded carriers, which release the active compound in vivo when such prodrug is administered to a mammalian subject. Prodrugs of an active compound, as described herein, are typically prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of a hydroxy functional group, or acetamide, formamide and benzamide derivatives of an amine functional group in the active compound and the like.

The term "in vivo" refers to an event that takes place in a subject's body.

The term "in vitro" refers to an event that takes places outside of a subject's body. For example, an in vitro assay encompasses any assay run outside of a subject. In vitro assays encompass cell-based assays in which cells alive or dead are employed. In vitro assays also encompass a cell-free assay in which no intact cells are employed.

"Optional" or "optionally" means that the subsequently described event of circumstances may or may not occur, and that the description includes instances where the event or circumstance occurs and instances in which it does not. For example, "optionally substituted aryl" means that the aryl group may or may not be substituted and that the description includes both substituted aryl groups and aryl groups having no substitution.

"Pharmaceutically acceptable carrier, diluent or excipient" includes without limitation any adjuvant, carrier, excipient, glidant, sweetening agent, diluent, preservative, dye, colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

Compounds

The compounds, compositions, and methods provided herein may be useful in treating a metabolic disease or disorder, including but not limited to diabetes, metabolic syndrome, obesity, hyperlipidemia, and non-alcoholic steatohepatitis.

In certain embodiments, provided herein is a compound of Formula (I-a) or Formula (II-a):

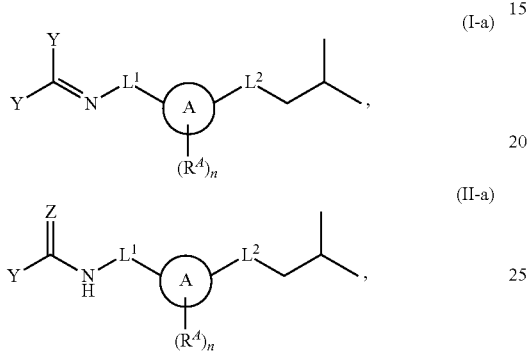

or a pharmaceutically acceptable salt thereof, wherein:

A is selected from a bond, $C_{3-12}$ carbocycle, and 3- to 12-membered heterocycle, wherein the carbocycle or heterocycle is monocyclic or multicyclic;

Y is selected from $N(R^1)_2$, $C(R^B)_3$, $OR^3$, and $SR^3$;

Z is selected from $NR^1$, $C(R^B)_2$, O, and S;

each of $L^1$ and $L^2$ is independently selected from a bond, —O—, —S—, —N(R$^1$)—, —N(R$^1$)CH$_2$—, —C(O)—, —C(O)O—, —OC(O)—, —OC(O)O—, —C(O)N(R$^1$)—, —C(O)N(R$^1$)C(O)—, —C(O)N(R$^1$)C(O)N(R$^1$)—, —N(R$^1$)C(O)—, —N(R$^1$)C(O)N(R$^1$)—, —N(R$^1$)C(O)O—, —OC(O)N(R$^1$)—, —C(NR$^1$)—, —N(R$^1$)C(NR$^1$)—, —C(NR$^1$)N(R$^1$)—, —N(R$^1$)C(NR$^1$)N(R$^1$)—, —S(O)$_2$—, —OS(O)—, —S(O)O—, —S(O)—, —OS(O)$_2$—, —S(O)$_2$O—, —N(R$^1$)S(O)$_2$—, —S(O)$_2$N(R$^1$)—, —N(R$^1$)S(O)—, —S(O)N(R$^1$)—, —N(R$^1$)S(O)$_2$N(R$^1$)—, —N(R$^1$)S(O)N(R$^1$)—, alkylene, alkenylene, alkynylene, heteroalkylene, heteroalkenylene, and heteroalkynylene, wherein one or more hydrogen atoms are optionally substituted with $R^2$ and wherein two $R^2$ groups attached to the same atom or different atoms can optionally join together to form a $C_{3-8}$ carbocycle or 3- to 8-membered heterocycle;

$R^A$ is independently selected at each occurrence from $R^2$;

n is an integer from 0 to 10;

$R^B$ is independently selected at each occurrence from hydrogen and $R^2$, and/or two $R^B$ groups attached to the same atom can optionally join together to form a $C_{3-8}$ carbocycle or 3- to 8-membered heterocycle;

$R^1$ is independently selected at each occurrence from: hydrogen, —C(O)R$^3$, —C(O)OR$^3$, —C(O)N(R$^3$)$_2$, —C(O)NR$^4$R$^5$;

$C_{1-6}$ alkyl, $C_{2-6}$ alkenyl, and $C_{2-6}$ alkynyl, each of which is independently optionally substituted at each occurrence with one or more substituents selected from halogen, —NO$_2$, —CN, —OR$^3$, —SR$^3$, —N(R$^3$)$_2$, —NR$^4$R$^5$, —S(=O)R$^3$, —S(=O)$_2$R$^3$, —S(=O)$_2$N(R$^3$)$_2$, —S(=O)$_2$NR$^4$R$^5$, —NR$^3$S(=O)$_2$R$^3$, —NR$^3$S(=O)$_2$N(R$^3$)$_2$, —NR$^3$S(=O)$_2$NR$^4$R$^5$, —C(O)R$^3$, —C(O)OR$^3$, —OC(O)R$^3$, —OC(O)OR$^3$, —OC(O)N(R$^3$)$_2$, —OC(O)NR$^4$R$^5$, —NR$^3$C(O)R$^3$, —NR$^3$C(O)OR$^3$, —NR$^3$C(O)N(R$^3$)$_2$, —NR$^3$C(O)NR$^4$R$^5$, —C(O)N(R$^3$)$_2$, —C(O)NR$^4$R$^5$, —P(O)(OR$^3$)$_2$, —P(O)(R$^3$)$_2$, =O, =S, =N(R$^3$), $C_{3-12}$ carbocycle and 3- to 12-membered heterocycle; and $C_{3-12}$ carbocycle and 3- to 12-membered heterocycle, wherein each $C_{3-12}$ carbocycle and 3- to 12-membered heterocycle in $R^1$ is independently optionally substituted with one or more substituents selected from halogen, —NO$_2$, —CN, —OR$^3$, —SR$^3$, —N(R$^3$)$_2$, —NR$^4$R$^5$, —S(=O)R$^3$, —S(=O)$_2$R$^3$, —S(=O)$_2$N(R$^3$)$_2$, —S(=O)$_2$NR$^4$R$^5$, —NR$^3$S(=O)$_2$R$^3$, —NR$^3$S(=O)$_2$N(R$^3$)$_2$, —NR$^3$S(=O)$_2$NR$^4$R$^5$, —C(O)R$^3$, —C(O)OR$^3$, —OC(O)R$^3$, —OC(O)OR$^3$, —OC(O)N(R$^3$)$_2$, —OC(O)NR$^4$R$^5$, —NR$^3$C(O)R$^3$, —NR$^3$C(O)OR$^3$, —NR$^3$C(O)N(R$^3$)$_2$, —NR$^3$C(O)NR$^4$R$^5$, —C(O)N(R$^3$)$_2$, —C(O)NR$^4$R$^5$, —P(O)(OR$^3$)$_2$, —P(O)(R$^3$)$_2$, =O, =S, =N(R$^3$), $C_{1-6}$ alkyl, $C_{1-6}$ haloalkyl, $C_{2-6}$ alkenyl, and $C_{2-6}$ alkynyl;

$R^2$ is independently selected at each occurrence from: halogen, —NO$_2$, —CN, —OR$^3$, —SR$^3$, —N(R$^3$)$_2$, —NR$^4$R$^5$, —S(=O)R$^3$, —S(=O)$_2$R$^3$, —S(=O)$_2$N(R$^3$)$_2$, —S(=O)$_2$NR$^4$R$^5$, —NR$^3$S(=O)$_2$R$^3$, —NR$^3$S(=O)$_2$N(R$^3$)$_2$, —NR$^3$S(=O)$_2$NR$^4$R$^5$, —C(O)R$^3$, —C(O)OR$^3$, —OC(O)R$^3$, —OC(O)OR$^3$, —OC(O)N(R$^3$)$_2$, —OC(O)NR$^4$R$^5$, —NR$^3$C(O)R$^3$, —NR$^3$C(O)OR$^3$, —NR$^3$C(O)N(R$^3$)$_2$, —NR$^3$C(O)NR$^4$R$^5$, —C(O)N(R$^3$)$_2$, —C(O)NR$^4$R$^5$, —P(O)(OR$^3$)$_2$, —P(O)(R$^3$)$_2$, =O, =S, =N(R$^3$);

$C_{1-10}$ alkyl, $C_{2-10}$ alkenyl, and $C_{2-10}$ alkynyl, each of which is independently optionally substituted at each occurrence with one or more substituents selected from halogen, —NO$_2$, —CN, —OR$^3$, —SR$^3$, —N(R$^3$)$_2$, —NR$^4$R$^5$, —S(=O)R$^3$, —S(=O)$_2$R$^3$, —S(=O)$_2$N(R$^3$)$_2$, —S(=O)$_2$NR$^4$R$^5$, —NR$^3$S(=O)$_2$R$^3$, —NR$^3$S(=O)$_2$N(R$^3$)$_2$, —NR$^3$S(=O)$_2$NR$^4$R$^5$, —C(O)R$^3$, —C(O)OR$^3$, —OC(O)R$^3$, —OC(O)OR$^3$, —OC(O)N(R$^3$)$_2$, —OC(O)NR$^4$R$^5$, —NR$^3$C(O)R$^3$, —NR$^3$C(O)OR$^3$, —NR$^3$C(O)N(R$^3$)$_2$, —NR$^3$C(O)NR$^4$R$^5$, —C(O)N(R$^3$)$_2$, —C(O)NR$^4$R$^5$, —P(O)(OR$^3$)$_2$, —P(O)(R$^3$)$_2$, =O, =S, =N(R$^3$), $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^2$ is independently optionally substituted with one or more substituents selected from halogen, —NO$_2$, —CN, —OR$^3$, —SR$^3$, —N(R$^3$)$_2$, —NR$^4$R$^5$, —S(=O)R$^3$, —S(=O)$_2$R$^3$, —S(=O)$_2$N(R$^3$)$_2$, —S(=O)$_2$NR$^4$R$^5$, —NR$^3$S(=O)$_2$R$^3$, —NR$^3$S(=O)$_2$N(R$^3$)$_2$, —NR$^3$S(=O)$_2$NR$^4$R$^5$, —C(O)R$^3$, —C(O)OR$^3$, —OC(O)R$^3$, —OC(O)OR$^3$, —OC(O)N(R$^3$)$_2$, —OC(O)NR$^4$R$^5$, —NR$^3$C(O)R$^3$, —NR$^3$C(O)OR$^3$, —NR$^3$C(O)N(R$^3$)$_2$, —NR$^3$C(O)NR$^4$R$^5$, —C(O)N(R$^3$)$_2$, —C(O)NR$^4$R$^5$, —P(O)(OR$^3$)$_2$, —P(O)(R$^3$)$_2$, =O, =S, =N(R$^3$), $C_{1-6}$ alkyl, $C_{1-6}$ haloalkyl, $C_{2-6}$ alkenyl, and $C_{2-6}$ alkynyl;

$R^3$ is independently selected at each occurrence from hydrogen; and $C_{1-20}$ alkyl, $C_{2-20}$ alkenyl, $C_{2-20}$ alkynyl, 1- to 6-membered heteroalkyl, $C_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, $C_{3-12}$ carbocycle, or 3- to 6-membered heterocycle; and $R^4$ and $R^5$ are taken together with the nitrogen atom to which they are attached to form a 3- to 8-membered heterocycle, optionally substituted with one or more $R^2$.

In some cases, the compound is a compound of Formula (I-b) or Formula (II-b):

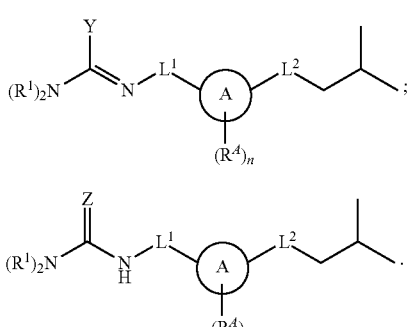

In some cases, the compound is a compound of Formula (I-c) or Formula (II-c):

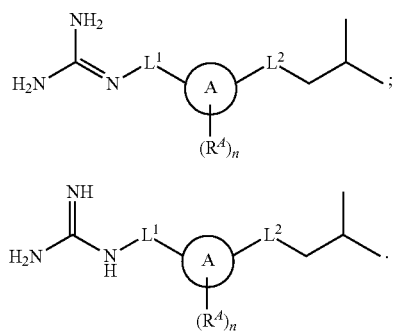

In some cases, the compound is a compound of Formula (III):

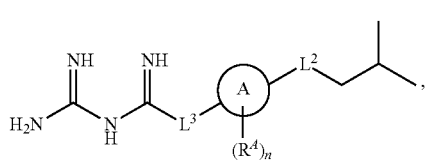

or a pharmaceutically acceptable salt thereof, wherein:

$L^3$ is selected from a bond, —O—, —S—, —N($R^1$)—, —N($R^1$)CH$_2$—, —C(O)—, —C(O)O—, —OC(O)—, —OC(O)O—, —C(O)N($R^1$)—, —C(O)N($R^1$)C(O)—, —C(O)N($R^1$)C(O)N($R^1$)—, —N($R^1$)C(O)—, —N($R^1$)C(O)N($R^1$)—, —N($R^1$)C(O)O—, —OC(O)N($R^1$)—, —C(N$R^1$)—, —N($R^1$)C(N$R^1$)—, —C(N$R^1$)N($R^1$)—, —N($R^1$)C(N$R^1$)N($R^1$)—, —S(O)$_2$—, —OS(O)—, —S(O)O—, —S(O)—, —OS(O)$_2$—, —S(O)$_2$O—, —N($R^1$)S(O)$_2$—, —S(O)$_2$N($R^1$)—, —N($R^1$)S(O)—, —S(O)N($R^1$)—, —N($R^1$)S(O)$_2$N($R^1$)—, —N($R^1$)S(O)N($R^1$)—, alkylene, alkenylene, alkynylene, heteroalkylene, heteroalkenylene, and heteroalkynylene, wherein one or more hydrogen atoms of $L^3$ are optionally substituted with $R^2$ and wherein two $R^2$ groups attached to the same atom or different atoms of $L^3$ can optionally join together to form a $C_{3-8}$ carbocycle or 3- to 8-membered heterocycle.

In some cases, the compound is a compound of Formula (IV):

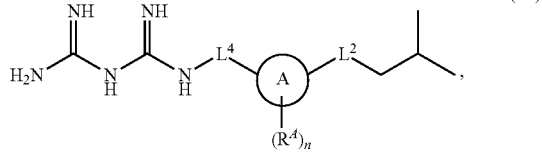

or a pharmaceutically acceptable salt thereof, wherein:

$L^4$ is selected from a bond, —O—, —S—, —N($R^1$)—, —N($R^1$)CH$_2$—, —C(O)—, —C(O)O—, —OC(O)—, —OC(O)O—, —C(O)N($R^1$)—, —C(O)N($R^1$)C(O)—, —C(O)N($R^1$)C(O)N($R^1$)—, —N($R^1$)C(O)—, —N($R^1$)C(O)N($R^1$)—, —N($R^1$)C(O)O—, —OC(O)N($R^1$)—, —C(N$R^1$)—, —N($R^1$)C(N$R^1$)—, —C(N$R^1$)N($R^1$)—, —N($R^1$)C(N$R^1$)N($R^1$)—, —S(O)$_2$—, —OS(O)—, —S(O)O—, —S(O)—, —OS(O)$_2$—, —S(O)$_2$O—, —N($R^1$)S(O)$_2$—, —S(O)$_2$N($R^1$)—, —N($R^1$)S(O)—, —S(O)N($R^1$)—, —N($R^1$)S(O)$_2$N($R^1$)—, —N($R^1$)S(O)N($R^1$)—, alkylene, alkenylene, alkynylene, heteroalkylene, heteroalkenylene, and heteroalkynylene, wherein one or more hydrogen atoms of $L^4$ are optionally substituted with $R^2$ and wherein two $R^2$ groups attached to the same atom or different atoms of $L^4$ can optionally join together to form a $C_{3-8}$ carbocycle or 3- to 8-membered heterocycle.

In some cases, the compound is a biguanide.

In some cases, A is a bond. In some cases, A is monocyclic. In some cases, A is multicyclic. In some cases, A is a $C_{3-8}$ carbocycle or 3- to 8-membered heterocycle. In some cases, A is a $C_{3-6}$ carbocycle or 3- to 6-membered heterocycle. In some cases, A is a $C_{5-6}$ carbocycle or 5- to 6-membered heterocycle. In some cases, A is a $C_{3-12}$ carbocycle. In some cases, A is a 3- to 12-membered heterocycle. In some cases, A is a monocyclic heterocycle. In some cases, A is a 5-membered or 6-membered heterocycle. In some cases, A is saturated. In some cases, A is unsaturated. In some cases, A is aromatic. In some cases, A is not aromatic.

In some cases, A has one of the following structures:

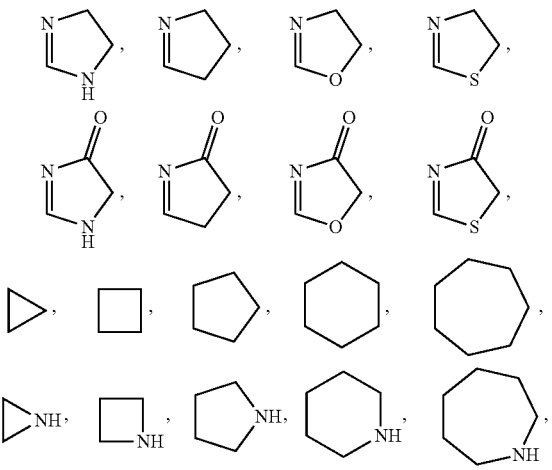

-continued

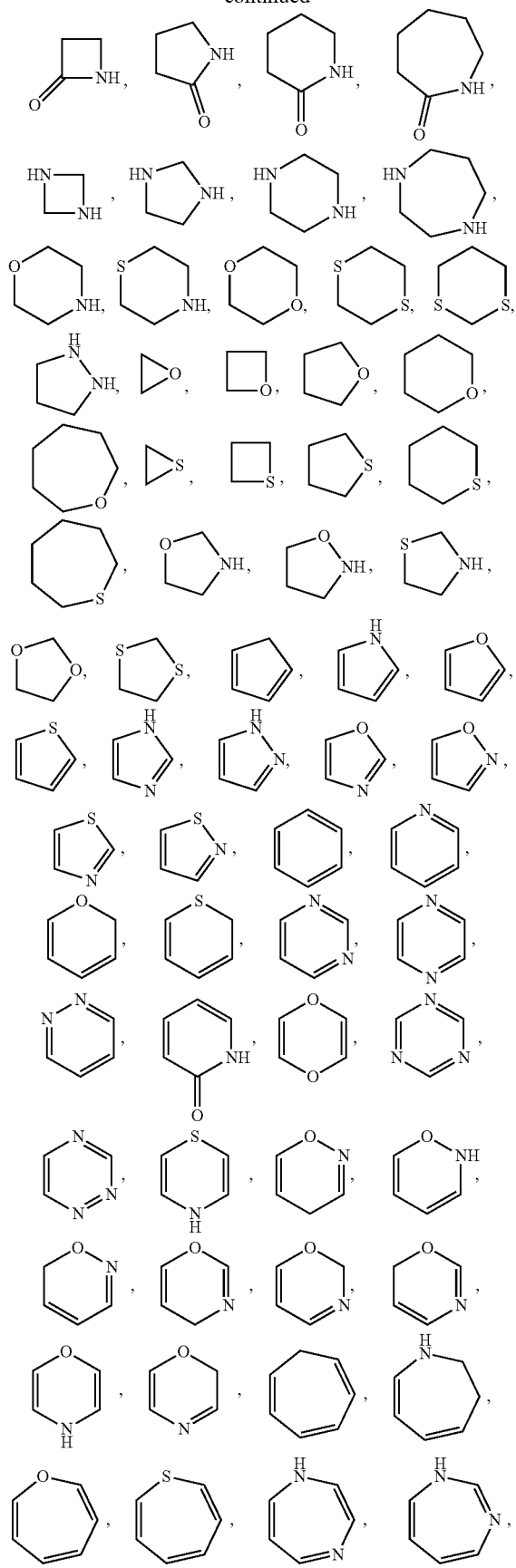

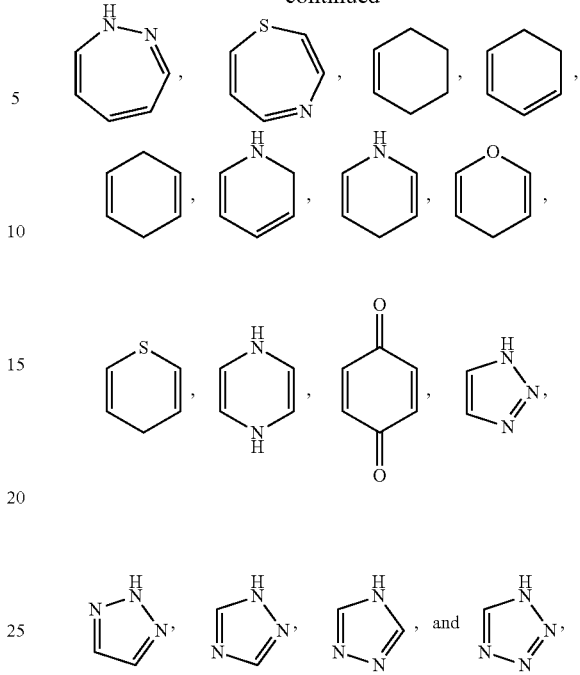

wherein the H of any CH or NH may be replaced with a bond to $R^A$.

In some cases, $L^2$ is a bond. In some cases, $L^2$ is an alkylene. In some cases, $L^2$ is a $C_{1-6}$ alkylene, such as a $C_{1-3}$ alkylene.

In some cases, the compound is a compound of Formula (V):

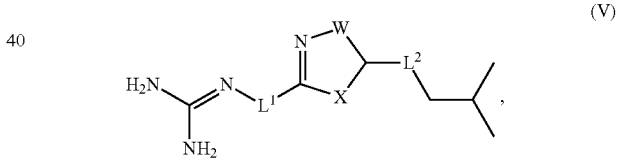

(V)

wherein:

each of W and X is independently selected from the group consisting of —O—, —S—, —N($R^1$)—, —N($R^1$)$CH_2$—, —C(O)—, —C(O)O—, —OC(O)—, —OC(O)O—, —C(O)N($R^1$)—, —C(O)N($R^1$)C(O)—, —C(O)N($R^1$)C(O)N($R^1$)—, —N($R^1$)C(O)—, —N($R^1$)C(O)N($R^1$)—, —N($R^1$)C(O)O—, —OC(O)N($R^1$)—, —C(N$R^1$)—, —N($R^1$)C(N$R^1$)—, —C(N$R^1$)N($R^1$)—, —N($R^1$)C(N$R^1$)N($R^1$)—, —S(O)$_2$—, —OS(O)—, —S(O)O—, —S(O)—, —OS(O)$_2$—, —S(O)$_2$O—, —N($R^1$)S(O)$_2$—, —S(O)$_2$N($R^1$)—, —N($R^1$)S(O)—, —S(O)N($R^1$)—, —N($R^1$)S(O)$_2$N($R^1$)—, —N($R^1$)S(O)N($R^1$)—, $C_{1-8}$ alkylene, $C_{1-8}$ alkenylene, $C_{1-8}$ alkynylene, $C_{1-7}$ heteroalkylene, $C_{1-7}$ heteroalkenylene, and $C_{1-7}$ heteroalkynylene, wherein one or more hydrogen atoms are optionally substituted with $R^2$ and wherein two $R^2$ groups attached to the same atom or different atoms can optionally join together to form a $C_{3-8}$ carbocycle or 3- to 8-membered heterocycle.

In some cases, W is selected from the group consisting of —C(O)— and —C($R^B$)$_2$—.

In some cases, the compound is a compound of Formula (VI):
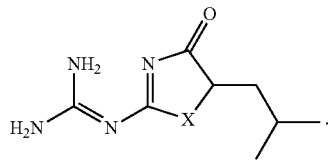
(VI)
In some cases, X is selected from the group consisting of —O—, —S—, —N(R$^1$)—, —C(R$^B$)$_2$—, and any combination thereof.
In some cases, the compound is
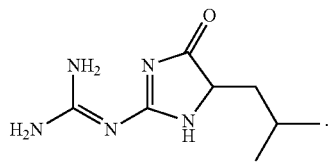
In some cases, the compound is
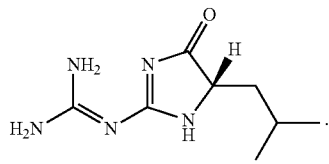
In some cases, the compound is selected from Table 1 or Table 3, or a pharmaceutically acceptable salt thereof.
TABLE 1
| No. | Structure | MW (calc'd) |
|---|---|---|
| 1 |  | 197.24 |
| 2 |  | 197.24 |
| 3 |  | 197.24 |
| 4 | 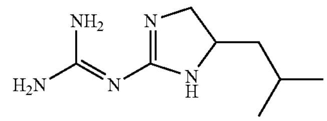 | 183.25 |
| 5 | 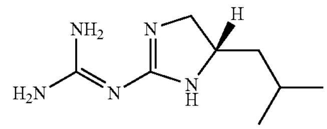 | 183.25 |
| 6 | 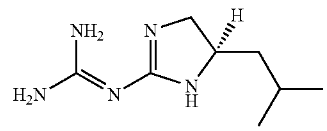 | 183.25 |
| 7 | 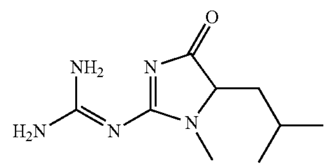 | 211.26 |
| 8 | 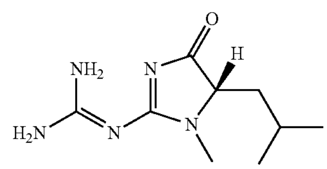 | 211.26 |
| 9 | 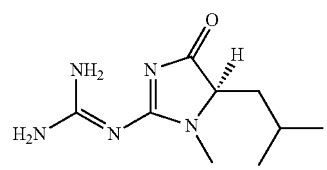 | 211.26 |
| 10 | 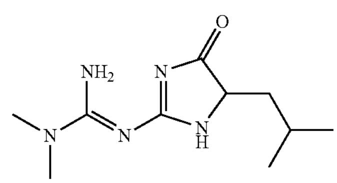 [SMILES: CC(C)CC1NC(/N=C(\N)N(C)C)=NC1=O] | 225.29 |
| 11 | 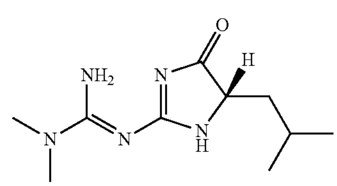 [SMILES: CC(C)C[C@@H]1NC(/N=C(\N)N(C)C)=NC1=O] | 225.29 |
| 12 | 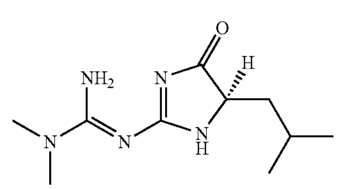 [SMILES: CC(C)C[C@H]1NC(/N=C(\N)N(C)C)=NC1=O] | 225.29 |

TABLE 1-continued

Exemplary compounds

| No. | Structure | MW (calc'd) |
|---|---|---|
| 13 | 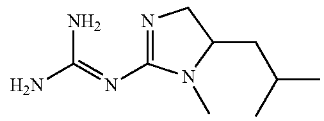 | 197.28 |
| 14 | 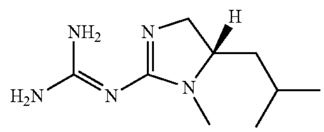 | 197.28 |
| 15 | 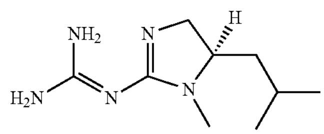 | 197.28 |
| 16 | 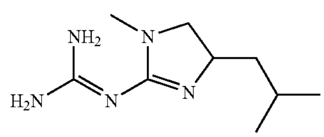 | 197.28 |
| 17 | 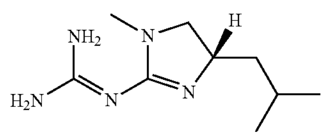 | 197.28 |
| 18 | 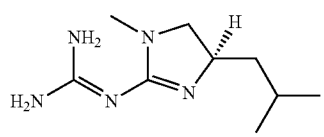 | 197.28 |
| 19 | 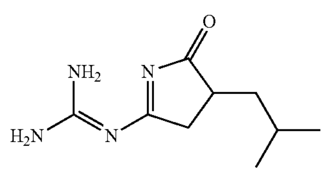 | 196.25 |
| 20 | 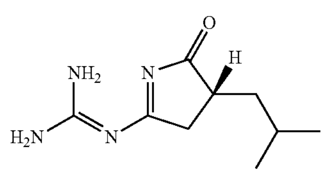 | 196.25 |
| 21 | 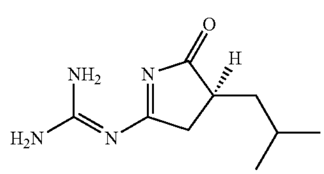 | 196.25 |
| 22 | 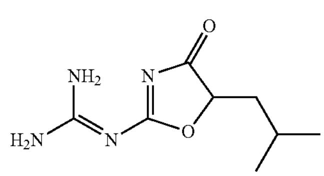 | 198.22 |
| 23 | | 198.22 |
| 24 | | 198.22 |
| 25 | | 214.29 |
| 26 | | 214.29 |
| 27 | | 214.29 |
| 28 | | 171.24 |
| 29 | | 157.22 |
| 30 | | 185.27 |
| 31 | | 171.24 |
| 32 | | 201.27 |

TABLE 1-continued

Exemplary compounds

| No. | Structure | MW (calc'd) |
|---|---|---|
| 33 | (structure) | 215.30 |

TABLE 2

Exemplary biguanide drugs

| No. | Name | Structure | MW (calc'd) |
|---|---|---|---|
| 34 | Metformin | (structure) | 129.16 |
| 35 | Phenformin | (structure) | 205.26 |
| 36 | Buformin | (structure) | 157.22 |

TABLE 3

Exemplary compounds

| No. | Structure | MW (calc'd) |
|---|---|---|
| 37 | (structure) | 183.21 |
| 38 | (structure) | 197.24 |
| 39 | (structure) | 183.25 |

TABLE 3-continued

Exemplary compounds

| No. | Structure | MW (calc'd) |
|---|---|---|
| 40 | (structure) | 281.38 |
| 41 | (structure) | 224.35 |
| 42 | (structure) | 311.38 |
| 43 | (structure) | 288.34 |
| 44 | (structure) | 344.45 |
| 45 | (structure) | 286.33 |

TABLE 3-continued

Exemplary compounds

| No. | Structure | MW (calc'd) |
|---|---|---|
| 46 | | 302.37 |
| 47 | | 302.37 |
| 48 | | 302.37 |
| 49 | | 332.35 |
| 50 | | 332.35 |
| 51 | 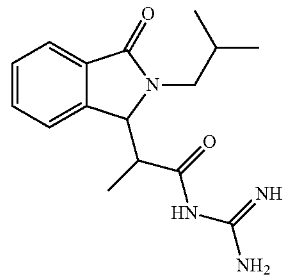 [SMILES: CC(C)CN1C(=O)c2ccccc2C1C(C)C(=O)NC(=N)N] | 302.37 |
| 52 | 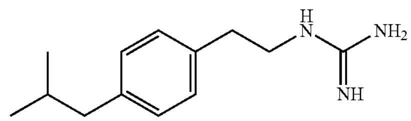 [SMILES: CC(C)Cc1ccc(CCNC(=N)N)cc1] | 219.33 |
| 53 | 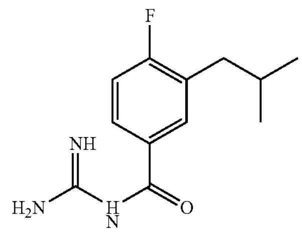 [SMILES: CC(C)Cc1cc(C(=O)NC(=N)N)ccc1F] | 237.27 |
| 54 | 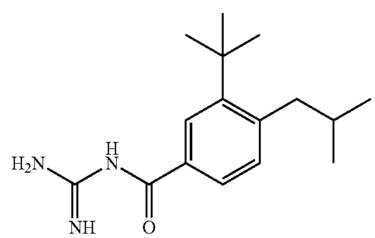 [SMILES: CC(C)Cc1ccc(C(=O)NC(=N)N)cc1C(C)(C)C] | 275.39 |
| 55 | 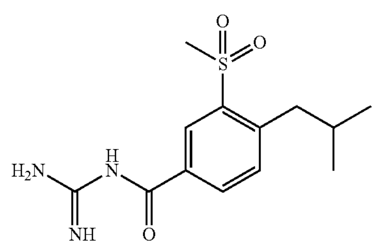 [SMILES: CC(C)Cc1ccc(C(=O)NC(=N)N)cc1S(C)(=O)=O] | 297.37 |
| 56 | 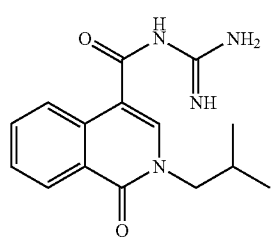 [SMILES: CC(C)Cn1cc(C(=O)NC(=N)N)c2ccccc2c1=O] | 286.33 |

TABLE 3-continued

Exemplary compounds

| No. | Structure | MW (calc'd) |
|---|---|---|
| 57 | (pyrrole-NH, 3-isobutyl, 4-methylsulfonyl, 2-carboxamidoguanidine) | 286.35 |
| 58 | (N-methylpyrrole, 3-isobutyl, 4-methylsulfonyl, 2-carboxamidoguanidine) | 300.38 |
| 59 | (furan, 3-isobutyl, 4-methylsulfonyl, 2-carboxamidoguanidine) | 287.34 |
| 60 | (thiophene, 3-isobutyl, 4-methylsulfonyl, 2-carboxamidoguanidine) | 303.40 |
| 61 | (pyrrole-NH, 3-isobutyl, 4-acetyl, 2-carboxamidoguanidine) | 250.30 |
| 62 | (N-methylpyrrole, 3-isobutyl, 4-acetyl, 2-carboxamidoguanidine) | 264.32 |
| 63 | (furan, 3-isobutyl, 4-acetyl, 2-carboxamidoguanidine) | 251.28 |
| 64 | (thiophene, 3-isobutyl, 4-acetyl, 2-carboxamidoguanidine) | 267.35 |
| 65 | (pyrrole-NH, 3-neopentyl, 2-carboxamidoguanidine) | 264.37 |
| 66 | (N-methylpyrrole, 3-neopentyl, 2-carboxamidoguanidine) | 278.39 |
| 67 | (furan, 3-neopentyl, 2-carboxamidoguanidine) | 265.35 |
| 68 | (thiophene, 3-neopentyl, 2-carboxamidoguanidine) | 281.42 |

TABLE 3-continued

Exemplary compounds

| No. | Structure | MW (calc'd) |
|---|---|---|
| 69 | 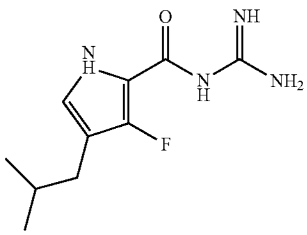 [SMILES: CC(C)Cc1c[nH]c(C(=O)NC(=N)N)c1F] | 226.25 |
| 70 | 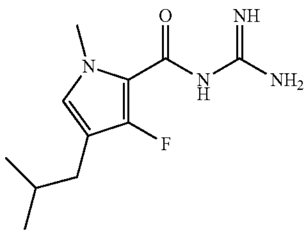 [SMILES: CC(C)Cc1cn(C)c(C(=O)NC(=N)N)c1F] | 240.28 |
| 71 | 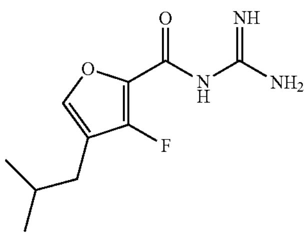 [SMILES: CC(C)Cc1coc(C(=O)NC(=N)N)c1F] | 227.24 |
| 72 | 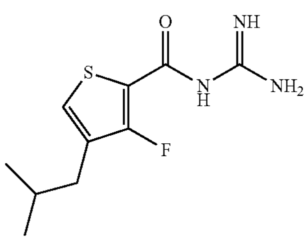 [SMILES: CC(C)Cc1csc(C(=O)NC(=N)N)c1F] | 243.30 |
| 73 | 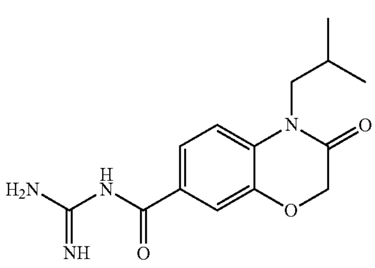 [SMILES: CC(C)CN1C(=O)COc2cc(C(=O)NC(=N)N)ccc21] | 290.32 |
| 74 | 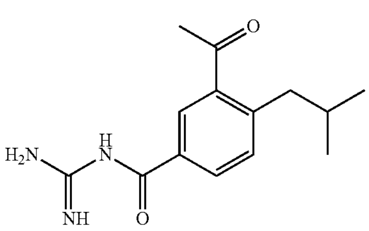 [SMILES: CC(=O)c1cc(C(=O)NC(=N)N)ccc1CC(C)C] | 261.32 |
| 75 | | 336.39 |
| 76 | | 344.43 |
| 77 | | 311.40 |
| 78 | | 346.43 |
| 79 | | 197.32 |
| 80 | | 205.30 |

TABLE 3-continued

Exemplary compounds

| No. | Structure | MW (calc'd) |
|---|---|---|
| 81 | (isobutyl-piperazinyl guanidine) | 226.32 |
| 82 | (cyclopropylmethyl-piperazinyl guanidine) | 224.31 |
| 83 | (guanidino-methyl-isobutylcyclopropane) | 169.27 |
| 84 | (isobutyl-cyclopropyl-methyl guanidine) | 169.27 |
| 85 | (sialic acid analog with isobutyryl group) | 358.39 |
| 86 | (4-isobutylphenyl guanidine) | 191.27 |
| 87 | (6-isobutyl-4-methylquinazolin-2-yl guanidine) | 257.33 |
| 88 | (acetamido-isobutyryl-dihydropyridazine carboxylic acid with guanidine) | 312.32 |
| 89 | (4-(cyclopropylmethyl)thiazol-2-yl guanidine) | 196.27 |
| 90 | (4-isobutylthiazol-2-yl guanidine) | 198.29 |
| 91 | (isobutyryl-tetrahydrothiazolopyridine guanidine) | 267.35 |
| 92 | (methyl-isobutyl-tetrahydrobenzothiazole guanidine) | 266.41 |
| 93 | (4,5-diisobutyloxazol-2-yl guanidine) | 238.33 |
| 94 | (isobutyl-tetrahydrobenzothiazole guanidine) | 252.38 |

TABLE 3-continued

Exemplary compounds

| No. | Structure | MW (calc'd) |
|---|---|---|
| 95 | 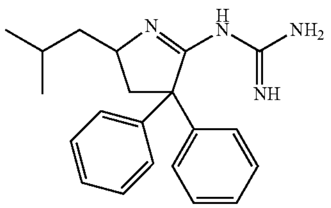 [SMILES: CC(C)CC1CC(c2ccccc2)(c2ccccc2)C(NC(=N)N)=N1] | 334.46 |
| 96 | 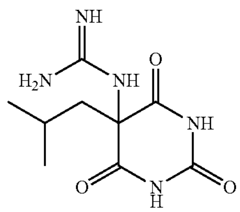 [SMILES: CC(C)CC1(NC(=N)N)C(=O)NC(=O)NC1=O] | 241.25 |
| 97 | 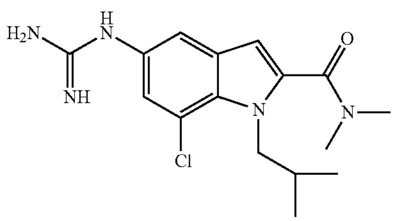 [SMILES: CC(C)Cn1c(C(=O)N(C)C)cc2cc(NC(=N)N)cc(Cl)c21] | 335.83 |
| 98 | 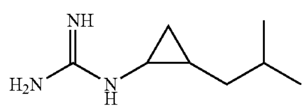 | 155.24 |
| 99 | 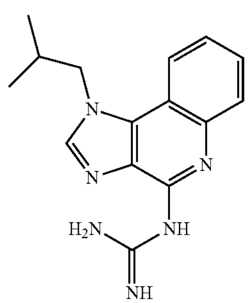 [SMILES: CC(C)Cn1cnc2c(NC(=N)N)nc3ccccc3c21] | 282.34 |
| 100 | 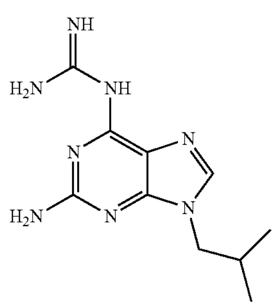 [SMILES: CC(C)Cn1cnc2c(NC(=N)N)nc(N)nc21] | 248.29 |

Methods

In certain embodiments, provided herein is a method of treating a metabolic disease or disorder in a subject in need thereof, the method comprising administering to the subject a compound described herein (e.g., a compound of Formula I-a, I-b, I-c, II-a, II-b, II-c, III, IV, V, or VI) or selected from Table 1 or Table 3, or a pharmaceutically acceptable salt thereof, thereby treating the metabolic disease or disorder in the subject. In some cases, the metabolic disease or disorder is selected from the group consisting of diabetes, metabolic syndrome, obesity, hyperlipidemia, high cholesterol, arteriosclerosis, hypertension, non-alcoholic steatohepatitis, non-alcoholic fatty liver, non-alcoholic fatty liver disease, hepatic steatosis, and any combination thereof.

In some cases, the method further comprises administering a second therapeutic agent. In some cases, the second therapeutic agent is selected from the group consisting of a phosphodiesterase (PDE) inhibitor, sirtuin pathway activator, anti-diabetic agent, anti-hyperlipidemic agent, glucagon-like peptide-1 (GLP-1) agonist, dipeptidyl peptidase-4 (DPP-4) inhibitor, sodium-glucose cotransporter-2 (SGLT2) inhibitor or gliflozin, a fibrate, a nitric oxide (NO) donor, nicotinic acid, nicotinamide riboside, nicotinic acid metabolite, and any combination thereof. In some cases of a method described herein, the second therapeutic agent is selected from the group consisting of sildenafil, nicotinic acid, nicotinamide riboside, and nicotinic acid metabolite.

In some cases, the compound is administered to the subject at a dose of about 0.1-5,000 mg/day. In some cases, the compound is administered to the subject to achieve a circulating concentration in the subject within the range of about 1 nM to about 5 mM.

Provided herein is a method of treating a disease or condition in a subject in need thereof, the method comprising: administering to the subject a therapeutically effective amount of a compound described herein.

Provided herein is a method of treating a disease or condition in a subject, comprising administering to the subject a therapeutically effective amount of a pharmaceutical composition of a compound described herein. In some cases of a method described herein, the disease or condition is selected from the group consisting of diabetes, metabolic syndrome, obesity, hyperlipidemia, high cholesterol, arteriosclerosis, hypertension, non-alcoholic steatohepatitis, non-alcoholic fatty liver, non-alcoholic fatty liver disease, hepatic steatosis, and any combination thereof.

Examples of diabetic symptoms include, but are not limited to, polyuria, polydipsia, weight loss, polyphagia, blurred vision, hypertension, abnormalities of lipoprotein metabolism, and periodontal disease.

A compound or composition described herein can be particularly useful for diabetes control and ameliorating a hyperlipidemic condition. In one embodiment, the disclosure provides for methods for increasing insulin sensitivity, increasing glucose uptake, increasing glucose utilization, lowering blood glucose level, increasing fat oxidation, lowering lipid accumulation, reducing total lipid content or lowering level of total cholesterol, LDL, or triglyceride, increasing HDL level, or reducing atherosclerotic plaque size comprising administering to a subject in need thereof any of the subject compositions. The level or content described herein can be a circulating concentration in serum or blood stream, or a total amount in the subject's body. In some embodiments, the subject composition is useful in increasing weight loss of the subject, and increasing Sirt1 activation of the subject. In various embodiments, a composition is administered to the subject in an amount that delivers synergizing amounts of a compound of Formula I-a, I-b, I-c, II-a, II-b, II-c, III, IV, V, or VI or a compound listed in Table 1 or 3 and one or more agents sufficient to ameliorate a hyperlipidemic condition and for diabetes control of the subject. In some embodiments, nicotinic acid or nicotinic acid metabolites can induce a side effect (e.g., cutaneous vasodilation) if administered to a subject at its therapeutic dose without a compound of Formula I-a, I-b, I-c, II-a, II-b, II-c, III, IV, V, or VI or a compound listed in Table 1 or 3 or an anti-diabetic agent such as metformin or any analogs thereof. In some embodiments, an anti-diabetic agent such as metformin or any analogs thereof can cause a side effect (e.g., gastrointestinal distress) if it is administered to a subject at its therapeutic dose without a compound of Formula I-a, I-b, I-c, II-a, II-b, II-c, III, IV, V, or VI or a compound listed in Table 1 or 3 or nicotinic acid. Methods described herein can also be useful for ameliorating the side-effect without losing the therapeutic effectiveness of nicotinic acid, nicotinamide riboside or nicotinic acid metabolites. A description of various aspects, features, embodiments, and examples, is provided herein.

The subject methods can be applicable for administering to a subject that is suffering from diabetes mellitus and/or hyperlipidemia, at risk of suffering from diabetes mellitus and/or hyperlipidemia, and/or suffering from a condition that is associated with diabetes mellitus and/or hyperlipidemia such as cardiovascular conditions. In some cases, an effective amount of an additional therapeutic or a pharmaceutically active agent that is known in the medical art (e.g., an anti-hyperlipidemic agent) can be administered to a subject in conjunction with any of the subject compositions.

Hyperlipidemia can be characterized by a high level of total lipid content or level in a subject. Hyperlipidemia can also be accompanied by a high level of body weight or BMI of a subject. The types of lipid can include cholesterol, cholesterol esters, phospholipids and triglycerides. The content or level of the lipids can be a circulating level that is measured in the bloodstream, plasma or serum of the subject. These lipids can be transported in the blood as large lipoproteins including chylomicrons, very low-density lipoproteins (VLDL), intermediate-density lipoprotein (IDL), low-density lipoproteins (LDL) and high-density lipoproteins (HDL) based on their density. Most triglycerides can be transported in chylomicrons or VLDL and most cholesterol can be carried in LDL and HDL. High levels of lipid in the circulation can cause lipid accumulation on the walls of arteries, and further result in atherosclerotic plaque formation and therefore narrow the arteries. The subject that is suffering from hyperlipidemia can be at high risk of acquiring a cardiovascular condition. Hyperlipidemia can also be characterized by a high level of some lipoproteins or a low level of HDL. The condition that the subject is suffering from or at risk of suffering from can be a condition that is associated with an abnormal level of lipoproteins or lipids in the subject. The subject composition can be used to change the level of the one or more lipids or lipoproteins in the subject. In some embodiments, the type of lipids or lipoproteins that its level can be affected by the subject compositions and methods can be one or more lipoproteins and/or lipids including but not limited to: total cholesterol, triglyceride, HDL, IDL, VLDL or LDL.

A number of methods can be used to assess the levels of lipoproteins and/or lipids in a subject. These methods can differ from one another in the type of sample and the analytical technique used. The type of sample that can be used to measure such levels include but are not limited to: serum, plasma, whole blood, red blood cells or tissue samples. Where desired, the level of lipoproteins and/or lipids can be measured under a fasting condition, e.g., without taking food for at least about 8 hours, 10 hours, 12 hours, or even longer.

The size of atherosclerotic plaque or lesion can be measured by any methods that are known in the art. For examples, methods described in Phan B A et al., "Effects of niacin on glucose levels, coronary stenosis progression, and clinical events in subjects with normal baseline glucose levels (100 mg/dl): a combined analysis of the Familial Atherosclerosis Treatment Study (FATS), HDL-Atherosclerosis Treatment Study (HATS), Armed Forces Regression Study (AFREGS), and Carotid Plaque Composition by MRI during lipid-lowering (CPC) study", Am J Cardiol. 2013 Feb. 1; 111(3):352-5, and Lehman S J et al., "Assessment of Coronary Plaque Progression in Coronary CT Angiography Using a Semi-Quantitative Score", JACC Cardiovasc Imaging. 2009 November; 2(11): 1262-1270. A non-limiting example of the method to measure the size of atherosclerotic plaque or lesion can be quantitative coronary angiography.

In some embodiments, the amounts of a secondary therapeutic agent in the composition, if administered to a subject alone and without a compound of Formula I-a, I-b, I-c, II-a, II-b, II-c, III, IV, V, or VI or a compound listed in Table 1 or 3, can cause no therapeutic effect in the subject. However, when administered in conjunction with a compound of Formula I-a, I-b, I-c, II-a, II-b, II-c, III, IV, V, or VI or a compound listed in Table 1 or 3, a therapeutic effect can be observed. The "therapeutic effect" described herein is a lowered total lipid content, decreased total cholesterol level, decreased triglyceride level, increased HDL level, decreased LDL level or reduced atherosclerotic plaque in the subject administered.

In some embodiments, a therapeutic amount of nicotinic acid and/or nicotinic acid metabolites can cause a side effect that can be characterized by an increased in cutaneous vasodilation. The increase in the cutaneous vasodilation can be clinically significant. A sub-therapeutic amount of nicotinic acid, nicotinamide riboside and/or nicotinic acid metabolites cannot cause a clinically significant cutaneous vasodilation, or can reduce the degree of cutaneous vasodilation in the subject administered as compared to a therapeutic amount of nicotinic acid, nicotinamide riboside and/or nicotinic acid metabolites. The subject compositions and methods described herein can comprise a sub-therapeutic amount of nicotinic acid, nicotinamide riboside and/or nicotinic acid metabolites, to be used with a compound of Formula I-a, I-b, I-c, II-a, II-b, II-c, III, IV, V, or VI or a compound listed in Table 1 or 3 to result a therapeutic degree of effect of the sub-therapeutic amount of the nicotinic acid, nicotinamide riboside and/or nicotinic acid metabolites without causing the degree of side effect that can normally be caused by a therapeutic amount of nicotinic acid, nicotinamide riboside and/or nicotinic acid metabolites when used without a compound of Formula I-a, I-b, I-c, II-a, II-b, II-c, III, IV, V, or VI or a compound listed in Table 1 or 3. Levels of cutaneous vasodilation can be measured by any methods known in the medical art, such as the methods including laser-Doppler flowmeter. With the same level of therapeutic effect (e.g., lowering cholesterol level by at least 5%), the level of cutaneous vasodilation caused by the subject compositions as compared to nicotinic acid, nicotinamide riboside and/or nicotinic acid metabolites without a compound of Formula I-a, I-b, I-c, II-a, II-b, II-c, III, IV, V, or VI or a compound listed in Table 1 or 3 can be lower. For example, less than about 1%, 5%, 10%, 15%, 20%, 25%, 30%, 35%, 40%, 45%, 50%, 60%, 70%, 80% or 90% of the level that is caused by a therapeutic amount of nicotinic acid, nicotinamide riboside and/or nicotinic acid metabolites.

In some embodiments, the amount of a compound of Formula I-a, I-b, I-c, II-a, II-b, II-c, III, IV, V, or VI or a compound listed in Table 1 or 3 can be at least about 25, 50, 75, 100, 150, 200, 250, 300, 350, 400, 450, or 500 mg. In some embodiments, a unit dosage can comprise a compound of Formula I-a, I-b, I-c, II-a, II-b, II-c, III, IV, V, or VI or a compound listed in Table 1 or 3 in about, less than about, or more than about the indicated amounts (e.g., 25, 50, 100, 150, 200, 250, 300, 400, 500, or more mg) in combination with one or more other components in about, less than about, or more than about the indicated amounts. In some embodiments, a composition further comprises a PDE inhibitor in a synergizing amount. In some embodiments, a composition further comprises a sirtuin pathway activator in a synergizing amount. In some embodiments, resveratrol in an example composition is replaced with a PDE inhibitor or a sirtuin pathway activator in a synergizing amount. In compositions comprising a PDE inhibitor or methods comprising administration of a PDE inhibitor (separately from or concurrently with one or more other components), the PDE inhibitor may be provided in an amount that produces a peak plasma concentration of about, less than about, or more than about 0.1, 1, 5, 10, 25, 50, 100, 500, 1000, 2550, 5000, 10000, or more nM.

Accordingly, the multi-component compositions described herein can have a beneficial or synergistic effect on increasing insulin sensitivity, increasing glucose uptake, increasing glucose utilization, lowering blood glucose level, lowering total lipid content, lowering lipid accumulation, decreasing total cholesterol level, decreasing triglyceride level, increasing HDL level, increasing fat oxidation, and/or decreasing LDL level. In some embodiments, a compound, composition, or method described herein can be effective to change the level of lipoproteins and/or lipids in the subject by at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60% or even higher as compared to an initial level of lipoproteins and/or lipids prior to administration of it to a subject. The level can be lowered by about 19%-24%, 14%-29%, 12%-35%, 10-40%, 8%-45%, 5%-50%, 2%-60%, or 1%-70%. The level can be a circulating level.

Accordingly, the multi-component compositions described herein can have a beneficial or synergistic effect on increasing insulin sensitivity, increasing glucose uptake, increasing glucose utilization, lowering blood glucose level, lowering total lipid content, lowering lipid accumulation, decreasing total cholesterol level, decreasing triglyceride level, increasing HDL level, increasing fat oxidation, and/or decreasing LDL level. In some embodiments, a compound, composition, or method described herein can be effective to change the insulin sensitivity and/or glucose utilization in the subject by at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60% or even higher as compared to an initial level of lipoproteins and/or lipids prior to administration of it to a subject. The level can be lowered by about 19%-24%, 14%-29%, 12%-35%, 1040%, 8%-45%, 5%-50%, 2%-60%, or 1%-70%. The level can be a circulating level.

In some embodiments, a compound, composition, or method described herein can be effective to reduce the atherosclerotic plaque size in a subject by at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60% or even higher as compared to an initial size of atherosclerotic plaque prior to administration of it to a subject. The level can be reduced by about 19%-24%, 14%-29%, 12%-35%, 1040%, 8%-45%, 5%-50%, 2%-60%, or 1%-70%.

The disclosure provides for a method of treating diabetes, comprising administering to the subject any of the compounds or compositions described herein over a time period, wherein the insulin sensitivity in the subject is increased over the time period. Insulin sensitivity can be increased by about or greater than about 1, 2, 3, 5, 10, 20, 50, 100, or 200%. In some embodiments, a therapeutic agent (e.g., a phosphodiesterase (PDE) inhibitor, sirtuin pathway activator, anti-diabetic agent, anti-hyperlipidemic agent, glucagon-like peptide-1 (GLP-1) agonist, dipeptidyl peptidase-4 (DPP-4) inhibitor, sodium-glucose cotransporter-2 (SGLT2) inhibitor or gliflozin, a fibrate, a nitric oxide (NO) donor, nicotinic acid, nicotinamide riboside, or nicotinic acid metabolite) is administered in an amount that reduces the therapeutically effective dose of a compound of Formula I-a, I-b, I-c, II-a, II-b, II-c, III, IV, V, or VI or a compound listed in Table 1 or 3 for a subject. In some embodiments, the therapeutically effective dose of a compound of Formula I-a, I-b, I-c, II-a, II-b, II-c, III, IV, V, or VI or a compound listed in Table 1 or 3 is reduced by about or more than about 50%, 60%, 70%, 80%, 90%, 95%, 97.5%, 99.9%, 99.99%, or more. In some embodiments, administration of compositions described herein reduces body fat (e.g., visceral fat) by about or more than about 5%, 10%, 15%, 20%, 25%, 50%, or more.

Insulin sensitivity can be measured using a variety of techniques, including $HOMA_{IR}$. $HOMA_{IR}$, which is the homeostasis model assessment of insulin resistance can be used as a screening index of changes in insulin sensitivity. $HOMA_{IR}$ can be calculated via standard formula from fasting plasma insulin and glucose as follows: $HOMA_{IR}$=[Insulin (uU/mL)×glucose (mM)]/22.5.

In some embodiments, insulin signaling can also be measured. Insulin signaling can be measured by measuring total and phosphorylated Akt, GSK-3β, IGF-1R, IR, IRS-1, p70S6K and PRAS40 in tissue lysates via the Luminex Kits "Akt Pathway Total 7-Plex Panel" (Cat #LHO0002) and "Akt Pathway Phospho 7-Plex Panel" (Cat #LHO0001) from Invitrogen Life Science.

Administration of compositions disclosed herein that increase SIRT1 and SIRT3 activity can be useful in any subject in need of metabolic activation of hepatocytes, adipocytes or one or more of their muscles, e.g., skeletal muscle, smooth muscle or cardiac muscle or muscle cells thereof. A subject can be a subject having cachexia or muscle wasting. Increasing SIRT1 and/or SIRT3 activity is beneficial for treating hyperlipidemia, diabetes mellitus and impaired glucose tolerance and reducing inflammatory responses in a subject. Increase in metabolic activation of hepatocytes, adipocytes or one or more of their muscles can be useful in lowering the lipid content and increasing weight loss of the subject. The content or levels of the lipids and lipoproteins can be lowered.

Increasing SIRT3 activity can also be used for treating or preventing hyperlipidemia, cardiovascular diseases, reducing blood pressure by vasodilation, increasing cardiovascular health, and increasing the contractile function of vascular tissues, e.g., blood vessels and arteries (e.g., by affecting smooth muscles). Generally, activation of SIRT3 can be used to stimulate the metabolism of hepatocytes, adipocytes or any type of muscle, e.g., muscles of the gut or digestive system, or the urinary tract, and thereby can be used to control gut motility, e.g., constipation, and incontinence. SIRT3 activation can also be useful in erectile dysfunction. It can also be used to stimulate sperm motility, e.g., and be used as a fertility drug. Other embodiments in which it would be useful to increase SIRT3 include repair of muscle, such as after a surgery or an accident, increase of muscle mass; and increase of athletic performance.

The disclosure provides methods in which beneficial effects are produced by a compound of Formula I-a, I-b, I-c, II-a, II-b, II-c, III, IV, V, or VI or a compound listed in Table 1 or 3, optionally in combination with one or more therapeutic agents, that increase the protein or activity level of a sirtuin (e.g., SIRT1 or SIRT3). The activity of SIRT1 and SIRT3 can be increased in muscle cells and/or hepatocytes in the subject. These methods effectively facilitate, increase or stimulate one or more of the following: mimic the benefits of calorie restriction or exercise in the hepatocyte or muscle cells, increase mitochondrial biogenesis or metabolism, increase mitochondrial activity and/or endurance in the hepatocytes or muscle cells, sensitize the muscle cells to insulin, increase fatty acid oxidation in the muscle cell, decrease reactive oxygen species (ROS) in the muscle cell, increase PGC-1α and/or UCP3 and/or GLUT4 expression in the hepatocytes or muscle cells, and activate AMP activated protein kinase (AMPK) in the hepatocytes or muscle cells. Various types of muscle cells can be contacted in accordance with the disclosure. In some embodiments, the muscle cell is a skeletal muscle cell. In certain embodiments, the muscle cell is a cell of a slow-twitch muscle, such as a soleus muscle cell.

Glucose uptake can be measured using in vivo or in vitro techniques. For example, glucose uptake can be measure in vivo using a PET scan in conjunction with labeled glucose or glucose analog. Measurements of glucose uptake can be quantified from the PET scan or by any other technique known in the art. In some embodiments, the glucose uptake can be measured by quantitation of exogenously administered 18-F-deoxyglucose uptake via PET.

ROS/Oxidative Stress can be measured by drawing blood into EDTA-treated tubes, centrifuging to separate plasma, and aliquoting samples for individual assays. Plasma can be maintained at −80° C. under nitrogen to prevent oxidative changes prior to measurements. Plasma malonaldehyde (MDA) can be measured using a fluorometric assay, and plasma 8-isoprostane $F_{2\alpha}$ was measured by ELISA (Assay Designs, Ann Arbor, Mich.).

Another embodiment provides for the administration of a composition comprising synergizing amounts of a compound of Formula I-a, I-b, I-c, II-a, II-b, II-c, III, IV, V, or VI or a compound listed in Table 1 or 3 and resveratrol to the subject in an amount sufficient to increase fatty acid oxidation within the cells of the subject. Yet other embodiments provide for the administration of a composition comprising synergizing amounts of a compound of Formula I-a, I-b, I-c, II-a, II-b, II-c, III, IV, V, or VI or a compound listed in Table 1 or 3 and resveratrol to a subject in an amount sufficient to increase fatty acid oxidation in the subject.

Another aspect of the disclosure provides for achieving desired effects in one or more subjects after administration of a combination composition described herein for a specified time period. For example, the beneficial effects of the compositions described herein can be observed after administration of the compositions to the subject for 1, 2, 3, 4, 6, 8, 10, 12, 24, or 52 weeks.

The disclosure provides for a method of treating subjects, comprising identifying a pool of subjects amenable to treatment. The identifying step can include one or more screening tests or assays. For example, subjects that are identified as diabetic or hyperlipidemic, or that have above average or significantly greater than average body mass indices (BMI) and/or weight can be selected for treatment. The subject can be overweight or obese, which can be indicated by an above ideal body weight of the subject or a BMI that is higher than 25, 30, 40, or 50. The subject can weight more than about 50, 75, 100, 125, 150, 160, 170, 180, 190, 200, 210, 220, 230, 240, 250, 260, 270, 280, 290, 300, 310, 320, 330, 340, 350, 360, 370, 380, 390, or 400 lbs. The subjects that have been on a high fat diet can be selected for treatment as well. The identified subjects can then be treated with one or more compositions described herein.

The disclosure also provides for methods of manufacturing the compositions described herein. In some embodiments, the manufacture of a composition described herein comprises mixing or combining two or more components. These components can include a phosphodiesterase (PDE) inhibitor, sirtuin pathway activator, anti-diabetic agent, anti-hyperlipidemic agent, glucagon-like peptide-1 (GLP-1) agonist, dipeptidyl peptidase-4 (DPP-4) inhibitor, sodium-glucose cotransporter-2 (SGLT2) inhibitor or gliflozin, a fibrate, a nitric oxide (NO) donor, nicotinic acid, nicotinamide riboside, or nicotinic acid metabolite.

Assessment of NAFLD, NASH and Hepatic Steatosis

NALFD, NASH and/or hepatic steatosis can be assessed by any means known to those of skill in the art or otherwise described herein. In some embodiments, reduction of NALFD, NASH and/or hepatic steatosis is assessed by a change of one or more physiological indicators. Non-limiting physiological indicator can include a change of liver morphology, liver stiffness, accumulation of fat in the liver, and size or weight of the liver. Non-alcoholic steatohepatitis (NASH) or hepatic steatosis in a subject can be evidenced, e.g., by an accumulation of fat in the liver of the subject (e.g., by an accumulation of fat in hepatic cells of the subject). Accumulation of fat in the liver can be indicated by several means, for example, by ultrasonography, computed tomography (CT), and magnetic resonance imaging, measurement of liver size or weight, or biopsy. For example, a subject with NASH or hepatic steatosis can exhibit a hepatic fat content of 5% or higher, 10% or higher, 20% or higher, 30% or higher, 40% or higher, 50% or higher, 60% or higher, or 70% or higher. In general, a subject with stage 1 hepatic steatosis typically exhibits 5%-33% fat accumulation in the liver. A subject with stage 2 hepatic steatosis can exhibit 33%-66% fat accumulation in the liver. A subject with stage 3 hepatic steatosis can exhibit over 66% fat accumulation in the liver.

Techniques used for assessing hepatic steatosis (including those described herein) can be used in conjunction with measurements of alcohol consumption to assess NAFLD. In some embodiments, NAFLD is assessed by determination of an average daily amount of alcohol consumption by the subject. In some cases, a subject with NAFLD has hepatic steatosis and is assessed by determination of an average of less than 20 grams of alcohol consumption per day (e.g., an average of less than 25 ml alcohol/day). NAFLD in a subject may progress to non-alcoholic steatohepatitis (NASH).

Techniques used for assessing NALFD in conjunction with measurements of liver inflammation can be used to assess NASH. In some embodiments, NASH is assessed by determination of inflammation in the liver of a subject concurrent with hepatic steatosis, for example, upon detection of hepatic fat accumulation (steatosis) and one or more of the following liver conditions: inflammation, ballooning degeneration of hepatocytes (sometimes with identifiable Mallory bodies), glycogenated hepatocyte nuclei, and pericellular fibrosis. Pericellular fibrosis can be identified by trichome strain. Pericellular fibrosis can exhibit upon trichrome staining, for example, a characteristic "chicken wire" pattern. NASH in a subject may progress to cirrhosis.

A subject with NASH or hepatic steatosis can be suffering from a symptom of NASH or hepatic steatosis. Exemplary symptoms include, but are not limited to fatigue, malaise, unexplained weight loss, weakness, lack of appetite, nausea, appearance of small, red spider veins under the skin, easy bruising, jaundice, internal bleeding (e.g., bleeding from engorged veins in the esophagus or intestines), loss of sex drive, ascites, itching, edema, mental confusion, and pain or ache (e.g., pain or ache of the upper right abdomen). In some embodiments, the subject is asymptomatic.

Reduction and sustained reduction of NASH can be assessed by any ultrasonography methods known to those of skill in the art or otherwise described herein. Ultrasonography assessment of NASH and/or hepatic steatosis (e.g., fat accumulation in liver) can comprise use of conventional B-mode ultrasonography. Assessment of various hepatic ultrasonography parameters can be used for the assessment of hepatic steatosis. Exemplary ultrasonography parameters for the assessment of NASH and/or hepatic steatosis include, but are not limited to (1) parenchymal brightness, (2) liver-to-kidney contrast, (3) deep beam attenuation, (4) bright vessel walls, and (5) gallbladder wall definition. Assessment of such ultrasonography parameters can be used to calculate an ultrasonographic steatosis score (USS). USS can be calculated, e.g., as follows: absent (score 0) steatosis was defined as normal liver echotexture; mild (score 1) steatosis as slight and diffuse increase in fine parenchymal echoes with normal visualization of diaphragm and portal vein borders; moderate (score 2) steatosis as moderate and diffuse increase in fine echoes with slightly impaired visualization of portal vein borders and diaphragm; and severe (score 3) steatosis as fine echoes with poor or no visualization of portal vein borders, diaphragm, and posterior portion of the right lobe.

Reduction and sustained reduction of NASH can be assessed by any computed tomography (CT) known to those of skill in the art or otherwise described herein. CT images can be assessed by, e.g., a radiologist. CT images of the liver of a subject can be assessed by, e.g., measuring density of regions of interest in the images. Regions of interest within images can be selected so as not to contain blood vessels or other artifacts (e.g., motion artifacts). Density of regions of interest in a CT image can be measured in Hounsfield units (HU). Normal liver tissue can have a HU measurement of 40-60 HU. By contrast, fat typically has a lower density. For example, fat can have an HU measurement of, e.g., about −100 to about −500. NASH or hepatic steatosis can be evidenced by an HU measurement less than 40 HU. NASH or hepatic steatosis can be evidenced by an HU measurement that is between −500 and 40 HU, for example, an HU measurement that is −500-1 HU, −100-10 HU, 0-20 HU, 5-30 HU, or 20-39.9 HU. NASH or hepatic steatosis can be assessed by a subject exhibiting an HU measurement of 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, 0, or less than 0 HU. NASH or hepatic steatosis can be evidenced by a difference in HU measurement between spleen and liver (e.g., $HU_{spleen}$−$HU_{liver}$) For example, hepatic steatosis can be evidenced if $HU_{spleen}$−$HU_{liver}$ is greater than 0, for example, if $HU_{spleen}$−$HU_{liver}$ is between 1-10, 10-20, or more than 20. In some embodiments, a difference in HU measurement between spleen and liver of 18.5 is used to determine NASH or hepatic steatosis in a subject. In some embodiments, a reduction of difference in $HU_{spleen}$−$HU_{liver}$ indicates a sustained reduction of NASH or hepatic steatosis.

Reduction and sustained reduction of NASH can be assessed by any MRI methods known to those of skill in the art or otherwise described herein. Exemplary methods of using MRI to determine steatosis, e.g., hepatic steatosis, are described in US Patent Application Pub. No. 20050215882, which is hereby incorporated by reference.

Reduction and sustained reduction of NASH or hepatic steatosis can be evidenced by measurement of liver weight and/or size. Methods of measuring liver weight and/or size can be any known to those of skill in the art or otherwise described herein. Reduction of NASH or hepatic steatosis can be indicated by a decrease in liver weight and/or size as compared to the subject before commencement of methods and compositions described herein, or to a control subject with NASH or hepatic steatosis. In some embodiments, a decrease in liver weight/size by 10% or more, 15% or more, 20%, or more, 25% or more, 30%, or more, 35% or more, 40% or more, 45% or more, 50%, or more, 55% or more, 60%, or more, 65% or more, 70% or more, 75% or more, 80% or more, 85% or more, 90%, or more, 95% or more, 100%, or more than 100% as compared to the subject before commencement of methods and compositions described herein, or to a control subject with NASH or hepatic steatosis can indicate sustained reduction of NASH or hepatic steatosis in a subject.

Reduction and sustained reduction of NASH or hepatic steatosis can be evidenced by tissue biopsy. A liver biopsy sample can be obtained by any means known to those of skill in the art, for example, by needle biopsy. The sample can be processed by any means known to those of skill in the art or otherwise described herein. The sample can be fixed (e.g., with formalin) or may be unfixed. The sample may be snap-frozen. For example, the sample may be sectioned into thin sections. The sections may be stained, e.g., with hematoxylin and eosin. Accumulation of fat in the liver can be evidenced by appearance of vacuoles which are filled with lipids such as, by way of example only, triglycerides. Such vacuoles can appear to be optically "empty", since fats can dissolve during histological tissue processing. Accordingly, levels of NASH or hepatic steatosis can be determined by measuring the number, size, or density of hepatic lipid vacuoles.

Liver stiffness can be evaluated by performing Transient Elastography (TE) (Fibroscan®, Echosens®, Paris, France). TE (Fibroscan®, Echosens®, Paris, France) is a widely used noninvasive method for detecting liver disease. TE is painless and can provide results in less than 5 minutes and is highly acceptable for patients. The volume of liver tissue evaluated by TE approximates a cylinder 4×1 cm which is usually at least 100 times bigger than a liver biopsy. In general, vibrations of mild amplitude and low frequency are transmitted by the transducer inducing an elastic shear wave that propagates within the liver. Pulse-echo ultrasonic acquisitions are performed to follow the shear wave and measure its speed, which is directly related to the tissue stiffness (the harder the tissue, the faster the shear propagates). Results are usually expressed in Kilopascals (Kpa) and correspond to the median value of ten validated measurements ranging from 2.5 to 75 Kpa, with 5.5 Kpa reported to define normality.

Levels of reduction and sustained reduction of NASH or hepatic steatosis can be determined using any of the assessment methods described herein. Levels of reduction and sustained reduction of NASH or hepatic steatosis can be quantified, by way of non-limiting example only, as a percentage of fat accumulation (e.g., fat content) in the liver. In some embodiments, NASH or hepatic steatosis is scored according to a 0-3 score, with 0=<5% fat accumulation in the liver, 1=5%–33% fat accumulation in the liver, 2=33%–66% fat accumulation in the liver, and 3=>66% fat accumulation in the liver. Liver fat content can be assessed by any means known to those of skill in the art, including, e.g., by proton magnetic resonance spectroscopy, by biopsy, or by any other methods described herein.

In one aspect, reduction and sustained reduction of NASH or hepatic steatosis can be evaluated by measuring one or more biomarkers selected from the group consisting of transforming growth factor (TGF)-β, cytokeratin 18, serum aspartate transaminase (AST), serum alanine transaminase (ALT), and gamma glutamyl transferase (GGT). Methods of measuring biomarkers can be any known to those of skill in the art or otherwise described herein. Reduction and sustained reduction of NASH or hepatic steatosis can be indicated by a decrease of expression level of one or more biomarkers as compared to the subject before commencement of methods and compositions described herein, or to a control subject with NASH or hepatic steatosis. In some cases, reduction and sustained reduction of NASH or hepatic steatosis is indicated by a aspartate transaminase to alanine transaminase ratio that is greater than at least 1, at least 2, at least 3, at least 4, at least 5, at least 10, or more.

Levels of liver inflammation, indicative of hepatic steatosis and/or NASH, can be determined using any of the assessment methods described herein. Levels of liver inflammation can be quantified, by way of non-limiting example only, as a percentage, a fold change or a ratio, of biomarkers such as expression level of liver inflammation biomarkers in the liver. Expression of a biomarker can be achieved by way of measuring, quantifying, and monitoring the expression level of the gene or mRNA encoding said biomarker, and/or the peptide, or protein of said biomarker. In general, assessment of biomarker expression can be achieved by way of measuring, quantifying, monitoring or comparing results prior to, during and after treatment. Exemplary of biomarkers indicative of liver inflammation include, but are not limited to, interleukin-(IL) 6, interleukin-(IL) 1β, tumor necrosis factor (TNF)-α, transforming growth factor (TGF)-β, monocyte chemotactic protein (MCP)-1, C-reactive protein (CRP), PAI-1, collagen isoforms such as Col1a1, Col1a2, and Col4a1. Liver inflammation can also be assessed by change of macrophage infiltration, for example, measuring a change of CD68 expression level. In some cases, liver inflammation can be assessed by examining liver fibrosis and using liver picrosirius red staining. In some cases, liver inflammation can be assessed by measuring or monitoring serum levels or circulating levels of interleukin-(IL) 6, interleukin-(IL) 1β, tumor necrosis factor (TNF)-α, transforming growth factor (TGF)-β, monocyte chemotactic protein (MCP)-1, and C-reactive protein (CRP).

Levels of liver fat content can be determined using any of the assessment methods described herein. Levels of liver fat content can be quantified, by way of non-limiting example only, as a percentage, a fold change or a ratio, of liver lipogenic gene expression in the liver. In general, assessment of gene expression can be achieved by way of measuring, quantifying, monitoring or comparing results prior to, during and after treatment. Exemplary of biomarkers indicative of liver fat content include, but are not limited to, acetyl-CoA carboxylase (ACC), stearoyl-CoA desaturase 1 (SCD1), fatty acid synthase (FAS), and liver fatty oxidation genes such as PPAR-α, ACOX1, COX1, and CPT1B.

Level of reduction of biomarkers using the methods and composition described herein can indicate a sustained reduction of NASH or hepatic steatosis. In some embodiments, a decrease in biomarker expression by 10% or more, 15% or more, 20%, or more, 25% or more, 30%, or more, 35% or more, 40% or more, 45% or more, 50%, or more, 55% or more, 60%, or more, 65% or more, 70%, or more, 75% or more, 80% or more, 85% or more, 90%, or more, 95% or more, 100%, or more than 100% as compared to the subject before commencement of methods and compositions described herein, or to a control subject with NASH or hepatic steatosis can indicate sustained reduction of NASH or hepatic steatosis in a subject.

In some embodiments, the reduction of one or more biomarkers or physiological indicators is monitored for a period time before, during or after commencement of the methods and compositions described herein. The biomarker expression can be measured and monitored for at least 1 week, at least 2 weeks, at least 3 weeks, at least 4 weeks, at least 5 weeks, at least 6 weeks, at least 7 weeks, at least 8 weeks, at least 9 weeks, at least 10 weeks, at least 11 weeks, at least 12 weeks, at least 1 month, at least 2 months, at least 3 months, at least 4 months, at least 5 months, at least 6 months, at least 7 months, at least 8 months, at least 9 months, at least 10 months, at least 11 months, at least 12 months, at least 2 years, at least 5 years, at least 10 years, or more. In some embodiments, the sustained reduction of one or more biomarkers or physiological indicators is monitored periodically before, during or after commencement of the methods or compositions described herein. The biomarker expression can be measured and monitored for every week, every 2 weeks, every 3 weeks, every 4 weeks, every 5 weeks, every 6 weeks, every 7 weeks, every 8 weeks, every 9 weeks, every 10 weeks, every 11 weeks, every 12 weeks, every month, every 2 months, every 3 months, every 4 months, every 5 months, every 6 months, every 7 months, every 8 months, every 9 months, every 10 months, every 11 months, every 12 months, every 2 years, every 5 years, every 10 years, or more.

Administration and/or co-administration of any of the compounds described herein can reduce NASH or hepatic steatosis in a subject in need thereof. Exemplary subjects in need of NASH or hepatic steatosis reduction can include subjects who have NASH or hepatic steatosis.

Reduction of NASH or hepatic steatosis can be determined by comparison to the subject before commencement of the methods and compositions described herein, or to a control subject and/or control population. Reduction of NASH or hepatic steatosis in a subject can be considered if any one or more of hepatic fat content, as measured by any of the methods described herein, liver size or weight, liver vacuole number, size of a liver vacuole, liver vacuole density, expression of biomarkers such as, interleukin-(IL) 6, interleukin-(IL) 1β, tumor necrosis factor (TNF)-α, transforming growth factor (TGF)-β, monocyte chemotactic protein (MCP)-1, C-reactive protein (CRP), PAI-1, Col1a1, Col1a2, Col4a1, CD68, acetyl-CoA carboxylase (ACC), stearoyl-CoA desaturase 1 (SCD1), fatty acid synthase (FAS), PPAR-α, ACOX1, COX1, CPT1B, cytokeratin 18, gamma glutamyl transferase (GGT), serum alanine transaminase (ALT) and/or serum aspartate transaminase levels in the subject are reduced as compared to a control subject and/or control population. A control subject can be an individual that has not been administered one or more compounds described herein. Likewise, a control population can encompass a plurality of individuals that have not been administered one or more compounds described herein. The control subject can be a subject having hepatic steatosis, that is not administered one or more compounds described herein. The control subject can be a different subject.

It is not necessary for the control subject to be a different individual from said subject. For example, the control subject can be the same subject at an earlier time point, for example, prior to receiving a first dose of any of the compounds described herein. In some embodiments, a level of hepatic steatosis in the subject following administration of one or more compounds described herein is compared to a level of hepatic steatosis in the subject prior to first administration of the one or more compounds.

An exemplary method of assessing NASH or hepatic steatosis reduction in a subject can comprise measuring a level of NASH hepatic steatosis in the subject or in a biological sample derived from the subject at a first time point. The first time point may be a time point prior to administration of one or more compounds described herein. The method may further comprise measuring a level of NASH or hepatic steatosis in the subject or in a biological sample derived from the subject at a second time point. The second time point may follow administration of the one or more compounds described herein. The level measured at the second time point may be compared to the level measured at the first time point to determine whether reduction has occurred. Reduction of NASH hepatic steatosis can indicate clinical efficacy of the administration of the one or more compounds described herein. Reduction of NASH hepatic steatosis can indicate a sustained reduction of NASH or hepatitis steatosis. The method may further comprise administering additional doses of the one or more compounds described herein if the level of NASH or hepatic steatosis in the subject is reduced.

Practice of any one of the methods described herein can reduce NASH or hepatic steatosis by at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or more than 99%. For example, practice of any one of the methods described herein can reduce NASH or hepatic steatosis by 5-20%, 10-40%, 30-60%, 40-80%, 60-95%, or 75-99%. In some embodiments, administration of any combination of agents described herein reduces NASH or hepatic steatosis in about 1 week, 2 weeks, 3 weeks, 4 weeks, 5 weeks, 6 weeks, 8 weeks, or less. Administration of any combination of agents described herein can, for example, reduce liver weight by at least 10% in about 1 week, 2 weeks, 3 weeks, 4 weeks, 5 weeks, 6 weeks, 8 weeks, or less. In some cases, administration of any combination of agents described herein can, for example, reduce liver weight by at least 20% in about six weeks. Administration of any combination of agents described herein can, by way of example only, reduce liver vacuole number, size, and/or density by over 10%, 20%, 25%, over 50%, over 75%, or over 90% in about 1 week, 2 weeks, 3 weeks, 4 weeks, 5 weeks, 6 weeks, 8 weeks, or less.

Practice of any one of the methods described herein can sustain reduction of NASH or hepatic steatosis by at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or more than 99%. For example, practice of any one of the methods described herein can sustain reduction of NASH or hepatic steatosis by 5-20%, 10-40%, 30-60%, 40-80%, 60-95%, or 75-99%. In some embodiments, administration of any combination of agents described herein sustains reduction of NASH or hepatic steatosis in about 1 week, 2 weeks, 3 weeks, 4 weeks, 5 weeks, 6 weeks, 8 weeks, or less. Administration of any combination of agents described herein can, for example, sustain reduction of liver weight by at least 10% in about 1 week, 2 weeks, 3 weeks, 4 weeks, 5 weeks, 6 weeks, 8 weeks, or less. In some cases, administration of any combination of agents described herein can, for example, sustain reduction of liver weight by at least 20% in about six weeks. Administration of any combination of agents described herein can, by way of example only, sustain reduction of liver vacuole number, size, and/or density by over 10%, 20%, 25%, over 50%, over 75%, or over 90% in about 1 week, 2 weeks, 3 weeks, 4 weeks, 5 weeks, 6 weeks, 8 weeks, or less.

Practice of any one of the methods described herein can reduce liver inflammation by at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or more than 99%. For example, practice of any one of the methods described herein can reduce liver inflammation by 5-20%, 10-40%, 30-60%, 40-80%, 60-95%, or 75-99%. In some embodiments, administration of any combination of agents described herein reduces liver inflammation in about 1 week, 2 weeks, 3 weeks, 4 weeks, 5 weeks, 6 weeks, 8 weeks, or less. Administration of any combination of agents described herein can, for example, reduce macrophage infiltration by at least 10% in about six weeks. Administration of any combination of agents described herein can, for example, reduce macrophage infiltration by at least 20% in about six weeks. Administration of any combination of agents described herein can, by way of example only, reduce liver inflammation, macrophage infiltration, and/or liver fibrosis, by number, size or density by over 25%, over 50%, over 75%, or over 90% in about twelve weeks.

Practice of any one of the methods described herein can sustain reduction of liver inflammation by at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or more than 99%. For example, practice of any one of the methods described herein can sustain reduction of liver inflammation by 5-20%, 10-40%, 30-60%, 40-80%, 60-95%, or 75-99%. In some embodiments, administration of any combination of agents described herein sustains reduction of liver inflammation in about 1 week, 2 weeks, 3 weeks, 4 weeks, 5 weeks, 6 weeks, 8 weeks, or less. Administration of any combination of agents described herein can, for example, sustain reduction of macrophage infiltration by at least 10% in about six weeks. Administration of any combination of agents described herein can, for example, sustain reduction of macrophage infiltration by at least 20% in about six weeks. Administration of any combination of agents described herein can, by way of example only, sustain reduction of liver inflammation, macrophage infiltration, and/or liver fibrosis, by number, size or density by over 25%, over 50%, over 75%, or over 90% in about twelve weeks.

Practice of any one of the methods described herein can reduce liver fat content by at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or more than 99%. For example, practice of any one of the methods described herein can reduce liver fat content by 5-20%, 10-40%, 30-60%, 40-80%, 60-95%, or 75-99%. In some embodiments, administration of any combination of agents described herein reduces liver fat content in about 1 week, 2 weeks, 3 weeks, 4 weeks, 5 weeks, 6 weeks, 8 weeks, or less. Administration of any combination of agents described herein can, for example, reduce lipogenic gene expression by at least 10% in about six weeks. Administration of any combination of agents described herein can, for example, reduce lipogenic gene expression by at least 20% in about six weeks. Administration of any combination of agents described herein can, by way of example only, reduce liver fat content, and/or increase liver fatty acid oxidation, by number, size or density by over 25%, over 50%, over 75%, or over 90% in about six weeks.

Practice of any one of the methods described herein can sustain reduction of liver fat content by at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or more than 99%. For example, practice of any one of the methods described herein can sustain reduction of liver fat content by 5-20%, 10-40%, 30-60%, 40-80%, 60-95%, or 75-99%. In some embodiments, administration of any combination of agents described herein sustains reduction of liver fat content in about 1 week, 2 weeks, 3 weeks, 4 weeks, 5 weeks, 6 weeks, 8 weeks, or less. Administration of any combination of agents described herein can, for example, sustain reduction of lipogenic gene expression by at least 10% in about six weeks. Administration of any combination of agents described herein can, for example, sustain reduction of lipogenic gene expression by at least 20% in about six weeks. Administration of any combination of agents described herein can, by way of example only, sustain reduction of liver fat content, and/or increase liver fatty acid oxidation, by number, size or density by over 25%, over 50%, over 75%, or over 90% in about six weeks.

In some cases, the effectiveness of reducing NASH, reducing hepatic steatosis, reducing liver fibrosis, reducing macrophage infiltration, reducing expression of lipogenic genes, reducing expression of hepatic inflammatory genes, and increasing expression of liver fatty acid oxidation genes by practice of any one of the methods described herein can be maintained for at least 1 week, at least 2 weeks, at least 3 weeks, at least 4 weeks, at least 5 weeks, at least 6 weeks, 8 weeks, at least 8 weeks, at least 12 weeks, or more. In some cases, the effectiveness can be maintained for at least 1 month, at least 2 months, at least 3 months, at least 4 months, at least 5 months, at least 6 months, at least 12 months, at least 1 year, at least 2 years, at least 5 years, at least 10 years, or longer. In some cases, the sustainable effect is detectable after administering a composition described herein for at least 1 dose, at least 2 doses, at least 3 doses, at least 4 doses, at least 5 doses, at least 6 doses, at least 8 doses, at least 10 doses, or more.

In some cases, the effectiveness of sustaining reduction of NASH, sustaining reduction of hepatic steatosis sustaining reduction of liver fibrosis, sustaining reduction of macrophage infiltration, sustaining reduction of expression of lipogenic genes, sustaining reduction of expression of hepatic inflammatory genes, and sustaining reduction of increased expression of liver fatty acid oxidation genes by practice of any one of the methods described herein can be maintained for at least 1 week, at least 2 weeks, at least 3 weeks, at least 4 weeks, at least 5 weeks, at least 6 weeks, 8 weeks, at least 8 weeks, at least 12 weeks, or more. In some cases, the effectiveness can be maintained for at least 1 month, at least 2 months, at least 3 months, at least 4 months, at least 5 months, at least 6 months, at least 12 months, at least 1 year, at least 2 years, at least 5 years, at least 10 years, or longer. In some cases, the sustainable effect is detectable after administering a composition described herein for at least 1 dose, at least 2 doses, at least 3 doses, at least 4 doses, at least 5 doses, at least 6 doses, at least 8 doses, at least 10 doses, or more.

Administration and/or co-administration of any of the compounds described herein can prevent NASH or hepatic steatosis in a subject in need thereof. Exemplary subjects in need of hepatic steatosis reduction can include subjects exhibiting a propensity for, or having a high risk of developing, hepatic steatosis.

A number of environmental and genetic risk factors have been found to increase propensity of a subject to develop NASH or hepatic steatosis. A subject can exhibit a propensity for developing NASH or hepatic steatosis if the subject exhibits any combination of risk factors described herein. A greater number of risk factors exhibited by a subject can indicate a higher propensity for developing NASH or hepatic steatosis, as compared to a subject that exhibits a lower number of risk factors. It is understood that a subject can be considered to exhibit a propensity for developing NASH or hepatic steatosis if the subject exhibits even one, two, three, or more of the risk factors described herein.

An exemplary risk factor for developing hepatic steatosis is obesity. Accordingly, a subject can be considered to exhibit an increased propensity to develop NASH or hepatic steatosis if the subject is obese. Obesity in a subject can be assessed using a body mass index (BMI) measurement. A subject's BMI can be calculated by dividing the subject's body weight (in kg) by the square of the subject's height ($m^2$). A subject can be considered overweight if the subject exhibits a BMI that is over 25 $kg/m^2$, over 26 $kg/m^2$, over 27 $kg/m^2$, over 28 $kg/m^2$, or over 29 $kg/m^2$, and can be considered obese if the subject exhibits a BMI that is over 30 $kg/m^2$, over 31 $kg/m^2$, over 32 $kg/m^2$, over 33 $kg/m^2$, over 34 $kg/m^2$, over 35 $kg/m^2$, over 36 $kg/m^2$, over 37 $kg/m^2$, over 38 $kg/m^2$, over 39 $kg/m^2$, over 40 $kg/m^2$, or over 45 $kg/m^2$. A subject can also be considered to exhibit a propensity to develop NASH or hepatic steatosis if the subject exhibits abdominal obesity. Abdominal obesity can be assessed by measuring the circumference of the subject's waist. For example, if the subject is an adult male, the subject can be considered to exhibit abdominal obesity if the subject exhibits a waist circumference of 102 cm or greater. For other example, if the subject is an adult female, the subject can be considered to exhibit abdominal obesity if the subject exhibits a waist circumference of 88 cm or greater.

Another exemplary risk factor for developing NASH or hepatic steatosis is insulin resistance. Accordingly, a subject can be considered to exhibit an increased propensity to develop NASH or hepatic steatosis if the subject exhibits insulin resistance. Insulin resistance in a subject can be assessed by any means known in the art or otherwise described herein. By way of example only, insulin resistance may be assessed by measuring Homeostatic Assessment of Insulin Resistance ($HOMA_{IR}$) in the subject. $HOMA_{IR}$ can be determined by any means known in the art, for example, by the following equation: $HOMA_{IR}$=Insulin (uU/mL)× glucose (mM)]/22.5. The $HOMA_{IR}$ value increases with increasing insulin resistance, and values above (2.6) are generally considered to be insulin resistant. A subject can be considered to exhibit insulin resistance if the subject exhibits a $HOMA_{IR}$ above the $75^{th}$ percentile, or a $HOMA_{IR}$ value of over 2.6. Insulin resistance may also be assessed by measuring fasting serum insulin levels in the subject. A subject may be considered to exhibit insulin resistance if the subject exhibits a fasting serum insulin level of 60 pmol/L or higher.

Insulin resistance may also be assessed by measuring a quantitative insulin sensitivity check index (QUICKI) in the subject. QUICKI can be determined by the following equation: QUICKI=1/(log(fasting insulin µU/mL)+log(fasting glucose mg/dL)). A subject may be considered to exhibit insulin resistance if the subject exhibits a QUICKI of 0.30 or less. For other example, insulin resistance can be determined by measuring blood glucose levels in a subject, in some cases over a period of time, following administration of a bolus of insulin. Subjects with insulin resistance typically exhibit an attenuated drop in blood glucose levels following insulin administration, as compared to subject without insulin resistance.

Another exemplary risk factor for developing NASH or hepatic steatosis is diabetes. Accordingly, a subject can be considered to exhibit an increased propensity to develop NASH or hepatic steatosis if the subject has or is diagnosed with diabetes. The diabetes can be Type I or Type II diabetes. Diabetes may be diagnosed by any means known to those of skill in the art, or otherwise described herein. For example, a subject may be diagnosed with diabetes if the subject exhibits high fasting plasma glucose levels (e.g., 126 mg/dl or higher). A subject may be diagnosed with diabetes if the subject exhibits high plasma glucose levels following administration of a bolus of glucose (e.g., in a glucose tolerance test). For example, a subject may be diagnosed with diabetes if the subject exhibits 200 mg/dl plasma glucose or higher two hours after administration of a 75 g bolus of glucose.

Genetics may be a risk factor for developing NASH or hepatic steatosis. For example, males of Indian, Asian, and/or Mexican descent may have a higher risk of developing hepatic steatosis. Accordingly, a subject can be considered to exhibit an increased propensity to develop NASH or hepatic steatosis if the subject is a male of Indian, Asian, and/or Mexican descent. Genetic polymorphisms may also be associated with an increased propensity to develop NASH or hepatic steatosis. For example, a subject may be considered to exhibit an increased propensity to develop NASH or hepatic steatosis if the subject exhibits a T455C or C482T polymorphism in the APOC3 gene.

Certain medications increase risk for developing NASH or hepatic steatosis. Such medications increase risk for developing NASH or hepatic steatosis include, but are not limited to oral corticosteroids (e.g., prednisone, hydrocortisone, among others), synthetic estrogens (e.g., Premarin, Ortho-Est, tamoxifen, among others), amiodarone (Cordarone, Pacerone), diltiazem, anti-retroviral drugs such as, e.g., indinavir, and methotrexate. Accordingly, a subject may be considered to exhibit an increased propensity to develop NASH or hepatic steatosis if the subject has taken any of the medications described herein as increasing risk for developing NASH or hepatic steatosis.

In some embodiments, the subject exhibiting a propensity for developing NASH or hepatic steatosis has not yet developed hepatic steatosis. For example, the subject may not have exhibited a symptom of NASH or hepatic steatosis. For other example, the subject may not exhibit increased fat content of the liver. In some embodiments, the subject has not been diagnosed with NASH or hepatic steatosis. In some embodiments, the subject does not exhibit an increase in serum ALT levels as compared to a control subject without NASH or hepatic steatosis.

Practice of any one of the methods described herein can prevent or reduce occurrence of NASH or hepatic steatosis in at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or more than 99% of treated subjects. For example, practice of any one of the methods described herein can prevent NASH or hepatic steatosis or reduce occurrence of hepatic steatosis by 5-20%, 10-40%, 30-60%, 40-80%, 60-95%, or 75-99%. In some embodiments, administration of any combination of agents described herein to a subject prevents or reduces occurrence of NASH or hepatic steatosis in the subjects for at least about 1, 2, 3, 4, 5, 6, 7, 8 weeks or 2, 4, 6, 12 or 24 months. Prevention of NASH or hepatic steatosis can be determined by comparison to a reference subject and/or reference population. NASH or hepatic steatosis in a subject can be considered to be prevented or to have reduced occurrence if any one or more of hepatic fat content, as measured by any of the methods described herein, liver size or weight, liver vacuole number, size of a liver vacuole, liver vacuole density, serum alanine transaminase (ALT) and/or aspartate transaminase levels in the subject does not increase or increases to a lesser extent as compared to a reference subject and/or reference population. The reference subject and/or reference population can be another subject or population of subjects exhibiting a comparable propensity for developing NASH or hepatic steatosis who has not developed NASH or hepatic steatosis, and who is not treated with one or more compounds described herein.

Compositions and Co-Administration

In certain embodiments, provided herein is a composition comprising a compound described herein (e.g., a compound of Formula I-a, I-b, I-c, II-a, II-b, II-c, III, IV, V, or VI or a compound listed in Table 1 or 3) and one or more therapeutic agents. In some cases, the one or more agents are selected from the group consisting of a phosphodiesterase (PDE) inhibitor, sirtuin pathway activator, anti-diabetic agent, anti-hyperlipidemic agent, glucagon-like peptide-1 (GLP-1) agonist, dipeptidyl peptidase-4 (DPP-4) inhibitor, sodium-glucose cotransporter-2 (SGLT2) inhibitor or gliflozin, a fibrate, a nitric oxide (NO) donor, nicotinic acid, nicotinamide riboside, nicotinic acid metabolite, and any combination thereof.

Provided herein is a pharmaceutical composition comprising a compound described herein and a pharmaceutically acceptable carrier. In some cases of a pharmaceutical composition described herein, the pharmaceutical composition is formulated for oral administration. In some cases of a pharmaceutical composition described herein, the pharmaceutical composition is formulated for injection.

In some embodiments, the particular choice of compounds depends upon the diagnosis of the attending physicians and their judgment of the condition of the individual and the appropriate treatment protocol. The compounds are optionally administered concurrently (e.g., simultaneously, essentially simultaneously or within the same treatment protocol) or sequentially, depending upon the nature of the disease, disorder, or condition, the condition of the individual, and the actual choice of compounds used. In certain instances, the determination of the order of administration, and the number of repetitions of administration of each therapeutic agent during a treatment protocol, is based on an evaluation of the disease being treated and the condition of the individual.

In some embodiments, therapeutically-effective dosages vary when the drugs are used in treatment combinations. Methods for experimentally determining therapeutically-effective dosages of drugs and other agents for use in combination treatment regimens are described in the literature.

In some embodiments of the combination therapies described herein, dosages of the co-administered compounds vary depending on the type of co-drug employed, on the specific drug employed, on the disease or condition being treated and so forth. In addition, when co-administered with one or more biologically active agents, the compound provided herein is optionally administered either simultaneously with the biologically active agent(s), or sequentially. In certain instances, if administered sequentially, the attending physician will decide on the appropriate sequence of therapeutic compound described herein in combination with the additional therapeutic agent.

The multiple therapeutic agents are optionally administered in any order or even simultaneously. If simultaneously, the therapeutic agents are optionally provided in a single, unified form, or in multiple forms (by way of example only, either as a single pill or as two separate pills). In certain instances, one of the therapeutic agents is optionally given in multiple doses. In other instances, both are optionally given as multiple doses. If not simultaneous, the timing between the multiple doses is any suitable timing, e.g., from more than zero weeks to less than four weeks. In addition, the combination methods, compositions and formulations are not to be limited to the use of only two agents; the use of multiple therapeutic combinations is also envisioned (including two or more compounds described herein).

Any of the components described herein, including nicotinic acid, nicotinamide riboside, and resveratrol can be used in a subject composition in free form, isolated form, purified from a natural source, and/or purified or prepared from a synthetic source. The natural source can be an animal source or plant source. The components can be pure to at least about 95, 97, 99, 99.5, 99.9, 99.99, or 99.999%.

Certain embodiments provide compositions that can comprise any combination of agents, such as a compound of Formula I-a, I-b, I-c, II-a, II-b, II-c, III, IV, V, or VI, a compound listed in Table 1 or 3, a phosphodiesterase (PDE) inhibitor, sirtuin pathway activator, anti-diabetic agent, antihyperlipidemic agent, glucagon-like peptide-1 (GLP-1) agonist, dipeptidyl peptidase-4 (DPP-4) inhibitor, sodium-glucose cotransporter-2 (SGLT2) inhibitor or gliflozin, a fibrate, a nitric oxide (NO) donor, nicotinic acid, nicotinamide riboside, or nicotinic acid metabolite that have been isolated from one or more sources. The agents can be isolated from natural sources or created from synthetic sources and then enriched to increase the purity of the components. For example, sildenafil can be created from a synthetic source and then enriched by one or more purification methods. The isolated and enriched components, such as, e.g., metformin, resveratrol, icariin, and sildenafil, can then be formulated for administration to a subject in any combination.

Any of the above unit dosage compositions can further comprise an additional agent. The additional agent can be a sirtuin pathway activator and/or PDE inhibitor. In some embodiments, a weight % of the additional agent in the composition, excluding excipients (e.g., fillers) is 5-50%. In particular embodiments, the additional agent is metformin. The metformin can be present in the unit dosage composition in a therapeutic or sub-therapeutic dose. For example, the unit dosage composition can further comprise about 2.5 to about 500 mg of metformin (e.g., about 2.5, 5, 10, 20, 25, 50, 100, 125, 150, 175, 200, 250, 300, 350, 400, 450, or 500 mg of metformin). In some embodiments, the additional agent is a PDE inhibitor (e.g., a PDE5 inhibitor). In some embodiments, the additional agent is icariin. The icariin can be present in the unit dosage composition in a therapeutic or sub-therapeutic dose. For example, the unit dosage composition can further comprise about 1 to about 2000 mg of icariin (e.g., about 1, 5, 10, 20, or 25 mg of icariin). In some embodiments, the additional agent is sildenafil. The sildenafil can be present in the unit dosage composition in a therapeutic or sub-therapeutic dose. For example, the unit dosage composition can further comprise about 1 to about 2000 mg of sildenafil (e.g., about 1, 5, 10, 20, or 25 mg of sildenafil). The unit dosage can comprise about 0.01 to about 100 mg of a NO donor. The unit dosage can optionally further comprise resveratrol.

Exemplary Glucagon-Like Peptide-1 (GLP-1) Agonists

In some cases of a composition described herein, the glucagon-like peptide-1 (GLP-1) agonist is selected from the group consisting of exenatide, liraglutide, lixisenatide, albiglutide, dulaglutide, taspoglutide, semaglutide, and any combination thereof.

Glucagon-like peptide-1 receptor agonists, also known as GLP-1 receptor agonists or incretin mimetics, are agonists of the GLP-1 receptor. This class of drugs can be used to treat type 2 diabetes.

Exemplary Dipeptidyl Peptidase-4 (DPP-4) Inhibitors

In some cases of a composition described herein, the dipeptidyl peptidase-4 (DPP-4) inhibitor is selected from the group consisting of sitagliptin, vildagliptin, saxagliptin, linagliptin, gemigliptin, anagliptin, teneligliptin, alogliptin, trelagliptin, dutogliptin, omarigliptin, berberine, lupeol, and any combination thereof.

Dipeptidyl peptidase 4 inhibitors, also known as gliptins, are a class of oral hypoglycemics that block DPP-4 (DPP-IV). DPP-4 inhibitors reduce glucagon, thereby lowering blood glucose levels. Their mechanism of action is to increase incretin levels (e.g., GLP-1 and GIP), thereby inhibiting glucagon release, increasing insulin secretion, decreasing gastric emptying, and decreasing blood glucose levels. DPP-4 inhibitors can be used to treat diabetes mellitus type 2.

Exemplary Sodium-Glucose Cotransporter-2 (SGLT2) Inhibitors or Gliflozins

In some cases of a composition described herein, the sodium-glucose cotransporter-2 (SGLT2) inhibitor or gliflozin is selected from the group consisting of dapagliflozin, empagliflozin, canagliflozin, ipragliflozin, tofogliflozin, sergliflozin etabonate, remogliflozin etabonate, ertugliflozin, and any combination thereof.

Sodium-glucose cotransporter-2 (SGLT2) inhibitors or gliflozins are a class of medications that inhibit reabsorption of glucose in the kidney, thereby lowering blood sugar, by inhibiting sodium-glucose transport protein 2 (SGLT2). They are used to treat type II diabetes mellitus (T2DM). They may enhance blood sugar control or reduce body weight and systolic and diastolic blood pressure.

Exemplary Fibrates

In some cases of a composition described herein, the fibrate is selected from the group consisting of bezafibrate, ciprofibrate, clofibrate, aluminium clofibrate, etofibrate, gemfibrozil, fenofibrate, clinofibrate, and any combination thereof.

Fibrates are a class of amphipathic carboxylic acids and are used to treat a range of metabolic disorders, including hypercholesterolemia (high cholesterol). They are hypolipidemic agents. Fibrates activate PPAR (peroxisome proliferator-activated receptors), including PPARa. The PPARs are intracellular receptors that modulate carbohydrate and fat metabolism and adipose tissue differentiation. Activating PPARs induces the transcription of genes that facilitate lipid metabolism.

Exemplary Sirtuin Pathway Activators

In some cases of a composition described herein, the sirtuin pathway activator is a biguanide, resveratrol, a sirtuin activator, an AMPK activator, or a PGC-1α activator. In some cases of a composition described herein, the PGC-1α activator is a thiazolidinedione. In some cases of a composition described herein, the thiazolidinedione is selected from the group consisting of rosiglitazone, pioglitazone, lobeglitazone, and any combination thereof.

An increase in mitochondrial biogenesis can be evidenced by an increase in the formation of new mitochondria and/or by an increase in mitochondrial functions, such as increased fatty acid oxidation, increased heat generation, increased insulin sensitivity, increased glucose uptake, increased vasodilation, decreased weight, decreased adipose volume, and decreased inflammatory response or biomarkers in a subject.

In some embodiments, the sirtuin pathway activator is a sirtuin activator. The sirtuin activator can be a Sirt1 activator, or an activator of another sirtuin (e.g., Sirt2, Sirt3, Sirt4, Sirt5, Sirt6). Sirt1 activity can be determined by measuring deacetylation of a substrate, which can be detected using a fluorophore. An increase in sirt1, sirt2, sirt3, sirt4, sirt5, sirt6, or another sirtuin is observed by applying a corresponding substrate in a deacylation assay conducted in vitro. The substrate for measuring SIRT1 activity can be any substrate known in the art (for example, a peptide containing amino acids 379-382 of human p53 (Arg-His-Lys-Lys[Ac]). The substrate for measuring SIRT3 activity can be any substrate known in the art (for example a peptide containing amino acids 317-320 of human p53 (Gln-Pro-Lys-Lys[Ac])).

Exemplary sirtuin activators can include those described in Howitz et al. (2003) Nature 425: 191 and include, for example, resveratrol (3,5,4'-Trihydroxy-trans-stilbene), butein (3,4,2',4'-Tetrahydroxychalcone), piceatannol (3,5,3', 4'-Tetrahydroxy-trans-stilbene), isoliquiritigenin (4,2',4'-Trihydroxychalcone), fisetin (3,7,3',4'-Tetrahyddroxyflavone), quercetin (3,5,7,3',4'-Pentahydroxyflavone), Deoxyrhapontin (3,5-Dihydroxy-4'-methoxystilbene 3-O-β-D-glucoside); trans-Stilbene; Rhapontin (3,3',5-Trihydroxy-4'-methoxystilbene 3-O-β-D-glucoside); cis-Stilbene; Butein (3,4,2',4'-Tetrahydroxychalcone); 3,4,2'4'6'-Pentahydroxychalcone; Chalcone; 7,8,3',4'-Tetrahydroxyflavone; 3,6,2',3'-Tetrahydroxyflavone; 4'-Hydroxyflavone; 5,4'-Dihydroxyflavone 5,7-Dihydroxyflavone; Morin (3,5,7,2',4'-Pentahydroxyflavone); Flavone; 5-Hydroxyflavone; (−)-Epicatechin (Hydroxy Sites: 3,5,7,3',4'); (−)-Catechin (Hydroxy Sites: 3,5,7,3',4'); (−)-Gallocatechin (Hydroxy Sites: 3,5,7,3',4',5') (+)-Catechin (Hydroxy Sites: 3,5,7,3', 4'); 5,7,3',4',5'-pentahydroxyflavone; Luteolin (5,7,3',4'-Tetrahydroxyflavone); 3,6,3',4'-Tetrahydroxyflavone; 7,3',4',5'-Tetrahydroxyflavone; Kaempferol (3,5,7,4'-Tetrahydroxyflavone); 6-Hydroxyapigenin (5,6,7,4'-Tetrahydoxyflavone); Scutellarein); Apigenin (5,7,4'-Trihydroxyflavone); 3,6,2',4'-Tetrahydroxyflavone; 7,4'-Dihydroxyflavone; Daidzein (7,4'-Dihydroxyisoflavone); Genistein (5,7,4'-Trihydroxyflavanone); Naringenin (5,7,4'-Trihydroxyflavanone); 3,5,7,3',4'-Pentahydroxyflavanone; Flavanone; Pelargonidin chloride (3,5,7,4'-Tetrahydroxyflavylium chloride); Hinokitiol (b-Thujaplicin; 2-hydroxy-4-isopropyl-2,4,6-cycloheptatrien-1-one); L-(+)-Ergothioneine ((S)-a-Carboxy-2,3-dihydro-N,N,N-trimethyl-2-thioxo-1H-imidazole-4-ethanaminium inner salt); Caffeic Acid Phenyl Ester; MCI-186 (3-Methyl-1-phenyl-2-pyrazolin-5-one); HBED (N,N'-Di-(2-hydroxybenzyl) ethylenediamine-N,N'-diacetic acid-H2O); Ambroxol (trans-4-(2-Amino-3,5-dibromobenzylamino) cyclohexane-HCl; and U-83836E ((−)-2-((4-(2,6-di-1-Pyrrolidinyl-4-pyrimidinyl)-1-piperzainyl)methyl)-3,4-dihydro-2,5,7,8-tetramethyl-2H-1-benzopyran-6-01.2HCl). Analogs and derivatives thereof can also be used.

In some embodiments, the sirtuin pathway activator is an AMPK pathway activator. AMPK activity can be determined by any means known in the art, such as, e.g., measuring AMPK phosphorylation via an ELISA assay or by Western blot. The AMPK pathway activator can be a biguanide. Examples of biguanides include and are not limited to metformin, buformin, phenformin, proguanil or the like.

In some embodiments, the sirtuin pathway activator (e.g., AMPK pathway activator) is a polyphenol. Exemplary polyphenols include, e.g., chlorogenic acid, resveratrol, caffeic acid, piceatannol, ellagic acid, epigallocatechin gallate (EGCG), stilbene, cinnamic acid, hydroxycinnamic acid, grape seed extract, or any analog thereof. In some embodiments, the sirtuin pathway activator is resveratrol, an analog thereof, or a metabolite thereof. For example, the activator can be pterostilbene or a small molecule analog of resveratrol. Examples of small molecule analogs of resveratrol are described in U.S. Patent Application Nos. 20070014833, 20090163476, and 20090105246, which are incorporated herein by reference in its entirety.

The polyphenol can be a substantially homogeneous population of polyphenols. The polyphenol can be one type of polyphenol, wherein the composition can exclude all other types of polyphenols. In some embodiments, a method described herein comprises administration one type of polyphenol, and exclude all other types of polyphenols. In some embodiments, a method described herein comprises administration of two, three, or four types of polyphenols, and exclude all other types of polyphenols. In some embodiments, a method described herein comprises administration of 1, 2, 3, or 4 types of polyphenols and less than 0.1, 0.5, 1, or 2% of any other types of polyphenols.

Sirtuin pathway activators can also include PDE inhibitors. PDE inhibitors can include non-specific PDE inhibitors. PDE inhibitors can be naturally occurring or non-naturally occurring (e.g., manufactured), and may be provided in the form of a natural source comprising the PDE inhibitor, or an extract thereof (e.g., purified). Examples of non-specific PDE inhibitors include, but are not limited to, caffeine, theophylline, theobromine, 3-isobutyl-1-methylxanthine (IBMX), pentoxifylline (3,7-dihydro-3,7-dimethyl-1-(5oxohexyl)-1H-purine-2,6-dione), aminophylline, paraxanthine, and salts, derivatives, metabolites, catabolites, anabolites, precursors, and analogs thereof. Non-limiting examples of natural sources of PDE inhibitors include coffee, tea, guarana, yerba mate, cocoa, and chocolate (e.g., dark chocolate).

Sirtuin pathway activators can include quinic acid, cinnamic acid, ferulic acid, fucoxanthin, rosiglitazone, or any analog thereof. Sirtuin-pathway activators can also include isoflavones, pyroloquinoline (PQQ), quercetin, L-carnitine, lipoic acid, coenzyme Q10, pyruvate, 5-aminoimidazole-4-carboxamide ribotide (AICAR), bezfibrate, oltipraz, and/or genistein.

Sirtuin pathway activators can agents that stimulate expression of the Fndc5, PGC1-α, or UCP1. The expression can be measured in terms of the gene or protein expression level. Alternatively, the sirtuin pathway activator can be irisin. Methods for increasing the level of irisin are described in Boström et al., "A PGC1-α-dependent myokine that drives brown-fat-like development of white fat and thermogenesis," Nature, Jan. 11, 2012.

Sirtuin pathway activators can include thiazolidinediones. Exemplary thiazolidinediones include, e.g., rosiglitazone, pioglitazone, troglitazone, and any analogs thereof.

Nicotinic Acid, Nicotinamide Riboside and Nicotinic Acid Metabolites

The disclosure provides for compositions that include one or more agents selected from the group consisting of nicotinic acid, nicotinamide riboside, and nicotinic acid metabolite. The one or more agents selected from the group consisting of nicotinic acid, nicotinamide riboside, and nicotinic acid metabolite can be used in free form. The term "free", as used herein in reference to a component, indicates that the component is not incorporated into a larger molecular complex. In some embodiments, the nicotinic acid can be comprised in niacin. Alternatively, the one or more agents selected from the group consisting of nicotinic acid, nicotinamide riboside, and nicotinic acid metabolite can be in a salt form.

In some embodiments, the compositions can be substantially free of nicotinamide and/or nicotinamide metabolites. The nicotinamide and/or nicotinamide metabolites can counteract the effects of nicotinic acid or nicotinamide riboside. Nicotinamide can be harmful to the liver in high doses (as disclosed in http://www.livestrong.com/article/448906-therapeutic-levels-of-niacin-to-lower-cholesterol-levels/#ixzz2NO3KhDZu). The mass or molar amount of nicotinamide and/or nicotinamide metabolites can be less than about 0.01, 0.1, 0.5, 1, 2, 5, or 10% of the total composition. The mass or molar amount of nicotinamide and/or nicotinamide metabolites can be less than about 0.01, 0.1, 0.5, 1, 2, 5, or 10% of the total composition.

Without being limited to theory, ingestion of one or more agents selected from the group consisting of nicotinic acid, nicotinamide riboside, and nicotinic acid metabolite can lower lipid content, lower triglyceride level, lower LDL level, lower total cholesterol level, lower lipid accumulation, or increase HDL level. The ingestion of one or more agents selected from the group consisting of nicotinic acid, nicotinamide riboside, and nicotinic acid metabolite can also increase fat oxidation or stimulate sirtuin signaling, including increase activation of Sirt1 and Sirt3. In some embodiments, any of the compositions described herein can include salts, derivatives, metabolites, catabolites, anabolites, precursors, and analogs of nicotinic acid. For example, the metabolites can include nicotinyl CoA, nicotinuric acid, nicotinate mononucleotide, nicotinate adenine dinucleotide, or nicotinamide adenine dinucleotide. In some embodiments, the compositions cannot comprise nicotinamide. In some embodiments, the compositions comprise nicotinamide. In some embodiments, the compositions can be substantially free of nicotinic acid metabolites.

Exemplary Anti-Diabetic Agents

In some cases of a composition described herein, the anti-diabetic agent is selected from the group consisting of biguanide, meglitinide, sulfonylurea, thiazolidinedione, alpha glucosidase inhibitor, ergot alkaloid, and any combination thereof. In some cases of a composition described herein, the sulfonylurea is glipizide. In some cases of a composition described herein, the biguanide is metformin.

Anti-diabetic agents, also known as drugs used to treat diabetes mellitus, or diabetes as normally referred to, by lowering glucose levels in the blood. Examples of anti-diabetic agents include biguanides (such as metformin), guanidine and/or derivatives thereof (such as galegine), thiazolidinediones and meglitinides (such as repaglinide, pioglitazone, and rosiglitazone), alpha glucosidase inhibitors (such as acarbose), sulfonylureas (such as tolbutamide, acetohexamide, tolazamide, chlorpropamide, glipizide, glyburide, glimepiride, gliclazide), incretins, ergot alkaloids (such as bromocriptine), and DPP inhibitors (such as sitagliptin, vildagliptin, saxagliptin, lingliptin, dutogliptin, gemigliptin, alogliptin, and berberine). In some embodiments, the guanide may comprise a dimethyl structure. The guanide with a dimethyl structure can include dimethylguanidine, galegine, and metformin. In some embodiments, the guanide can include a dimethyl structure that activates the Sirt1/AMPK pathway. The anti-diabetic agent can be an oral anti-diabetic agent and thus are called oral hypoglycemic agents or oral antihyperglycemic agents. The anti-diabetic agent can also be injectable anti-diabetic drugs, including insulin, amylin analogues (such as pramlintide), and inretin mimetics (such as exenatide and liraglutide).

In some embodiments, the anti-diabetic agent is a biguanide including, metformin, phenformin, and buformin. Without being limited to theory, ingestion of a biguanide, such as metformin, has pharmaceutical efficacy in preventing the production of glucose in the liver, increasing sensitivity to insulin and helping the body respond better to its own insulin, and reducing sugar absorption by the intestines. In some embodiments, a biguanide can be a sirtuin pathway activator or an AMPK pathway activator, which increases sensitivity to insulin, hence improving the efficiency of glucose uptake from the blood. In a preferred embodiment, a biguanide is metformin. Metformin can be synthesized from equimolar amounts of 2-cyanoguanidine and dimethylamine in the presence of hydrochloric acid to yield the biguanide, metformin hydrochloride. A common characteristic of metformin, biguanides and guanides is the presence of dimethyl structure. Examples of guanides containing dimethyl structure include, but are not limited to, galegine and dimethylguanidine.

Metformin is known as a medicament for influencing the body's sensitivity to insulin and lowering blood glucose level, and is a FDA approved anti-diabetic agent to treat diabetes and related diseases such as heart disease, blindness and kidney diseases. Commercially available metformin includes Glucophage, Glucopage XR, Glumetza, Fortamet and Riomet. Currently, there are two forms of manufactured metformin, the immediate release Metformin IR and the slow release Metformin SR. Common side effects of metformin include gastrointestinal discomfort, bloating, flatulence, nausea/vomiting and diarrhea. Less common reactions include hypoglycemia, myalgia, lightheadedness, dyspnea, rash, increased sweating, taste disorder, and flu-like syndrome. Lactic acidosis is a rare side effect of anti-diabetic medicaments containing metformin. In general, metformin does not increase insulin concentration in the blood or cause hypoglycemia when used alone. Treatment of metformin has good effect on LDL cholesterol while has no effect on blood pressure. In addition, treatment of metformin can decrease triglycerides. In some cases, metformin can be administrated as a monotherapy or in combination with other medicaments, for example, metformin with sitagliptin (commercially known as Janumet), metformin with pioglitazone (commercially known as Competact), and metformin with vildagliptin (commercially known as Eucreas).

In a preferred embodiment, a compound or composition described herein can be administered to lower lipid levels, to lower lipid accumulation, to increase fat oxidation, to increase glucose utilization and to increase insulin sensitivity for diabetes control in a subject with a reduction in side effects such as lactic acidosis and/or hypoglycemia. In some embodiments, a compound, composition, or method described herein is sufficient to lower lipid levels, to lower lipid accumulation, to increase fat oxidation, to increase glucose utilization and to increase insulin sensitivity for diabetes control without causing a clinically significant lactic acidosis and/or hypoglycemia.

In some embodiments, the compositions can comprise guanidine and guanidine derivatives, including the alkaloid galegine, which can be isolated from the French lilac, also known as Goats rue (*Galega officinalis*) as described in Witters L. A., "The blooming of the French lilac," J. Clin Invest 108, 1105-1107 Oct. 15, 2001. In some cases, the toxicity of guanidine can preclude its development as a therapeutic, and the galegine effects can be less potent than those of metformin. In some embodiments, galegine and metformin can act via the same pathway, by dose-responsive activation of AMPK, as described in Mooney et al., "Mechanisms underlying the metabolic actions of galegine that contribute to weight loss in mice," Br. J Pharmacol 153, 1669-1677 Feb. 25, 2008. In some embodiments, guanides containing the dimethyl structure, such as galegine and dimethylguanidine, synergize with leucine, thereby increasing the efficacy of the guanide, which allows for use of such guanides for as a therapeutic treatment for diabetes at non-toxic doses of such guanides.

Exemplary PDE Inhibitors

In some cases of a composition described herein, the phosphodiesterase (PDE) inhibitor is a phosphodiesterase type 5 (PDE5) inhibitor. In some cases of a composition described herein, the phosphodiesterase type 5 (PDE5) inhibitor is selected from the group consisting of avanafil, iodenafil, mirodenafil, sildenafil, tadalafil, icariin, vardenafil, udenafil, zaprinst, benzamidenafil, dasantafil, and any combination thereof.

One or more PDE inhibitors can be used with the compositions or methods described herein. In certain embodiments, one or more methods can further comprise administering to a subject a PDE inhibitor. A PDE inhibitor can act as a sirtuin pathway activator. The PDE inhibitor can be selective or non-selective. The PDE inhibitor can exhibit selective inhibition to a PDE subclass, for example PDE 5. Examples of selective PDE inhibitors include inhibitors to PDE 1, 2, 3, 4, 5, 6, 7, 8, 9, 10, or 11. A non-selective PDE inhibitor can be one that does not distinguish among subclasses of phosphodiesterases. In addition, some non-selective PDE inhibitors may interact with more than one metabolic pathway. For examine, some non-selective PDE inhibitors may be xanthine derivatives and serve as adenosine antagonists and have unknown interactions with other metabolic pathways. Selective PDE inhibitors can be PDE inhibitors that exhibit preferential interaction with a selected PDE. For example, a PDE inhibitor can have a strong interaction with PDE 5, and very little interaction with other PDE sub-classes.

PDE inhibitors can be naturally occurring or non-naturally occurring (e.g., manufactured), and may be provided in the form of a natural source comprising the PDE inhibitor, or an extract thereof (e.g., purified). In some embodiments, the PDE inhibitor is a non-specific PDE inhibitor. Examples of non-specific PDE inhibitors include, but are not limited to, caffeine, theophylline, theobromine, 3-isobutyl-1-methylxanthine (IBMX), pentoxifylline (3,7-dihydro-3,7-dimethyl-1-(5oxohexyl)-1H-purine-2,6-dione), aminophylline, paraxanthine, and salts, derivatives, metabolites, catabolites, anabolites, precursors, and analogs thereof. The PDE inhibitor can be sourced from a natural source of PDE inhibitors. Non-limiting examples of natural sources of PDE inhibitors include coffee, tea, guarana, yerba mate, cocoa, and chocolate (e.g., dark chocolate).

Any agents that selectively and negatively regulate a PDE subclass, such as PDE 5, expression or activity can be used as selective PDE inhibitors in the compositions and methods described herein.

For example, a selective PDE inhibitor alternatively can be an agent that exhibits a 50% inhibitory concentration (IC50) with respect to a PDE subclass, such as PDE 5, that is at least at least 10-fold, at least 20-fold, at least 50-fold, at least 100-fold, at least 1000-fold, at least 10,000-fold lower than the inhibitor's IC50 with respect to one, two, three, or more other PDE subclasses. In some embodiment, a selective PDE inhibitor can be an agent that exhibits a 50% inhibitory concentration (IC50) with respect to a PDE subclass, such as PDE 5, that is at least at least 10-fold, at least 20-fold, at least 50-fold, at least 100-fold, at least 1000-fold, at least 10,000-fold, or more, lower than the inhibitor's IC50 with respect to all other PDE subclasses.

In one aspect, IC50 is a determination of the concentration at which 50% of a given PDE is inhibited in a cell-based assay. IC50 determinations can be accomplished using any suitable techniques. In general, an IC50 can be determined by measuring the activity of a given enzyme in the presence of a range of concentrations of the inhibitor under study. The experimentally obtained values of enzyme activity then are plotted against the inhibitor concentrations used. The concentration of the inhibitor that shows 50% enzyme activity (as compared to the activity in the absence of any inhibitor) is taken as the "IC50" value. Analogously, other inhibitory concentrations can be defined through appropriate determinations of activity. For example, in some settings it can be desirable to establish a 90% inhibitory concentration, i.e., IC90, etc.

Methods for measuring, assessing, assaying, interrogating or analyzing selectivity of PDE inhibitors are described in "Phosphodiesterase-5 Gln-817 is critical for cGMP, vardenafil, or sildenafil affinity: its orientation impacts cGMP but not cAMP affinity" by Zoraghi (2006) and "Cyclic Nucleotide Phosphodiesterases: Molecular Regulation to Clinical Use" by Bender (2006) which are incorporated herein in its entirety by reference.

The selective PDE inhibitor may inhibit PDE activity with an IC50 value of about 100 nM or less, preferably about 50 nM, about 25 nM, about 10 nM, about 5 nM, about 1 nM, 100 pM, 50 pM, 25 pM, 10 pM, 1 pM, or less, as ascertained in a cell-based assay or an in vitro kinase assay.

In some embodiments, the PDE inhibitor is a PDE1 inhibitor such as nimodipine, vinopocetine, and IC224. The PDE 1 inhibitor can interact with PDE1, which is a Ca2+/calmodulin-regulated phosphodiesterase that serves to degrade both cAMP and cGMP. The vinopocetine can be derived from periwinkle extract, and it can serve as a cerebrovascularvasodilator. Vinopocetine can be in the form of a dietary supplement.

In other embodiments, the PDE inhibitor is a PDE3 inhibitor such as meribendan, arinone and cilostamide. The PDE inhibitor can be a PDE4 inhibitor, such as apremilast, mesembrine, ibudilast, piclamilast, luteolin, roflumilast, cilomilast, diazepam, rolipram and YM796. The PDE inhibitor can be a PDE4 inhibitor, such as rolipram and YM796. The PDE4 inhibitor can interact with PDE 4, which is a cAMP-specific phosphodiesterase that predominates in immune cells.

In some embodiments, the PDE inhibitor is a PDE5 specific inhibitor, icariin, sildenafil, tadalafil, vardenafil, avanafil, iodenafil, mirodenafil, udenafil, and zaprinast. In some embodiments, the PDE5 inhibitor is icariin. In some embodiments, the PDE5 inhibitor is sildenafil. In some embodiments, the PDE5 inhibitor is tadalafil. In some embodiments, the PDE5 inhibitor is vardenafil. In some embodiments, the PDE5 inhibitor is avanafil. In some embodiments, the PDE5 inhibitor is iodenafil. In some embodiments, the PDE5 inhibitor is mirodenafil. In some embodiments, the PDE5 inhibitor is udenafil. In some embodiments, the PDE5 inhibitor is zaprinast. The PDE 5 inhibitor can interact with PDE 5, which is a cGMP-specific PDE. Increases in cGMP signaling can increase mitochondrial biogenesis both in vitro and in vivo. A PDE 5 inhibitor can increase nitric oxide signaling and be an effective vasodilator. Other examples of PDE 5 inhibitors are described in U.S. Pat. Nos. 5,250,534 and 6,469,012, which are each incorporated by reference in their entirety.

In some embodiments, a PDE inhibitor is administered in place of or in addition to resveratrol or other sirtuin pathway activator. In some embodiments, compositions comprising one or more components described herein comprise a PDE inhibitor in place of or in addition to resveratrol or other sirtuin pathway activator.

Exemplary NO (Nitric Oxide) Donors

In some cases of a composition described herein, the nitric oxide (NO) donor is selected from the group consisting of an organic nitrate, a diazeniumdiolate (NONOate), an S-nitrosothiol, an active pharmaceutical agent comprising an NO group, an NO-zeolite, arginine, sodium nitroprusside (SNP), and any combination thereof. In some cases of a composition described herein, the organic nitrate is selected from the group consisting of:

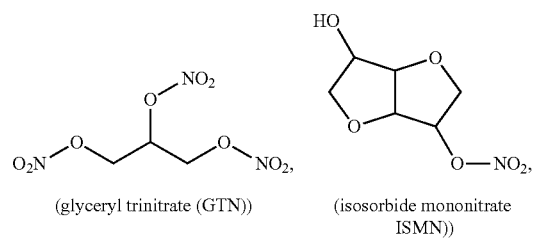

(glyceryl trinitrate (GTN))   (isosorbide mononitrate ISMN))

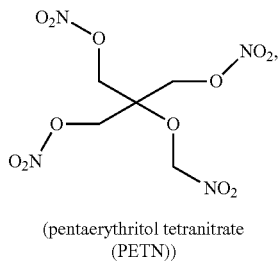

(pentaerythritol tetranitrate (PETN))

and BiDil (isosorbide dinitrate with hydralazine). In some cases of a composition described herein, the diazeniumdiolate is selected from the group consisting of:

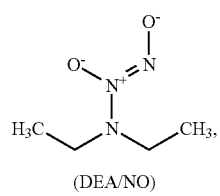

(DEA/NO)

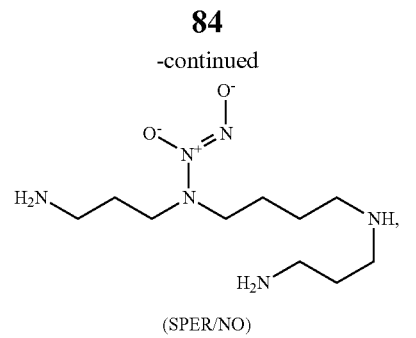

(SPER/NO)

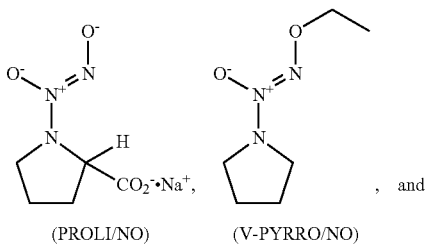

(PROLI/NO)   (V-PYRRO/NO)   , and

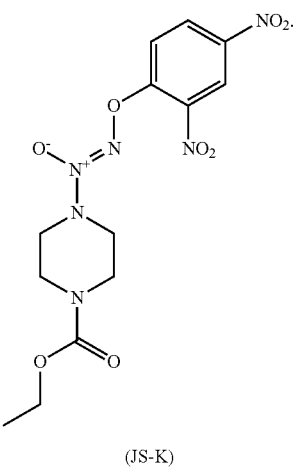

(JS-K)

In some cases of a composition described herein, the S-nitrosothiol is selected from the group consisting of:

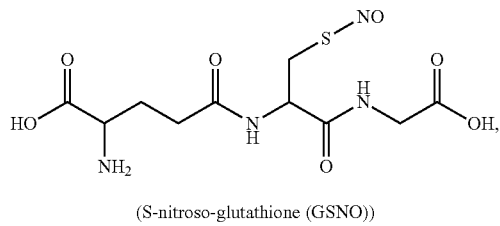

(S-nitroso-glutathione (GSNO))

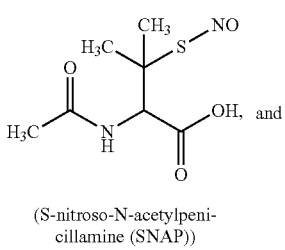

(S-nitroso-N-acetylpenicillamine (SNAP))

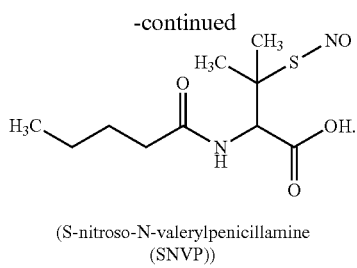

(S-nitroso-N-valerylpenicillamine (SNVP))

The NO donor can be an organic nitrate or nitrite selected from the group consisting of amyl nitrate, ethyl nitrite, ethyl nitrate, isosorbide mononitrate, isosorbide dinitrate, nitroglycerin, nitrosothiols and nitroprussides. In certain embodiments, at least one of the NO donors is arginine. In other embodiments, at least one of the NO donors is L-arginine. In certain embodiments, at least one of the NO donors has

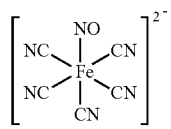

(nitroprusside). In further embodiments, at least one of the NO donors is sodium nitroprusside (SNP).

For examples, nitric oxide donors for use in certain aspects include without limitation, isosorbide dinitrate, L-arginine, linsidomine, minoxidil, nicorandil, nitroglycerin, nitroprusside, nitrosoglulthathione, and S-nitroso-N-acetylpenicillamine (SNAP) or glyceryl trinitrate. In certain aspects, isosorbide mononitrate, glyceryl trinitrate, or L-arginine is used as organic NO donor.

In certain embodiments, the nitric oxide donor is a compound selected from the group consisting of an organic nitrite, an organic nitrate, a nitrite ester of a polyol, a nitrate ester of a polyol molsidomine and its metabolites, a diazeniumdiolate, a S-nitrosothiol, an iron-sulphur nitrosyl, sodium nitrite, ethylene glycol dinitrate, isopropyl nitrate, amyl nitrite, amyl nitrate, ethyl nitrite, butyl nitrite, isobutyl nitrite, octyl nitrite, glyceryl-1-monoitrate, glyceryl-1,2-dinitrate, glyceryl-1,3-dinitrate, nitroglycerin, butane-1,2,4-triol-trinitrate, erythrityl tetranitrate, pentaerythrityl tetranitrate, sodium nitroprusside, clonitrate, erythrityl tetranitrate, isosorbide mononitrate, isosorbide dinitrate, mannitol hexanitrate, mesoionic oxatriazole, pentaerythritol tetranitrate, penetrinitol, triethanolamine trinitrate, trolnitrate phosphate (triethanolamine trinitrate diphosphate), propatylnitrate, nitrite esters of sugars, nitrate esters of sugars, sodium nitroprusside, nicorandil, apresoline, diazoxide, hydralazine, hydrochlorothiazide, minoxidil, pentaerythritol, tolazoline, scoparone (6,7-dimethoxycoumarin) sinitrodil, sildenafil, vardenafil, tadalafil, 4-Ethyl-2-[(Z)-hydroxyiminol]-5-nitro-3(E)-hexeneamide, L-arginine, pharmaceutically acceptable salts, derivatives, isomers and any combinations thereof.

In particular embodiments, NO donors include L-arginine. L-arginine is converted in the body into a chemical called nitric oxide. NO donors also include agents that stimulate endogenous NO or elevate levels of endogenous endothelium-derived relaxing factor (EDRF) in vivo or are substrates for nitric oxide synthase. Such compounds include, for example, L-arginine, L-homoarginine, and N-hydroxy-L-arginine, including their nitrosated and nitrosylated analogs (e.g., nitrosated L-arginine, nitrosylated L-arginine, nitrosated N-hydroxy-L-arginine, nitrosylated N-hydroxy-L-arginine, nitrosated L-homoarginine and nitrosylated L-homoarginine), precursors of L-arginine and/or physiologically acceptable salts thereof, including, for example, citrulline, omithine or glutamine, inhibitors of the enzyme arginase (e.g., N-hydroxy-L-arginine and 2(S)-amino-6-boronohexanoic acid) and the substrates for nitric oxide synthase, cytokines, adenosin, bradykinin, calreticulin, bisacodyl, and phenolphthalein. EDRF is a vascular relaxing factor secreted by the endothelium, and has been identified as nitric oxide (NO) or a closely related derivative thereof.

In certain embodiments, NO donors can be molsidomine and its active metabolite linsidomine, as well as sodium nitroprusside. These substances do not need to be reduced to donate NO. Sodium nitroprusside is an inorganic compound with the formula $Na_2[Fe(CN)_5NO]$, usually encountered as the dihydrate, $Na_2[Fe(CN)_5NO] \cdot 2H_2O$. This red-colored sodium salt dissolves in water ethanol to give solutions containing the free complex dianion $[Fe(CN)_5NO]^{2-}$. This compound is used as a drug. In this role it is abbreviated SNP, and it has tradenames like Nitropress. It acts as a drug by releasing nitric oxide; it belongs to the class of NO-releasing drugs as a result. This drug is used as a vasodilator to reduce blood pressure.

In certain embodiments, at least one of the NO donors is an organic nitrate. In certain embodiments, the organic nitrate is selected from the group consisting of:

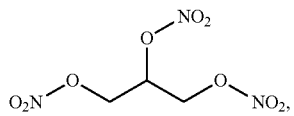

(glyceryl trinitrate (GTN))

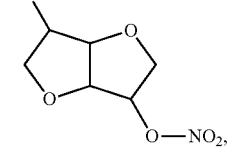

(isosorbide mononitrate (ISMN))

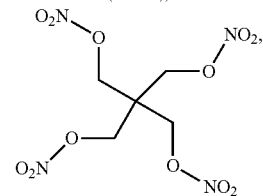

(pentaerythritol tetranitrate (PETN))

and BiDil (isosorbide dinitrate with hydralazine).

The organic nitrates are the most commonly used NO donor drugs. In certain embodiments, the NO donor is an organic nitrate such as glyceryl trinitrate (GTN; also known as nitroglycerin). GTN is the best-studied nitrate, used mainly in acute relief of pain associated with angina. GTN ointments are also routinely used for the treatment of anal fissure, transdermal patches in heart failure and chronic angina, whereas nebulized GTN may have benefits in certain subgroups with pulmonary hypertension. GTN contains three nitro-oxy ester (referred to as nitrate) groups, but releases only one molar equivalent of NO from the terminal position after bioactivation.

In certain embodiments, the NO donor is an organic nitrate such as isosorbide mononitrate (ISMN) used for the treatment of chronic angina. In certain embodiments, organic nitrates can include BiDil (isosorbide dinitrate with hydralazine).

In additional embodiments, the NO donor includes at least one organic nitrate which includes esters of nitric acid and can be an acyclic or cyclic compound, such as represented by the following general formula: $R(\text{—CR'R''—O—NO}_2)_x$, wherein: R is an organic or H (hydro) moiety or covalent bond, particularly a 2 to about 12 carbon hydrocarbon or oxygen-substituted hydrocarbon, especially one having 2 to 6 carbons and from 0 to 2 oxygen(s); R' is an organic or hydro moiety or covalent bond, and preferably methyl; lower alkyl, to include ethyl, propyl, butyl, pentyl, and hexyl; methoxy; lower alkoxy; or hydro; R" is an organic or hydro moiety or covalent bond, preferably methyl, lower alkyl, methoxy, lower alkoxy, or hydro, and especially hydro; and X is an integer from 1 to about 12, and preferably from 2 to 6.

For instance, the organic nitrate can be ethylene glycol dinitrate, isopropyl nitrate; glyceryl-1-mononitrate; glyceryl-1,2-dinitrate; glyceryl-1,3-dinitrate; nitroglycerin (GTN); butane-1,2,4-triol-trinitrate; erythrityl tetranitrate (ETN); pentaerythrityl tetranitrate (PETN); isosorbide mononitrate (ISMN), which may include isosorbide-2-mononitrate (IS2N) and/or isosorbide-5-mononitrate (ISSN); and/or isosorbide dininitrate (ISDN), and so forth and the like. An advantageous organic nitrate is GTN, and advantageous, other organic nitrates include ISDN, ETN, PETN, etc., which may have been given regulatory approval for use in treatments in other fields of medicine on human subjects.

In certain embodiments, at least one of the NO donors is a diazeniumdiolate (NONOate). In certain embodiments, the diazeniumdiolate is selected from the group consisting of:

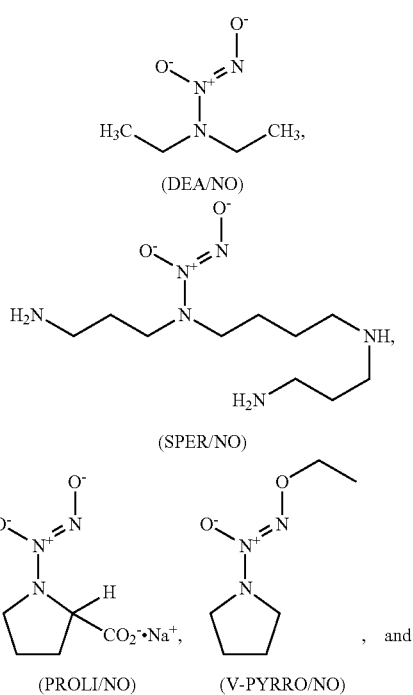

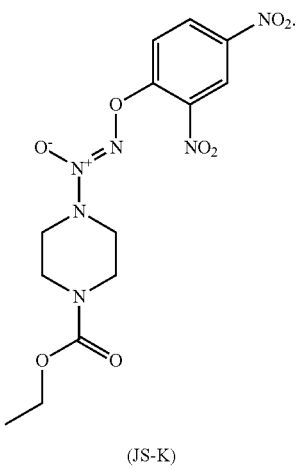

Any suitable diazeniumdiolates (also known as 'NONOates') can be used in certain embodiments. The first of this class to be described was an adduct of diethylamine and NO (diethylamine NONOate; DEA/NO). Diazeniumdiolates consist of a diolate group [N(O—)N═O] bound to a nucleophile adduct (a primary or secondary amine or polyamine) via a nitrogen atom. NONOates decompose spontaneously in solution at physiological pH and temperature, to generate up to 2 molar equivalents of NO. The rate of decomposition is dependent on the structure of the nucleophile. A range of NONOates has now been described with half-lives varying from seconds to hours. An attractive feature of this class of compounds is that their decomposition is not catalysed by thiols or biological tissue, unless specifically designed to (see below) and, because NO release follows simple first-order kinetics, the rate of NO release can be accurately predicted.

In certain embodiments, at least one of the NO donors is an S-nitrosothiol. In certain embodiments, the S-nitrosothiol is selected from the group consisting of:

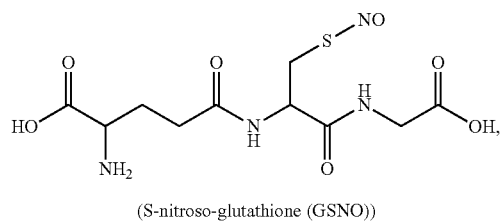

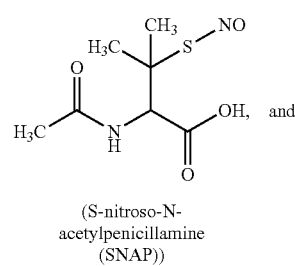

-continued

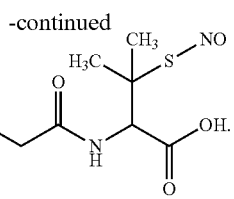

(S-nitroso-N-valerylpenicillamine (SNVP))

S-nitrosothiol is a class of NO donors which contain a single chemical bond between a thiol (sulphydryl) group (R—SH) and the NO moiety. Biological activity of S-nitrosothiols is highly influenced by the molecular environment of the parent thiol. That said, the complex chemistry of NO release from even the most basic S-nitrosothiol gives these compounds several means by which they can confer NO bioactivity. For instance, S-nitrosothiols are considered to be $NO^+$ donors and transfer of $NO^+$ across the plasma membrane via protein disulphide isomerases may allow even large molecule weight S-nitrosothiols to transfer oxides of nitrogen across cell membranes to subcellular targets.

In additional aspects, S-nitrosothiols have advantages over other classes of NO donors, such as the nitrates, as they have far less stringent metabolic requirements and this may be the reason that they do not induce tolerance with long-term use.

S-nitrosothiols have a number of potential advantages over other classes of NO donors. Firstly, some examples show tissue selectivity: S-nitroso-glutathione (GSNO) is selective for arteries over veins, giving them a different haemodynamic profile of action than those of classical organic nitrates. Additionally, S-nitrosothiols are potent antiplatelet agents, inhibiting aggregation at doses that do not influence vascular tone. Furthermore, the ability of S-nitrosothiols to directly transfer $NO^+$ species allows biological activity to be passed on through a chain of other thiols without the release of free NO. This mechanism of bioactivation may make S-nitrosothiols less susceptible to conditions of oxidative stress by effectively protecting the NO moiety from attack by oxygen-centered free radicals.

In certain embodiments, the nitric oxide donor is a small molecule.

Compounds that contain S-nitroso groups, O-nitroso-groups, and N-nitroso groups are all known to release nitric oxide and are thus exemplary NO donors.

O-nitroso compounds are compounds having one or more —O—NO groups, and are also referred to as O-nitrosylated compounds and nitrite compounds.

S-nitroso compounds are compounds with one or more —S—NO groups and are also referred to as nitrosothiols and S-nitrosylated compounds. An —S—NO group is also referred to in the art as a sulfonyl nitrite, a thionitrous acid ester, an S-nitrosothial or a thionitrite.

Compounds having an =N—NO group are referred to herein as N-nitroso compounds. Other NO compound includes NONOates, nitroprusside, nitrates, furoxans, etc.

In addition, nitro compounds —Y—$NO_2$ are included in the embodiment (where Y is N, C, O, S or transition metal).

In certain embodiments, at least one of the NO donors is a pharmaceutical agent comprising one or more NO groups, such as a pharmaceutical agent modified to be covalently or non-covalently bound to one or more NO groups. In certain embodiments, at least one of the NO groups is a nitro-oxy group, an S-nitrosothiol group, or a furoxan group. In certain embodiments, at least one of the NO groups is a nitro-oxy group. In certain embodiments, at least one of the NO donors is selected from the group consisting of:

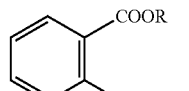
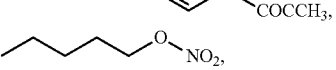

(NCX4215)

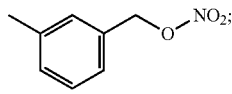

(NCX4016)

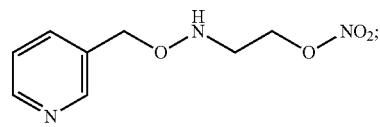

(nicorandil)

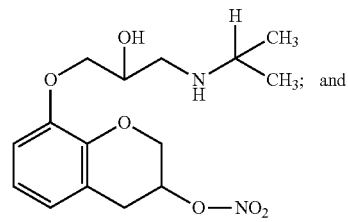

(Nipradilol (K-351))

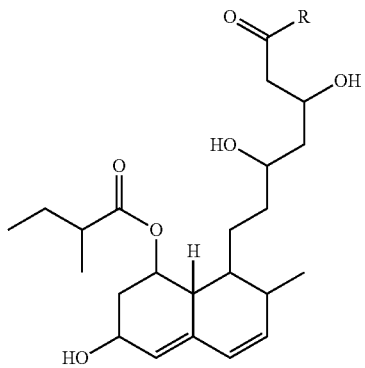

wherein R=OH (nitro-pravastatin), or R=O(CH2)4ONO2 (nitro-fluvastatin).

In certain embodiments, at least one of the NO groups is an S-nitrosothiol group, and the NO donor can include

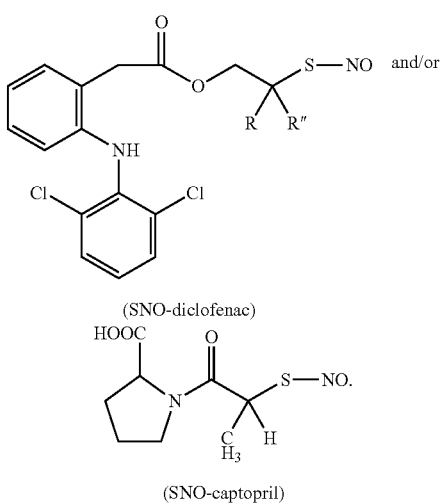

(SNO-diclofenac)

(SNO-captopril)

In certain embodiments, at least one of the NO groups is a furoxan group, and the NO donor can be

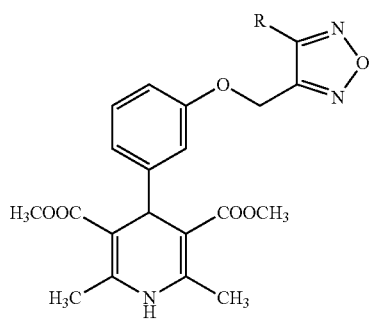

(furoxan bound to 4-phenyl-1,4-dihydropyridine).

In certain embodiments, the pharmaceutical agent comprising one or more NO groups is a PDE inhibitor comprising one or more NO groups, a biguanide comprising one or more NO groups, or a sirtuin pathway activator comprising one or more NO groups, or any combination thereof. For example, the PDE inhibitor comprising one or more NO groups is a PDE5 inhibitor comprising one or more NO groups. In certain embodiments, the PDE5 inhibitor comprising one or more NO groups is sildenafil comprising one or more NO groups. In certain embodiments, the biguanide comprising one or more NO groups is metformin comprising one or more NO groups. In certain embodiments, the sirtuin pathway activator comprising one or more NO groups is a PGC-1α activator comprising one or more NO groups. In certain embodiments, the PGC-1α activator comprising one or more NO groups is a thiazolidinedione comprising one or more NO groups. In certain embodiments, the thiazolidinedione comprising one or more NO groups is rosiglitazone comprising one or more NO groups. In certain embodiments, a compound of Formula I-a, I-b, I-c, II-a, II-b, II-c, III, IV, V, or VI or a compound listed in Table 1 or 3 comprises one or more NO groups.

Exemplary anti-hyperlipidemic agents

The anti-hyperlipidemic agents and/or anti-diabetic agent can be in a sub-therapeutic amount in lowering levels of total lipid content or triglyceride, LDL or cholesterol levels, or increasing the HDL level, or increasing glucose utilization, or increasing insulin sensitivity, or increasing fat oxidation. The anti-hyperlipidemic agent can be a lipid-lowering agent or hypolipidemic agent. The anti-hyperlipidemic agent can be an oral agent or injectable agent. The types of the anti-hyperlipidemic agents can include, but are not limited to, HMG-CoA inhibitors (or statins), fibrates, nicotinic acid, bile acid sequestrants (resins), cholesterol absorption inhibitors (e.g., ezetimibe), lomitapide, phytosterols, orlistat, CETP inhibitors, squalene synthase inhibitors, ApoA-1 Milano, Apoprotein-B inhibitors, PCSK9 inhibitors, or others. The statin type anti-hyperlipidemic agents can include but are not limited to: atorvastatin, fluvastatin, pravastatin, lovastatin, simvastatin, pitavastatin, cerivastatin, rosuvastatin, or lovastatin/niacin ER. The cholesterol absorption inhibitors can include but are not limited to ezetimibe, and combination of ezetimibe with simvastatin. The fibrate type of anti-hyperlipidemic agents can include but are not limited to: gemfibrozil, fenofibrate, fenofibric acid, clofibrate, or micronized fenofibrate. The bile acid sequestrants can include but are not limited to: colestipol, cholestyramine, or colesevelam. Other types of anti-hyperlipidemic agent can include dextrothyroxine sodium or icosapent.

Therapeutic Agents

Compositions described herein can further include one or more pharmaceutically active agent or therapeutic agents other than one or more agents selected from the group consisting of a phosphodiesterase (PDE) inhibitor, sirtuin pathway activator, anti-diabetic agent, anti-hyperlipidemic agent, glucagon-like peptide-1 (GLP-1) agonist, dipeptidyl peptidase-4 (DPP-4) inhibitor, sodium-glucose cotransporter-2 (SGLT2) inhibitor or gliflozin, a fibrate, a nitric oxide (NO) donor, nicotinic acid, nicotinamide riboside, nicotinic acid metabolite, and any combination thereof. The therapeutic agents or pharmaceutically active agents can be any agent that is known in the art. For example, the combination compositions can further comprise a dietary supplement that also has beneficial effects on lipid content, and/or insulin sensitivity.

Compositions described herein can further comprise one or more therapeutic agents that are herbs and/or supplements. The examples of the herbs and/or the supplements can be, but are not limited to: Acai, Alfalfa, Aloe, Aloe Vera, Aristolochic Acids, Asian Ginseng, Astragalus, Bacillus coagulans, Belladonna, Beta-carotene, Bifidobacteria, Bilberry, Bilberry, Biotin, Bitter Orange, Black Cohosh, Black Cohosh, Black psyllium, Black tea, Bladderwrack, Blessed thistle, Blond psyllium, Blueberry, Blue-green algae, Boron, Bromelain, Butterbur, Calcium, Calendula, Cancell/Cantron/Protocel, Cartilage (Bovine and Shark), Cassia cinnamon, Cat's Claw, Chamomile, Chasteberry, Chondroitin sulfate, Chromium, Cinnamon, Clove, Coenzyme Q-10, Colloidal Silver Products, Cranberry, Creatine, Dandelion, Dandelion, Devil's claw, DHEA, Dong quai, Echinacea, Ephedra, Essiac/Flor-Essence, Eucalyptus, European Elder (Elderberry), European Mistletoe, Evening Primrose Oil, Fenugreek, Feverfew, Fish oil, Flaxseed, Flaxseed oil, Folate, Folic acid, Garlic, Ginger, Gingko, Ginseng, Glucosamine hydrochloride, Glucosamine sulfate, Goldenseal, Grape Seed Extract, Green Tea, Hawthorn, Hoodia, Horse Chestnut, Horsetail, Hydrazine Sulfate, Iodine, Iron, Kava, Lactobacillus, Laetrile/Amygdalin, L-arginine, Lavender, Licorice, Lycium, Lycopene, Magnesium, Manganese, Melatonin, Milk Thistle, Mistletoe Extracts, Noni, Oral Probiotics, Pantothenic acid (Vitamin B5), Passionflower, PC-SPES, Pennyroyal, Peppermint, Phosphate salts, Pomegranate, Propolis, Pycnogenol, Pyridoxine (Vitamin B6), Red Clover, Red yeast, Riboflavin (Vitamin B2), Roman chamomile, Saccharomyces boulardii, S-Adenosyl-L-Methionine (SAMe), Sage, Saw Palmetto, Selected Vegetables/Sun's Soup, Selenium, Senna, Soy, St. John's Wort, sweet orange essence, Tea Tree Oil, Thiamine (Vitamin B1), Thunder God Vine, Turmeric, Valerian, Vitamin A, Vitamin B12, Vitamin C, Vitamin D, Vitamin E, Vitamin K, Wild yam, Yohimbe, Zinc or 5-HTP.

In various other embodiments, compositions for use in practicing one or more methods described herein are formulated such that they do not contain (or exclude) one or more of the following ingredients: caffeine, green tea extract or extracts from guarana seed or guarana plants. Compositions can also be formulated such that they are substantially free of high glycemic index carbohydrate, such as, e.g., simple carbohydrates, including sugars such as but not limited to sucrose, glucose, dextrose, maltose, fructose, and galactose, among others.

Dosage Amounts

In some embodiments, the dosing of a compound of Formula I-a, I-b, I-c, II-a, II-b, II-c, III, IV, V, or VI, a compound listed in Table 1 or 3, a phosphodiesterase (PDE) inhibitor, sirtuin pathway activator, anti-diabetic agent, anti-hyperlipidemic agent, glucagon-like peptide-1 (GLP-1) agonist, dipeptidyl peptidase-4 (DPP-4) inhibitor, sodium-glucose cotransporter-2 (SGLT2) inhibitor or gliflozin, a fibrate, a nitric oxide (NO) donor, nicotinic acid, nicotinamide riboside, or nicotinic acid metabolite can be designed to achieve a specified physiological concentration or circulating level. The physiological concentration can be a circulating level as measured in the serum or blood stream of a subject. The subject can be a human or an animal. A selected dosing can be altered based on the characteristics of the subject, such as weight, rate of energy metabolism, genetics, ethnicity, height, or any other characteristic.

In some embodiments, a selected dose of a composition can be administered to a subject such that the subject achieves a desired circulating level of a particular component. The desired circulating level of a component can be either a therapeutically effective level or a sub-therapeutic level.

In certain embodiments, a dosage regimen to treat, prevent, or ameliorate the condition(s) for which relief is sought, is modified in accordance with a variety of factors. These factors include the disorder from which the subject suffers, as well as the age, weight, sex, diet, and medical condition of the subject. Thus, in various embodiments, the dosage regimen actually employed varies and deviates from the dosage regimens set forth herein.

In some embodiments, the pharmaceutical agents that make up the combination therapy described herein are provided in a combined dosage form or in separate dosage forms intended for substantially simultaneous administration. In certain embodiments, the pharmaceutical agents that make up the combination therapy are administered sequentially, with either therapeutic compound being administered by a regimen calling for two-step administration. In some embodiments, two-step administration regimen calls for sequential administration of the active agents or spaced-apart administration of the separate active agents. In certain embodiments, the time period between the multiple administration steps varies, by way of non-limiting example, from a few minutes to several hours, depending upon the properties of each pharmaceutical agent, such as potency, solubility, bioavailability, plasma half-life and kinetic profile of the pharmaceutical agent.

The amount of pharmaceutical agent, or any other component used in a combination composition described herein, can be an amount that is therapeutically effective. The therapeutic amount can be assessed for individual subjects, or for groups of subjects. The group of subjects can be all potential subjects, or subjects having a particular characteristic such as age, weight, race, gender, or physical activity level.

The amount of pharmaceutical agent, or any other component used in a combination composition described herein, can be an amount that is sub-therapeutic. In some embodiments, using sub-therapeutic amounts of an agent or component can reduce the side-effects of the agent. Use of sub-therapeutic amounts can still be effective, particularly when used in synergy with other agents or components. A sub-therapeutic amount of the agent or component can be such that it is an amount below which would be considered therapeutic. For example, FDA guidelines can suggest a specified level of dosing to treat a particular condition, and a sub-therapeutic amount would be any level that is below the FDA suggested dosing level. The sub-therapeutic amount can be about 1, 5, 10, 15, 20, 25, 30, 35, 50, 75, 90, or 95% less than the amount that is considered to be a therapeutic amount.

In some embodiments, a dosing can be designed to achieve a specified physiological concentration or circulating level. The physiological concentration can be a circulating level as measured in the blood stream of a subject. The subject can be a human or an animal. A selected dosing can be altered based on the characteristics of the subject, such as weight, rate of energy metabolism, genetics, ethnicity, height, or any other characteristic.

In some embodiments, a composition comprises an amount of one or more agents selected from the group consisting of a phosphodiesterase (PDE) inhibitor, sirtuin pathway activator, anti-diabetic agent, anti-hyperlipidemic agent, glucagon-like peptide-1 (GLP-1) agonist, dipeptidyl peptidase-4 (DPP-4) inhibitor, sodium-glucose cotransporter-2 (SGLT2) inhibitor or gliflozin, a fibrate, a nitric oxide (NO) donor, nicotinic acid, nicotinamide riboside, nicotinic acid metabolite, and any combination thereof. The amount of one or more agents selected from the group consisting of a phosphodiesterase (PDE) inhibitor, sirtuin pathway activator, anti-diabetic agent, anti-hyperlipidemic agent, glucagon-like peptide-1 (GLP-1) agonist, dipeptidyl peptidase-4 (DPP-4) inhibitor, sodium-glucose cotransporter-2 (SGLT2) inhibitor or gliflozin, a fibrate, a nitric oxide (NO) donor, nicotinic acid, nicotinamide riboside, nicotinic acid metabolite, and any combination thereof can be a sub-therapeutic amount, and/or an amount that is synergistic with one or more other compounds in the composition or one or more of the compounds administered simultaneously or in close temporal proximity with the composition, such as a compound of Formula I-a, I-b, I-c, II-a, II-b, II-c, III, IV, V, or VI or a compound listed in Table 1 or 3. In some embodiments, the one or more agents selected from the group consisting of a phosphodiesterase (PDE) inhibitor, sirtuin pathway activator, anti-diabetic agent, anti-hyperlipidemic agent, glucagon-like peptide-1 (GLP-1) agonist, dipeptidyl peptidase-4 (DPP-4) inhibitor, sodium-glucose cotransporter-2 (SGLT2) inhibitor or gliflozin, a fibrate, a nitric oxide (NO) donor, nicotinic acid, nicotinamide riboside, nicotinic acid metabolite, and any combination thereof is administered in a low dose, a medium dose, or a high dose, which describes the relationship between two doses, and generally do not define any particular dose range. The compositions can be administered to a subject such that the subject is administered a selected total daily dose of the composition. The total daily dose can be determined by the sum of doses administered over a 24 hour period.

In some embodiments, the dosing can be recommended by a healthcare provider including, but not limited to a patient's physician, nurse, nutritionist, pharmacist, or other health care professional. A health care professional may include a person or entity that is associated with the health care system. Examples of health care professionals may include surgeons, dentists, audiologists, speech pathologists, physicians (including general practitioners and specialists), physician assistants, nurses, midwives, pharmaconomists/pharmacists, dietitians, therapists, psychologists, physical therapists, phlebotomists, occupational therapists, optometrists, chiropractors, clinical officers, emergency medical technicians, paramedics, medical laboratory technicians, radiographers, medical prosthetic technicians social workers, and a wide variety of other human resources trained to provide some type of health care service.

Dosage of a Compound of Formula I-a, I-b, I-c, II-a, II-b, II-c, III, IV, V, or VI or a Compound Listed in Table 1, 2, or 3

Any of the methods described herein can comprise administering an effective dose of a compound of Formula I-a, I-b, I-c, II-a, II-b, II-c, III, IV, V, or VI or a compound listed in Table 1 or 3. The dose of a compound of Formula I-a, I-b, I-c, II-a, II-b, II-c, III, IV, V, or VI or a compound listed in Table 1 or 3 can be a therapeutic dose or a sub-therapeutic dose.

The dose of a compound of Formula I-a, I-b, I-c, II-a, II-b, II-c, III, IV, V, or VI or a compound listed in Table 1 or 3 can be about, less than about, or more than about 0.01 mg, 0.02 mg, 0.03 mg, 0.04 mg, 0.05 mg, 0.1 mg, 0.2 mg, 0.3 mg, 0.4 mg, 0.5 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 20 mg, 25 mg, 50 mg, 75 mg, 100 mg, 125 mg, 145 mg, 150 mg, 175 mg, 200 mg, 225 mg, 250 mg, 300 mg, 350 mg, 500 mg, 1 g, 2 g, 3 g, 4 g, 5 g, 6 g, 7 g, 8 g, 9 g, or 10 g (per administration or per day) or any intermediate numbers or ranges.

Any of the methods described herein can comprise administering a dose of a compound of Formula I-a, I-b, I-c, II-a, II-b, II-c, III, IV, V, or VI or a compound listed in Table 1 or 3. The dose of a compound of Formula I-a, I-b, I-c, II-a, II-b, II-c, III, IV, V, or VI or a compound listed in Table 1 or 3 can be a therapeutic dose. The therapeutic dose can be above 500 mg, above 600 mg, above 700 mg, above 800 mg, above 900 mg, or above 1000 mg (1 g). A therapeutic dose of a compound of Formula I-a, I-b, I-c, II-a, II-b, II-c, III, IV, V, or VI or a compound listed in Table 1 or 3 can be about 1 g, about 1.1 g, about 1.2 g, about 1.3 g, about 1.4 g, about 1.5 g, about 1.6 g, about 1.7 g, about 1.8 g, about 1.9 g, about 2 g, or more than 2 g. The therapeutic dose can be above 500 mg/day, above 600 mg/day, above 700 mg/day, above 800 mg/day, above 900 mg/day, above 1000 mg/day (1 g/day). A therapeutic dose of a compound of Formula I-a, I-b, I-c, II-a, II-b, II-c, III, IV, V, or VI or a compound listed in Table 1 or 3 can be about 1 g/day, about 1.1 g/day, about 1.2 g/day, about 1.3 g/day, about 1.4 g/day, about 1.5 g/day, about 1.6 g/day, about 1.7 g/day, about 1.8 g/day, about 1.9 g/day, about 2 g/day, or more than 2 g/day. The dose of a compound of Formula I-a, I-b, I-c, II-a, II-b, II-c, III, IV, V, or VI or a compound listed in Table 1 or 3 can be a sub-therapeutic dose. The sub-therapeutic dose of a compound of Formula I-a, I-b, I-c, II-a, II-b, II-c, III, IV, V, or VI or a compound listed in Table 1 or 3 can be about 1-1000 mg, about 5-500 mg, about 10-100 mg, about 30-90 mg, about 50-70 mg, or about 62.5 mg. The sub-therapeutic dose of a compound of Formula I-a, I-b, I-c, II-a, II-b, II-c, III, IV, V, or VI or a compound listed in Table 1 or 3 can be, e.g., 1, 5, 10, 15, 25, 50, 125, 250, or 500 mg. The dose of a compound of Formula I-a, I-b, I-c, II-a, II-b, II-c, III, IV, V, or VI or a compound listed in Table 1 or 3 can be a sub-therapeutic dose. The sub-therapeutic dose of a compound of Formula I-a, I-b, I-c, II-a, II-b, II-c, III, IV, V, or VI or a compound listed in Table 1 or 3 can be about 40-70, 25-1000 mg/day, about 50-500 mg/day, about 100-500 mg/day. The sub-therapeutic dose of a compound of Formula I-a, I-b, I-c, II-a, II-b, II-c, III, IV, V, or VI or a compound listed in Table 1 or 3 can be about, less than about, or greater than about 1, 5, 10, 15, 25, 50, 60 125, 250, or 500 mg/day. The compound of Formula I-a, I-b, I-c, II-a, II-b, II-c, III, IV, V, or VI or a compound listed in Table 1 or 3 can be administered as a unit dose. The unit dose of a compound of Formula I-a, I-b, I-c, II-a, II-b, II-c, III, IV, V, or VI or a compound listed in Table 1 or 3 can be 1, 5, 10, 15, 25, 50, 62.5, 125 or 250 mg.

Dosage of NO Donors

Any of the methods described herein can comprise administering an effective dose of a NO donors, e.g., L-arginine and/or SNP. The dose of NO donors can be a therapeutic dose or a sub-therapeutic dose.

The dose of a NO donor can be about, less than about, or more than about 0.01 mg, 0.02 mg, 0.03 mg, 0.04 mg, 0.05 mg, 0.1 mg, 0.2 mg, 0.3 mg, 0.4 mg, 0.5 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 20 mg, 25 mg, 50 mg, 75 mg, 100 mg, 125 mg, 145 mg, 150 mg, 175 mg, 200 mg, 225 mg, 250 mg, 300 mg, 350 mg, 500 mg, 1 g, 2 g, 3 g, 4 g, 5 g, 6 g, 7 g, 8 g, 9 g, or 10 g (per administration or per day) or any intermediate numbers or ranges.

The dose of L-arginine can be about, less than about, or more than about 0.01 mg, 0.02 mg, 0.03 mg, 0.04 mg, 0.05 mg, 0.1 mg, 0.2 mg, 0.3 mg, 0.4 mg, 0.5 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 20 mg, 25 mg, 50 mg, 75 mg, 100 mg, 125 mg, 145 mg, 150 mg, 175 mg, 200 mg, 225 mg, 250 mg, 300 mg, 350 mg, 500 mg, 1 g, 2 g, 3 g, 4 g, 5 g, 6 g, 7 g, 8 g, 9 g, or 10 g (per administration or per day) or any intermediate numbers or ranges.

The dose of SNP can be about, less than about, or more than about 0.01 mg, 0.02 mg, 0.03 mg, 0.04 mg, 0.05 mg, 0.1 mg, 0.2 mg, 0.3 mg, 0.4 mg, 0.5 mg, 1 mg, 2 mg, 3 mg, 4 mg, 5 mg, 6 mg, 7 mg, 8 mg, 9 mg, 10 mg (per administration or per day) or any intermediate numbers or ranges.

The dose of an organic nitrate can be about, less than about, or more than about 0.01 mg, 0.02 mg, 0.03 mg, 0.04 mg, 0.05 mg, 0.1 mg, 0.2 mg, 0.3 mg, 0.4 mg, 0.5 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 20 mg, 25 mg, 50 mg, 75 mg, 100 mg, 125 mg, 145 mg, 150 mg, 175 mg, 200 mg, 225 mg, 250 mg, 300 mg, 350 mg, or 500 mg (per administration or per day) or any intermediate numbers or ranges.

The dose of a diazeniumdiolate (NONOate) can be about, less than about, or more than about 0.01 mg, 0.02 mg, 0.03 mg, 0.04 mg, 0.05 mg, 0.1 mg, 0.2 mg, 0.3 mg, 0.4 mg, 0.5 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 20 mg, 25 mg, 50 mg, 75 mg, 100 mg, 125 mg, 145 mg, 150 mg, 175 mg, 200 mg, 225 mg, 250 mg, 300 mg, 350 mg, 500 mg (per administration or per day) or any intermediate numbers or ranges.

The dose of a S-nitrosothiol can be about, less than about, or more than about 0.01 mg, 0.02 mg, 0.03 mg, 0.04 mg, 0.05 mg, 0.1 mg, 0.2 mg, 0.3 mg, 0.4 mg, 0.5 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 20 mg, 25 mg, 50 mg, 75 mg, 100 mg, 125 mg, 145 mg, 150 mg, 175 mg, 200 mg, 225 mg, 250 mg, 300 mg, 350 mg, 500 mg (per administration or per day) or any intermediate numbers or ranges.

The dose of a pharmaceutical agent comprising one or more NO groups can be about, less than about, or more than about 0.01 mg, 0.02 mg, 0.03 mg, 0.04 mg, 0.05 mg, 0.1 mg, 0.2 mg, 0.3 mg, 0.4 mg, 0.5 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 20 mg, 25 mg, 50 mg, 75 mg, 100 mg, 125 mg, 145 mg, 150 mg, 175 mg, 200 mg, 225 mg, 250 mg, 300 mg, 350 mg, 500 mg, 1 g, 2 g, 3 g, 4 g, 5 g, 6 g, 7 g, 8 g, 9 g, or 10 g (per administration or per day) or any intermediate numbers or ranges.

The dose can be administered daily. The dose can be a low dose, a medium dose, or a high dose. A low dose of L-arginine may comprise about, less than about, or more than about 20 mg, 25 mg, 50 mg, 75 mg, 100 mg, 125 mg, 145 mg, or more (or any intermediate numbers or ranges); a medium dose of L-arginine may comprise about, less than about, or more than about 150 mg, 175 mg, 200 mg, 225 mg, 250 mg, 300 mg, 350 mg, 500 mg, or more (or any intermediate numbers or ranges); and a high dose of L-arginine may comprise about, less than about or more than about 600 mg, 700 mg. 800 mg, 900 mg, 1 g, 2 g, 3 g, 4 g, 5 g, 6 g, 7 g, 8 g, 9 g, or 10 g or more (or any intermediate numbers or ranges). A daily low dose of L-arginine may comprise about, less than about, or more than about 20 mg, 25 mg, 50 mg, 75 mg, 100 mg, 125 mg, 140 mg, or more (or any intermediate numbers or ranges); a daily medium dose of L-arginine may comprise about, less than about, or more than about 150 mg, 175 mg, 200 mg, 225 mg, 250 mg, 300 mg, 350 mg, 500 mg, or more (or any intermediate numbers or ranges); and a daily high dose of L-arginine may comprise about, less than about or more than about 600 mg, 700 mg. 800 mg, 900 mg, 1 g, 2 g, 3 g, 4 g, 5 g, 6 g, 7 g, 8 g, 9 g, or 10 g or more (or any intermediate numbers or ranges).

A low dose of SNP may comprise about, less than about, or more than about 0.01 mg, 0.02 mg, 0.03 mg, 0.04 mg, 0.05 mg, 0.1 mg, 0.2 mg, 0.3 mg, 0.4 mg, 0.5 mg, 1 mg, or more (or any intermediate numbers or ranges); a medium dose of SNP may comprise about, less than about, or more than about 2 mg, 3 mg, 4 mg, 5 mg, 6 mg, 7 mg, 8 mg, or more (or any intermediate numbers or ranges); and a high dose of SNP may comprise about, less than about, or more than about 9 mg, 10 mg, 11 mg, 12 mg, 13 mg, 14 mg, 15 mg, or more. A daily low dose of SNP may comprise about, less than about, or more than about 0.01 mg, 0.02 mg, 0.03 mg, 0.04 mg, 0.05 mg, 0.1 mg, 0.2 mg, 0.3 mg, 0.4 mg, 0.5 mg, 1 mg, or more (or any intermediate numbers or ranges); a daily medium dose of SNP may comprise about, less than about, or more than about 2 mg, 3 mg, 4 mg, 5 mg, 6 mg, 7 mg, 8 mg, or more (or any intermediate numbers or ranges); and a daily high dose of L-arginine may comprise about, less than about, or more than about 9 mg, 10 mg, 11 mg, 12 mg, 13 mg, 14 mg, 15 mg, or more (or any intermediate numbers or ranges).

A composition comprising a unit dosage form can be formulated to provide a dosage of an NO donor. The dosage of the NO donor can be an amount of about 0.05 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 1.1 mg, about 1.2 mg, about 1.3 mg, about 1.4 mg, about 1.5 mg, about 1.6 mg, about 1.7 mg, about 1.8 mg, about 1.9 mg, about 2 mg, about 2.1 mg, about 2.5 mg, about 3 mg, about 4 mg, about 5 mg, about 10 mg, about 20 mg, about 30 mg, about 40 mg, about 50 mg, about 60 mg, about 70 mg, about 80 mg, about 90 mg, about 100 mg, about 150 mg, about 160 mg, about 180 mg, about 200 mg, about 250 mg, about 300 mg, about 350 mg, about 400 mg, about 500 mg, about 600 mg, about 700 mg, about 800 mg, about 900 mg, about 1 g, about 2 g, about 3 g, about 4 g, about 5 g, about 6 g, about 7 g, about 8 g, about 9 g, about 10 g, about 15 g, about 20 g or any intermediate ranges or values.

An sub-therapeutic dosage of the NO donor can be an amount of about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 1.1 mg, about 1.2 mg, about 1.3, about 1.4 mg, about 1.5 mg, about 1.6 mg, about 1.7 mg, about 1.8 mg, about 1.9 mg, about 2 mg, about 2.1 mg, about 2.5 mg, about 3 mg, about 4 mg, about 5 mg, about 10 mg, about 20 mg, about 30 mg, about 40 mg, about 50 mg, about 60 mg, about 70 mg, about 80 mg, about 90 mg, about 100 mg, about 150 mg, about 160 mg, about 180 mg, about 200 mg or any intermediate ranges or values.

Dosage of Sirtuin Pathway Activators

Any of the methods described herein can comprise administering a dose of sirtuin pathway activators. In some embodiments, the sirtuin pathway activator is a sirtuin activator. In some embodiments, the sirtuin activator is resveratrol. In some embodiments, the sirtuin activator is a polyphenol selected from the group consisting of chlorogenic acid, resveratrol, caffeic acid, stilbenes, cinnamic acid, hydroxycinnamic acids, ferulic acid, piceatannol, ellagic acid, epigallocatechin gallate, grape seed extract, and any analog thereof. In some embodiments, the sirtuin pathway activator is an AMPK activator. In some embodiments, AMPK activator is a biguanide. In some embodiments, the biguanide is metformin. The dose of a sirtuin pathway activator can be about, less than about, or more than about 0.01 mg, 0.02 mg, 0.03 mg, 0.04 mg, 0.05 mg, 0.1 mg, 0.2 mg, 0.3 mg, 0.4 mg, 0.5 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 20 mg, 25 mg, 50 mg, 75 mg, 100 mg, 125 mg, 145 mg, 150 mg, 175 mg, 200 mg, 225 mg, 250 mg, 300 mg, 350 mg, 500 mg, 1 g, 2 g, 3 g, 4 g, 5 g, 6 g, 7 g, 8 g, 9 g, 10 g, 20 g, 30 g, 40 g, 50 g, 60 g, 70 g, 80 g, 90 g, or 100 g (per administration or per day) or any intermediate numbers or ranges.

In some embodiments, a composition comprises an amount of a sirtuin pathway activator, such as a polyphenol (e.g., resveratrol) or a biguanide (e.g., metformin and any analogs thereof). The amount of sirtuin pathway activator may be a sub-therapeutic amount, and/or an amount that is synergistic with one or more other compounds in the composition or one or more other compounds administered simultaneously or in close temporal proximity with the composition. In some embodiments, the sirtuin pathway activator is administered in a low dose, a medium dose, or a high dose, which describes the relationship between two doses, and generally do not define any particular dose range.

Dosage of Anti-Diabetic Agents

A dose of the anti-diabetic agent, which can be a unit dose, can comprise a thiazolidinedione, guanide or a biguanide such as dimethylguanidine, galegine, rosiglitazone, metformin or any analogs thereof, that can be about, more than about, or less than about 0.01, 0.05, 0.1, 0.5, 1, 5, 10, 25, 50, 100, 150, 200, 250, 300, 350, 400, 450, 500, 1000, 1500, 2000, or 2550 mg per day. A dose of the anti-diabetic agent, which can be a unit dose, can comprise a guanide such as galegine or dimethylguanidine, or a biguanide such as metformin or any analogs thereof that can be between about 1-2550, 5-500, 5-50, 10-25, 20-50, 30-75, 10-100, 0.01-10, 0.05-20, 0.05-50, 0.1-10, 1-10, 1-20 or 25-2550 mg per day. The particular dosing of the anti-diabetic agent for a subject can be determined by a physician or a health care provider as described herein.

The desired circulating level of the of the anti-diabetic agent can be at least about, less than about, or more than about 0.01, 0.03, 0.05, 0.08, 0.1, 0.12, 0.15, 0.2, 0.25, 0.3, 1, 5, 10, 20, 30, 40, 50, 75, 100, 150, 200, 500 µM or more of the anti-diabetic agent such as galegine, dimethylguanidine, metformin or any analogs thereof. The desired circulating level of the of the anti-diabetic agent can be between about 0.01-500, 0.01-1, 1-10, 10-100, 100-500, 1-100 or 1-200 µM of the anti-diabetic agent such as galegine, dimethylguanidine, metformin or any analogs thereof.

In the case of metformin, a physician suggested starting dose can be 1000 mg daily, with subject specific dosing having a range of 500 mg to a maximum of 2550 mg daily (metformin hydrochloride extended-release tablets label www.accessdatafda.gov/drugsatfda_docs/label/2008/021574s0101bl.pdf). The particular dosing for a subject can be determined by a clinician by titrating the dose and measuring the therapeutic response. The therapeutic dosing level can be determined by measuring fasting plasma glucose levels and measuring glycosylated hemoglobin. A sub-therapeutic amount can be any level that would be below the recommended dosing of metformin. For example, if a subject's therapeutic dosing level is determined to be 700 mg daily, a dose of 600 mg would be a sub-therapeutic amount. Alternatively, a sub-therapeutic amount can be determined relative to a group of subjects rather than an individual subject. For example, if the average therapeutic amount of metformin for subjects with weights over 300 lbs is 2000 mg, then a sub-therapeutic amount can be any amount below 2000 mg.

Any of the methods described herein can comprise administering a dose of metformin. The dose of metformin can be a therapeutic dose. The therapeutic dose can be above 500 mg, above 600 mg, above 700 mg, above 800 mg, above 900 mg, or above 1000 mg (1 g). A therapeutic dose of metformin can be about 1 g, about 1.1 g, about 1.2 g, about 1.3 g, about 1.4 g, about 1.5 g, about 1.6 g, about 1.7 g, about 1.8 g, about 1.9 g, about 2 g, or more than 2 g. The therapeutic dose can be above 500 mg/day, above 600 mg/day, above 700 mg/day, above 800 mg/day, above 900 mg/day, above 1000 mg/day (1 g/day). A therapeutic dose of metformin can be about 1 g/day, about 1.1 g/day, about 1.2 g/day, about 1.3 g/day, about 1.4 g/day, about 1.5 g/day, about 1.6 g/day, about 1.7 g/day, about 1.8 g/day, about 1.9 g/day, about 2 g/day, or more than 2 g/day. The dose of metformin can be a sub-therapeutic dose. The sub-therapeutic dose of metformin can be about 1-1000 mg, about 5-500 mg, about 10-100 mg, about 30-90 mg, about 50-70 mg, or about 62.5 mg. The sub-therapeutic dose of metformin can be, e.g., 1, 5, 10, 15, 25, 50, 125, 250, or 500 mg. The dose of metformin can be a sub-therapeutic dose. The sub-therapeutic dose of metformin can be about 40-70, 25-1000 mg/day, about 50-500 mg/day, about 100-500 mg/day. The sub-therapeutic dose of metformin can be about, less than about, or greater than about 1, 5, 10, 15, 25, 50, 60 125, 250, or 500 mg/day. The metformin can be administered as a unit dose. The unit dose of metformin can be 1, 5, 10, 15, 25, 50, 62.5, 125 or 250 mg.

An oral dosing of about 50 mg metformin or any analogs thereof can achieve a circulating level of metformin in a subject that is about 1-3 µM metformin or any analogs thereof. An oral dosing of about 1000 mg metformin or any analogs thereof can achieve a circulating level of metformin or any analogs thereof in a subject that is about 10 µM. The desired circulating level of the metformin can be about 1, 2, 4, 5 µM or more of metformin.

Dosage of Nicotinic Acid, Nicotinamide Riboside, or Nicotinic Acid Metabolites

In the case of nicotinic acid administered alone to lower lipid content, the physician suggested starting dose is 1000-3000 mg daily, with subject specific dosing having a range of 1 mg to 1000 mg daily. The particular dosing for a subject can be determined by a clinician by titrating the dose and measuring the therapeutic response. The therapeutic dosing level can be determined by measuring fasting plasma cholesterol and LDL levels without causing clinically significant cutaneous vasodilation. A sub-therapeutic amount can be any level that would be below the recommended dosing of nicotinic acid. For example, if a subject's therapeutic dosing level is determined to be 700 mg daily, a dose of 600 mg would be a sub-therapeutic amount. Alternatively, a sub-therapeutic amount can be determined relative to a group of subjects rather than an individual subject. For example, if the average therapeutic amount of nicotinic acid, nicotinamide riboside or nicotinic acid metabolites for subjects with weights over 300 lbs is 2000 mg, then a sub-therapeutic amount can be any amount below 2000 mg.

In the case of nicotinic acid, nicotinamide riboside, or nicotinic acid metabolites, the therapeutically effective level of the nicotinic acid, nicotinamide riboside, nicotinic acid metabolites can be a circulating level between about 1-100 nM. A sub-therapeutic level of the nicotinic acid, nicotinamide riboside, or nicotinic acid metabolites, by itself or in any combination, can be any circulating level at least about, less than about, or more than about 1, 2.5, 5, 10, 15, 20, 25, 30, 35, 40, 45, 50, 60, 70, 80, 90 or 100 nM. The sub-therapeutic level of the one or more agents selected from the group consisting of nicotinic acid, nicotinamide riboside, and nicotinic acid metabolite, in a subject composition formulated for administration can be less than about 1, 5, 10, 20, 30, 50, 60, 70, 80, 90, 100, 125, 150, 175, 200, 250, 300, 350, 400, 450, 500, 600, 700, 750, 800, 900 or 1000 mg of the one or more agents selected from the group consisting of nicotinic acid, nicotinamide riboside, and nicotinic acid metabolite.

A dose, which can be a unit dose, can comprise nicotinic acid, nicotinamide riboside or nicotinic acid metabolites, that can be about, more than about, or less than about 0.01, 0.05, 0.1, 0.5, 1, 2, 5, 10, 20, 40, 60, 80, 100, 200, 250, 400, 500, 800, 1000, or 1500 mg of the nicotinic acid, nicotinamide riboside, or nicotinic acid metabolites. The composition can comprise between about 1-100, or 5-50, or 10-20 mg of the one or more agents selected from the group consisting of nicotinic acid, nicotinamide riboside, and nicotinic acid metabolite. In some embodiments, a unit dose can comprise at least about 1 mg of one or more agents selected from the group consisting of nicotinic acid, nicotinamide riboside, and nicotinic acid metabolite. In some embodiments, a unit dose can comprise less than 250 mg of one or more agents selected from the group consisting of nicotinic acid, nicotinamide riboside, and nicotinic acid metabolite. The dosage can be adjusted for the intended subject administered. For example, a dose that is suitable for a canine can be less than the dose that is suitable for a human. The amount of nicotinic acid, nicotinamide riboside and/or nicotinic acid metabolites as described herein can be administered daily or simultaneously. The amount as described herein can be administered in one dose or separately in multiple doses daily.

In some embodiments, the composition comprises both nicotinic acid and nicotinamide riboside, and the total amount of nicotinic acid and nicotinamide riboside can be about, more than about, or less than about 0.01, 0.05, 0.1, 0.5, 1, 2, 5, 10, 20, 40, 60, 80, 100, 200, 250, 400, 500, 600, 800, 900, 1000, or 1500 mg.

In other embodiments, a daily dose of one or more agents selected from the group consisting of nicotinic acid, nicotinamide riboside, and nicotinic acid metabolite can be about, more than about, or less than about 0.0001 mg/kg (mg of one or more agents selected from the group consisting of nicotinic acid, nicotinamide riboside, and nicotinic acid metabolite/kg of the subject receiving the dose), 0.005 mg/kg, 0.01 mg/kg, 0.5 mg/kg, 1 mg/kg, 2.5 mg/kg, 5 mg/kg, 7.5 mg/kg, 10 mg/kg, 12.5 mg/kg, 15 mg/kg, 20 mg/kg, 25 mg/kg, 50 mg/kg, 75 mg/kg, 100 mg/kg, or more.

An oral dosing of about 3,000 mg nicotinic acid or nicotinamide riboside can achieve a circulating level of nicotinic acid or nicotinamide riboside in a subject that is about 10 µM nicotinic acid or nicotinamide riboside. An oral dosing of about 50 mg nicotinic acid or nicotinamide riboside can achieve a circulating level of nicotinic acid or nicotinamide riboside in a subject that is about 10-100 nM nicotinic acid or nicotinamide riboside.

The desired circulating or serum level of the one or more agents selected from the group consisting of nicotinic acid, nicotinamide riboside, and nicotinic acid metabolite can be at least about, less than about, or more than about 0.1, 0.25, 0.5, 0.75, 1, 10, 20, 40, 60, 80, 100, 120, 200, 400, 500, 1000, 1500, 2000, 2550, or 3000 nM or more of the one or more agents selected from the group consisting of nicotinic acid, nicotinamide riboside, and nicotinic acid metabolite. The desired circulating or serum level of the one or more agents selected from the group consisting of nicotinic acid, nicotinamide riboside, and nicotinic acid metabolite can be between about 0.1-3000, 0.1-10, 10-100, 10-500, 100-1000, 1-10, 1-100, 1000-3000 or 1-1000 nM of the one or more agents selected from the group consisting of nicotinic acid, nicotinamide riboside, and nicotinic acid metabolite. The therapeutically effective level of one or more agents selected from the group consisting of nicotinic acid, nicotinamide riboside, and nicotinic acid metabolite can be between 44-111 µM, which corresponds to about 10-20 µg/mL.

The sub-therapeutic amount of nicotinic acid, nicotinamide riboside, and/or nicotinic acid metabolites can be less than 1 g, 500, 250, 100, 50 or 10 mg. The amount of nicotinic acid, nicotinamide riboside, and/or nicotinic acid metabolites can be between about 1-100 mg. The amount of nicotinic acid, nicotinamide riboside, and/or nicotinic acid metabolites can be capable of achieving a circulating level of nicotinic acid, nicotinamide riboside, and/or nicotinic acid metabolites that is about 1-100 nM, higher than about 100 nM or at least about 10 nM.

Dosage of Polyphenols

Any of the methods described herein can comprise administering a dose of a polyphenol, e.g., resveratrol. The dose may be administered daily. The dose can be a low dose, a medium dose, or a high dose. A low dose of resveratrol may comprise about, less than about, or more than about 0.5 mg, 1 mg, 2.5 mg, 5 mg, 7.5 mg, 10 mg, 12.5 mg, 15 mg, 20 mg, 25 mg, 50 mg, 75 mg, 100 mg, or more; a medium dose of resveratrol may comprise about, less than about, or more than about 20 mg, 25 mg, 50 mg, 75 mg, 100 mg, 125 mg, 150 mg, 175 mg, 200 mg, 250 mg, or more; and a high dose of resveratrol may comprise about, less than about, or more than about 150 mg, 175 mg, 200 mg, 225 mg, 250 mg, 300 mg, 350 mg, 400 mg, or more. A daily low dose of resveratrol may comprise about, less than about, or more than about 0.5 mg, 1 mg, 2.5 mg, 5 mg, 7.5 mg, 10 mg, 12.5 mg, 15 mg, 20 mg, 25 mg, 50 mg, 75 mg, 100 mg, or more; a daily medium dose of resveratrol may comprise about, less than about, or more than about 20 mg, 25 mg, 50 mg, 75 mg, 100 mg, 125 mg, 150 mg, 175 mg, 200 mg, 250 mg, or more; and a daily high dose of resveratrol may comprise about, less than about, or more than about 150 mg, 175 mg, 200 mg, 225 mg, 250 mg, 300 mg, 350 mg, 400 mg, or more.

A dose, which can be a unit dose, can comprise about, less than about, or more than about 1, 5, 10, 25, 35, 50, 51, 75, 100, 150, 200, 250, 300, 350, 400, 450, 500, or more mg of resveratrol. The composition can comprise between about 5-500, 30-250, or 35-100 mg of resveratrol. In some embodiments, a unit dose can comprise at least about 35 mg of resveratrol. The amount of resveratrol as described herein can be administered daily or simultaneously. The amount as described herein can be administered in one dose or separately in multiple doses daily.

A daily low dose of resveratrol can comprise about, less than about, or more than about 0.5 mg/kg (mg of resveratrol/kg of the subject receiving the dose), 1 mg/kg, 2.5 mg/kg, 5 mg/kg, 7.5 mg/kg, 10 mg/kg, 12.5 mg/kg, 15 mg/kg, 20 mg/kg, 25 mg/kg, 50 mg/kg, or more; a daily medium dose of resveratrol can comprise about, less than about, or more than about 20 mg/kg, 25 mg/kg, 50 mg/kg, 75 mg/kg, 100 mg/kg, 125 mg/kg, 150 mg/kg, 175 mg/kg, 200 mg/kg, 250 mg/kg, or more; and a daily high dose of resveratrol can comprise about, less than about, or more than about 150 mg/kg, 175 mg/kg, 200 mg/kg, 225 mg/kg, 250 mg/kg, 300 mg/kg, 350 mg/kg, 400 mg/kg, or more. The dosing range as defined to low, medium or high can be dependent on the subject receiving the dose and vary from subject to subject.

The desired circulating level of the resveratrol can be at least about, less than about, or more than about 40, 60, 80, 100, 120, 150, 200, 300, 400, 800, 1600, 3000, or 5000 nM or more of the resveratrol. The desired circulating level of the resveratrol can be between about 40-5000 nM of the resveratrol.

An oral dosing of about 1100 mg of resveratrol can achieve a circulating level of resveratrol in a subject that is about 0.5 mM resveratrol. An oral dosing of about 50 mg of resveratrol can achieve a circulating level of resveratrol in a subject that is about 200 nM resveratrol.

Dosage of Thiazoladinediones

Any of the methods described herein can comprise administering a dose of a thiazolidinedione. Exemplary thiazoladinediones are described herein. The dose of thiazolidinedione can be a therapeutic dose or a sub-therapeutic dose. The thiazolidinedione can be rosiglitazone. The dose of the rosiglitazone can be at least 100 µg. The dose of the rosiglitazone can be about or less than about 4 mg. The dose of the rosiglitazone can be 100 µg-4 mg, can be 200 µg-2 mg, can be 400 µg to 1000 µg. The desired circulating level of the rosiglitazone can be about 1, 10, 25, 50, 100, 400 nM or more of rosiglitazone. The thiazolidinedione can be pioglitazone. The dose of the pioglitazone can be at least 100 µg. The dose of the pioglitazone can be about or less than about 15 mg. The dose of the pioglitazone can be 100 µg-45 mg, can be 200 µg-10 mg, can be 400 µg to 5 mg, can be 500 µg to 1 mg. The desired circulating level of the pioglitazone can be about 0.25, 0.50, 1.0, 2.0 µM or more of pioglitazone.

Dosage of PDE Inhibitors

In some embodiments, a composition comprises an amount of a selective PDE inhibitor (e.g., PDE-5 inhibitor including but not limited to sildenafil or icariin). The amount of a PDE inhibitor may be a subtherapeutic amount, and/or an amount that is synergistic with one or more other compounds in the composition or one or more of the compounds administered simultaneously or in close temporal proximity with the composition. In some embodiments, the PDE inhibitor is administered in a low dose, a medium dose, or a high dose, which describes the relationship between two doses, and generally do not define any particular dose range.

A dose or daily dose of sildenafil can be about or less than about 0.05, 0.1, 0.5, 1, 2, 3, 4, 5, 10, 20, 40, 60, 80, or 100 mg of sildenafil. A dose or daily dose of sildenafil can be about 0.05-100, 1-50, or 5-20 mg of sildenafil. A dose or daily dose of icariin can be about or less than about 1, 10, 12.5, 20, 25, 50, or 100 mg of icariin. A dose or daily dose of icariin can be about 1-100, 5-60, or 10-30 mg of icariin. A dose or daily dose of tadalafil can be about 0.01, 0.05, 0.1, 0.5, 1, 15, 2, 2.5, 5, 10, 15, or 20 mg. A dose or daily dose of tadalafil can be about 0.1-50, 0.5-20, or 1-10 mg. A dose or daily dose of vardenafil can be about 0.01, 0.05, 0.1, 0.5, 1, 15, 2, 2.5, 5, 10, 15, or 20 mg. A dose or daily dose of vardenafil can be about 0.1-50, 0.5-20, or 1-10 mg. A dose or daily dose of avanafil can be about 1, 10, 20, 50, or 100 mg. A dose or daily dose of avanafil can be about 1-100, 5-50, or 10-40 mg. A dose or daily dose of lodenafil can be about 0.05, 0.1, 0.5, 1, 2, 5, 10, 20 or 50 mg. A dose or daily dose of lodenafil can be about 0.05-100, 1-50, or 5-20 mg. A dose or daily dose of mirodenafil can be about 0.05, 0.1, 0.5, 1, 2, 5, 10, 20, 50, 80, or 100 mg. A dose or daily dose of mirodenafilcan be about 0.05-100, 1-50, or 5-20 mg. A dose or daily dose of udenafil can be about 0.05, 0.1, 0.5, 1, 2, 5, 10, 20, or 50 mg. A dose or daily dose of udenafil can be about 0.05-100, 1-50, or 5-20 mg.

The dosing of sildenafil can achieve a circulating concentration of about or less than about 0.1, 0.5, 1, 2, 5, or 10 nM. In some embodiments, the target or achieved circulating concentration of sildenafil is less than about 1 nM. A unit dose of about 20 mg of sildenafil can achieve a circulating concentration of about 100 nM of sildenafil. A unit dose of about 0.2 mg of sildenafil can achieve a circulating concentration of about 1 nM of sildenafil. The dosing of about icariin can achieve a circulating concentration of about or less than about 0.1, 0.5, 1, 2, 5, or 10 nM. In some embodiments, the target or achieved circulating concentration of icariin is less than about 1 nM. A unit dose of about 20 mg of icariin can achieve a circulating concentration of about 100 nM of icariin. A unit dose of about 0.1 mg of icariin can achieve a circulating concentration of about 1 nM of icariin.

Another aspect of the disclosure provides compositions comprising synergizing amounts of PDE-5 inhibitor, such as, e.g., sildenafil, icariin, tadalafil, vardenafil, avanafil, lodenafil, mirodenafil and udenafil, in combination with a compound of Formula I-a, I-b, I-c, II-a, II-b, II-c, III, IV, V, or VI or a compound listed in Table 1 or 3. Thus, one embodiment provides a composition comprising a compound of Formula I-a, I-b, I-c, II-a, II-b, II-c, III, IV, V, or VI or a compound listed in Table 1 or 3 in an amount of about 0.25 to about 3.0 g and sildenafil in an amount of about 0.05 to about 100 mg. In compositions comprising a PDE inhibitor or methods comprising administration of a PDE inhibitor (separately from or concurrently with one or more other components), the PDE inhibitor may be provided in an amount that produces a peak plasma concentration of about, less than about, or more than about 0.1, 1, 5, 10, 25, 50, 100, 500, 1000, 2500, 5000, 10000, or more nM.

Some embodiments of a method described herein comprise co-administering a compound of Formula I-a, I-b, I-c, II-a, II-b, II-c, III, IV, V, or VI or a compound listed in Table 1 or 3 in an amount of about 0.25 to about 3.0 g/day and a PDES inhibitor in an amount of about 0.05 to about 2000 mg/day. The PDES inhibitor can be any of the PDES inhibitors described herein, such as sildenafil. The daily dose of the PDES inhibitor can be as described herein. In some embodiments, such methods further comprise co-administering resveratrol in an amount of about 50 to about 500 mg/day or co-administering metformin in an amount of about 25 and about 500 mg/day.

Ratio of Dosages

In some embodiments, the composition administered to a subject can be optimized for a given subject. For example, the ratio of a compound of Formula I-a, I-b, I-c, II-a, II-b, II-c, III, IV, V, or VI or a compound listed in Table 1 or 3 to a phosphodiesterase (PDE) inhibitor, sirtuin pathway activator, anti-diabetic agent, anti-hyperlipidemic agent, glucagon-like peptide-1 (GLP-1) agonist, dipeptidyl peptidase-4 (DPP-4) inhibitor, sodium-glucose cotransporter-2 (SGLT2) inhibitor or gliflozin, a fibrate, a nitric oxide (NO) donor, nicotinic acid, nicotinamide riboside, nicotinic acid metabolite, or the particular components in a combination composition can be adjusted. The ratio and/or particular components can be selected after evaluation of the subject after being administered one or more compositions with varying ratios of a compound of Formula I-a, I-b, I-c, II-a, II-b, II-c, III, IV, V, or VI or a compound listed in Table 1 or 3 to a phosphodiesterase (PDE) inhibitor, sirtuin pathway activator, anti-diabetic agent, anti-hyperlipidemic agent, glucagon-like peptide-1 (GLP-1) agonist, dipeptidyl peptidase-4 (DPP-4) inhibitor, sodium-glucose cotransporter-2 (SGLT2) inhibitor or gliflozin, a fibrate, a nitric oxide (NO) donor, nicotinic acid, nicotinamide riboside, nicotinic acid metabolite, or varying combination composition components.

In some embodiments, the molar or mass ratios are circulating molar or mass ratios achieved after administration one or more compositions to a subject. The compositions can be a combination composition described herein. The molar ratio of a combination composition in a dosing form can be adjusted to achieve a desired circulating molar ratio. The molar ratio can be adjusted to account for the bioavailability, the uptake, and the metabolic processing of the one or more components of a combination composition. For example, if the bioavailability of a component is low, then the molar amount of a that component can be increased relative to other components in the combination composition. In some embodiments, the circulating molar or mass ratio is achieved within about 0.1, 0.5, 0.75, 1, 3, 5, or 10, 12, 24, or 48 hours after administration. The circulating molar or mass ratio can be maintained for a time period of about or greater than about 0.1, 1, 2, 5, 10, 12, 18, 24, 36, 48, 72, or 96 hours.

In some embodiments, the combination compositions can have a specified ratio of components. The specified ratio can provide for effective and/or synergistic treatment of hyperlipidemic conditions, which, for example, can be measured as a reduction in total lipid content, reduction in cholesterol level, reduction in triglyceride level, reduction in LDL level, reduction in body weight, reduction in lipid accumulation, increase in HDL level, increase in fat oxidation, increase in insulin sensitivity, and/or increase in glucose utilization. The ratio can be a mass ratio, a molar ratio, or a volume ratio.

In certain embodiments, there are provided compositions with (a) a compound of Formula I-a, I-b, I-c, II-a, II-b, II-c, III, IV, V, or VI or a compound listed in Table 1 or 3; and (b)

a therapeutic agent selected from the group consisting of a phosphodiesterase (PDE) inhibitor, sirtuin pathway activator, anti-diabetic agent, anti-hyperlipidemic agent, glucagon-like peptide-1 (GLP-1) agonist, dipeptidyl peptidase-4 (DPP-4) inhibitor, sodium-glucose cotransporter-2 (SGLT2) inhibitor or gliflozin, a fibrate, a nitric oxide (NO) donor, nicotinic acid, nicotinamide riboside, nicotinic acid metabolite, and any combination thereof. In some embodiments, the molar ratio of (a) to (b) is about, less than about, or greater than about 0.00001, 0.00005, 0.0001, 0.0005, 0.001, 0.005, 0.01, 0.05, 0.1, 0.5, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 120, 130, 140, 150, 160, 170, 180, 190, 200, 220, 250, 300, 350, 400, or 500 or any intermediate ranges or numbers. In some embodiments, the molar ratio of component (a) to (b) in said composition is greater than about 20, 40, 60, 80, 100, 120, or 150.

In some embodiments, the circulating molar ratio of a compound of Formula I-a, I-b, I-c, II-a, II-b, II-c, III, IV, V, or VI or a compound listed in Table 1 or 3 to sildenafil is about or greater than about 100, 1,000, 2,5000, 5,000, 10,000, 50,000, 100,000, 250,000, 500,000, 750,000 or more. In some embodiments, the circulating molar ratio of resveratrol to sildenafil is about or greater than about 50, 100, 200, 400, 800 or more.

Dosage Administration

The dosing of the combination compositions can be administered about, less than about, or more than about 1, 2, 3, 4, 5, 6, 7, 8, 9, 10 or more times a daily. A subject can receive dosing for a period of about, less than about, or greater than about 1, 2, 3, 4, 5, 6, 7, 8, 9, 10, 11, 12, 13, 14 or more days, weeks or months.

Any of the above agents can be administered in unit doses. Any of the above agents in the amounts described herein can be administered in unit doses. A unit dose can be a fraction of the daily dose, such as the daily dose divided by the number of unit doses to be administered per day. A unit dose can be a fraction of the daily dose that is the daily dose divided by the number of unit doses to be administered per day and further divided by the number of unit doses (e.g., tablets) per administration. The number of unit doses per administration may be about, less than about, or more than about 1, 2, 3, 4, 5, 6, 7, 8, 9, 10, or more. The number of doses per day may be about, less than about, or more than about 1, 2, 3, 4, 5, 6, 7, 8, 9, 10, or more. The number of unit doses per day may be determined by dividing the daily dose by the unit dose, and may be about, less than about, or more than about 1, 2, 3, 4, 5, 6, 7, 8, 9, 10, 11, 12, 13, 14, 15, 6, 17, 18, 19, 20, or more unit doses per day. For example, a unit dose can be about the daily dose or about ½, ⅓, ¼, ⅕, ⅙, ⅐, ⅛, ⅑, ⅒ of the daily dose. A unit dose can be about one-third of the daily amount and administered to the subject three times daily. A unit dose can be about one-half of the daily amount and administered to the subject twice daily. A unit dose can be about one-fourth of the daily amount with two unit doses administered to the subject twice daily. In some embodiments, a unit dose comprises about, less than about, or more than about 50 mg resveratrol. In some embodiments, a unit dose comprises about, less than about, or more than about 50 mg metformin. In some embodiments, a unit dose comprises about, less than about, or more than about 550 mg of a compound of Formula I-a, I-b, I-c, II-a, II-b, II-c, III, IV, V, or VI or a compound listed in Table 1 or 3. In some embodiments, a unit dose is administered as two unit doses two times per day. In some embodiments, a unit dose is administered as one unit dose two times per day.

Administration

The length of the period of administration and/or the dosing amounts can be determined by a physician or any other type of clinician. The physician or clinician can observe the subject's response to the administered compositions and adjust the dosing based on the subject's performance. For example, dosing for subjects that show reduced effects in energy regulation can be increased to achieve desired results.

The agents, compounds, or compositions described herein can be administered to a subject orally or by any other methods, such as intravenous, intraarterial, parenteral, buccal, topical, transdermal, rectal, intramuscular, subcutaneous, intraosseous, transmucosal, or intraperitoneal administration. Methods of oral administration include administering the composition as a liquid, a solid, or a semi-solid that can be taken in the form of a dietary supplement or a food stuff.

The agents described herein can be co-administered. The agents can be administered simultaneously, e.g., in a single composition, or can be administered sequentially. The agents can be administered sequentially within 1, 2, 3, 4, 5, 6, 7, 8, 9, 10, 11, 12, 13, 14, 15, 30, 60, 90, or 120 minutes from each other.

In some embodiments, the components in the compositions can be administered together at the same time in the same route, or administered separately. The components in the compositions can also be administered subsequently. In some embodiments, a compound of Formula I-a, I-b, I-c, II-a, II-b, II-c, III, IV, V, or VI or a compound listed in Table 1 or 3 in the compositions can be administered to a subject in conjunction with one or more therapeutic agents. In some embodiments, the components in the compositions can be administered at the same or different administration route. For example, a compound of Formula I-a, I-b, I-c, II-a, II-b, II-c, III, IV, V, or VI or a compound listed in Table 1 or 3, and/or biguanide (e.g., metformin or any analog thereof) can be administered orally while nicotinic acid, nicotinamide riboside and/or nicotinic acid metabolites can be administered via intravenous injection. Each of the metabolites can be administered via the same or different administration routes.

The agents, compounds, or compositions described herein can be administered periodically. For example, the agents, compounds, or compositions can be administered one, two, three, four times a day, or even more frequent. The subject can be administered every 1, 2, 3, 4, 5, 6 or 7 days. In some embodiments, the agents, compounds, or compositions are administered three times daily. The administration can be concurrent with meal time of a subject. The period of treatment or diet supplementation can be for about 1, 2, 3, 4, 5, 6, 7, 8, or 9 days, 2 weeks, 1-11 months, or 1 year, 2 years, 5 years or even longer. In some embodiments, the subject is administered the agents for six weeks or more. In some embodiments, the dosages that are administered to a subject can change or remain constant over the period of treatment. For example, the daily dosing amounts can increase or decrease over the period of administration.

The length of the period of administration and/or the dosing amounts can be determined by a physician, a nutritionist, or any other type of clinician. The physician, nutritionist, or clinician can observe the subject's response to the administered compositions and adjust the dosing based on the subject's performance. For example, dosing for subjects that show reduced effects in energy regulation can be increased to achieve desired results.

Formulations

Any of the agents described herein can be administered to the subject in one or more compositions. A composition for use in practicing any of the methods described herein can comprise any combination of the agents described herein. For example, a composition described herein can comprise one, two, three, four, or more than four of the agents described herein.

Compositions described herein can be compounded into a variety of different dosage forms. For example, compositions can be formulated for oral administration, e.g., as a tablet, chewable tablet, caplets, capsule, soft gelatin capsules, lozenges or solution. Compositions can be formulated as a nasal spray or for injection when in its solution form. In some embodiments, the composition is a liquid composition suitable for oral consumption.

In some embodiments, the agents are formulated into a composition suitable for oral administration. Compositions described herein suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion, including liquid dosage forms (e.g., a suspension or slurry), and oral solid dosage forms (e.g., a tablet or bulk powder). Oral dosage forms may be formulated as tablets, pills, dragees, capsules, emulsions, lipophilic and hydrophilic suspensions, liquids, gels, syrups, slurries, suspensions and the like, for oral ingestion by an individual or a patient to be treated. Such dosage forms can be prepared by any of the methods of formulation. For example, the active ingredients can be brought into association with a carrier, which constitutes one or more necessary ingredients. Capsules suitable for oral administration include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. Optionally, the inventive composition for oral use can be obtained by mixing a composition a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The compositions may be in liquid form. Exemplary liquid forms, which may be formulated for oral administration or for administration by injection, include aqueous solution, suitably flavored syrups, aqueous or oil suspensions, and flavored emulsions with edible oils such as cottonseed oil, sesame oil, coconut oil, or peanut oil as well as elixirs and similar pharmaceutical vehicles. Suitable dispersing or suspending agents for aqueous suspensions include synthetic natural gums, such as tragacanth, acacia, alginate, dextran, sodium carboxymethyl cellulose, methylcellulose, polyvinylpyrrolidone or gelatin. A method described herein may comprise administering to a subject a combination of an injectable composition and a composition for oral administration.

Liquid preparations for oral administration may take the form of, for example, solutions, syrups or suspensions, or they may be presented as a dry product for reconstitution with water or other suitable vehicles before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); preservatives (e.g., methyl or propyl p-hydroxybenzoates or sorbic acid); and artificial or natural colors and/or sweeteners.

The preparation of pharmaceutical compositions described herein can be conducted in accordance with generally accepted procedures for the preparation of pharmaceutical preparations. See, for example, Remington's Pharmaceutical Sciences 18th Edition (1990), E. W. Martin ed., Mack Publishing Co., PA. Depending on the intended use and mode of administration, it may be desirable to process the magnesium-counter ion compound further in the preparation of pharmaceutical compositions. Appropriate processing may include mixing with appropriate non-toxic and non-interfering components, sterilizing, dividing into dose units, and enclosing in a delivery device.

Embodiments further encompass anhydrous compositions and dosage forms comprising an active ingredient, since water can facilitate the degradation of some compounds. For example, water may be added (e.g., 5%) in the arts as a means of simulating long-term storage in order to determine characteristics such as shelf-life or the stability of formulations over time. Anhydrous compositions and dosage forms described herein can be prepared using anhydrous or low moisture containing ingredients and low moisture or low humidity conditions. Compositions and dosage forms described herein which contain lactose can be made anhydrous if substantial contact with moisture and/or humidity during manufacturing, packaging, and/or storage is expected. An anhydrous composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An agent described herein can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Binders suitable for use in dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Lubricants which can be used to form compositions and dosage forms described herein include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the composition.

Lubricants can be also be used in conjunction with tissue barriers which include, but are not limited to, polysaccharides, polyglycans, seprafilm, interceed and hyaluronic acid.

Disintegrants may be used in the compositions described herein to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition.

Disintegrants that can be used to form compositions and dosage forms described herein include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Examples of suitable fillers for use in the compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Compositions may include a solubilizer to ensure good solubilization and/or dissolution of a compound described herein and to minimize precipitation of the compound. This can be useful for compositions for non-oral use, e.g., compositions for injection. A solubilizer may also be added to increase the solubility of the hydrophilic drug and/or other components, such as surfactants, or to maintain the composition as a stable or homogeneous solution or dispersion.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof. A non-exhaustive list of examples of excipients includes monoglycerides, magnesium stearate, modified food starch, gelatin, microcrystalline cellulose, glycerin, stearic acid, silica, yellow beeswax, lecithin, hydroxypropylcellulose, croscarmellose sodium, and crospovidone.

Release

The compositions described herein can also be formulated as extended-release, sustained-release or time-release such that one or more components are released over time. Delayed release can be achieved by formulating the one or more components in a matrix of a variety of materials or by microencapsulation. The compositions can be formulated to release one or more components over a time period of 4, 6, 8, 12, 16, 20, or 24 hours. The release of the one or more components can be at a constant or changing rate.

Using the controlled release dosage forms provided herein, the one or more cofactors can be released in its dosage form at a slower rate than observed for an immediate release formulation of the same quantity of components. In some embodiments, the rate of change in the biological sample measured as the change in concentration over a defined time period from administration to maximum concentration for an controlled release formulation is less than about 80%, 70%, 60%, 50%, 40%, 30%, 20%, or 10% of the rate of the immediate release formulation. Furthermore, in some embodiments, the rate of change in concentration over time is less than about 80%, 70%, 60%, 50%, 40%, 30%, 20%, or 10% of the rate for the immediate release formulation.

In some embodiments, the rate of change of concentration over time is reduced by increasing the time to maximum concentration in a relatively proportional manner. For example, a two-fold increase in the time to maximum concentration may reduce the rate of change in concentration by approximately a factor of 2. As a result, the one or more cofactors may be provided so that it reaches its maximum concentration at a rate that is significantly reduced over an immediate release dosage form. The compositions described herein may be formulated to provide a shift in maximum concentration by 24 hours, 16 hours, 8 hours, 4 hours, 2 hours, or at least 1 hour. The associated reduction in rate of change in concentration may be by a factor of about 0.05, 0.10, 0.25, 0.5 or at least 0.8. In certain embodiments, this is accomplished by releasing less than about 30%, 50%, 75%, 90%, or 95% of the one or more cofactors into the circulation within one hour of such administration.

Optionally, the controlled release formulations exhibit plasma concentration curves having initial (e.g., from 2 hours after administration to 4 hours after administration) slopes less than 75%, 50%, 40%, 30%, 20% or 10% of those for an immediate release formulation of the same dosage of the same cofactor.

In some embodiments, the rate of release of the cofactor as measured in dissolution studies is less than about 80%, 70%, 60% 50%, 40%, 30%, 20%, or 10% of the rate for an immediate release formulation of the same cofactor over the first 1, 2, 4, 6, 8, 10, or 12 hours.

The controlled release formulations provided herein can adopt a variety of formats. In some embodiments, the formulation is in an oral dosage form, including liquid dosage forms (e.g., a suspension or slurry), and oral solid dosage forms (e.g., a tablet or bulk powder), such as, but not limited to those, those described herein.

The controlled release tablet of a formulation disclosed herein can be of a matrix, reservoir or osmotic system. Although any of the three systems is suitable, the latter two systems can have more optimal capacity for encapsulating a relatively large mass, such as for the inclusion of a large amount of a single cofactor, or for inclusion of a plurality of cofactors, depending on the genetic makeup of the individual. In some embodiments, the slow-release tablet is based on a reservoir system, wherein the core containing the one or more cofactors is encapsulated by a porous membrane coating which, upon hydration, permits the one or more cofactors to diffuse through. Because the combined mass of the effective ingredients is generally in gram quantity, an efficient delivery system can provide optimal results.

Thus, tablets or pills can also be coated or otherwise compounded to provide a dosage form affording the advantage of prolonged action. For example, the tablet or pill can comprise an inner dosage an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings such materials including a number of polymeric acids and mixtures of polymeric acids with such materials as shellac, cetyl alcohol and cellulose acetate. In some embodiments, a formulation comprising a plurality of cofactors may have different cofactors released at different rates or at different times. For example, there can be additional layers of cofactors interspersed with enteric layers.

Methods of making sustained release tablets are known in the art, e.g., see U.S. Patent Publications 2006/051416 and 2007/0065512, or other references disclosed herein. Methods such as described in U.S. Pat. Nos. 4,606,909, 4,769,027, 4,897,268, and 5,395,626 can be used to prepare sustained release formulations of the one or more cofactors determined by the genetic makeup of an individual. In some embodiments, the formulation is prepared using OROS® technology, such as described in U.S. Pat. Nos. 6,919,373, 6,923,800, 6,929,803, and 6,939,556. Other methods, such as described in U.S. Pat. Nos. 6,797,283, 6,764,697, and 6,635,268, can also be used to prepare the formulations disclosed herein.

Pharmaceutical Compositions

The compositions and methods of the present disclosure may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound or salt of Formula I-a, I-b, I-c, II-a, II-b, II-c, III, IV, V, or VI or a compound listed in Table 1 or 3 and a pharmaceutically acceptable carrier.

In some embodiments, the pharmaceutical composition is formulated for oral administration. In other embodiments, the pharmaceutical composition is formulated for injection. In still more embodiments, the pharmaceutical compositions comprise a compound as disclosed herein and an additional therapeutic agent (e.g., anticancer agent). Non-limiting examples of such therapeutic agents are described herein below.

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a composition of a compound or salt of Formula I-a, I-b, I-c, II-a, II-b, II-c, III, IV, V, or VI or a compound listed in Table 1 or 3 is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, a compound or salt of Formula I-a, I-b, I-c, II-a, II-b, II-c, III, IV, V, or VI or a compound listed in Table 1 or 3 is delivered in a targeted drug delivery system, for example, in a liposome coated with organ-specific antibody. In such embodiments, the liposomes are targeted to and taken up selectively by the organ. In yet other embodiments, the composition is provided in the form of a rapid release formulation, in the form of an extended release formulation, or in the form of an intermediate release formulation. In yet other embodiments, the composition is administered topically.

The compound of Formula I-a, I-b, I-c, II-a, II-b, II-c, III, IV, V, or VI or a compound listed in Table 1 or 3, or a pharmaceutically acceptable salt thereof, may be effective over a wide dosage range. For example, in the treatment of adult humans, dosages from 0.01 to 1000 mg per day, from 0.5 to 100 mg per day, from 1 to 50 mg per day, and from 5 to 40 mg per day are examples of dosages that may be used in some embodiments. The exact dosage will depend upon the route of administration, the form in which the compound is administered, the subject to be treated, the body weight of the subject to be treated, and the preference and experience of the attending physician.

In some embodiments, a compound or salt of Formula I-a, I-b, I-c, II-a, II-b, II-c, III, IV, V, or VI or a compound listed in Table 1 or 3 is administered in a single dose. Typically, such administration will be by injection, e.g., intravenous injection, in order to introduce the agent quickly. However, other routes are used as appropriate. In some embodiments, a single dose of a compound or salt of Formula I-a, I-b, I-c, II-a, II-b, II-c, III, IV, V, or VI or a compound listed in Table 1 or 3 is used for treatment of an acute condition.

In some embodiments, a compound or salt of Formula I-a, I-b, I-c, II-a, II-b, II-c, III, IV, V, or VI or a compound listed in Table 1 or 3 is administered in multiple doses. In some embodiments, dosing is about once, twice, three times, four times, five times, six times, or more than six times per day. In other embodiments, dosing is about once a month, once every two weeks, once a week, or once every other day. In another embodiment, a compound or salt of Formula I-a, I-b, I-c, II-a, II-b, II-c, III, IV, V, or VI or a compound listed in Table 1 or 3 and another agent are administered together about once per day to about 6 times per day. In another embodiment, the administration of a compound or salt of Formula I-a, I-b, I-c, II-a, II-b, II-c, III, IV, V, or VI or a compound listed in Table 1 or 3 and an agent continues for less than about 7 days. In yet another embodiment, the administration continues for more than about 6 days, more than about 10 days, more than about 14 days, more than about 28 days, more than about two months, more than about six months, or one year or more. In some cases, continuous dosing is achieved and maintained as long as necessary.

Administration of a compound or salt of Formula I-a, I-b, I-c, II-a, II-b, II-c, III, IV, V, or VI or a compound listed in Table 1 or 3 may continue as long as necessary. In some embodiments, a compound described herein is administered for more than 1, more than 2, more than 3, more than 4, more than 5, more than 6, more than 7, more than 14, or more than 28 days. In some embodiments, a compound described herein is administered 28 days or less, 14 days or less, 7 days or less, 6 days or less, 5 days or less, 4 days or less, 3 days or less, 2 days or less, or 1 day or a part thereof. In some embodiments, a compound or salt of Formula I-a, I-b, I-c, II-a, II-b, II-c, III, IV, V, or VI or a compound listed in Table 1 or 3 is administered chronically on an ongoing basis, e.g., for the treatment of chronic effects.

In some embodiments, a compound or salt of Formula I-a, I-b, I-c, II-a, II-b, II-c, III, IV, V, or VI or a compound listed in Table 1 or 3 is administered in dosages. It is known in the art that due to intersubject variability in compound pharmacokinetics, individualization of dosing regimen is necessary for optimal therapy. Dosing for a compound or salt of Formula I-a, I-b, I-c, II-a, II-b, II-c, III, IV, V, or VI or a compound listed in Table 1 or 3 may be found by routine experimentation in light of the instant disclosure.

In some embodiments, a compound or salt of Formula I-a, I-b, I-c, II-a, II-b, II-c, III, IV, V, or VI or a compound listed in Table 1 or 3 is formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins1999).

Provided herein are pharmaceutical compositions comprising a compound or salt of Formula I-a, I-b, I-c, II-a, II-b, II-c, III, IV, V, or VI or a compound listed in Table 1 or 3 and a pharmaceutically acceptable diluent(s), excipient(s), or carrier(s). In certain embodiments, the compounds or salts described are administered as pharmaceutical compositions in which a compound or salt of Formula I-a, I-b, I-c, II-a, II-b, II-c, III, IV, V, or VI or a compound listed in Table 1 or 3 is mixed with other active ingredients, as in combination therapy. Encompassed herein are all combinations of actives set forth in the combination therapies section below and throughout this disclosure. In specific embodiments, the pharmaceutical compositions include one or more compounds of Formula I-a, I-b, I-c, II-a, II-b, II-c, III, IV, V, or VI or a compound listed in Table 1 or 3, or a pharmaceutically acceptable salt thereof.

A pharmaceutical composition, as used herein, refers to a mixture of a compound or salt of Formula I-a, I-b, I-c, II-a, II-b, II-c, III, IV, V, or VI or a compound listed in Table 1 or 3 with other chemical components, such as carriers, stabilizers, diluents, dispersing agents, suspending agents, thickening agents, and/or excipients. In certain embodiments, the pharmaceutical composition facilitates administration of the compound to an organism. In some embodiments, practicing the methods of treatment or use provided herein, therapeutically effective amounts of a compound or salt of Formula I-a, I-b, I-c, II-a, II-b, II-c, III, IV, V, or VI or a compound listed in Table 1 or 3 are administered in a pharmaceutical composition to a mammal having a disease, disorder or medical condition to be treated. In specific embodiments, the mammal is a human. In certain embodiments, therapeutically effective amounts vary depending on the severity of the disease, the age and relative health of the subject, the potency of the compound used and other factors. A compound or salt of Formula I-a, I-b, I-c, II-a, II-b, II-c, III, IV, V, or VI or a compound listed in Table 1 or 3 may be used singly or in combination with one or more therapeutic agents as components of mixtures.

In one embodiment, a compound or salt of Formula I-a, I-b, I-c, II-a, II-b, II-c, III, IV, V, or VI or a compound listed in Table 1 or 3 is formulated in an aqueous solution. In specific embodiments, the aqueous solution is selected from, by way of example only, a physiologically compatible buffer, such as Hank's solution, Ringer's solution, or physiological saline buffer. In other embodiments, a compound or salt of Formula I-a, I-b, I-c, II-a, II-b, II-c, III, IV, V, or VI or a compound listed in Table 1 or 3 is formulated for transmucosal administration. In specific embodiments, transmucosal formulations include penetrants that are appropriate to the barrier to be permeated. In still other embodiments wherein a compound or salt of Formula I-a, I-b, I-c, II-a, II-b, II-c, III, IV, V, or VI or a compound listed in Table 1 or 3 is formulated for other parenteral injections, appropriate formulations include aqueous or nonaqueous solutions. In specific embodiments, such solutions include physiologically compatible buffers and/or excipients.

In another embodiment, a compound or salt of Formula I-a, I-b, I-c, II-a, II-b, II-c, III, IV, V, or VI or a compound listed in Table 1 or 3 is formulated for oral administration. A compound or salt of Formula I-a, I-b, I-c, II-a, II-b, II-c, III, IV, V, or VI or a compound listed in Table 1 or 3 may be formulated by combining the active compounds with, e.g., pharmaceutically acceptable carriers or excipients. In various embodiments, a compound or salt of Formula I-a, I-b, I-c, II-a, II-b, II-c, III, IV, V, or VI or a compound listed in Table 1 or 3 is formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipient with a compound or salt of Formula I-a, I-b, I-c, II-a, II-b, II-c, III, IV, V, or VI or a compound listed in Table 1 or 3, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, a therapeutically effective amount of a compound or salt of Formula I-a, I-b, I-c, II-a, II-b, II-c, III, IV, V, or VI or a compound listed in Table 1 or 3 is formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, a therapeutically effective amount of a compound or salt of Formula I-a, I-b, I-c, II-a, II-b, II-c, III, IV, V, or VI or a compound listed in Table 1 or 3 is formulated for buccal or sublingual administration. Formulations suitable for buccal or sublingual administration include, by way of example only, tablets, lozenges, or gels. In still other embodiments, a compound or salt of Formula I-a, I-b, I-c, II-a, II-b, II-c, III, IV, V, or VI or a compound listed in Table 1 or 3 is formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical compositions are formulated in a form suitable for parenteral injection as sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, a suspension of a compound or salt of Formula I-a, I-b, I-c, II-a, II-b, II-c, III, IV, V, or VI or a compound listed in Table 1 or 3 is prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. In certain embodiments, the active agent is in powder form for constitution with a suitable vehicle, e.g., sterile pyrogen-free water, before use.

In still other embodiments, a compound or salt of Formula I-a, I-b, I-c, II-a, II-b, II-c, III, IV, V, or VI or a compound listed in Table 1 or 3 is administered topically. A compound or salt of Formula I-a, I-b, I-c, II-a, II-b, II-c, III, IV, V, or VI or a compound listed in Table 1 or 3 may be formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In yet other embodiments, a compound or salt of Formula I-a, I-b, I-c, II-a, II-b, II-c, III, IV, V, or VI or a compound listed in Table 1 or 3 is formulated for transdermal administration. Transdermal formulations may employ transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on demand delivery of pharmaceutical agents. In additional embodiments, the transdermal delivery of a compound or salt of Formula I-a, I-b, I-c, II-a, II-b, II-c, III, IV, V, or VI or a compound listed in Table 1 or 3 is accomplished by means of iontophoretic patches and the like. In certain embodiments, transdermal patches provide controlled delivery of a compound or salt of Formula I-a, I-b, I-c, II-a, II-b, II-c, III, IV, V, or VI or a compound listed in Table 1 or 3. In specific embodiments, the rate of absorption is slowed by using rate-controlling membranes or by trapping the compound within a polymer matrix or gel. In alternative embodiments, absorption enhancers are used to increase absorption. Absorption enhancers or carriers include absorbable pharmaceutically acceptable solvents that assist passage through the skin. For example, in one embodiment, transdermal devices are in the form of a bandage comprising a backing member, a reservoir containing a compound or salt of Formula I-a, I-b, I-c, II-a, II-b, II-c, III, IV, V, or VI or a compound listed in Table 1 or 3, optionally with carriers, optionally a rate controlling barrier to deliver the compound to the skin of the host at a controlled and predetermined rate over a prolonged period of time, and means to secure the device to the skin.

In other embodiments, a compound or salt of Formula I-a, I-b, I-c, II-a, II-b, II-c, III, IV, V, or VI or a compound listed in Table 1 or 3 is formulated for administration by inhalation. Various forms suitable for administration by inhalation include, but are not limited to, aerosols, mists or powders. Pharmaceutical compositions of a compound or salt of Formula I-a, I-b, I-c, II-a, II-b, II-c, III, IV, V, or VI or a compound listed in Table 1 or 3 are conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In specific embodiments, the dosage unit of a pressurized aerosol is determined by providing a valve to deliver a metered amount. In certain embodiments, capsules and cartridges of, such as, by way of example only, gelatin for use in an inhaler or insufflator are formulated containing a powder mix of a compound or salt of Formula I-a, I-b, I-c, II-a, II-b, II-c, III, IV, V, or VI or a compound listed in Table 1 or 3 and a suitable powder base such as lactose or starch.

In still other embodiments, a compound or salt of Formula I-a, I-b, I-c, II-a, II-b, II-c, III, IV, V, or VI or a compound listed in Table 1 or 3 is formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In certain embodiments, pharmaceutical compositions are formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients may be optionally used as suitable. Pharmaceutical compositions comprising a compound or salt of Formula I-a, I-b, I-c, II-a, II-b, II-c, III, IV, V, or VI or a compound listed in Table 1 or 3 are manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable carrier, diluent or excipient and a compound or salt of Formula I-a, I-b, I-c, II-a, II-b, II-c, III, IV, V, or VI or a compound listed in Table 1 or 3, sometimes referred to herein as an active agent or ingredient. The active ingredient may be in free-acid or free-base form, or in a pharmaceutically acceptable salt form. Additionally, a compound or salt of Formula I-a, I-b, I-c, II-a, II-b, II-c, III, IV, V, or VI or a compound listed in Table 1 or 3 may be in unsolvated or solvated forms with pharmaceutically acceptable solvents such as water and ethanol. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising a compound or salt of Formula I-a, I-b, I-c, II-a, II-b, II-c, III, IV, V, or VI or a compound listed in Table 1 or 3 include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound or salt of Formula I-a, I-b, I-c, II-a, II-b, II-c, III, IV, V, or VI or a compound listed in Table 1 or 3. Semi-solid compositions include, but are not limited to, gels, suspensions and creams. The form of the pharmaceutical compositions of a compound or salt of Formula I-a, I-b, I-c, II-a, II-b, II-c, III, IV, V, or VI or a compound listed in Table 1 or 3 include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, pharmaceutical composition comprising a compound or salt of Formula I-a, I-b, I-c, II-a, II-b, II-c, III, IV, V, or VI or a compound listed in Table 1 or 3 illustratively takes the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, aqueous suspensions contain one or more polymers as suspending agents. Polymers include water-soluble polymers such as cellulosic polymers, e.g., hydroxypropyl methylcellulose, and water-insoluble polymers such as cross-linked carboxyl-containing polymers. Certain pharmaceutical compositions described herein comprise a mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Pharmaceutical compositions also, optionally, include solubilizing agents to aid in the solubility of a compound described herein. The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, useful compositions also, optionally, include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Pharmaceutical compositions may include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Pharmaceutical compositions may include one or more antioxidants to enhance chemical stability where required. Suitable antioxidants include, by way of example only, ascorbic acid and sodium metabisulfite.

In certain embodiments, aqueous suspension compositions are packaged in single-dose non-reclosable containers. Alternatively, multiple-dose reclosable containers are used, in which case it is typical to include a preservative in the composition.

In certain embodiments, delivery systems for hydrophobic pharmaceutical compounds are employed. Liposomes and emulsions are examples of delivery vehicles or carriers useful herein. In certain embodiments, organic solvents such as N-methylpyrrolidone are also employed. In additional embodiments, a compound or salt of Formula I-a, I-b, I-c, II-a, II-b, II-c, III, IV, V, or VI or a compound listed in Table 1 or 3 is delivered using a sustained-release system, such as semipermeable matrices of solid hydrophobic polymers containing the therapeutic agent. Various sustained-release materials may be used herein. In some embodiments, sustained-release capsules release the compounds for a few weeks up to over 100 days. Depending on the chemical nature and the biological stability of the therapeutic reagent, additional strategies for protein stabilization are employed.

In certain embodiments, the formulations described herein comprise one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

In some embodiments, the concentration of a compound or salt of Formula I-a, I-b, I-c, II-a, II-b, II-c, III, IV, V, or VI or a compound listed in Table 1 or 3 provided in a pharmaceutical compositions is less than about: 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of a compound or salt of Formula I-a, I-b, I-c, II-a, II-b, II-c, III, IV, V, or VI or a compound listed in Table 1 or 3 provided in a pharmaceutical composition is greater than about: 90%, 80%, 70%, 60%, 50%, 40%, 30%, 20%, 19.75%, 19.50%, 19.25%, 19%, 18.75%, 18.50%, 18.25%, 18%, 17.75%, 17.50%, 17.25%, 17%, 16.75%, 16.50%, 16.25%, 16%, 15.75%, 15.50%, 15.25%, 15%, 14.75%, 14.50%, 14.25%, 14%, 13.75%, 13.50%, 13.25%, 13%, 12.75%, 12.50%, 12.25%, 12%, 11.75%, 11.50%, 11.25%, 11%, 10.75%, 10.50%, 10.25%, 10%, 9.75%, 9.50%, 9.25%, 9%, 8.75%, 8.50%, 8.25%, 8%, 7.75%, 7.50%, 7.25%, 7%, 6.75%, 6.50%, 6.25%, 6%, 5.75%, 5.50%, 5.25%, 5%, 4.75%, 4.50%, 4.25%, 4%, 3.75%, 3.50%, 3.25%, 3%, 2.75%, 2.50%, 2.25%, 2%, 1.75%, 1.50%, 1.25%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of a compound or salt of Formula I-a, I-b, I-c, II-a, II-b, II-c, III, IV, V, or VI or a compound listed in Table 1 or 3 is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of a compound or salt of Formula I-a, I-b, I-c, II-a, II-b, II-c, III, IV, V, or VI or a compound listed in Table 1 or 3 is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of a compound or salt of Formula I-a, I-b, I-c, II-a, II-b, II-c, III, IV, V, or VI or a compound listed in Table 1 or 3 is equal to or less than about: 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of a compound or salt of Formula I-a, I-b, I-c, II-a, II-b, II-c, III, IV, V, or VI or a compound listed in Table 1 or 3 is more than about: 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of one or more compounds described herein is in the range of 0.0001-10 g, 0.0005-9 g, 0.001-8 g, 0.005-7 g, 0.01-6 g, 0.05-5 g, 0.1-4 g, 0.5-4 g, or 1-3 g.

Kits

Certain embodiments provide kits. In some embodiments, a kit comprises a pharmaceutical composition described herein and instructions for using the composition to treat a subject suffering from a disease or condition. The kits include one or more compounds or compositions described herein, in suitable packaging, and written material that can include instructions for use, discussion of clinical studies, listing of side effects, and the like. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials.

The kit may further contain another agent. In some embodiments, two or more agents are provided as separate compositions in separate containers within the kit. In some embodiments, two or more agents are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in some embodiments, be marketed directly to the consumer.

In some embodiments, a kit can comprise a multi-day supply of unit dosages. The unit dosages can be any unit dosage described herein. The kit can comprise instructions directing the administration of the multi-day supply of unit dosages over a period of multiple days. The multi-day supply can be a one-month supply, a 30-day supply, or a multi-week supply. The multi-day supply can be a 90-day, 180-day, 3-month or 6-month supply. The kit can include packaged daily unit dosages, such as packages of 1, 2, 3, 4, or 5 unit dosages. The kit can be packaged with other dietary supplements, vitamins, and meal replacement bars, mixes, and beverages.

In some embodiments, a kit can further comprise a wearable activity monitor. The wearable activity monitor can monitor physical and/or ambulatory activity via a pedometer, accelerometer, or Exemplary wearable activity monitors include, e.g.; a Fitbit®, Jawbone UP®, LarkLife™, Nike FuelBand, Striiv Play, BodyMedia Fit-Core, among others. Such wearable activity monitors are described in U.S. Pat. Nos: 8,403,845; 8,398,546; 8,382,590; 8,369,936; 8,275,635; 8,157,731; 8,073,707; 7,959,567; 7,689,437; 7,502,643; 7,285,090; 7,261,690; 7,153,262; 7,020,508; 6,605,038; 6,595,929; 6,527,711; 8,562,489; 8,517,896; 8,469,862; 8,408,436; 8,370,549; 8,088,044; 8,088,043, and US Patent Application Publication Nos. 20130158369 and 20130151196, all of which are hereby incorporated by reference. Such kits can further comprise instructions for the subject to engage in a physical activity regimen in addition to instructions for use of the composition. Such kits can further comprise instructions for use of the wearable activity monitors. Such kits can also comprise wearable activity monitor accessories, such as, e.g., a charger, and/or a port or wireless for communicating data from the activity monitor to a computer or server.

For use in the therapeutic applications described herein, kits and articles of manufacture are also provided. In some embodiments, such kits comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from a variety of materials such as glass or plastic.

The articles of manufacture provided herein contain packaging materials. Packaging materials for use in packaging pharmaceutical products include those found in, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. For example, the container(s) includes a compound or salt of Formula I-a, I-b, I-c, II-a, II-b, II-c, III, IV, V, or VI or a compound listed in Table 1 or 3, optionally in a composition or in combination with another agent as disclosed herein. The container(s) optionally have a sterile access port (for example the container is an intravenous solution bag or a vial having a stopper pierceable by a hypodermic injection needle). Such kits optionally comprising a compound with an identifying description or label or instructions relating to its use in the methods described herein.

For example, a kit typically includes one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included. A label is optionally on or associated with the container. For example, a label is on a container when letters, numbers or other characters forming the label are attached, molded or etched into the container itself, a label is associated with a container when it is present within a receptacle or carrier that also holds the container, e.g., as a package insert. In addition, a label is used to indicate that the contents are to be used for a specific therapeutic application. In addition, the label indicates directions for use of the contents, such as in the methods described herein. In certain embodiments, the pharmaceutical composition is presented in a pack or dispenser device which contains one or more unit dosage forms containing a compound provided herein. The pack, for example, contains metal or plastic foil, such as a blister pack. Or, the pack or dispenser device is accompanied by instructions for administration. Or, the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some embodiments, compositions containing a compound provided herein formulated in a compatible pharmaceutical carrier are prepared, placed in an appropriate container, and labeled for treatment of an indicated condition.

EXAMPLES

The chemical entities described herein can be synthesized according to one or more illustrative schemes herein and/or techniques known in the art. Materials used herein are either commercially available or prepared by synthetic methods generally known in the art. These schemes are not limited to the compounds listed in the examples or by any particular substituents, which are employed for illustrative purposes. Although various steps are described and depicted in Example 1, the steps in some cases may be performed in a different order than the order shown in Example 1. Various modifications to these synthetic reaction schemes may be made and will be suggested to one skilled in the art having referred to the disclosure contained in this Application. Numberings or R groups in each scheme do not necessarily correspond to that of the claims or other schemes or tables herein.

Example 1: Synthesis of Compound 2

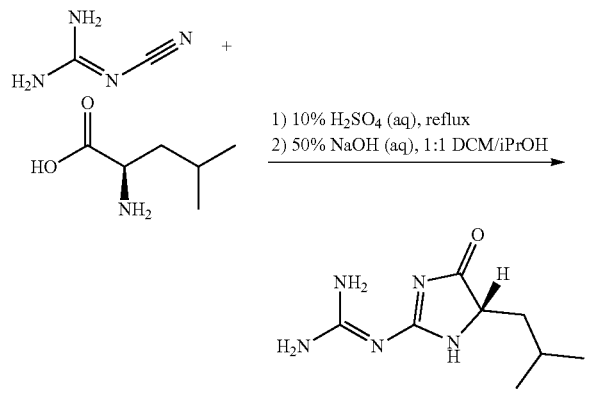

2-Cyanoguanidine (63.1 g, 0.75 mol) and L-leucine (65.6 g, 0.50 mol) were combined in 500 mL of 10 wt % aqueous $H_2SO_4$ and refluxed for 2 hr. The starting materials did not dissolve completely until solution temperature reached approximately 55° C. The solution reached approximately 110° C. at reflux. The reaction mixture was then placed in the freezer overnight. A large amount of precipitate (unreacted starting material) formed as the solution cooled. The mixture was filtered and pressed, and the filtrate was collected. The filtrate was cooled in an ice bath, and 50 wt % aqueous NaOH was added in 5 mL portions until the solution pH reached 11, requiring approximately 35-40 mL of NaOH solution. As the pH increased, additional precipitate formed (unreacted leucine). The mixture was filtered again, and the filtrate was collected. 500 mL of 1:1 dichloromethane:isopropanol was added to the filtrate with constant stirring in an ice bath. The solution became cloudy with precipitate, which was the desired product. The mixture was filtered and the solid product was collected and dried under vacuum. The solid collected from this step was pure by $^1H$ NMR and HPLC. The pure compound has a mass-to-charge ratio (m/z) of 198 (MH+).

Example 2: Effects of Compound 2 on Fat Oxidation

Cell Culture: C2C12 muscle cells were seeded with 40,000 cells per well on Seahorse tissue culture plates in Dulbecco's modified eagle's medium (DMEM) containing 10% fetal bovine serum (FBS) and antibiotics (1% penicillin-streptomycin) at 37° C. in 5% $CO_2$. After reaching confluency (24 hours), cells were induced to differentiate with DMEM containing 2% Horse Serum for 3 to 4 days until myotubes were fully formed. Cells were then treated with indicated concentration of Compound 2 for 24 hours.

Compound 2 was dissolved in 100% DMSO to a stock concentration of 100 mM. This stock was further diluted to indicated concentrations in DMEM media.

Fatty acid oxidation: Baseline and palmitate-stimulated oxygen consumption rates were measured with XF-24 analyzer (Seahorse Bioscience (now part of Agilent Technologies), MA, USA). After 24 hour treatment with Compound 2 of differentiated C2C12 muscle cells, cells were washed twice with non-buffered carbonate-free pH 7.4 low glucose (2.5 mM) DMEM containing carnitine (0.5 mM), equilibrated with 600 µl of the same media in a non-$CO_2$ incubator for 45 minutes, and then inserted into the instrument for 15 minutes of further equilibration, followed by $O_2$ consumption measurement. Three successive baseline measures at five-minute intervals were taken prior to injection of palmitate (200 µM final concentration). Sets of three five-minute intervals followed by 10-minute time delay were continued over a 2 to 3 hour period after palmitate injection. The area under the curve of $O_2$ consumption change from baseline for each sample was then calculated and used for subsequent analysis. Data are represented as mean±SD for each treatment group.

Statistics: Data were analyzed via one-way analysis of variance and least significant difference test was used to separate significantly different group means.

Figure 2:
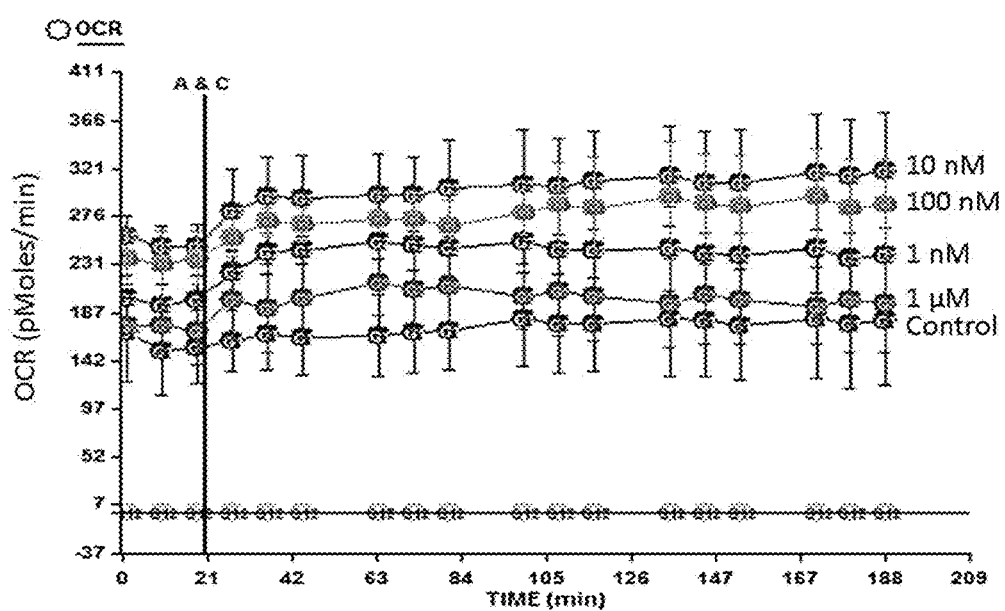
FIG. 2 shows effects of different concentrations of Compound 2 on fatty acid oxidation in C2C12 muscle cells.

Results:
In C2C12 Muscle Cells:
The data demonstrate a dose-response relationship on both baseline and palmitate-stimulated oxygen consumption rate (OCR) at low concentrations, with diminishing responses at higher concentrations (>100 nM Compound 2) (FIG. 2). Concentrations in excess of 1uM (not shown)

exhibited no effect. FIG. 2 shows effects of different concentrations of Compound 2 on fatty acid oxidation in C2C12 muscle cells. The vertical line indicates the time at which palmitate was injected.

Figure 3A:
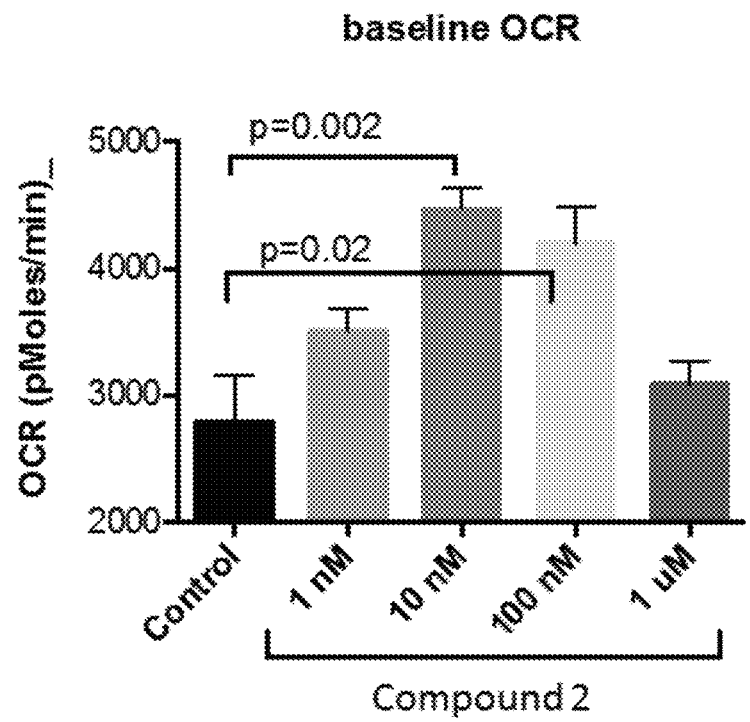
FIGS. 3A and 3B show area under the curve quantification of different concentrations of Compound 2 on fatty acid oxidation in C2C12 muscle cells.
Figure 3B:
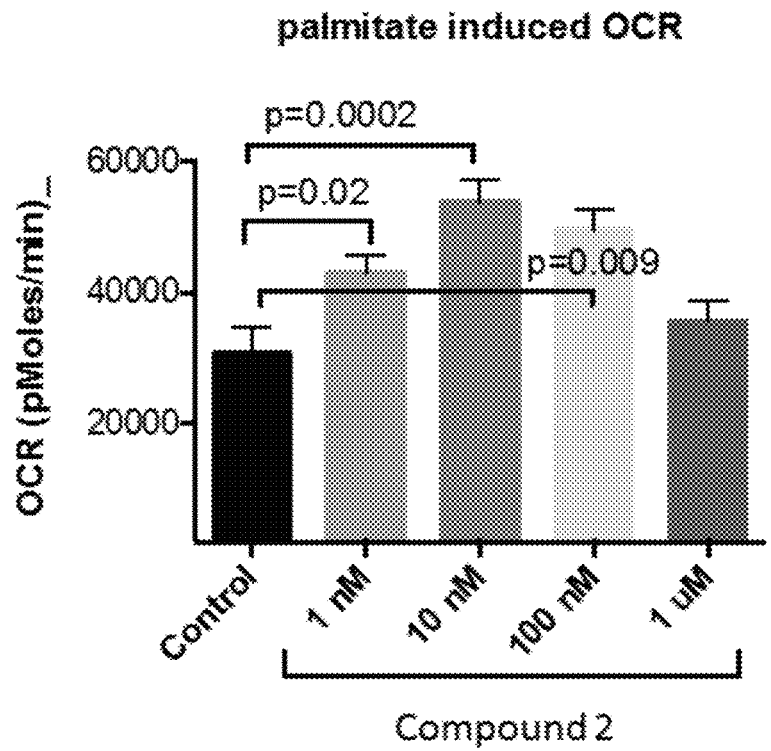

The quantification of the area under the curve showed a 60% increase of the baseline oxygen consumption rate with 10 nM Compound 2 prior to palmitate injection (p=0.002). Palmitate injection increased oxygen consumption ~10-fold compared to baseline in the control condition (FIG. 3B vs. FIG. 3A), and this was further increased by ~75% by Compound 2 (p=0.002). These effects were dose-responsive only in the very low concentration range (0-10 nM) and plateaued between 10 and 100 nM (FIGS. 3A and 3B). FIGS. 3A and 3B show area under the curve quantification of different concentrations of Compound 2 on fatty acid oxidation in C2C12 muscle cells. Data are represented as mean±SEM (n=3 to 4).

These data indicate a potent effect of Compound 2 on fat oxidation in skeletal muscle. In comparison, metformin alone does not stimulate fat oxidation in the same system at concentrations below 1 mM (e.g., 100,000-fold higher concentration), and combining leucine with metformin to potentiate metformin action still requires a concentration of 100 µM (e.g., 10,000-fold higher concentration) as shown in Banerjeee J, Bruckbauer A, Zemel MB. Activation of the AMPK/Sirt1 pathway by a leucine-metformin combination increases insulin sensitivity in skeletal muscle, and stimulates glucose and lipid metabolism and increases lifespan in *Caenorhabditis elegans*. Metabolism 2016, (http://dx-.doi.org/10.1016/j metabol.2016.06.011); in press.

Figure 9:
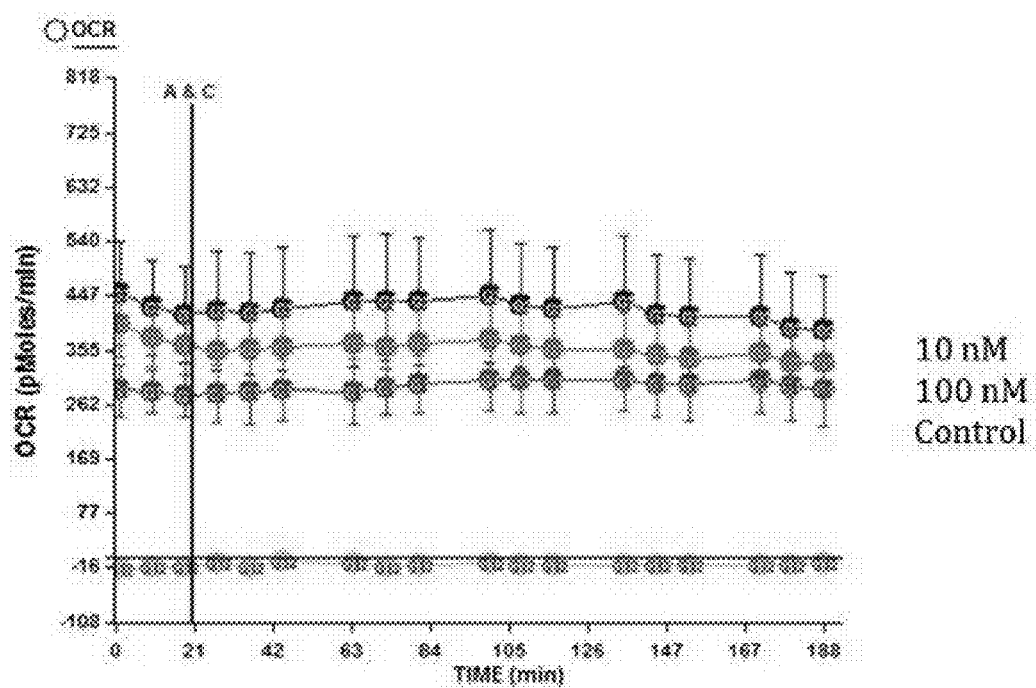
FIG. 9 depicts a graphical representation that shows the effects of different concentrations of Compound 2 on fatty acid oxidation in 3T3L1 adipocytes. The vertical line indicates the injection of palmitate.
Figure 10A:
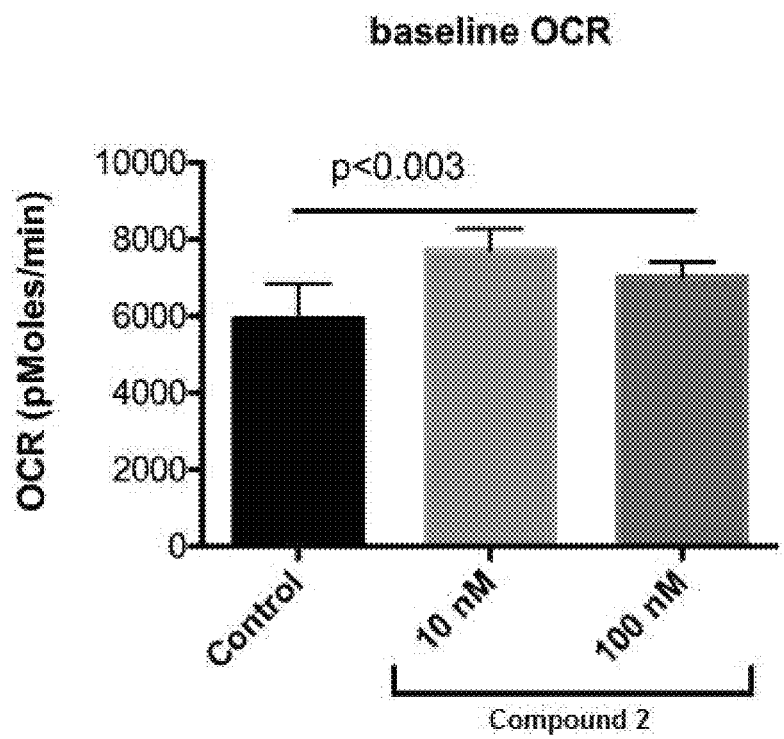
FIGS. 10A and 10B depict graphical representations that show area under the curve quantification of different concentrations of Compound 2 on fatty acid oxidation in 3T3L1 adipocytes. Data are represented as mean±SEM.
Figure 10B:
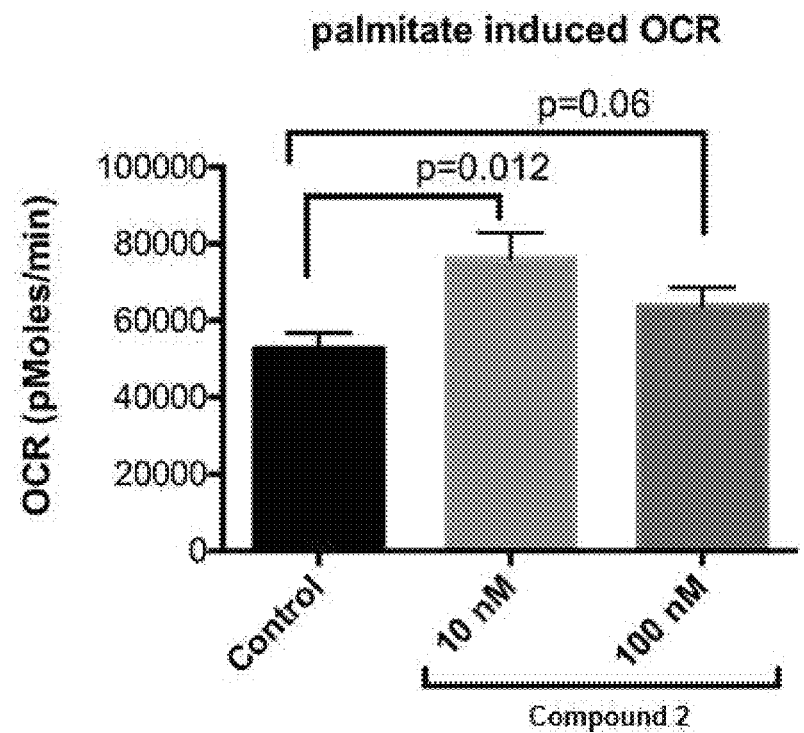

In 3T3L1 Adipocytes:

The data demonstrates that the baseline and palmitate stimulated OCR in 3T3L1 adipocytes were increased by 50% and 43%, respectively, after 48 hours of treatment with 10 nM Compound 2. A smaller effect was found with 100 nM Compound 2 (FIG. 9, and FIG. 10A and FIH. 10B). FIG. 9 depicts a graphical representation that shows the effects of different concentrations (10 nM and 100 nM) of Compound 2 on fatty acid oxidation in 3T3L1 adipocytes. The vertical line indicates the injection of palmitate. FIGS. 10A and 10B depicts graphical representations that show area under the curve quantification of different concentrations (10 nM and 100 nM) of Compound 2 on fatty acid oxidation in 3T3L1 adipocytes. As shown in FIG. 10A, the control had an OCR of approximately 6000 pMoles/min, 10 nM of Compound 2 had an OCR of approximately 7900 pMoles/min, and 100 nM of Compound 2 had an OCR of approximately 7000 pMoles/min. As shown in FIG. 10B, the control had an OCR of approximately 52000 pMoles/min, 10 nM of Compound 2 had an OCR of approximately 78000 pMoles/min, and 100 nM of Compound 2 had an OCR of approximately 62000 pMoles/min. Data are represented as mean±SEM.

The data indicates an extremely potent effect of Compound 2 on fat oxidation in skeletal muscle and adipocytes. In comparison, metformin alone does not stimulate fat oxidation in the same system at concentrations below 1 mM (i.e. 100,000-fold higher concentration), and combining leucine with metformin to potentiate metformin action still requires a concentration of 100 µM (i.e. 10,000-fold higher concentration). Banerjeee J, Bruckbauer A, and Zemel MB, Activation of the AMPK/Sirt1 pathway by a leucine-metformin combination increases insulin sensitivity in skeletal muscle, and stimulates glucose and lipid metabolism and increases lifespan in *Caenorhabditis elegans*, Metabolism (2016) 65(11):1679-1691.

Example 3: Effects of Compound 2 on Hepatic Steatosis

Cell Culture: HepG2 liver cells were seeded with 80,000 cells per well on 24-well tissue culture plates in low glucose (5 mM) DMEM containing 10% FBS and antibiotics. After 24 hours of attachment, lipid accumulation was induced by incubating cells with high glucose (25 mM) DMEM (10% FBS, 1% Pen-Strep) plus 100 nM insulin for 48 hours. Cells were then treated with indicated concentrations of Compound 2 for an additional 48 hours.

Compound 2 was dissolved in 100% DMSO to a stock concentration of 100 mM. This stock was further diluted to indicated concentrations in DMEM media.

Lipid accumulation (Oil Red Staining): HepG2 liver cells were seeded and treated as described above. After 48 hours of treatment with Compound 2, lipid accumulation in HepG2 was measured via Oil Red Staining. Cells were washed with phosphate buffered saline (PBS) once, then cells were fixated with 10% formalin for 1 hour. After removal of the formalin, cells were washed with ddH$_2$O twice, then washed with 60% isopropanol. Cells were dried completely. Cells were stained with Oil Red working solution (~5 mM) for 25 minutes, then immediately washed with ddH$_2$O four times, then dried completely again. Oil Red dye was eluted with 100% isopropanol and absorbance was read at 500 nm. Unstained cells plus isopropanol was used as a blank and subtracted from all readings. Data are represented as mean±SEM for each treatment group.

Statistics: Data were analyzed via one-way analysis of variance and least significant difference test was used to separate significantly different group means.

Results: Incubation of the cells with high glucose (25 mM) DMEM plus 100 nM insulin induced ~2-3 fold increase in fat accumulation in the cells (p<0.0001). This was significantly reduced by all tested concentrations of Compound 2 (1 nM to 10 uM) with the highest effect (up to 40%) achieved by 10 nM Compound 2 (FIG. 4; p<0.025).

Figure 4:
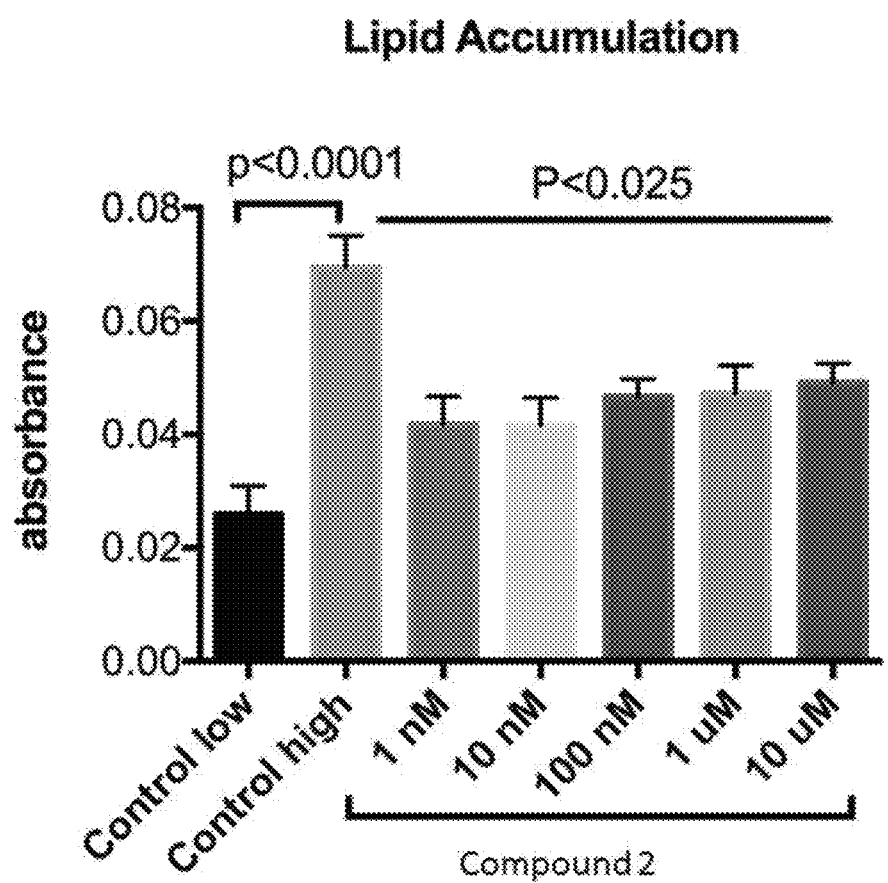
FIG. 4 shows effects of different concentrations of Compound 2 on lipid accumulation in HepG2 cells after induction with high glucose (25 mM) DMEM plus insulin.

FIG. 4 shows effects of different concentrations of Compound 2 on lipid accumulation in HepG2 cells after induction with high glucose (25 mM) DMEM plus insulin. Low glucose control cells were maintained in 5 mM glucose DMEM. Data are represented as mean±SEM (n=4 to 14).

These data indicate an extremely potent effect of Compound 2 on reducing steatosis in hepatocytes. In comparison, metformin alone does not reduce hepatic lipids in same system at concentrations below 1 mM (e.g., 100,000-fold higher concentration), and combining leucine with metformin to potentiate metformin action still requires a concentration of 100 µM (e.g., 10,000-fold higher concentration), as shown in Fu L, Bruckbauer A, Li F, Cao Q, Cui X, Wu R, Shi H, Zemel M B, Xue B. Interaction between metformin and leucine in reducing hyperlipidemia and hepatic lipid accumulation in diet-induced obese mice. Metabolism 2015; 64:1426-1434.

Example 4: Effects of Compound 2 on AMPK and Sirtuin Expression and Downstream Targets Cell Culture: C2C12 muscle cells were seeded with 400,000 cells per well on 6-well tissue culture plates in Dulbecco's modified eagle's medium (DMEM) containing 10% fetal bovine serum (FBS) and antibiotics (1% penicillin-streptomycin) at 37° C. in 5% CO$_2$. After reaching confluency (24 hours), cells were induced to differentiate with DMEM containing 2% Horse Serum for 5 to 6 days until myotubes were fully formed. Cells were then treated with indicated concentration of Compound 2 for 4 and 24 hours.

3T3L1 adipocytes were seeded with 200,000 cells per well on 6-well tissue culture plates in Dulbecco's modified eagle's medium (DMEM) containing 10% fetal bovine serum (FBS) and antibiotics (1% penicillin-streptomycin) at 37° C. in 5% $CO_2$. After reaching confluency (3 days), cells were induced to differentiate with a standard differentiation media (DM2-L1, Zen-Bio Inc., NC) for 3 days, then cells were maintained in DMEM (10% FBS, 1% penicillin-streptomycin) for another 11 days to induce lipid accumulation. Cells were then treated with indicated concentration of Compound 2 for 48 hours.

C. elegans culture: Synchronized L1 wild-type worms were transferred to NGM agar plates with the following treatments until adulthood (3 days): 1. control NGM plates, 2. NGM plate with 10 nM Compound 2 added to E. coli suspension, 3. NGM plate with 100 nM Compound 2 added to E. coli suspension.

Compound 2 was dissolved in 100% DMSO to a stock concentration of 100 mM. This stock was further diluted to indicated concentrations in DMEM media.

Western blots: Phospho-AMPK, AMPK, Phospho-ACC, ACC antibodies were obtained from Cell Signaling (Danvers, Mass.). Sir2 antibody was obtained from MyBiosource (San Diego, Calif.). Protein levels of cell extracts were measured by BCA kit (Thermo Scientific, Pittsburgh, Pa.). For Western blot, 10-50 µg protein was resolved on 4-15% gradient polyacrylaminde gels (Criterion precast gel, Bio-Rad Laboratories, Hercules, Calif.), transferred to either PVDF or nitrocellulose membranes, incubated in blocking buffer (3% BSA or 5% non-fat dry milk in TBS) and then incubated with primary antibody (1:1000 dilution), washed and incubated with horseradish peroxidase- or fluorescence-conjugated secondary antibody (1:10000 dilution). Visualization was conducted using BioRad ChemiDoc instrumentation and software (Bio-Rad Laboratories, Hercules, Calif.) and band intensity was assessed using Image Lab 4.0 with correction for background and loading controls.

Statistics: Data were analyzed via one-way analysis of variance and least significant difference test was used to separate significantly different group means.

Figure 5:
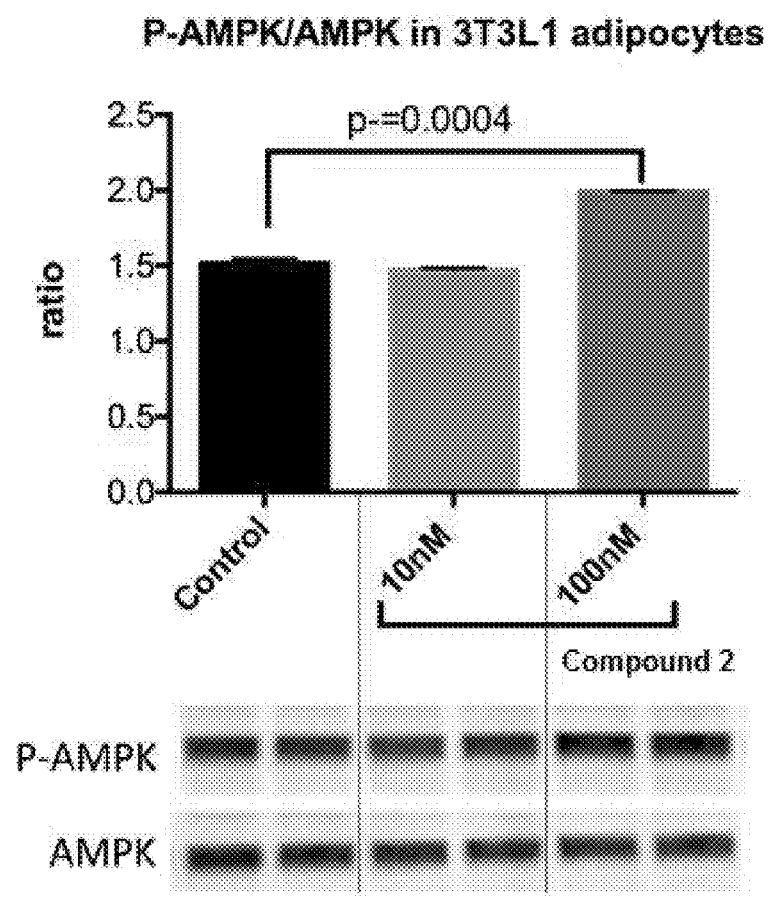
FIG. 5 depicts a graphical representation that shows the effects of different concentrations of Compound 2 on AMPK protein expression on 3T3L1 adipocytes after treatment for 48 hours, and a representative blot. Data are represented as mean±SEM of the ratio of phosphorylated/total AMPK.

Results: The data demonstrates that there was a 35% increase in the ratio of phosphorylated to total AMPK protein expression in 3T3L1 adipocytes treated with 100 nM of Compound 2 for 48 hours ((p=0.0004, FIG. 5). FIG. 5 shows the effects of different concentrations (10 nM and 100 nM) of Compound 2 on AMPK protein expression on 3T3L1 adipocytes after treatment for 48 hours, and a representative blot. Data are represented as mean±SEM of the ratio of phosphorylated/total AMPK. As shown in FIG. 5, the control had a ratio of approximately 1.52, 10 nM of Compound 2 had a ratio of approximately 1.5, and 100 nM of Compound 2 had a ratio of approximately 2.0.

Figure 6A:
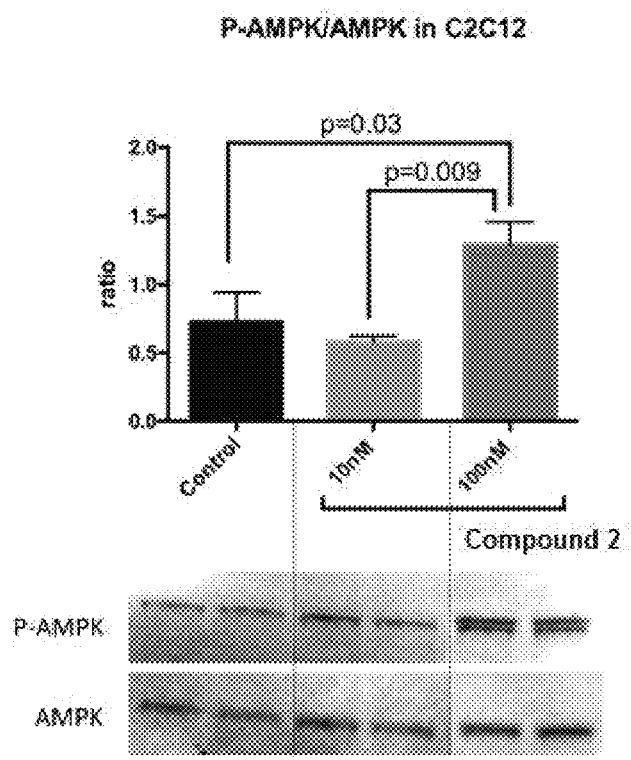
FIG. 6A depicts a graphical representation that shows the effects of different concentrations of Compound 2 on protein expression of AMPK in C2C12 muscle cells after treatment for 4 hours, and a representative blot.

The data also demonstrates that there was a 78% increase in the ratio of P-AMPK/AMPK in C2C12 muscle cell treated with 100 nM Compound 2 for 4 hours (p=0.03), while no effect was seen with 10 nM Compound 2 (FIG. 6A). FIG. 6A depicts a graphical representation that shows the effects of different concentrations (10 nM and 100 nM) of Compound 2 on protein expression of AMPK in C2C12 muscle cells after treatment for 4 hours, and a representative blot. As shown in FIG. 6A, the control had a ratio of approximately 0.75, 10 nM of Compound 2 had a ratio of approximately 0.65, and 100 nM of Compound 2 had a ratio of approximately 1.35.

Figure 6B:
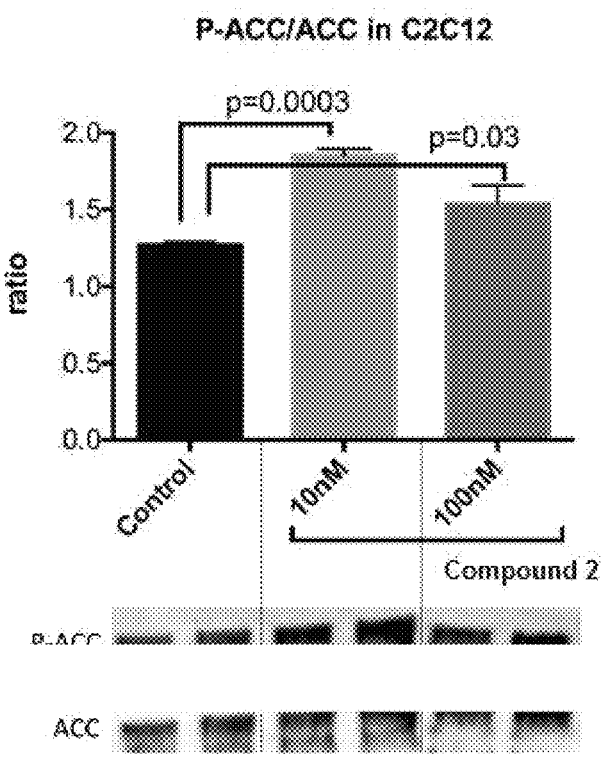
FIG. 6B depicts a graphical representation that shows the effects of different concentrations of Compound 2 on protein expression of Phospho-ACC in C2C12 muscle cells after treatment for 24 hours, and a representative blot. Data are represented as mean±SEM of the ratio of phosphorylated/total AMPK and ACC.

The ratio of the phosphorylated to total acetyl-CoA carboxylase (ACC), an AMPK-downstream target, was also increased by 46% and 21% in C2C12 muscle cells treated for 24 h with 10 nM and 100 nM Compound 2, respectively (FIG. 6B). FIG. 6B depicts a graphical representation that shows the effects of different concentrations (10 nM and 100 nM) of Compound 2 on protein expression of Phospho-ACC in C2C12 muscle cells after treatment for 24 hours, and a representative blot. Data are represented as mean±SEM of the ratio of phosphorylated/total AMPK and ACC. As shown in FIG. 6B, the control had a ratio of approximately 1.25, 10 nM of Compound 2 had a ratio of approximately 1.8, and 100 nM of Compound 2 had a ratio of approximately 1.52.

Figure 7A:
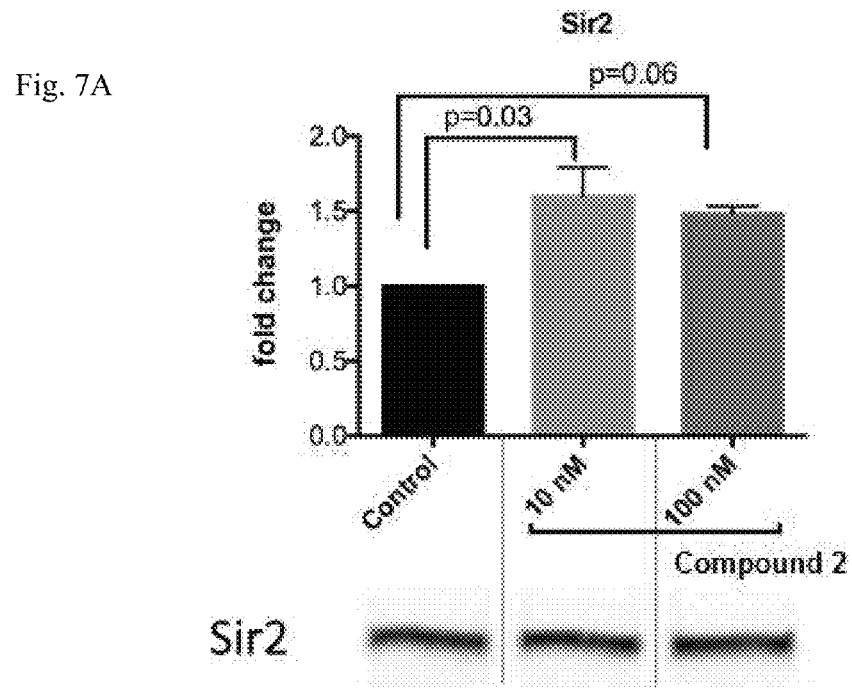
FIG. 7A depicts a graphical representation that shows the effects of different concentrations of Compound 2 on Sir2 protein expression after treatment L1 stage to adulthood (3 days), and a representative blot.
Figure 7B:
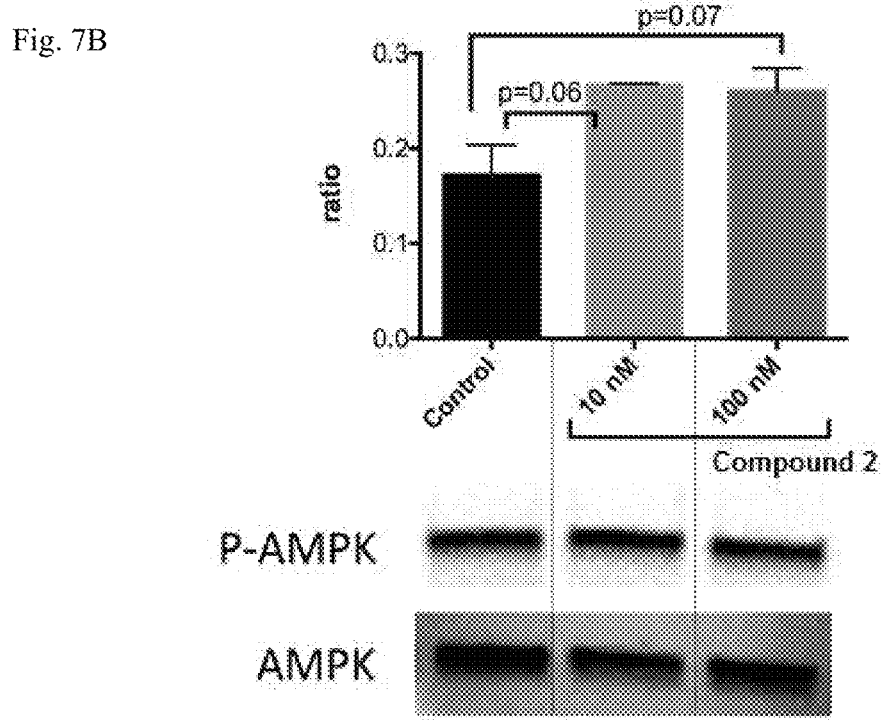
FIG. 7B depicts a graphical representation that shows the effects of different concentrations of Compound 2 on AMPK protein expression after treatment L1 stage to adulthood (3 days), and representative blot. Data are represented as mean±SEM of the ratio of phosphorylated/total AMPK and fold change of control for Sir2.

The data demonstrates that there was an increase of approximately 50% of P-AMPK/AMPK protein expression in C. elegans treated with Compound 2 from L1 stage to adulthood (p=0.06; FIG. 7B). FIG. 7B depicts a graphical representation that shows the effects of different concentrations (10 nM and 100 nM) of Compound 2 on AMPK protein expression after treatment L1 stage to adulthood (3 days), and representative blot. As shown in FIG. 7B, the control had a ratio of approximately 0.18, 10 nM of Compound 2 had a ratio of approximately 0.27, and 100 nM of Compound 2 had a ratio of approximately 0.26.

The upward trend for AMPK protein expression was associated with up to 60% increase in Sir2 protein expression (p=0.03; FIG. 7A). FIG. 7A depicts a graphical representation that shows the effects of different concentrations (10 nM and 100 nM) of Compound 2 on Sir2 protein expression after treatment L1 stage to adulthood (3 days), and a representative blot. As shown in FIG. 7A, the control had a fold change of approximately 1.0, 10 nM of Compound 2 had a fold change of approximately 1.65, and 100 nM of Compound 2 had a fold change of approximately 1.5. Data are represented as mean±SEM of the ratio of phosphorylated/total AMPK and fold change of control for Sir2.

Example 5: Effects of Compound 2 on Adiponectin Expression

Cell Culture: 3T3L1 adipocytes were seeded with 20,000 cells per well on 96-well tissue culture plates in DMEM containing 10% FBS and 1% penicillin-streptomycin. After reaching confluency (3 days), cells were induced to differentiate with a standard differentiation media (DM2-L1, Zen-Bio Inc., NC) for 3 days, then cells were maintained in DMEM (10% FBS, 1% penicillin-streptomycin) for another 8 days to induce lipid accumulation. Cells were then treated with indicated concentration of Compound 2 for 48 hours.

Compound 2 was dissolved in 100% DMSO to a stock concentration of 100 mM. This stock was further diluted to indicated concentrations in DMEM media.

Gene Expression: 3T3L1 adipocytes were grown and treated as described above. The medium was removed and the cells were washed with cold PBS. Cells Lysis, reverse transcription and real-time PCR was performed according to the instructions of the TaqMan® Gene Expression Cells-to-$C_T$™ Kit manual (Life Technologies Inc, Cat #4399002). cDNA was probed with adiponectin and normalized to 18S.

Statistics: Data were analyzed via one-way analysis of variance and least significant difference test was used to separate significantly different group means.

Figure 8:
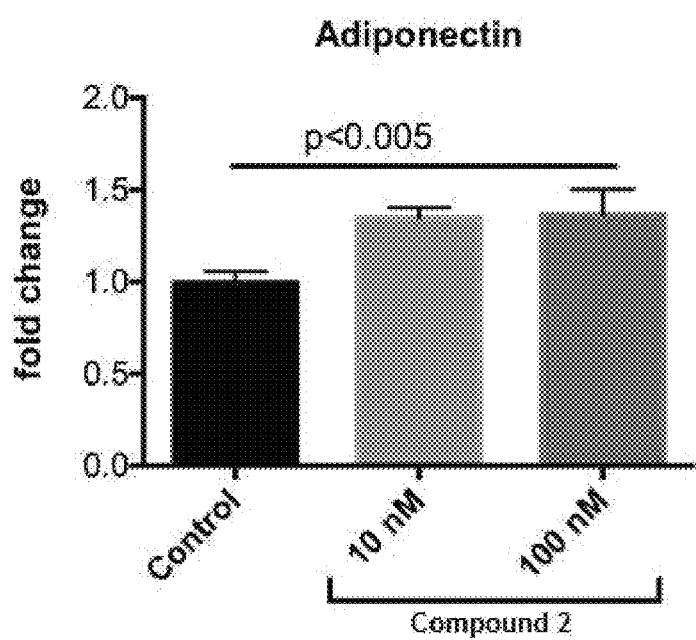
FIG. 8 depicts a graphical representation that shows the effects of different concentrations of Compound 2 on adiponectin protein expression in 3T3L1 adipocytes after treatment for 48 hours. Data are calculated as fold change to control and represented as mean±SEM.

Results: The data demonstrates that a 48 hour treatment of 3T3L1 adipocytes with Compound 2 (10 nM and 100 nM) significantly increased adiponectin gene expression by approximately 35% (FIG. 8). FIG. 8 depicts a graphical representation that shows the effects of different concentrations (10 nM and 100 nM) of Compound 2 on adiponectin protein expression in 3T3L1 adipocytes after treatment for 48 hours. Data are calculated as fold change to control and represented as mean±SEM. As shown in FIG. 8, the control had a fold change of approximately 1.0, 10 nM of Compound 2 had a fold change of approximately 1.35, and 100 nM of Compound 2 had a fold change of approximately 1.4.

Example 6: Effects on Lipid Accumulation in Adipocytes and *C. Elegans*

3T3L1 adipocytes:
Cell Culture: 3T3L1 adipocytes were seeded with 80,000 cells per well on 24-well tissue culture plates in high glucose (25 mM) DMEM containing 10% FBS and antibiotics. After reaching confluency (3 days), cells were induced to differentiate with a standard differentiation media (DM2-L1, Zen-Bio Inc., NC) for 3 days, then cells were maintained in DMEM (10% FBS, 1% penicillin-streptomycin) for another 8 days to induce lipid accumulation. Cells were then treated with indicated concentration of Compound 2 for 72 hours.

Compound 2 was dissolved in 100% DMSO to a stock concentration of 100 mM. This stock was further diluted to indicated concentrations in DMEM media.

Lipid accumulation (Oil Red Staining): 3T3L1 adipocytes were seeded and treated as described above. After 72 hours of treatment with Compound 2, lipid accumulation in adipocytes was measured via Oil Red Staining. Cells were washed with phosphate buffered saline (PBS) once, then cells were fixated with 10% formalin for 1 hour. After removal of the formalin, cells were washed with ddH$_2$O twice, then washed with 60% isopropanol. Cells were dried completely. Cells were stained with Oil Red working solution (~5 mM) for 25 minutes, then immediately washed with ddH$_2$O four times, then dried completely again. Oil Red dye was eluted with 100% isopropanol and absorbance was read at 500 nm. Unstained cells plus isopropanol was used as a blank and subtracted from all readings. Data are represented as mean±SEM for each treatment group.

Statistics: Data were analyzed via one-way analysis of variance and least significant difference test was used to separate significantly different group means.

Figure 11:
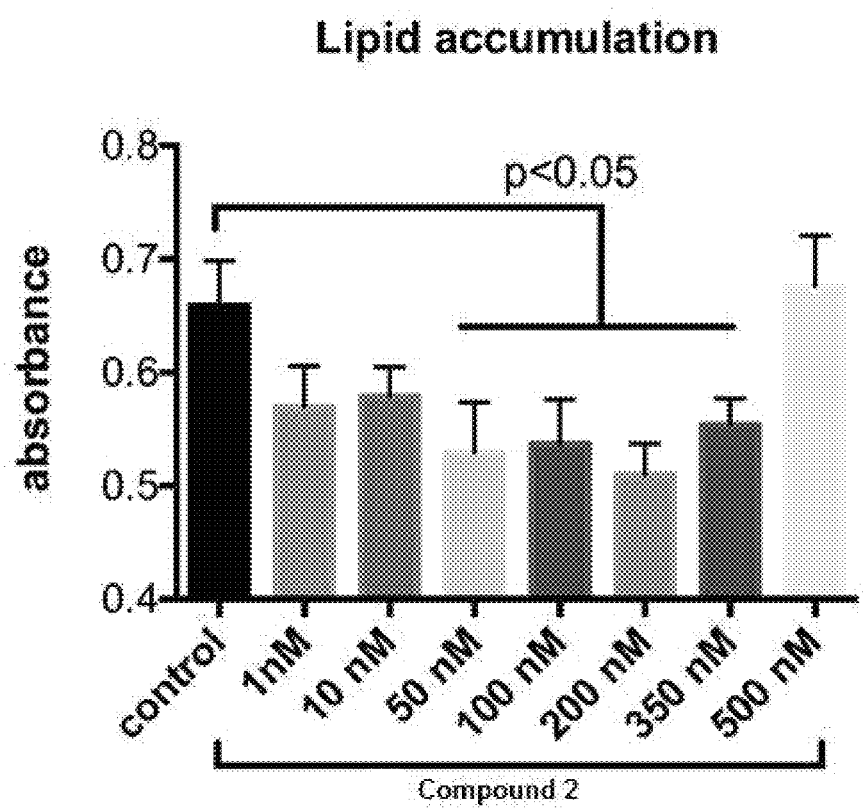
FIG. 11 depicts a graphical representation that shows the effects of different concentrations of Compound 2 on lipid accumulation in 3T3L1 adipocytes after treatment for 72 hours. Data are represented as mean±SEM.

Results: The data demonstrates that there was a dose-responsive reduction in lipid accumulation with a plateau effect (up to 23%) achieved by 50 to 350 nM Compound 2 (FIG. 11; p<0.05). The lipid reducing effect was lost with higher concentration of Compound 2 (500 nM). FIG. 11 depicts a graphical representation that shows the effects of different concentrations of Compound 2 on lipid accumulation in 3T3L1 adipocytes after treatment for 72 hours. Data are represented as mean±SEM. As shown in FIG. 11, the control had an absorbance of approximately 0.66, 1 nM of Compound 2 had an absorbance of approximately 0.57, 10 nM of Compound 2 had an absorbance of approximately 0.58, 50 nM of Compound 2 had an absorbance of approximately 0.53, 100 nM of Compound 2 had an absorbance of approximately 0.54, 200 nM of Compound 2 had an absorbance of approximately 0.51, 350 nM of Compound 2 had an absorbance of approximately 0.55, and 500 nM of Compound 2 had an absorbance of approximately 0.68.

*C. elegans*:
*C. elegans* culture: Synchronized L1 wild-type worms were transferred to NGM agar plates with the following treatments until adulthood (3 days): 1. control NGM plates, 2. NGM plate with 10 nM Compound 2 added to *E. coli* suspension, 3. NGM plate with 100 nM Compound 2 added to *E. coli* suspension.

Lipid accumulation (Oil Red Staining): Worms were washed off the plate with 2×5 ml PBS and collected in centrifuge tubes. The tubes were centrifuged at 1000 g for 30 seconds, then the supernatant was removed and the worm pellet was washed again with 5 ml PBS. Then the supernatant was discarded except approximately 400 ul, to which 200 ul of 10% paraformaldehyde was added and then gently rocked for 60 minutes at room temperature. To remove the paraformaldehyde, worms were centrifuged at 1500 g for 30 sec, then washed 1× with 5 ml PBS, centrifuged and supernatant removed except 400 ul, to which 600 ul of 100% isopropanol was added and mixed by inverting the tube and incubated for 15 minutes at room temperature. After centrifugation, the isopropanol was removed, then 1 ml of 60% filtered OilRed (4 vol ddH2O and 6 vol of OilRed stock (OilRed stock: dilute 0.35 g OilRed O (Sigma Cat #0-0625, FW 408.5) in 100 ml 100% isopropanol, stirred overnight, then filtered (0.2 um) and stored at room temperature), let stand for 15 to 20 min and filter with 0.2 um) was added. Worms were rotated on shaker overnight at room temperature and protected from light. Next day, the worms were centrifuged at 1200 g for 30 seconds, the dye was removed, and worms were washed 4 times with ddH$_2$O. At last washing step, 2 ml of ddH$_2$O was added and worms were counted under microscope in 3×20 ul drops. The worm number was multiplied by 100 to calculate the total worm number for normalization of the absorbance data. Then worm solution was centrifuged again, supernatant removed and 300 ul of 100% isopropanol was added to elute the OilRed. 100 ul aliquots of OilRed-isopropanol in transferred to 96-well plate and the absorbance was measured at 500 nm.

Statistics: Data were analyzed via one-way analysis of variance and least significant difference test was used to separate significantly different group means.

Figure 12:
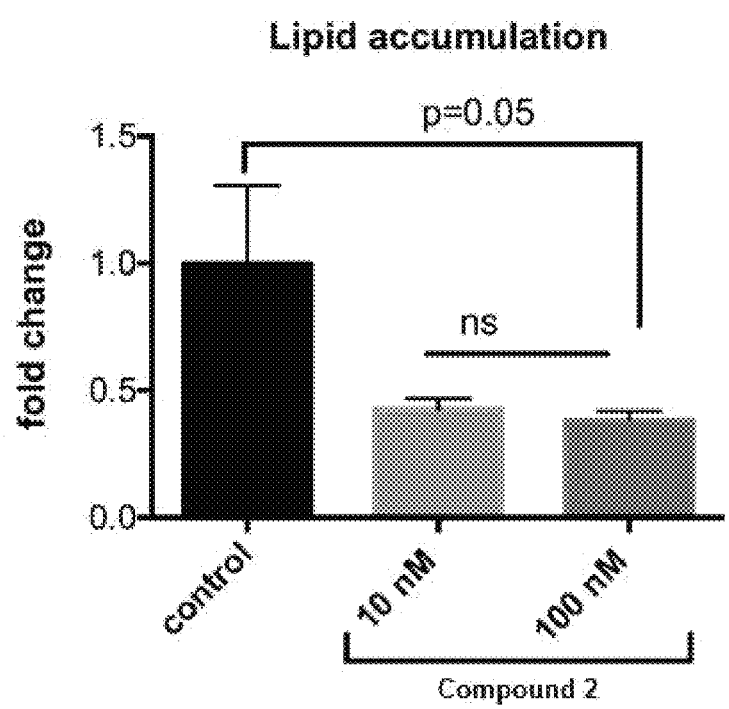
FIG. 12 depicts a graphical representation that shows the effects of different concentrations of Compound 2 on lipid accumulation in *C. elegans* after the worms were treated from L1 stage to adulthood (3 days). Absorbance values were normalized to worm number and transformed to fold change of control. Data are represented as mean±SEM.

Results: The date demonstrates that there was a significant 60% reduction in lipid accumulation in the worms treated with 100 nM Compound 2 (p<0.05) which was evident both quantitatively (FIG. 12) and visually (FIG. 13). FIG. 12 depicts a graphical representation that shows the effects of different concentrations of Compound 2 on lipid accumulation in *C. elegans* after the worms were treated from L1 stage to adulthood (3 days). Absorbance values were normalized to worm number and transformed to fold change of control. Data are represented as mean±SEM. As shown in FIG. 12, the control had a fold change of approximately 1.0, 10 nM of Compound 2 had a fold change of approximately 0.45, and 100 nM of Compound 2 had a fold change of approximately 0.35.

Figure 13A:
FIGS. 13A and 13B depict representative microscopic images of the effects of different concentrations of Compound 2 on lipid accumulation in *C. elegans*.
Figure 13B:
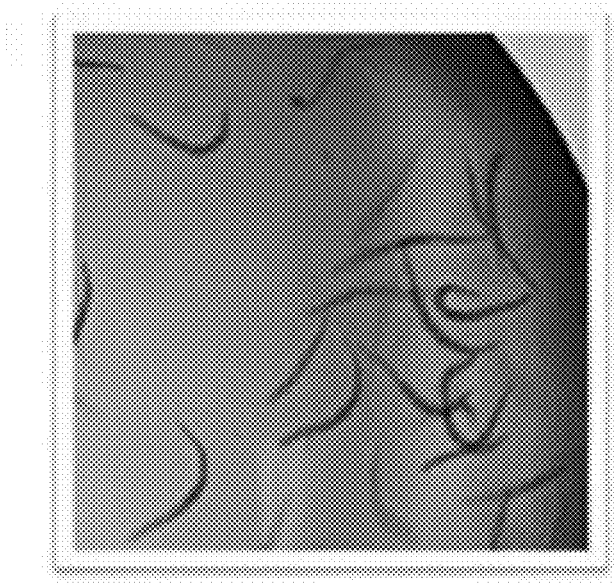

FIGS. 13A and 13B depict representative microscopic images of the effects of different concentrations of Compound 2 on lipid accumulation in *C. elegans*. FIG. 13A represents the control and FIG. 13B represents the significant reduction of lipid accumulation in in *C. elegans* when treated with 100 nM of Compound 2.

Example 7: Effects of Compound 2 on Lifespan

Lifespan Protocol: Wild-type worms were synchronized and hatched L1s were transferred to normal NGM agar plates until L4/young adult stage (3 days). 100 synchronized stage L4 worms per group were picked and placed on NGM agar plates seeded with *E. coli* strain OP-50 (=day 1 of study). Paraquat was added in the indicated concentration to the agar plates, the Compound 2 concentrations were dissolved in the *E. coli* suspension. The worms were maintained at 21° C. throughout the duration of the study. Live worms were placed on new plates every day to eliminate progeny. Worms were scored as dead if they did not respond to repeated touches with the platinum pick and scored as censored if they crawled off the plate.

Statistics: For the statistical analysis of the lifespan study with *C. elegans*, data were analyzed via Kaplan-Meier survival curves and statistical significance between curves was determined with the Log-rank (Mantel_Cox) test using Prism 6 (GraphPad Software, La Jolla Calif., USA, www.graphpad.com).

Results: The data demonstrates that Compound 2 (10 nM and 100 nM) significantly increased the median lifespan by 18% and 30% under normal (FIGS. 14A and 14B) and mild oxidative stress (FIGS. 14C and 14D) conditions (500 uM Paraquat), respectively (p<0.0002). In addition, Compound 2 increased the maximum lifespan by 14% under mild oxidative stress conditions (FIGS. 14C and 14D). FIGS. 14A, 14B, 14C and 14D show the effects of 10 nM and 100 nM Compound 2 on lifespan in *C. elegans* under normal and mild oxidative stress (500 uM Paraquat) conditions.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A compound having the structural formula of:

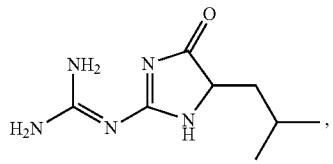

or a pharmaceutically acceptable salt thereof.

2. The compound of claim 1, wherein the compound is

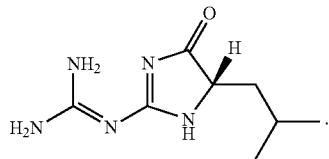

3. A compound or a pharmaceutically acceptable salt thereof selected from:

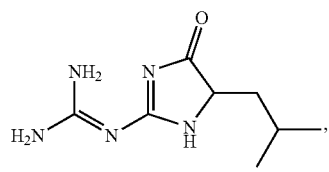

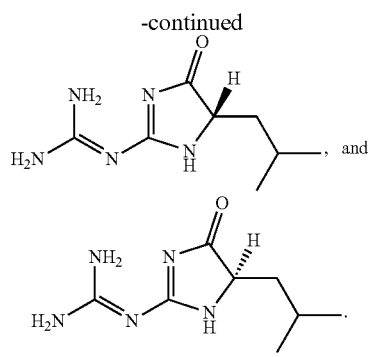

4. A pharmaceutical composition comprising a compound of claim 1 and a pharmaceutically acceptable carrier.

5. The pharmaceutical composition of claim 4, wherein the pharmaceutical composition is formulated for oral administration.

6. The pharmaceutical composition of claim 4, wherein the pharmaceutical composition is formulated for injection.

7. A kit comprising a pharmaceutical composition of claim 4 and instructions for using the composition to treat a subject suffering from a disease or condition, wherein the disease or condition is selected from the group consisting of diabetes, metabolic syndrome, obesity, hyperlipidemia, high cholesterol, arteriosclerosis, hypertension, non-alcoholic steatohepatitis, non-alcoholic fatty liver, non-alcoholic fatty liver disease, hepatic steatosis, and any combination thereof.

8. A method of treating a disease or condition in a subject in need thereof, wherein the disease or condition is selected from the group consisting of diabetes, metabolic syndrome, obesity, hyperlipidemia, high cholesterol, arteriosclerosis, hypertension, non-alcoholic steatohepatitis, non-alcoholic fatty liver, non-alcoholic fatty liver disease, hepatic steatosis, and any combination thereof, the method comprising: administering to the subject a therapeutically effective amount of a compound of claim 1.

9. A method of reducing, treating, or sustaining a reduction of a metabolic disease or disorder in a subject in need thereof, whether or not a diagnosis of this disease has been made, wherein the metabolic disease or disorder is selected from the group consisting of diabetes, metabolic syndrome, obesity, hyperlipidemia, high cholesterol, arteriosclerosis, hypertension, non-alcoholic steatohepatitis, non-alcoholic fatty liver, non-alcoholic fatty liver disease, hepatic steatosis, and any combination thereof, comprising administering to said subject a dose of the compound of claim 1 to effect a reduction, treatment, or sustainment in reduction of the metabolic disease or disorder.

10. A method of reducing adiposity in a subject in need thereof, comprising administering to said subject the compound of claim 1 to effect a reduction of adiposity in the subject.

11. A method of increasing insulin sensitivity in a subject in need thereof, comprising administering to said subject the compound of claim 1 to effect increasing insulin sensitivity in the subject.

12. A method of increasing glucose utilization in a subject in need thereof, comprising administering to said subject the compound of claim 1 to effect increasing glucose utilization in the subject.

13. A method of increasing fat oxidation in a subject in need thereof, comprising administering to said subject the compound of claim 1 to effect increasing fat oxidation in the subject.

14. A method of treating diabetes and/or hyperlipidemia comprising administering to the subject the compound of claim 1 over a time period, during which the subject exhibits one or more of (1) an increase in insulin sensitivity, glucose utilization, or fat oxidation or (2) a reduction in lipid accumulation.

15. A method of reducing atherosclerotic plaque size in a subject in need thereof, comprising administering to said subject a dose of the compound of claim 1 to effect a reduction in total atherosclerotic plaque size in the subject.

16. A method of reducing non-alcoholic steatohepatitis (NASH) in a subject in need thereof, comprising administering to said subject a dose of the compound of claim 1 to effect a reduction in non-alcoholic steatohepatitis (NASH) in the subject.

17. The method of claim 16, wherein the non-alcoholic steatohepatitis (NASH) is evidenced by reduction in hepatic fat, inflammation and/or fibrosis detectable by one or more methods selected from the group consisting of ultrasonography, computed tomography (CT), magnetic resonance imaging, measurement of serum alanine transaminase and aspartate transaminase, biopsy, transient elastography, magnetic resonance elastography, and related techniques.

18. The method of claim 16, wherein the subject exhibits a non-alcoholic fatty liver disease (NAFLD).

19. The method of claim 18, wherein the NAFLD is selected from the group consisting of non-alcoholic fatty liver (NAFL), NASH-related cirrhosis, and hepatic steatosis.

20. The method of claim 16, wherein the subject exhibits one or more symptoms of non-alcoholic steatohepatitis (NASH) selected from the group consisting of weakness, fatigue, unexplained weight loss, ache and jaundice.

21. A method of reducing, treating, or sustaining a reduction of a metabolic disease or disorder in a subject in need thereof, whether or not a diagnosis of this disease has been made, wherein the disease or condition is selected from the group consisting of diabetes, metabolic syndrome, obesity, hyperlipidemia, high cholesterol, arteriosclerosis, hypertension, non-alcoholic steatohepatitis, non-alcoholic fatty liver, non-alcoholic fatty liver disease, hepatic steatosis, and any combination thereof, comprising administering to said subject a dose of the pharmaceutical composition of claim 4 to effect a reduction, treatment, or sustainment in reduction of the metabolic disease or disorder.

22. A method of reducing adiposity in a subject in need thereof, comprising administering to said subject the pharmaceutical composition of claim 4 to effect a reduction of adiposity in the subject.

23. A method of increasing insulin sensitivity in a subject in need thereof, comprising administering to said subject the pharmaceutical composition of claim 4 to effect increasing insulin sensitivity in the subject.

24. A method of increasing glucose utilization in a subject in need thereof, comprising administering to said subject the pharmaceutical composition of claim 4 to effect increasing glucose utilization in the subject.

25. A method of increasing fat oxidation in a subject in need thereof, comprising administering to said subject the pharmaceutical composition of claim 4 to effect increasing fat oxidation in the subject.

26. A method of treating diabetes and/or hyperlipidemia comprising administering to the subject the pharmaceutical composition of claim 4 over a time period, during which the subject exhibits one or more of (1) an increase in insulin sensitivity, glucose utilization, or fat oxidation or (2) a reduction in lipid accumulation.

27. A method of reducing atherosclerotic plaque size in a subject in need thereof, comprising administering to said subject a dose of the pharmaceutical composition of claim 4 to effect a reduction in total atherosclerotic plaque size in the subject.

28. A method of reducing non-alcoholic steatohepatitis (NASH) in a subject in need thereof, comprising administering to said subject a dose of the pharmaceutical composition of claim 4 to effect a reduction in non-alcoholic steatohepatitis (NASH) in the subject.

29. The method of claim 28, wherein the non-alcoholic steatohepatitis (NASH) is evidenced by reduction in hepatic fat, inflammation and/or fibrosis detectable by one or more methods selected from the group consisting of ultrasonography, computed tomography (CT), magnetic resonance imaging, measurement of serum alanine transaminase and aspartate transaminase, biopsy, transient elastography, magnetic resonance elastography, and related techniques.

30. The method of claim 28, wherein the subject exhibits a non-alcoholic fatty liver disease (NAFLD).

31. The method of claim 30, wherein the NAFLD is selected from the group consisting of non-alcoholic fatty liver (NAFL), NASH-related cirrhosis, and hepatic steatosis.

32. The method of claim 28, wherein the subject exhibits one or more symptoms of non-alcoholic steatohepatitis (NASH) selected from the group consisting of weakness, fatigue, unexplained weight loss, ache and jaundice.

* * * * *